United States Patent
Markowitz et al.

(10) Patent No.: US 10,945,998 B2
(45) Date of Patent: Mar. 16, 2021

(54) INHIBITORS OF SHORT-CHAIN DEHYDROGENASE ACTIVITY FOR TREATING FIBROSIS

(71) Applicant: CASE WESTERN RESERVE UNIVERSITY, Cleveland, OH (US)

(72) Inventors: Sanford Markowitz, Pepper Pike, OH (US); Stanton Gerson, Hunting Valley, OH (US); Amar Desai, Cleveland, OH (US); Won Jin Ho, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 0 days.

(21) Appl. No.: 15/556,972

(22) PCT Filed: Mar. 8, 2016

(86) PCT No.: PCT/US2016/021374
§ 371 (c)(1),
(2) Date: Sep. 8, 2017

(87) PCT Pub. No.: WO2016/144958
PCT Pub. Date: Sep. 15, 2016

(65) Prior Publication Data
US 2018/0064694 A1    Mar. 8, 2018

Related U.S. Application Data

(60) Provisional application No. 62/129,885, filed on Mar. 8, 2015.

(51) Int. Cl.
*A61K 31/44*    (2006.01)
*A61K 31/4365*  (2006.01)
(Continued)

(52) U.S. Cl.
CPC ........ *A61K 31/4365* (2013.01); *A61K 31/426* (2013.01); *C07D 277/00* (2013.01); *C07D 277/02* (2013.01); *Y02A 50/30* (2018.01)

(58) Field of Classification Search
CPC .................................................. A61K 31/4365
(Continued)

(56) References Cited

U.S. PATENT DOCUMENTS 5,445,164 A    8/1995  Worthen et al.
6,214,533 B1   4/2001  Ho et al.
(Continued)

FOREIGN PATENT DOCUMENTS

EP    1080728 A1     3/2001
JP    2005325099 A  11/2005
(Continued)

OTHER PUBLICATIONS

Cho et al. "Inhibition of NAD+-dependent 15-hydroxtprostaglandin dehydrogenase (15-PGDH) by cyclooxygenase inhibitors and chemopreventive agents," Prostaglandins, Leukotrienes and Essential Fatty Acids, 2002, vol. 67, No. 6, pp. 461-465. (Year: 2002).*
(Continued)

*Primary Examiner* — Shengjun Wang
(74) *Attorney, Agent, or Firm* — Tarolli, Sundheim, Covell & Tummino LLP

(57) ABSTRACT

A method of treating or preventing a fibrotic disease, disorder or condition includes administering to a subject in need of treatment a 15-PGDH inhibitor.

14 Claims, 8 Drawing Sheets

(51) Int. Cl.
    *C07D 277/00* (2006.01)
    *A61K 31/426* (2006.01)
    *C07D 277/02* (2006.01)
(58) Field of Classification Search
    USPC .......................................................... 514/301
    See application file for complete search history.

(56) References Cited

U.S. PATENT DOCUMENTS

| | | | |
|---|---|---|---|
| 6,281,227 | B1 | 8/2001 | Choi-Sledeski et al. |
| 7,004,913 | B1 | 2/2006 | Rutenberg et al. |
| 7,131,958 | B2 | 11/2006 | Deverre |
| 7,147,626 | B2 | 12/2006 | Goodman et al. |
| 7,629,112 | B1 | 12/2009 | Zengerle et al. |
| 8,068,897 | B1 | 11/2011 | Gazdzinski |
| 8,202,882 | B2 | 6/2012 | Hoelzemann et al. |
| 9,789,116 | B2 | 10/2017 | Markowitz et al. |
| 9,790,233 | B2 | 10/2017 | Markowitz et al. |
| 9,801,863 | B2 | 10/2017 | Markowitz et al. |
| 10,301,320 | B2 | 5/2019 | Markowitz et al. |
| 10,420,752 | B2 | 9/2019 | Markowitz et al. |
| 2009/0118337 | A1* | 5/2009 | Davis .................. A61K 31/426 514/342 |
| 2010/0022521 | A1 | 1/2010 | Nogradi et al. |
| 2011/0034564 | A1* | 2/2011 | Parkkinen .......... A61K 36/9066 514/679 |
| 2011/0269954 | A1 | 11/2011 | Cho et al. |
| 2018/0064694 | A1 | 3/2018 | Markowitz et al. |
| 2018/0118756 | A1 | 5/2018 | Markowitz et al. |
| 2019/0275014 | A1 | 9/2019 | Markowitz et al. |
| 2019/0365769 | A1 | 12/2019 | Markowitz et al. |
| 2020/0030348 | A1 | 1/2020 | Markowitz et al. |
| 2020/0061073 | A1 | 2/2020 | Markowitz et al. |
| 2020/0095206 | A1 | 3/2020 | Markowitz et al. |
| 2020/0140453 | A1 | 5/2020 | Markowitz et al. |
| 2020/0147063 | A1 | 5/2020 | Markowitz et al. |

FOREIGN PATENT DOCUMENTS

| | | |
|---|---|---|
| JP | 2007527850 A | 10/2007 |
| JP | 2009520016 A | 5/2009 |
| JP | 2009535335 A | 10/2009 |
| JP | 2011500610 A | 1/2011 |
| JP | 2016524455 A | 12/2016 |
| JP | 2016537328 A | 12/2016 |
| JP | 2018511581 A | 4/2018 |
| JP | 6517197 B2 | 5/2019 |
| JP | 2019135253 A | 8/2019 |
| WO | 2001/017480 A1 | 3/2001 |
| WO | 2001017480 A2 | 3/2001 |
| WO | 2004012671 A2 | 2/2004 |
| WO | 2007/127183 A1 | 11/2007 |
| WO | 2009/029669 A1 | 3/2009 |
| WO | 2010/045017 A1 | 4/2010 |
| WO | 2011/042860 A2 | 4/2011 |
| WO | 2013/082243 A1 | 6/2013 |
| WO | 2013/158649 A1 | 10/2013 |
| WO | 2013158649 A1 | 10/2013 |
| WO | 2013/180336 A1 | 12/2013 |
| WO | 2014/160947 A1 | 10/2014 |
| WO | 2015/065716 A1 | 5/2015 |
| WO | 2016/124939 A1 | 8/2016 |
| WO | 2016/144958 D2 | 9/2016 |
| WO | 2016/168472 A1 | 10/2016 |

OTHER PUBLICATIONS

Kalugin, V. E. et al., "Functionalized sulfur-containing compounds. 13. Synthesis of substituted 3-amino-2-(sulfinyl) and (sulfonyl)thieno[2,3-b]pyridines", Russian Chemical Bulletin, 2006, vol. 55, No. 3, pp. 529-534.

Hall, P. R. et al., "Small molecule inhibitors of hantavirus infection", Bioorganic & Medicinal Chemistry Letters, 2010, vol. 20, No. 23, pp. 7085-7091.
Office action for Australian Patent Application No. 2014342811.
Blake et al., "Studies with Deuterated Drugs", Journal of Pharmaceutical Sciences, vol. 64, 1975, pp. 367-391.
Office Action for Japanese Patent Application No. 2016-524455.
Wu, et al., Synthesis and Biological Evaluation of Novel Thiazolidinedione Analogues as 15-Hydroxyprostaglandin Dehydrogenase Inhibitors, Journal of Medicinal Chemistry, 2011, vol. 54, pp. 5260-5264.
Tatsuwaki, et al., "Reduction of 15-hydroxyprostaglandin dehydrogenase expression us an independent predictor of poor survival associated with enhanced cell proliferation in gastric adenocarcinoma", Cancer Science, vol. 101, pp. 550-558.
Pubchem Database compound CID 1826991, 2-[(4-Cholorobezny)sulfonyl]-4-phenyl-6-(2-thienyl)thieno[2,3-b]pyridin-3-amine, Jul. 12, 2005.
Pubchem Database compound CID 3337993, 2-(Octylsulfonyl)-4-phenyl-6-thien-2-ylthieno[2,3-b]pyridin-3-amine, Sep. 7, 2005.
Pubchem Database compound CID 3337992, 2-(Octylsulfonyl)-4-phenyl-6-thiophen-2-ylthieno[2,3-b]pyridin-3-amine, Sep. 7, 2005.
Lakatos, et al., "The Role of PPARs in LUNG Fibrosis", PPAR Research, vol. 2007, pp. 1-10, Jan. 1, 2017.
Jadhav, et. al., "Potent and selective inhibitors of NAD+-dependent 15-hydroxyprostaglandin dehydrogenase (HPGD)", Molecular Libraries. Pathways to Discovery, Jan. 1, 2011.
U.S. Patent and Trademark Office, Office Action and 892 dated Mar. 8, 2019 in related U.S. Appl. No. 15/529,399.
U.S. Patent and Trademark Office, Office Action dated Sep. 21, 2018 in related U.S. Appl. No. 15/529,399.
U.S. Patent and Trademark Office, Office Action and 892 dated Mar. 1, 2019 in related U.S. Appl. No. 15/103,638.
U.S. Patent and Trademark Office, Office Action dated Aug. 13, 2018 in related U.S. Appl. No. 15/103,638.
U.S. Patent and Trademark Office, Office Action dated Feb. 2, 2018 in related U.S. Appl. No. 15/359,330.
U.S. Patent and Trademark Office, Office Action and 892 dated Aug. 17, 2017 in related U.S. Appl. No. 15/359,330.
U.S. Patent and Trademark Office, Office Action dated Jun. 22, 2016 in related U.S. Appl. No. 14/395,021.
U.S. Patent and Trademark Office, Office Action and 892 dated Oct. 19, 2015 in related U.S. Appl. No. 14/395,021.
U.S. Patent and Trademark Office, Office Action dated Mar. 31, 2017 in related U.S. Appl. No. 14/395,021.
U.S. Patent and Trademark Office, Office Action dated May 23, 2018 in related U.S. Appl. No. 15/799,307.
Somasundaram et al., Clinical Epigenetics vol. 10(127): 15 pages, 2018.
"A Guide to the Graphic Representation and Nomenclature of Chemical Formulae in the European Pharmacopoeia" European Pharmacopoeia 2011 2nd Edition.
Mayo Clinic Staff "Diseases and Conditions Chronic kidney disease" Jan. 30, 2015 Online"http://www.mayoclinic.org/diseasesconditions/kidneydisease/basics/causes/con2002677" accessed Dec. 11, 2015.
Galie et. al. "Guidelines for the diagnosis and treatment of pulmonary hypertension" European Heart Journal (2009)30, 2493-2537.
Healthline Online "http://www.healthline.com/health/inflammatory-bowel-disease", accessed Sep. 9, 2015.
Breyer "Prostanoid Receptors: Subtypes and Signaling" Annu. Rev. Pharmacol. Toxicol. 2001. 41 :661-90.
Kalugin "Functionalized sulfurcontaining compounds. 13.* Synthesis of substituted 3amino2(organylsulfinyl)and organylsulfonyl)thieno[2,3b]pyridines." Russian Chemical Bulletin, International Edition, vol. 55, No. 3, pp. 529-534, Mar. 2006.
Pubchem Database compound CI D 3337991, 2-butylsulfonyl-4-phenyl-6-thiophen-2-ylthieno[2,3-b]pyridin-3-amine, entered into the database on Sep. 7, 2005, Online "http://pubchem.ncbi.nlm.nih.gov/compound/3337991#section=Top" accessed Oct. 10, 2015.
Online"http://web.archive.org/web/20071219115313/http://www.akosgmbh.de/AKosSamples/index.html" 2011, accessed Oct. 10, 2015.

(56) References Cited

OTHER PUBLICATIONS

Online: "http://web.archive.org/web/20070630171813/http://www.enamine.net/index.php?option=comcontent&task=view&id=22&menuid=51&PHPSESSID=64a4f248f69d671a413f487bb62c4d90" dated Jun. 30, 2007, accessed Apr. 1, 2015.
Online "http://web.archive.org/web/20031225052253/http://www.specs.net/", accessed Apr. 1, 2015.
Online "http://web.archive.org/web/20130122020518/http://www.chembridge.com/screening_libraries/" 2011, accessed Oct. 10, 2015.
Zhang "Inhibition of the prostaglandin-degrading enzyme 15-PGDH potentiates tissue regeneration" Science Jun. 12, 2015 • vol. 348 Issue 6240 1223.
Supplementary European Search Report for Application No. 14859042.5-1462 / 3057973 dated Mar. 6, 2017.
A. Archelas et al: "Absolute Configuration of [alpha]-Methylstyrene Oxide: The Correct Absolute Configuration/Optical Rotation Correlation", The Journal of Organic Chemistry, vol. 64, No. 16, Aug. 1, 1999 (Aug. 1, 1999), pp. 6112-6114.
Japanese Office action for Application No. 2015-504681, dated Jan. 31, 2017.
Castellone, Maria, et al. "Prostaglandin E2 Promotes Colon Cancer Cell Growth Through a Gs-Axin-Catenin Signaling Axis", Dec. 2, 2005, vol. 310, Science.
Goessling, Wolfram, et al., "Genetic interaction of PGE2 and Wnt signaling regulates developmental specification of stem cells and regeneration", Cell. Mar. 20, 2009; 136(6): 1136-1147. doi:10.1016/j.cell.2009.01.015.
Frisch, Benjamin, et al., "In vivo prostaglandin E2 treatment alters the bone marrow microenvironment and preferentially expands short-term hematopoietic stem cells", Blood, Nov. 5, 2009 z vol. 114, No. 19,pp. 4054-4063.
Hoggati, Jonathan, et al., "Prostaglandin E2 enhances long-term repopulation but does not permanently alter inherent stem cell competitiveness", Blood, Oct. 24, 2013 x vol. 122, No. 17, pp. 2997-3000.
Jung, Peter, et al., "Isolation and in vitro expansion of human colonic stem cells", Nature Medicine 17, 1225-1227 (2011).
Brown, JR, et al., "COX-2: a molecular target for colorectal cancer prevention", J. Clin Oneal. Apr. 20, 2005;23(12):2840-55.
Obeid, J., et al., "Tyr-179 and Lys-183 are essential for enzymatic activity of 11 beta-hydroxysteroid dehydroxysteroid dehydrogenase", Biochem Biophys Res Commun. Oct. 15, 1992;188(1):222-7.
Ensor, CM, et al., "Site-directed mutagenesis of the conversed tyrosine 151 of human placental NAO(+)-dependent 15-hydroxyprostaglandin dehydrogenase yields a catalytically inactive enzyme", Biochem Biophys Res Commun. Apr. 30, 1991; 176(2):840-5.
Tanaka, N., et al., "Crystal Structures of the binary and ternary complexes of 7 alpha-hydroxysteroid dehydrogenase from *Escherichia coli*.", Biochemistry Jun. 18, 1996;35(24):7715-30.
Duveau, DY, et al., "Structure-activity relationship studies and biological characterization of human NAO(+)-dependent 15 hydroxyprostaglandin dehydrogenase", Bioorg Med Chem Lett. Jan. 15, 2014;24(2):630-5.
Piao, Yu Lan, et al., Wound healing effects of new 15-hydroxyprostaglandin dehydrogenase inhibitors, Prostaglandins, Leukotrienes and Essential Fatty Acids 91 (2014)325-332.
Bray, James E., et al. "The human short-chain dehydrogenase/reductase (SOR) superfamily: A bioinformatics Summary", Chemico-Biological Interactions 178(2009) 99-109.
Markowitz, Sanford, et al., "Molecular Basis of Colorectal Cancer", N Engl J Med 2009;361 :2449-60.
Yan, Min, et al., "15-Hydroxyprostaglandin dehydrogenase, a COX-2 oncogene antagonist, is a TGF-β-induced suppressor of human gastrointestinal cancers", PNAS, Dec. 14, 2004, vol. 101, No. 50, 17468-17473.

Ensor, Charles Mark, et al., "Bacterial expression and site-directed mutagenesis of two critical residues (tyrosine-151 and lysine-155) of human placental NAO +-dependent 15-hydroxyprostaglandin dehydrogenase", D Biochimica et Biophysica Acta 1208 (1994) 151-156.
Yan, Min, et al, "15-Hydroxyprostaglandin dehydrogenase inactivation as a mechanism of resistance to celecoxib chemoprevention of colon tumors", PNAS, Jun. 9, 2009, vol. 106, No. 23, 9409-9413.
Tai, Hsin-Hsiung, et al., "Prostaglandin catabolizing enzymes", Prostaglandins & other Lipid Mediators 68-69 (2002)483-493.
Choi, Dubok, et al., "Control of the intracellular levels of prostaglandin E2 through inhibition of the 15-hydroxyprostaglandin dehydrogenase for wound healing", Choi, D.; et al. Bioorg. Med. Chem. (2013), http://dx.doi.org/10.1016/j.bmc.2013.05.049.
Niesen, Frank H., et al., "High-Affinity Inhibitors of Human NAD+-Dependent 15-Hydroxyprostaglandin Dehydrogenase: Mechanisms of Inhibition and Structure-Activity Relationships", Nov. 2010, vol. 5, Issue 11.
Myung, Seung-Jae, et al., "15-Hydroxyprostaglandin dehydrogenase is an in vivo suppressor of colon tumorigenesis" PNAS, Aug. 8, 2006, vol. 103, No. 32, 12098-12102.
Otani, Taisuke, et al., "Levels of NAD+-dependent 15-hydroxyprostaglandin dehydrogenase are reduced in inflammatory bowel disease: evidence for involvement of TNF-a", Am J Physiol Gastrointest Liver Physiol 290: G361-DG368, 2006.
Cho, Hoon, et al., "Role of glutamine 148 of human 15-hydroxyprostaglandin dehydrogenase in catalytic oxidation of prostaglandin E2", Bioorganic & Medicinal Chemistry 14 (2006) 6486-6491.
Clifford, P.C., et al., "Treatment of Vasospastic disease with prostaglandin E1", British Medical Journal vol. 281, Oct. 18, 1980, pp. 1031-1034.
Jadhav, Ajit, et al., "Potent and Selective Inhibitors of NAD+-dependent 15-hydroxyprostaglandin dehydrogenase {HPGD)", Probe Report 2011.
Markowitz, Sanford, et al., "Aspirin and Colon Cancer—Targeting Prevention", N Engl J med 256;21, May 27, 2007.
North, Trista E., "PGE2-regulated wnt signaling and N-acetylcysteine are synergistically hepatoprotective in zebrafish acetaminophen injury", PNAS, Oct. 5, 2010, vol. 107, No. 40, pp. 17315-17320.
Wu, Ying, et al., "Synthesis and Biological Evaluation of Novel Thiazolidinedione Analogues as 15-Hydroxyprostaglandin Dehydrogenase Inhibitors", J Med Chem, Apr. 5, 2011, 54, 5260-5264.
Cho, et al., "Inhibition of NAD+-dependent 15-hydroxyprostaglandin dehydrogenase (15-PGDH) by cyclooxygenase inhibitors and chemopreventive agents", Prostaglandins, Leukotrienes and Essential FattyAcids {2002) 67(6), 461-465.
Hamza, Adel, et al., "Understanding human 15-hydroxyprostaglandin dehydrogenase binding with NAO+ and PGE2 by homology modeling, docking and molecular dynamics simulation", Bioorganic & Medicinal Chemistry 13 (2005) 4544-4551.
Berg, Daniel J., et al. "Rapid Development of Colitis in NSAID-Treated IL-10-Deficient Mice", Gastroenterology 2002; 123: 1527-1542.
Kabashima, Kenji, et al., "The prostaglandin receptor EP4 suppresses colitis, mucosal damage and CD4 cell activation in the gut", J. Clin. Invest 109:883-893 (2002).
Berk, L.B., et al., "16,16-Dimethyl Prostaglandin E2 and/or Syngeneic Bone Marrow Transplantation Increase Mouse Survival After Supra-Lethal Total Body Irradiation", Int. J Radiation Oncology Biol. Phys .. vol. 18. pp. 1387-1392.
Goessling, Wolfram, et al., "Prostaglandin E2 Enhances Human Cord Blood Stem Cell Xenotransplants and Shows Long-Term Safety in Preclinical Nonhuman Primate Transplant Models", Cell Stem Cell 8, 445-458, Apr. 8, 2011.
Porter, Rebecca L., et al., "Prostaglandin E2 Increases Hematopoietic Stem Cell Survival and Accelerates Hematopoietic Recovery After Radiation Injury", Stem Cells 2013;31 :372-383.
Kurland, JI, et al., "prostaglandin E in the positive and negative feedback control of myeloid Role for monocyte-macrophage-derived colony-stimulating factor and stem cell proliferation" Blood 1978 52: 388-407.

(56) References Cited

OTHER PUBLICATIONS

Hoffman, Corey M., et al., "Minireview: Complexity of Hematopoietic Stem Cell Regulation in the Bone Marrow Microenvironment", Mol Endocrinol, 2014.
Hoggati, Jonathan, et al., "Prostaglandin E2 enhances long-term repopulation but does not permanently alter inherent stem cell competitiveness," Blood 2013 122:2997-3000.
Frisch, Benjamin J., et al., "In vivo prostaglandin E2 treatment alters the bone marrow stem cells microenvironment and preferentially expands short-term hematopoietic", Blood 2009 114: 4054-4063.
Speth, Jennifer, et al., "Pharmacologic increase in HIF1 a enhances hematopoietic stem and progenitor homing and engraftment", Blood 2014 123: 203-207.
Hoggati, Jonathan, et al., "Prostaglandin E2 enhances hematopoietic stem cell homing, survival, and proliferation", Blood 2009 113: 5444-5455.
Hoggati, Jonathan, et al., "Recovery from hematopoietic injury by modulating prostaglandin E2 signaling post-irradiation", Blood Cells, Molecules and Diseases 50 (2013) 147-153.
Pelus, Louis, M., et al., Pleiotropic effects of prostaglandin E2 in hematopoiesis; prostaglandin E2 and other eicosanoids regulate hematopoietic stem and progenitor cell function, Prostaglandins & other Lipid Mediators 96 {2011) 3-9.
Pelus, L.M., et al., "Pulse exposure of haematopoietic grafts to prostaglandin E2 in vitro facilitates engraftment and recovery", Cell Prolif., 2011, 44 {Suppl. 1), 22-29.
Hoggati, Jonathan, et al., "Differential stem- and progenitor-cell trafficking by prostaglandin E2", Nature, 2011.
Sasaki, S., et al., "Prostaglandin E2 Inhibits Lesion Formation in Dextran Sodium Sulphate-Induced Colitis in Rats and Reduces the Levels of Mucosal Inflammatory Cytokines", Scand. J. Immunol. 51, 23-28, 2000.
Tessner, Teresa, G., et al., "Prostaglandins Prevent Decreased Epithelial Cell Proliferation Associated With Dextran Sodium Sulfate Injury in Mice", Gastroenterology 1998;115:874-882.
Cutler, Corey, et al., "Prostaglandin-modulated umbilical cord blood hematopoietic stem cell transplantation" Blood, 2013.
Geossling, Wolfram, et al., "Genetic Interaction of PGE2 and Wnt Signaling Regulates Developmental Specification of Stem Cells and Regeneration", Cell 136, 1136-1147, Mar. 20, 2009.
Hagedorn, Elliott J., et al., "Getting more for your marrow: Boosting hematopoietic stem cell numbers with PGE2", BoostinghematopoieticstemcellnumberswithPGE2, Exp Cell Res {2014), http://dx.doi.org/10.1016/j.yexcr.2014.07.030.
North, Trista E., et al., "Prostaglandin E2 regulates vertebrate haematopoietic stem cell homeostasis", vol. 447, Jun. 21, 2007.
Karna, Sandeep,et al., "Novel Potent 15-Hydroxyprostaglandin Dehydrogenase Inhibitors", J. of Advanced Engineering and Technology, vol. 3, No. 3 (2010) pp. 301-304.
Castellone, Maria Domenica, et al., "Prostaglandin E2 Promotes Colon Cancer Cell Growth Through a Gs-Axin-13-Catenin Signaling Axis", Science, vol. 310, Dec. 2, 2005.
Baker, Michael E., Licorice and enzymes other than 1 I !3-hydroxysteroid dehydrogenase: An evolutionary perspective. Department of Medicine, University of California, Steroids, Feb. 1994. vol. 59, p. 136-141.
Tatsuwaki, Hiroshi, et al., Reduction of 15-hydroxyprostaglandin dehydrogenase expression is an independent 6 ¬ehydrogenase expression is an independent predictor of poor survival associated with enhanced cell proliferation in gastric adenocarcinoma, Cancer Science, Feb. 2010, vol. 100, No. 2, p. 550-558.
International Search Report for Application No. PCT/US2013/036790, dated Jul. 29, 2013.
Supplementary European Search Report for Application No. EP 16780752, dated Nov. 23, 2018.
Pubchem Database compound CID 1826991, 2-[{4-Cholorobezny)sulfonyl]-4-phenyl-6-(2-thienyl)thieno[2,3-b]pyridin-3-mine, Jul. 12, 2005.
Pubchem Database compound CID 3337998, 2[{4-Tert-butylphenyl)sulfonyl]-4-phenyl-6-thien-2-ylthieno[2,3-b]pyridin-3-amine, Sep. 7, 2005.
Pubchem Database compound CID 3337993, 2-{0ctylsulfonyl)-4-phenyl-6-thien-2-ylthieno[2,3-b]pyridin-3-amine, Sep. 7, 2005.
Pubchem Database compound CID 3337995, 2-{Benzysulfonyl)-4-phenyl-6-thien-2-ylthieno[2,3-b]pyridin-3-amine, Sep. 7, 2005.
Pubchem Database compound CID 3337997, 2-[{4-Tert-butylphenyl)sulfinyl]-4-phenyl-6-thiophen-2-ylthieno[2,3-b]pyridin-3-amine, Sep. 7, 2005.
Pubchem Database compound CID 3337992, 2-{0ctylsulfonyl)-4-phenyl-6-thiophen-2-ylthieno[2,3-b]pyridin-3-amine, Sep. 7, 2005.
PubChem Substance summary for CID 52943190 Deposit dale Jun. 16, 2011 (Jun. 16, 2011) p. 1.
PubChem Substance summary for CID 3337839 Deposit dale Sep. 7, 2005 (Sep. 7, 2005) p. 1.
Lakatos, et al., "The Role of PPARs in Lung Fibrosis", PPAR Research, vol. 2007, pp. 1-10, Jan. 1, 2007.
Partial Supplementary European Search Report for Application No. 16762344.6/3267995, dated Oct. 22, 2018.
Partial Supplementary European Search Report for Application No. 16780752.8-1116/3283074, dated Aug. 14, 2018.
Examination Report for Australian Application No. 2018200368, dated Jul. 31, 2018.
Antczak et al Publication Date (Web): Apr. 11, 2017.
Randhawa Korean Journal of Physiology & Pharmacology (2014), 18(4), 279-288.
Solomon "The dextran sulphate sodium (DSS) model of colitis: an overview" Comp Clin Pathol (2010) 19:235-239.
Extended European Search Report for Application No. 16762344.6-1112/3267995, dated Jan. 28, 2019.
Supplementary European Search Report for Application No. 16780752.8-1116/3283074, dated Nov. 23, 2018.
Supplementary European Search Report for Application No. 16762344.6-1112/3267995, dated Feb. 14, 2019.
Office Action for Japanese Patent Application No. 2016-524455, dated Jun. 12, 2018.
Office Action for Canadian Patent Application No. 2870666, dated Jan. 22, 2019.
Examination Report for Australian Patent Application No. 2016248080, dated Dec. 23, 2019.
Australian Office action for Patent Application No. 2016229918, dated Oct. 18, 2019.
Office Action for Japanese Patent Application No. 2017-546676, dated Dec. 24, 2019.
Australian Office action for Patent Application No. 2016248080, dated Dec. 23, 2019.
Office action for Canadian Patent Application No. 2870666, dated Oct. 1, 2019.
Australian Office action for Patent Application No. 2019202208, dated Nov. 21, 2019.
Chinese Office Action for Application No. 201680034932.5 dated May 8, 2020.
European Office Action for Application No. 17 194 305.3-1110 dated Apr. 9, 2020.
Cho et al: "Thiazolidinediones as a novel class of NAD+dependent 15-hydroxyprostaglandin dehydrogenase inhibitors", Archives of Biochemistry and Biophysics, Academic Press, US, vol. 405, Jan. 1, 2002 (Jan. 1, 2002), pp. 247-251, XP002292688, ISSN: 0003-9861, DOI: 10.1016/S0003-9861 (02)00352-1.
Office action for Japanese Patent Application No. 2017-553122, dated Feb. 10, 2020.
Office action for Japanese Patent Application No. 2019-078488, dated Feb. 10, 2020.
"2-Octysulfonyl-4-phenyl-6-thiophen-2-ylthieno[2,3-b]pyridin-3-amine", Database PubChem Compound [online], NCBI Database accession No. CID 3337993, Sep. 7, 2005.
File Registry on STN, RN 457958-16-6, Entered STN: Oct. 2, 2002.
"2-[4-Chlorobenzyl)sulfonyl]-4-phenyl-6-(2-thienyl)thieno[2,3-b]pyridin-3-amine", Database PubChem Compound [online], NCBI Database accession No. 1826991, Jul. 12, 2005.

(56) References Cited

OTHER PUBLICATIONS

"2-[4-Tert-butylphenyl)sulfonyl-4-phenyl-6-thiophen-2-ylthieno[2,3-b]pyridin-3-amine", Database PubChem Compound [online], NCBI Database accession No. CID 3337998, Sep. 7, 2005.
"2-(Benzylsulfonyl)-4-phenyl-6-thien-2-ylthieno[2,3-b]pyridin-3-amine", Database PubChem Compound [online], NCBI Database accession No. CID 3337995, Sep. 7, 2005.
"2-[4-Tert-butylphenyl)sulfinyl-4-phenyl-6-thiophen-2-ylthieno[2,3-b]pyridin-3-amine", Database PubChem Compound [online], NCBI Database accession No. CID 3337997, Sep. 7, 2005.

\* cited by examiner

SWO33291 Application Increases Survival and Weight Maintenance in IPF
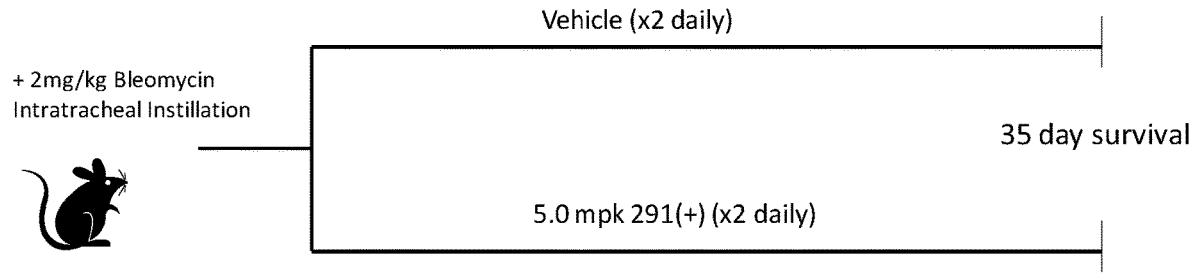
Fig. 1
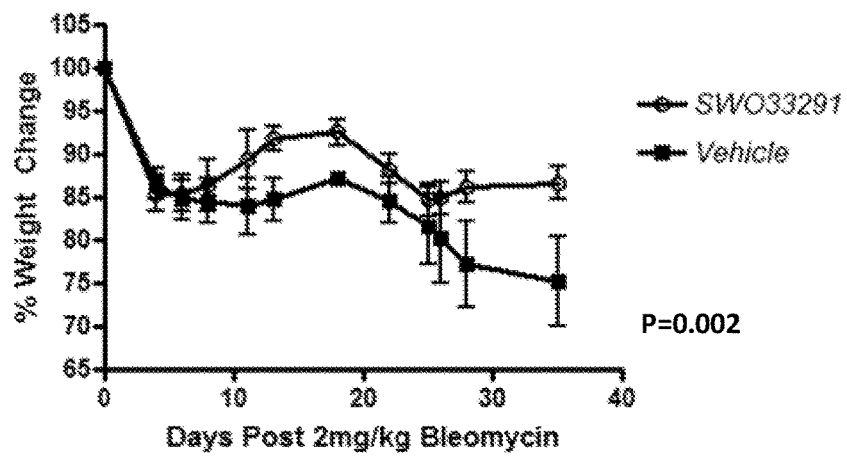
N= 10 mice/group
Fig. 2A
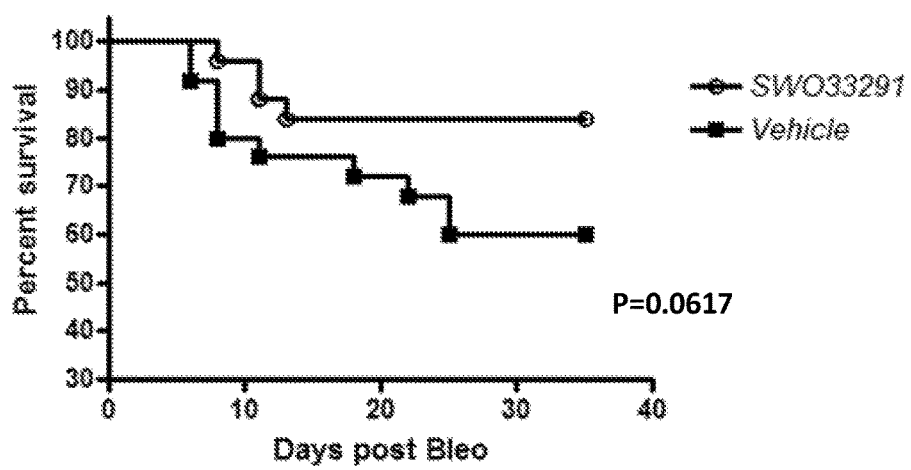
Fig. 2B   N= 25 mice/group SW033291 Treatment Decreases Collagen Deposition in IPF N= 9 untreated
N= 15 Vehicle
N= 20 SW033291

SWO33291 Decreases Inflammatory Response at Day 35

A

N= 2 untreated
N= 3 Vehicle
N= 5 SWO33291

B

SW033291 Decreases Inflammatory Response at Day 35

N= 2 untreated
N= 3 Vehicle
N= 5 SW033291

SWO33291 Decreases Inflammatory Response at Day 35

N= 2 untreated
N= 3 Vehicle
N= 5 SWO33291

Comparing fibrosis at Day 69 by Masson's Trichrome:
Two representative images of distal colon from each group

A

B

Comparing fibrosis at Day 69 by Masson's Trichrome:
Two representative images of distal colon from each group

INHIBITORS OF SHORT-CHAIN DEHYDROGENASE ACTIVITY FOR TREATING FIBROSIS

RELATED APPLICATION

This application claims priority from U.S. Provisional Application No. 62/129,885, filed Mar. 8, 2015, the subject matter of which is incorporated herein by reference in its entirety.

GOVERNMENT FUNDING

This invention was made with government support under Grant Nos. R01CA127306, R01CA127306-03S1, 1P01CA095471-10, AND 5P50CA150964, T32EB005583, F32DK107156, awarded by The National Institutes of Health. The United States government may have certain rights to the invention.

BACKGROUND

Fibrosis is a chronic and progressive process characterized by an excessive accumulation of extracellular matrix (ECM) leading to stiffening and/or scarring of the involved tissue. It develops through complex cell, extracellular matrix, cytokine and growth factor interactions. Distinct cell types are involved, such as resident mesenchymal cells (fibroblasts and myofibroblasts) and ECM-producing cells derived from epithelial and endothelial cells (through a process termed epithelial- and endothelial-mesenchymal transition), local or bone marrow-derived stem cells (fibrocytes). Myofibroblasts has long been regarded as a major cell type involved in normal wound healing, and as the key effector cell in fibrogenesis. They are highly synthetic for collagen and other ECM components, and are characterized by the de novo expression of α-smooth muscle actin α-SMA). The presence of myofibroblasts in fibrotic lesions in animal models of fibrosis correlates with the development of active fibrosis, and their persistence and localization to fibrotic foci in human disease is associated with disease progression. Myofibroblasts also exhibit an enhanced migratory phenotype and are capable of releasing numerous pro-fibrotic mediators.

Fibrotic diseases, including pulmonary fibrosis, systemic sclerosis, liver cirrhosis, and progressive kidney disease, are a leading cause of morbidity and mortality and can affect all tissues and organ systems. Fibrotic tissue remodeling can also influence cancer metastasis and accelerate chronic graft rejection in transplant recipients.

SUMMARY

Embodiments described herein relate to compositions and methods for treating and/or preventing fibrosis and various fibrotic diseases, disorders or conditions. As described in the Examples below, it was found that that inhibitors of short-chain dehydrogenase activity, such as 15-PGDH inhibitors, can be administered to a subject in need thereof to decrease fibrotic symptoms, such as collagen deposition, collagen accumulation, collagen fiber formation, inflammatory cytokine expression, and inflammatory cell infiltration, and treat and/or prevent various fibrotic diseases, disorders, and conditions characterized, in whole or in part, by the excess production of fibrous material, including excess production of fibrotic material within the extracellular matrix, or the replacement of normal tissue elements by abnormal, non-functional, and/or excessive accumulation of matrix-associated components.

Fibrotic diseases, disorders and conditions characterized, in whole or in part, by excess production of fibrotic material can include systemic sclerosis, multifocal fibrosclerosis, nephrogenic systemic fibrosis, scleroderma (including morphea, generalized morphea, or linear scleroderma), sclerodermatous graft-vs-host-disease, kidney fibrosis (including glomerular sclerosis, renal tubulointerstitial fibrosis, progressive renal disease or diabetic nephropathy), cardiac fibrosis (e.g., myocardial fibrosis), pulmonary fibrosis (e.g. pulmonary fibrosis, glomerulosclerosis pulmonary fibrosis, idiopathic pulmonary fibrosis, silicosis, asbestosis, interstitial lung disease, interstitial fibrotic lung disease, and chemotherapy/radiation induced pulmonary fibrosis), oral fibrosis, endomyocardial fibrosis, deltoid fibrosis, pancreatitis, inflammatory bowel disease, Crohn's disease, nodular fasciitis, eosinophilic fasciitis, general fibrosis syndrome characterized by replacement of normal muscle tissue by fibrous tissue in varying degrees, retroperitoneal fibrosis, liver fibrosis, liver cirrhosis, chronic renal failure; myelofibrosis (bone marrow fibrosis), drug induced ergotism, myelodysplastic syndrome, myeloproferative syndrome, collagenous colitis, acute fibrosis, organ specific fibrosis, and the like.

In some embodiments, a method of treating or preventing a fibrotic disease, disorder or condition includes administering to a subject in need thereof a therapeutically effect amount of a 15-PGDH inhibitor.

In some embodiments, the 15-PGDH inhibitors can be used to treat or prevent lung fibrosis. Lung fibrosis, which can be treated, can be selected from the group consisting of pulmonary fibrosis, pulmonary hypertension, chronic obstructive pulmonary disease (COPD), asthma, idiopathic pulmonary fibrosis, sarcoidosis, cystic fibrosis, familial pulmonary fibrosis, silicosis, asbestosis, coal worker's pneumoconiosis, carbon pneumoconiosis, hypersensitivity pneumonitides, pulmonary fibrosis caused by inhalation of inorganic dust, pulmonary fibrosis caused by an infectious agent, pulmonary fibrosis caused by inhalation of noxious gases, aerosols, chemical dusts, fumes or vapors, drug-induced interstitial lung disease, or pulmonary hypertension, and combinations thereof.

In other embodiments, the 15-PGDH inhibitors can be used to treat or prevent kidney fibrosis. The kidney fibrosis can result from dialysis following kidney failure, catheter placement, a nephropathy, glomerulosclerosis, glomerulonephritis, chronic renal insufficiency, acute kidney injury, end stage renal disease or renal failure, or combinations thereof.

In other embodiments, the 15-PGDH inhibitors can be used to treat or prevent liver fibrosis. The liver fibrosis can result from a chronic liver disease, viral induced hepatic cirrhosis, hepatitis B virus infection, hepatitis C virus infection, hepatitis D virus infection, schistosomiasis, primary biliary cirrhosis, alcoholic liver disease or non-alcoholic steatohepatitis (NASH), NASH associated cirrhosis obesity, diabetes, protein malnutrition, coronary artery disease, autoimmune hepatitis, cystic fibrosis, alpha-1-antitrypsin deficiency, primary biliary cirrhosis, drug reaction and exposure to toxins, or combinations thereof.

In some embodiments, the 15-PGDH inhibitors can be used to treat or prevent heart fibrosis, for example, cardiac fibrosis and endomyocardial fibrosis.

In some embodiments, the 15-PGDH inhibitors can be used to treat or prevent systemic sclerosis.

In some embodiments, the 15-PGDH inhibitors can be used to treat or prevent fibrotic diseases, disorders or conditions caused by post-surgical adhesion formation.

In some embodiments, the 15-PGDH inhibitors can used for reducing or preventing scar formation in a subject.

In other embodiments, the 15-PGDH inhibitors can be used to reduce or prevent scar formation on skin or scleroderma.

In various embodiments, the 15-PGDH inhibitors can be administered at a therapeutically effective amount such that at least one symptom or feature of a fibrotic disease, disorder or condition, or other related diseases, disorders or conditions, is reduced in intensity, severity, or frequency, or has delayed onset.

In other embodiments, the 15-PGDH inhibitors can be used in a method for decreasing or reducing collagen secretion, or collagen deposition, or collagen fiber accumulation, in a tissue or organ, such as the lung, the liver, the intestines, the colon, the skin or the heart, of a subject. The method can include administering a therapeutically effective amount of the 15-PGDH inhibitors to the subject in need thereof. The subject can have or be at risk of an excessive collagen secretion or collagen deposition in the tissue or organ, such as the kidney, the lung, the liver, the intestines, the colon, the skin or the heart. Usually, the excessive collagen secretion or collagen deposition in an organ results from an injury or an insult. Such injury and insult can be organ-specific. The 15-PGDH inhibitors can be administered over a sufficient period of time to decrease or reduce the level of collagen deposition in the tissue or organ, completely or partially. A sufficient period of time can be during one week, or between 1 week to 1 month, or between 1 to 2 months, or 2 months or more. For chronic condition, the 15-PGDH inhibitors can be advantageously administered for life time period.

In some embodiments, the 15-PGDH inhibitor can be administered to a tissue of a subject at an amount effective to increase prostaglandin levels in the tissue. The 15-PGDH inhibitor can include formula (I):

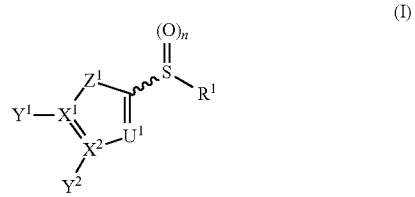

(I)

wherein n is 0-2;

$Y^1$, $Y^2$, and $R^1$ are the same or different and are each selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms (wherein from 1-3 of the ring atoms is independently selected from N, NH, N($C_1$-$C_6$ alkyl), NC(O) ($C_1$-$C_6$ alkyl), O, and S), $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—NH$_2$), carbamido (—NH—(CO)—NH$_2$), cyano(—CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N (aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), sulfonamide (—SO$_2$—NH$_2$, —SO$_2$NY$_2$ (wherein Y is independently H, arlyl or alkyl), phosphono (—P(O)(OH)$_2$), phosphonato (—P(O)(O$^-$)$_2$), phosphinato (—P(O)(O$^-$)), phospho (—PO$_2$), phosphino (—PH$_2$), polyalkylethers, phosphates, phosphate esters, groups incorporating amino acids or other moieties expected to bear positive or negative charge at physiological pH, combinations thereof, and wherein $Y^1$ and $Y^2$ may be linked to form a cyclic or polycyclic ring, wherein the ring is a substituted or unsubstituted aryl, a substituted or unsubstituted heteroaryl, a substituted or unsubstituted cycloalkyl, and a substituted or unsubstituted heterocyclyl;

$U^1$ is N, C—$R^2$, or C—$NR^3R^4$, wherein $R^2$ is selected from the group consisting of a H, a lower alkyl group, O, $(CH_2)_{n1}$OR' (wherein n1=1, 2, or 3), $CF_3$, $CH_2$—$CH_2$X, O—$CH_2$—$CH_2$X, $CH_2$—$CH_2$—$CH_2$X, O—$CH_2$—$CH_2$X, X, (wherein X=H, F, Cl, Br, or I), CN, (C=O)—R', (C=O)N(R')$_2$, O(CO)R', COOR' (wherein R' is H or a lower alkyl group), and wherein $R^1$ and $R^2$ may be linked to form a cyclic or polycyclic ring, wherein $R^3$ and $R^4$ are the same or different and are each selected from the group consisting of H, a lower alkyl group, O, $(CH_2)_{n1}$OR' (wherein n1=1, 2, or 3), $CF_3$, $CH_2$—$CH_2$X, $CH_2$—$CH_2$—$CH_2$X, (wherein X=H, F, Cl, Br, or I), CN, (C=O)—R', (C=O)N(R')$_2$, COOR' (wherein R' is H or a lower alkyl group), and $R^3$ or $R^4$ may be absent;

$X^1$ and $X^2$ are independently N or C, and wherein when $X^1$ and/or $X^2$ are N, $Y^1$ and/or $Y^2$, respectively, are absent;

$Z^1$ is O, S, $CR^aR^b$ or $NR^a$, wherein $R^a$ and $R^b$ are independently H or a $C_{1-8}$ alkyl, which is linear, branched, or cyclic, and which is unsubstituted or substituted;

and pharmaceutically acceptable salts thereof.

In other embodiments, the 15-PGDH inhibitor can include a compound having the following (V):

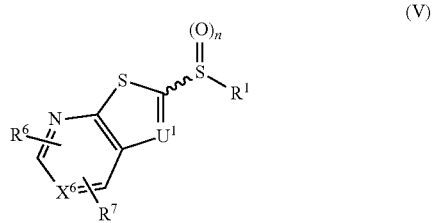

(V)

wherein n is 0-2

$X^6$ is independently is N or $CR^c$ $R^1$, $R^6$, $R^7$, and $R^c$ are each independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms (wherein from 1-3 of the ring atoms is independently selected from N, NH, N($C_1$-$C_6$ alkyl), NC(O)($C_1$-$C_6$ alkyl), O, and S), $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—NH$_2$), carbamido (—NH—(CO)—NH$_2$), cyano(—CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), sulfonamide (—SO$_2$—NH$_2$, —SO$_2$NY$_2$ (wherein Y is independently H, arlyl or alkyl), phosphono (—P(O)(OH)$_2$), phosphonato (—P(O)(O$^-$)$_2$), phosphinato (—P(O)(O$^-$)), phospho (—PO$_2$), phosphino (—PH$_2$), polyalkylethers, phosphates, phosphate esters, groups incorporating amino acids or other moieties expected to bear positive or negative charge at physiological pH, combinations thereof, and wherein $R^6$ and $R^7$ may be linked to form a cyclic or polycyclic ring, wherein the ring is a substituted or unsubstituted aryl, a substituted or unsubstituted heteroaryl, a substituted or unsubstituted cycloalkyl, and a substituted or unsubstituted heterocyclyl;

$U^1$ is N, C—$R^2$, or C—NR$^3$R$^4$, wherein $R^2$ is selected from the group consisting of a H, a lower alkyl group, O, (CH$_2$)$_{n1}$OR' (wherein n1=1, 2, or 3), CF$_3$, CH$_2$—CH$_2$X, O—CH$_2$—CH$_2$X, CH$_2$—CH$_2$—CH$_2$X, O—CH$_2$—CH$_2$X, X, (wherein X=H, F, Cl, Br, or I), CN, (C=O)—R', (C=O)N(R')$_2$, O(CO)R', COOR' (wherein R' is H or a lower alkyl group), and wherein $R^1$ and $R^2$ may be linked to form a cyclic or polycyclic ring, wherein $R^3$ and $R^4$ are the same or different and are each selected from the group consisting of H, a lower alkyl group, O, (CH$_2$)$_{n1}$OR' (wherein n1=1, 2, or 3), CF$_3$, CH$_2$—CH$_2$X, CH$_2$—CH$_2$—CH$_2$X, (wherein X=H, F, Cl, Br, or I), CN, (C=O)—R', (C=O)N(R')$_2$, COOR' (wherein R' is H or a lower alkyl group), and $R^3$ or $R^4$ may be absent;

and pharmaceutically acceptable salts thereof.

In some embodiments, $R^1$ is selected from the group consisting of branched or linear alkyl including —(CH$_2$)$_{n_1}$CH$_3$ ($n_1$=0-7),

wherein $n_2$=0-6 and X is any of the following: CF$_y$H$_z$ (y+z=3), CCl$_y$H$_z$ (y+z=3), OH, OAc, OMe, $R^{71}$, OR$^{72}$, CN, N(R$^{73}$)$_2$,

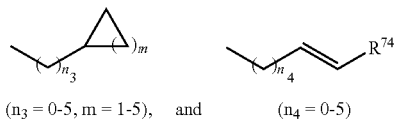

($n_3$ = 0-5, m = 1-5), and ($n_4$ = 0-5).

In other embodiments, $R^6$ and $R^7$ can each independently be one of the following:

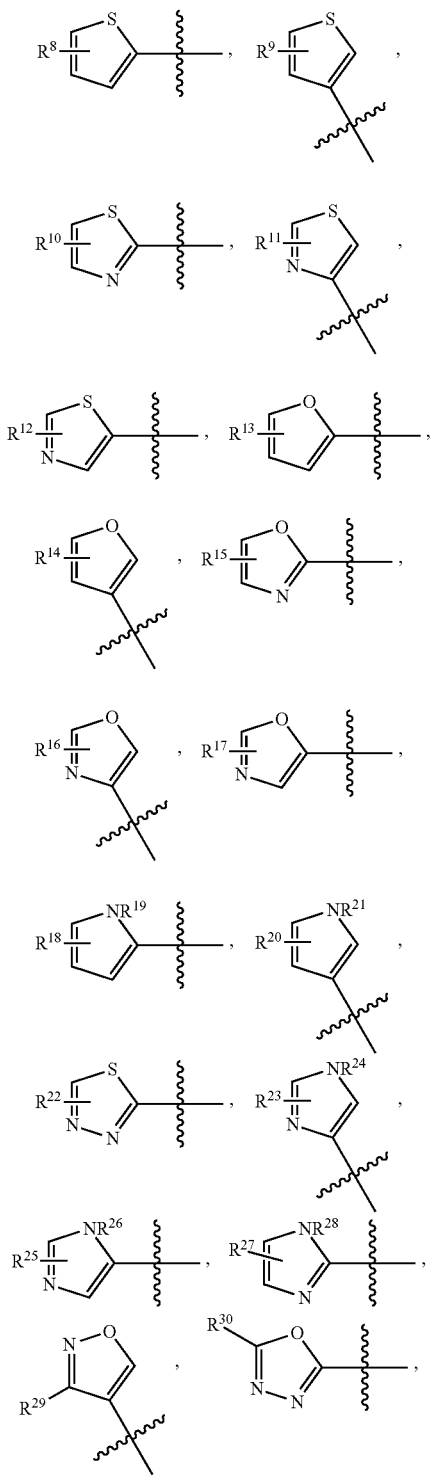

-continued

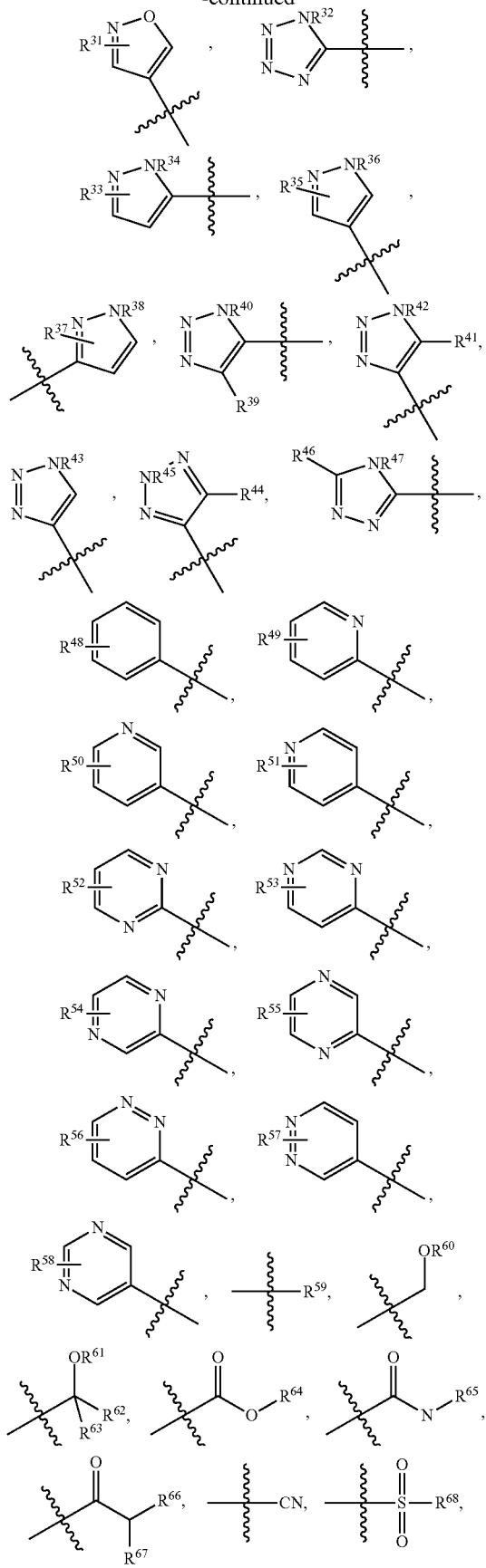

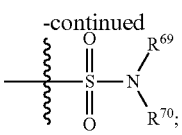

each $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, $R^{49}$, $R^{50}$, $R^{51}$, $R^{52}$, $R^{53}$, $R^{54}$, $R^{55}$, $R^{56}$, $R^{57}$, $R^{58}$, $R^{59}$, $R^{60}$, $R^{61}$, $R^{62}$, $R^{63}$, $R^{64}$, $R^{65}$, $R^{66}$, $R^{67}$, $R^{68}$, $R^{69}$, $R^{70}$, $R^{71}$, $R^{72}$, $R^{73}$, and $R^{74}$, are the same or different and are independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heterocycloalkenyl containing from 5-6 ring atoms, (wherein from 1-3 of the ring atoms is independently selected from N, NH, N($C_1$-$C_6$ alkyl), NC(O)($C_1$-$C_6$ alkyl), O, and S), heteroaryl or heterocyclyl containing from 5-14 ring atoms, (wherein from 1-6 of the ring atoms is independently selected from N, NH, N($C_1$-$C_3$ alkyl), O, and S), $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—NH$_2$), carbamido (—NH—(CO)—NH$_2$), cyano(—CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), sulfanamido (—SO$_2$N(R)$_2$ where R is independently H, alkyl, aryl or heteroaryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), sulfonamide (—SO$_2$—NH$_2$, —SO$_2$NY$_2$ (wherein Y is independently H, arlyl or alkyl), phosphono (—P(O)(OH)$_2$), phosphonato (—P(O)(O$^-$)$_2$), phosphinato (—P(O)(O$^-$)), phospho (—PO$_2$), phosphino (—PH$_2$), polyalkyl ethers (—[(CH$_2$)$_n$O]$_m$), phosphates, phosphate esters [—OP(O)(OR)$_2$ where R=H, methyl or other alkyl], groups incorporating amino acids or other moieties expected to bear positive or negative charge at physiological pH, and combinations thereof, and pharmaceutically acceptable salts thereof.

In some embodiments, the 15-PGDH inhibitor can inhibit the enzymatic activity of recombinant 15-PGDH at an IC$_{50}$ of less than 1 μM, or preferably at an IC$_{50}$ of less than 250 nM, or more preferably at an IC$_{50}$ of less than 50 nM, or more preferably at an IC$_{50}$ of less than 10 nM, or more preferably at an $IC_{50}$ of less than 5 nM at a recombinant 15-PGDH concentration of about 5 nM to about 10 nM.

BRIEF DESCRIPTION OF THE DRAWINGS

FIG. 1 illustrates a schematic diagram of an assay for measuring the effects of SW033291 on weight maintenance and survival in a mouse model of idiopathic pulmonary fibrosis.

FIGS. 2(A-B) illustrate plots showing (A) weight change and (B) survival of vehicle and SW033291 treated mouse models of idiopathic pulmonary fibrosis.

DETAILED DESCRIPTION

Figure 3:
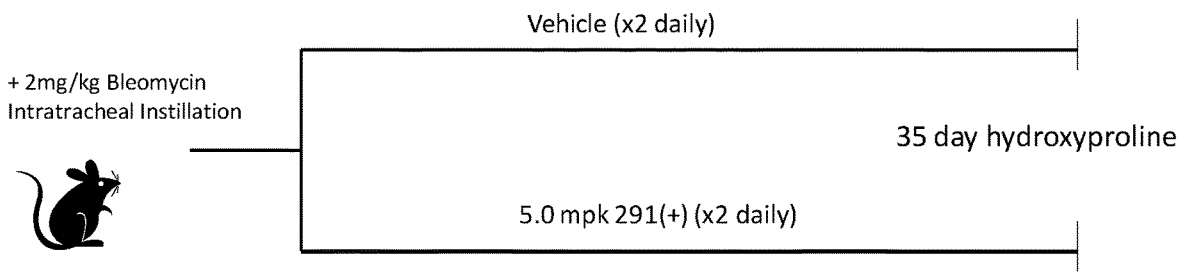
FIG. 3 illustrates a schematic diagram of an assay for measuring the effects of SW033291 on collagen deposition in a mouse model of idiopathic pulmonary fibrosis.

For convenience, certain terms employed in the specification, examples, and appended claims are collected here. Unless defined otherwise, all technical and scientific terms used herein have the same meaning as commonly understood by one of ordinary skill in the art to which this application belongs.

The articles "a" and "an" are used herein to refer to one or to more than one (i.e., to at least one) of the grammatical object of the article. By way of example, "an element" means one element or more than one element.

The terms "comprise," "comprising," "include," "including," "have," and "having" are used in the inclusive, open sense, meaning that additional elements may be included. The terms "such as", "e.g.", as used herein are non-limiting and are for illustrative purposes only. "Including" and "including but not limited to" are used interchangeably.

The term "or" as used herein should be understood to mean "and/or", unless the context clearly indicates otherwise.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length ±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

It will be noted that the structure of some of the compounds of the application include asymmetric (chiral) carbon or sulfur atoms. It is to be understood accordingly that the isomers arising from such asymmetry are included herein, unless indicated otherwise. Such isomers can be obtained in substantially pure form by classical separation techniques and by stereochemically controlled synthesis. The compounds of this application may exist in stereoisomeric form, therefore can be produced as individual stereoisomers or as mixtures.

The term "isomerism" means compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center" whereas a sulfur bound to three or four different substituents, e.g. sulfoxides or sulfinimides, is likewise termed a "chiral center".

The term "chiral isomer" means a compound with at least one chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has 2n–1 enantiomeric pairs, where n is the number of chiral centers. Compounds with more than one chiral center may exist as either an individual diastereomer or as a mixture of diastereomers, termed a "diastereomeric mixture". When one chiral center is present, a stereoisomer may be characterized by the absolute configuration (R or S) of that chiral center. Alternatively, when one or more chiral centers are present, a stereoisomer may be characterized as (+) or (–). Absolute configuration refers to the arrangement in space of the substituents attached to the chiral center. The substituents attached to the chiral center under consideration are ranked in accordance with the Sequence Rule of Cahn, Ingold and Prelog. (Cahn et al, Angew. Chem. Inter. Edit. 1966, 5, 385; errata 511; Cahn et al., Angew. Chem. 1966, 78, 413; Cahn and Ingold, J Chem. Soc. 1951 (London), 612; Cahn et al., Experientia 1956, 12, 81; Cahn, J., Chem. Educ. 1964, 41, 116).

The term "disorder" refer to any disorder, disease, or condition that would benefit from an agent that reduces or retards fibrosis. For example, included are diseases, disorders and conditions characterized by excess production of fibrous material, including excess production of fibrous material within the extracellular matrix. Also included are diseases, disorders and conditions characterized by replacement of normal tissue elements by abnormal, non-functional, and/or excessive accumulation of matrix-associated components.

The term "geometric Isomers" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules. Further, the structures and other compounds discussed in this application include all atropic isomers thereof.

The term "atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

The terms "crystal polymorphs" or "polymorphs" or "crystal forms" means crystal structures in which a compound (or salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

The term "derivative" refers to compounds that have a common core structure, and are substituted with various groups as described herein.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include acyl sulfonimides, tetrazoles, sulfonates, and phosphonates. See, e.g., Patani and LaVoie, Chem. Rev. 96, 3147-3176 (1996).

The phrases "parenteral administration" and "administered parenterally" are art-recognized terms, and include modes of administration other than enteral and topical administration, such as injections, and include, without limitation, intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrastemal injection and infusion.

The term "treating" is art-recognized and includes inhibiting a disease, disorder or condition in a subject, e.g., impeding its progress; and relieving the disease, disorder or condition, e.g., causing regression of the disease, disorder and/or condition. Treating the disease or condition includes ameliorating at least one symptom of the particular disease or condition, even if the underlying pathophysiology is not affected.

The term "preventing" is art-recognized and includes stopping a disease, disorder or condition from occurring in a subject, which may be predisposed to the disease, disorder and/or condition but has not yet been diagnosed as having it. Preventing a condition related to a disease includes stopping the condition from occurring after the disease has been diagnosed but before the condition has been diagnosed.

The term "pharmaceutical composition" refers to a formulation containing the disclosed compounds in a form suitable for administration to a subject. In a preferred embodiment, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of the disclosed compound or salts thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, intranasal, inhalational, and the like. Dosage forms for the topical or transdermal administration of a compound described herein includes powders, sprays, ointments, pastes, creams, lotions, gels, solutions, patches, nebulized compounds, and inhalants. In a preferred embodiment, the active compound is mixed under sterile conditions with a pharmaceutically acceptable carrier, and with any preservatives, buffers, or propellants that are required.

The term "flash dose" refers to compound formulations that are rapidly dispersing dosage forms.

The term "immediate release" is defined as a release of compound from a dosage form in a relatively brief period of time, generally up to about 60 minutes. The term "modified release" is defined to include delayed release, extended release, and pulsed release. The term "pulsed release" is defined as a series of releases of drug from a dosage form. The term "sustained release" or "extended release" is defined as continuous release of a compound from a dosage form over a prolonged period.

The phrase "pharmaceutically acceptable" is art-recognized. In certain embodiments, the term includes compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" is art-recognized, and includes, for example, pharmaceutically acceptable materials, compositions or vehicles, such as a liquid or solid filler, diluent, excipient, solvent or encapsulating material, involved in carrying or transporting any subject composition from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The compounds of the application are capable of further forming salts. All of these forms are also contemplated herein.

"Pharmaceutically acceptable salt" of a compound means a salt that is pharmaceutically acceptable and that possesses the desired pharmacological activity of the parent compound. For example, the salt can be an acid addition salt. One embodiment of an acid addition salt is a hydrochloride salt. The pharmaceutically acceptable salts can be synthesized from a parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile being preferred. Lists of salts are found in Remington's Pharmaceutical Sciences, 18th ed. (Mack Publishing Company, 1990).

The compounds described herein can also be prepared as esters, for example pharmaceutically acceptable esters. For example, a carboxylic acid function group in a compound can be converted to its corresponding ester, e.g., a methyl, ethyl, or other ester. Also, an alcohol group in a compound can be converted to its corresponding ester, e.g., an acetate, propionate, or other ester.

The compounds described herein can also be prepared as prodrugs, for example pharmaceutically acceptable prodrugs. The terms "pro-drug" and "prodrug" are used interchangeably herein and refer to any compound, which releases an active parent drug in vivo. Since prodrugs are known to enhance numerous desirable qualities of pharmaceuticals (e.g., solubility, bioavailability, manufacturing, etc.) the compounds can be delivered in prodrug form. Thus, the compounds described herein are intended to cover prodrugs of the presently claimed compounds, methods of delivering the same and compositions containing the same. "Prodrugs" are intended to include any covalently bonded carriers that release an active parent drug in vivo when such prodrug is administered to a subject. Prodrugs are prepared by modifying functional groups present in the compound in such a way that the modifications are cleaved, either in routine manipulation or in vivo, to the parent compound. Prodrugs include compounds wherein a hydroxy, amino, sulfhydryl, carboxy, or carbonyl group is bonded to any group that may be cleaved in vivo to form a free hydroxyl, free amino, free sulfhydryl, free carboxy or free carbonyl group, respectively. Prodrugs can also include a precursor (forerunner) of a compound described herein that undergoes chemical conversion by metabolic processes before becoming an active or more active pharmacological agent or active compound described herein.

Examples of prodrugs include, but are not limited to, esters (e.g., acetate, dialkylaminoacetates, formates, phosphates, sulfates, and benzoate derivatives) and carbamates (e.g., N,N-dimethylaminocarbonyl) of hydroxy functional groups, ester groups (e.g., ethyl esters, morpholinoethanol esters) of carboxyl functional groups, N-acyl derivatives (e.g., N-acetyl) N-Mannich bases, Schiff bases and enaminones of amino functional groups, oximes, acetals, ketals and enol esters of ketone and aldehyde functional groups in compounds, and the like, as well as sulfides that are oxidized to form sulfoxides or sulfones.

The term "protecting group" refers to a grouping of atoms that when attached to a reactive group in a molecule masks, reduces or prevents that reactivity. Examples of protecting groups can be found in Green and Wuts, Protective Groups in Organic Chemistry, (Wiley, 2.sup.nd ed. 1991); Harrison and Harrison et al., Compendium of Synthetic Organic Methods, Vols. 1-8 (John Wiley and Sons, 1971-1996); and Kocienski, Protecting Groups, (Verlag, $3^{rd}$ ed. 2003).

The term "amine protecting group" is intended to mean a functional group that converts an amine, amide, or other nitrogen-containing moiety into a different chemical group that is substantially inert to the conditions of a particular chemical reaction. Amine protecting groups are preferably removed easily and selectively in good yield under conditions that do not affect other functional groups of the molecule. Examples of amine protecting groups include, but are not limited to, formyl, acetyl, benzyl, t-butyldimethylsilyl, t-butyldiphenylsilyl, t-butyloxycarbonyl (Boc), p-methoxybenzyl, methoxymethyl, tosyl, trifluoroacetyl, trimethylsilyl (TMS), fluorenyl-methyloxycarbonyl, 2-trimethylsilyl-ethyoxycarbonyl, 1-methyl-1-(4-biphenylyl)ethoxycarbonyl, allyloxycarbonyl, benzyloxycarbonyl (CBZ), 2-trimethylsilyl-ethanesulfonyl (SES), trityl and substituted trityl groups, 9-fluorenylmethyloxycarbonyl (FMOC), nitro-veratryloxycarbonyl (NVOC), and the like. Those of skill in the art can identify other suitable amine protecting groups.

Representative hydroxy protecting groups include those where the hydroxy group is either acylated or alkylated such as benzyl, and trityl ethers as well as alkyl ethers, tetrahydropyranyl ethers, trialkylsilyl ethers and allyl ethers.

Additionally, the salts of the compounds described herein, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

The term "solvates" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

The compounds, salts and prodrugs described herein can exist in several tautomeric forms, including the enol and imine form, and the keto and enamine form and geometric isomers and mixtures thereof. Tautomers exist as mixtures of a tautomeric set in solution. In solid form, usually one tautomer predominates. Even though one tautomer may be described, the present application includes all tautomers of the present compounds. A tautomer is one of two or more structural isomers that exist in equilibrium and are readily converted from one isomeric form to another. This reaction results in the formal migration of a hydrogen atom accompanied by a switch of adjacent conjugated double bonds. In solutions where tautomerization is possible, a chemical equilibrium of the tautomers will be reached. The exact ratio of the tautomers depends on several factors, including temperature, solvent, and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs.

Tautomerizations can be catalyzed by: Base: 1. deprotonation; 2. formation of a delocalized anion (e.g., an enolate); 3. protonation at a different position of the anion; Acid: 1. protonation; 2. formation of a delocalized cation; 3. deprotonation at a different position adjacent to the cation.

The term "analogue" refers to a chemical compound that is structurally similar to another but differs slightly in composition (as in the replacement of one atom by an atom of a different element or in the presence of a particular functional group, or the replacement of one functional group by another functional group). Thus, an analogue is a compound that is similar or comparable in function and appearance, but not in structure or origin to the reference compound.

A "patient," "subject," or "host" to be treated by the subject method may mean either a human or non-human animal, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder.

The terms "prophylactic" or "therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic (i.e., it is intended to diminish, ameliorate, or stabilize the existing unwanted condition or side effects thereof).

The terms "therapeutic agent", "drug", "medicament" and "bioactive substance" are art-recognized and include molecules and other agents that are biologically, physiologically, or pharmacologically active substances that act locally or systemically in a patient or subject to treat a disease or condition. The terms include without limitation pharmaceutically acceptable salts thereof and prodrugs. Such agents may be acidic, basic, or salts; they may be neutral molecules, polar molecules, or molecular complexes capable of hydrogen bonding; they may be prodrugs in the form of ethers, esters, amides and the like that are biologically activated when administered into a patient or subject.

The phrase "therapeutically effective amount" or "pharmaceutically effective amount" is an art-recognized term. In certain embodiments, the term refers to an amount of a therapeutic agent that produces some desired effect at a reasonable benefit/risk ratio applicable to any medical treatment. In certain embodiments, the term refers to that amount necessary or sufficient to eliminate, reduce or maintain a target of a particular therapeutic regimen. The effective amount may vary depending on such factors as the disease or condition being treated, the particular targeted constructs being administered, the size of the subject or the severity of the disease or condition. One of ordinary skill in the art may empirically determine the effective amount of a particular compound without necessitating undue experimentation. In certain embodiments, a therapeutically effective amount of a therapeutic agent for in vivo use will likely depend on a number of factors, including: the rate of release of an agent from a polymer matrix, which will depend in part on the chemical and physical characteristics of the polymer; the identity of the agent; the mode and method of administration; and any other materials incorporated in the polymer matrix in addition to the agent.

The term "ED50" is art-recognized. In certain embodiments, ED50 means the dose of a drug, which produces 50% of its maximum response or effect, or alternatively, the dose, which produces a pre-determined response in 50% of test subjects or preparations. The term "LD50" is art-recognized. In certain embodiments, LD50 means the dose of a drug, which is lethal in 50% of test subjects. The term "therapeutic index" is an art-recognized term, which refers to the therapeutic index of a drug, defined as LD50/ED50.

The terms "$IC_{50}$," or "half maximal inhibitory concentration" is intended to refer to the concentration of a substance (e.g., a compound or a drug) that is required for 50% inhibition of a biological process, or component of a process, including a protein, subunit, organelle, ribonucleoprotein, etc.

With respect to any chemical compounds, the present application is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

When a bond to a substituent is shown to cross a bond connecting two atoms in a ring, then such substituent can be bonded to any atom in the ring. When a substituent is listed without indicating the atom via which such substituent is bonded to the rest of the compound of a given formula, then such substituent can be bonded via any atom in such substituent. Combinations of substituents and/or variables are permissible, but only if such combinations result in stable compounds.

When an atom or a chemical moiety is followed by a subscripted numeric range (e.g., $C_1$-6), it is meant to encompass each number within the range as well as all intermediate ranges. For example, "$C_{1-6}$ alkyl" is meant to include alkyl groups with 1, 2, 3, 4, 5, 6, 1-6, 1-5, 1-4, 1-3, 1-2, 2-6, 2-5, 2-4, 2-3, 3-6, 3-5, 3-4, 4-6, 4-5, and 5-6 carbons.

The term "alkyl" is intended to include both branched (e.g., isopropyl, tert-butyl, isobutyl), straight-chain e.g., methyl, ethyl, propyl, butyl, pentyl, hexyl, heptyl, octyl, nonyl, decyl), and cycloalkyl (e.g., alicyclic) groups (e.g., cyclopropyl, cyclopentyl, cyclohexyl, cycloheptyl, cyclooctyl), alkyl substituted cycloalkyl groups, and cycloalkyl substituted alkyl groups. Such aliphatic hydrocarbon groups have a specified number of carbon atoms. For example, $C_{1-6}$ alkyl is intended to include $C_1$, $C_2$, $C_3$, $C_4$, $C_5$, and $C_6$ alkyl groups. As used herein, "lower alkyl" refers to alkyl groups having from 1 to 6 carbon atoms in the backbone of the carbon chain. "Alkyl" further includes alkyl groups that have oxygen, nitrogen, sulfur or phosphorous atoms replacing one or more hydrocarbon backbone carbon atoms. In certain embodiments, a straight chain or branched chain alkyl has six or fewer carbon atoms in its backbone (e.g., $C_1$-$C_6$ for straight chain, $C_3$-$C_6$ for branched chain), for example four or fewer. Likewise, certain cycloalkyls have from three to eight carbon atoms in their ring structure, such as five or six carbons in the ring structure.

The term "substituted alkyls" refers to alkyl moieties having substituents replacing a hydrogen on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "aralkyl" moiety is an alkyl substituted with an aryl (e.g., phenylmethyl (benzyl)). If not otherwise indicated, the terms "alkyl" and "lower alkyl" include linear, branched, cyclic, unsubstituted, substituted, and/or heteroatom-containing alkyl or lower alkyl, respectively.

The term "alkenyl" refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, cyclopentenyl, cyclohexenyl, cyclooctenyl, and the like. Generally, although again not necessarily, alkenyl groups can contain 2 to about 18 carbon atoms, and more particularly 2 to 12 carbon atoms. The term "lower alkenyl" refers to an alkenyl group of 2 to 6 carbon atoms, and the specific term "cycloalkenyl" intends a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl or heterocycloalkenyl (e.g., heterocylcohexenyl) in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" refers to a linear or branched hydrocarbon group of 2 to 24 carbon atoms containing at least one triple bond, such as ethynyl, n-propynyl, and the like. Generally, although again not necessarily, alkynyl groups can contain 2 to about 18 carbon atoms, and more particularly can contain 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The terms "alkyl", "alkenyl", and "alkynyl" are intended to include moieties which are diradicals, i.e., having two points of attachment. A nonlimiting example of such an alkyl moiety that is a diradical is —$CH_2CH_2$—, i.e., a $C_2$ alkyl group that is covalently bonded via each terminal carbon atom to the remainder of the molecule.

The term "alkoxy" refers to an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Preferred substituents identified as "$C_1$-$C_6$ alkoxy" or "lower alkoxy" herein contain 1 to 3 carbon atoms, and particularly preferred such substituents contain 1 or 2 carbon atoms (i.e., methoxy and ethoxy).

The term "aryl" refers to an aromatic substituent containing a single aromatic ring or multiple aromatic rings that are fused together, directly linked, or indirectly linked (such that the different aromatic rings are bound to a common group such as a methylene or ethylene moiety). Aryl groups can contain 5 to 20 carbon atoms, and particularly preferred aryl groups can contain 5 to 14 carbon atoms. Examples of aryl groups include benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkylamino, dialkylamino, arylamino, diaryl amino, and al kylaryl amino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl). If not otherwise indicated, the term "aryl" includes unsubstituted, substituted, and/or heteroatom-containing aromatic substituents.

The term "alkaryl" refers to an aryl group with an alkyl substituent, and the term "aralkyl" refers to an alkyl group with an aryl substituent, wherein "aryl" and "alkyl" are as defined above. Exemplary aralkyl groups contain 6 to 24 carbon atoms, and particularly preferred aralkyl groups contain 6 to 16 carbon atoms. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. Alkaryl groups include, for example, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like.

The terms "heterocyclyl" or "heterocyclic group" include closed ring structures, e.g., 3- to 10-, or 4- to 7-membered rings, which include one or more heteroatoms. "Heteroatom" includes atoms of any element other than carbon or hydrogen. Examples of heteroatoms include nitrogen, oxygen, sulfur and phosphorus.

Heterocyclyl groups can be saturated or unsaturated and include pyrrolidine, oxolane, thiolane, piperidine, piperazine, morpholine, lactones, lactams, such as azetidinones and pyrrolidinones, sultams, and sultones. Heterocyclic groups such as pyrrole and furan can have aromatic character. They include fused ring structures, such as quinoline and isoquinoline. Other examples of heterocyclic groups include pyridine and purine. The heterocyclic ring can be substituted at one or more positions with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety. Heterocyclic groups can also be substituted at one or more constituent atoms with, for example, a lower alkyl, a lower alkenyl, a lower alkoxy, a lower alkylthio, a lower alkylamino, a lower alkylcarboxyl, a nitro, a hydroxyl, —CF$_3$, or —CN, or the like.

The term "halo" or "halogen" refers to fluoro, chloro, bromo, and iodo. "Counterion" is used to represent a small, negatively charged species such as fluoride, chloride, bromide, iodide, hydroxide, acetate, and sulfate. The term sulfoxide refers to a sulfur attached to 2 different carbon atoms and one oxygen and the S—O bond can be graphically represented with a double bond (S═O), a single bond without charges (S—O) or a single bond with charges [S(+)-O(−)].

The terms "substituted" as in "substituted alkyl," "substituted aryl," and the like, as alluded to in some of the aforementioned definitions, is meant that in the alkyl, aryl, or other moiety, at least one hydrogen atom bound to a carbon (or other) atom is replaced with one or more non-hydrogen substituents. Examples of such substituents include, without limitation: functional groups such as halo, hydroxyl, silyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO—), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_4$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—NH$_2$), carbamido (—NH—(CO)—NH$_2$), cyano (—CN), isocyano (—N$^+$C$^-$), cyanato (—O—CN), isocyanato (—ON$^+$C$^-$), isothiocyanato (—S—CN), azido (—N═N$^+$═N$^-$), formyl (—(CO)—H), thioformyl (—(CS)—H), amino (—NH$_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino (—CR═NH where R=hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR═N(alkyl), where R=hydrogen, alkyl, aryl, alkaryl, etc.), arylimino (—CR═N (aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O$^-$)$_2$), phosphinato (—P(O)(O$^-$)), phospho (—PO$_2$), and phosphino (—PH$_2$); and the hydrocarbyl moieties $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, and $C_6$-$C_{24}$ aralkyl.

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. For example, the phrase "substituted alkyl, alkenyl, and aryl" is to be interpreted as "substituted alkyl, substituted alkenyl, and substituted aryl." Analogously, when the term "heteroatom-containing" appears prior to a list of possible heteroatom-containing groups, it is intended that the term apply to every member of that group. For example, the phrase "heteroatom-containing alkyl, alkenyl, and aryl" is to be interpreted as "heteroatom-containing alkyl, substituted alkenyl, and substituted aryl.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

The terms "stable compound" and "stable structure" are meant to indicate a compound that is sufficiently robust to survive isolation, and as appropriate, purification from a reaction mixture, and formulation into an efficacious therapeutic agent.

The terms "free compound" is used herein to describe a compound in the unbound state.

Throughout the description, where compositions are described as having, including, or comprising, specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the compositions and methods described herein remains operable. Moreover, two or more steps or actions can be conducted simultaneously.

The term "small molecule" is an art-recognized term. In certain embodiments, this term refers to a molecule, which has a molecular weight of less than about 2000 amu, or less than about 1000 amu, and even less than about 500 amu.

All percentages and ratios used herein, unless otherwise indicated, are by weight.

The terms "gene expression" or "protein expression" includes any information pertaining to the amount of gene transcript or protein present in a sample, as well as information about the rate at which genes or proteins are produced or are accumulating or being degraded (e.g., reporter gene data, data from nuclear runoff experiments, pulse-chase data etc.). Certain kinds of data might be viewed as relating to both gene and protein expression. For example, protein levels in a cell are reflective of the level of protein as well as the level of transcription, and such data is intended to be included by the phrase "gene or protein expression information". Such information may be given in the form of amounts per cell, amounts relative to a control gene or protein, in unitless measures, etc.; the term "information" is not to be limited to any particular means of representation and is intended to mean any representation that provides relevant information. The term "expression levels" refers to a quantity reflected in or derivable from the gene or protein expression data, whether the data is directed to gene transcript accumulation or protein accumulation or protein synthesis rates, etc.

The terms "healthy" and "normal" are used interchangeably herein to refer to a subject or particular cell or tissue that is devoid (at least to the limit of detection) of a disease condition.

The term "nucleic acid" refers to polynucleotides such as deoxyribonucleic acid (DNA), and, where appropriate, ribonucleic acid (RNA). The term should also be understood to include analogues of either RNA or DNA made from nucleotide analogues, and, as applicable to the embodiment being described, single-stranded (such as sense or antisense) and double-stranded polynucleotides. In some embodiments, "nucleic acid" refers to inhibitory nucleic acids. Some categories of inhibitory nucleic acid compounds include antisense nucleic acids, RNAi constructs, and catalytic nucleic acid constructs. Such categories of nucleic acids are well-known in the art.

Embodiments described herein relate to compositions and methods for treating and/or preventing fibrosis and various fibrotic diseases, disorders or conditions. As described in the Examples below, it was found that that inhibitors of short-chain dehydrogenase activity, such as 15-PGDH inhibitors, can be administered to a subject in need thereof to decrease fibrotic symptoms, such as collagen deposition, inflammatory cytokine expression, and inflammatory cell infiltration, and treat and/or prevent various fibrotic diseases, disorders, and conditions.

In some embodiments, a method of treating or preventing a fibrotic disease, disorder or condition includes administering to a subject in need thereof a therapeutically effect amount of a 15-PGDH inhibitor such that at least one symptom or feature of a fibrotic disease, disorder or condition, or other related diseases, disorders or conditions, is reduced in intensity, severity, or frequency, or has delayed onset.

15-PGDH inhibitors are agents that, e.g., inhibit expression of 15-PGDH or bind to, partially or totally block stimulation, decrease, prevent, delay activation, inactivate, desensitize, or down regulate the activity of 15-PGDH, e.g., antagonists. 15-PGDH inhibitors described herein can provide a pharmacologic method for elevating prostaglandin levels in tissue.

As used herein, the term "fibrotic" diseases, disorders, or conditions include diseases, disorders, or conditions characterized, in whole or in part, by the excess production of fibrous material, including excess production of fibrotic material within the extracellular matrix, or the replacement of normal tissue elements by abnormal, non-functional, and/or excessive accumulation of matrix-associated components. The fibriotic disesases, disorders, or conditions, can include acute and chronic, clinical or subclinical presentation, in which fibrogenic associated biology or pathology is evident.

Examples of fibrotic diseases, disorders and conditions include systemic sclerosis, multifocal fibrosclerosis, nephrogenic systemic fibrosis, scleroderma (including morphea, generalized morphea, or linear scleroderma), sclerodermatous graft-vs-host-disease, kidney fibrosis (including glomerular sclerosis, renal tubulointerstitial fibrosis, progressive renal disease or diabetic nephropathy), cardiac fibrosis (e.g., myocardial fibrosis), pulmonary fibrosis (e.g., pulmonary fibrosis, glomerulosclerosis pulmonary fibrosis, idiopathic pulmonary fibrosis, silicosis, asbestosis, interstitial lung disease, interstitial fibrotic lung disease, and chemotherapy/radiation induced pulmonary fibrosis), oral fibrosis, endomyocardial fibrosis, deltoid fibrosis, pancreatitis, inflammatory bowel disease, Crohn's disease, nodular fasciitis, eosinophilic fasciitis, general fibrosis syndrome characterized by replacement of normal muscle tissue by fibrous tissue in varying degrees, retroperitoneal fibrosis, liver fibrosis, liver cirrhosis, chronic renal failure; myelofibrosis (bone marrow fibrosis), drug induced ergotism, myelodysplastic syndrome, myeloproferative syndrome, gynecological cancer, Kaposi's sarcoma, Hansen's disease, collagenous colitis, acute fibrosis, organ specific fibrosis, and the like.

Illustrative organ specific fibrotic disorders include, but are not limited to, pulmonary fibrosis, pulmonary hypertension, cystic fibrosis, asthma, chronic obstructive pulmonary disease, liver fibrosis, kidney fibrosis, NASH, and the like. Many fibrotic diseases, disorders or conditions have disordered and/or exaggerated deposition of extracellular matrix in affected tissues. Fibrosis may be associated with inflammation, occur as a symptom of underlying disease, and/or caused by surgical procedure or wound healing process. Unchecked fibrosis can result in destruction of the architecture of the underlying organ or tissue, commonly referred to as scarring.

In some embodiments, the 15-PGDH inhibitors can be used to treat or prevent lung fibrosis. The lung fibrosis can be selected from the group consisting of pulmonary fibrosis, pulmonary hypertension, chronic obstructive pulmonary disease (COPD), asthma, idiopathic pulmonary fibrosis, sarcoidosis, cystic fibrosis, familial pulmonary fibrosis, silicosis, asbestosis, coal worker's pneumoconiosis, carbon pneumoconiosis, hypersensitivity pneumonitides, pulmonary fibrosis caused by inhalation of inorganic dust, pulmonary fibrosis caused by an infectious agent, pulmonary fibrosis caused by inhalation of noxious gases, aerosols, chemical dusts, fumes or vapors, drug-induced interstitial lung disease, or pulmonary hypertension, and combinations thereof.

Pulmonary fibrosis is characterized by progressive scarring of lung tissue accompanied by fibroblast proliferation, excessive accumulation of extracellular matrix proteins, and abnormal alveolar structure. The thickened and stiff tissue makes it difficult for lungs to work properly, leading to breathing problems such as shortness of breath, and can ultimately be fatal. Pulmonary fibrosis may be caused by acute lung injury, viral infection, exposure to toxins, radiation, chronic disease, medications, or may be idiopathic (i.e., an undiscovered underlying cause).

The classic findings in idiopathic pulmonary fibrosis show diffuse peripheral scarring of the lungs with small bubbles (known as bullae) adjacent to the outer lining of the surface of the lung, often at the bases of the lungs. Idiopathic pulmonary fibrosis often has a slow and relentless progression. Early on, patients often complain of a dry unexplained cough. Next, shortness of breath (dyspnea) sets in and worsens over time triggered by less and less activity. Eventually, the shortness of breath becomes disabling, limiting all activity and even occurring while sitting still. In rarer cases, the fibrosis can be rapidly progressive, with dyspnea and disability occurring in weeks to months of onset of the disease. This form of pulmonary fibrosis has been referred to as Hamman-Rich syndrome.

Pulmonary hypertension is marked by an increase in the blood pressure of the lung vasculature, including the pulmonary artery, pulmonary vein, and/or pulmonary capillaries. Abnormally high pressure strains the right ventricle of the heart, causing it to expand. Over time, the right ventricle can weaken and lose its ability to pump enough blood to the lungs, leading to the development of heart failure. Pulmonary hypertension can occur as a result of other medical conditions, such as chronic liver disease and liver cirrhosis; rheumatic disorders such as scleroderma or systemic lupus erythematosus (lupus); and lung conditions including tumors, emphysema, chronic obstructive pulmonary disease (COPD), and pulmonary fibrosis. Pulmonary fibrosis may lead to narrowing of pulmonary vasculature resulting in pulmonary hypertension.

Chronic Obstructive Pulmonary Disease (COPD) is a common lung disease that is often associated with chronic bronchitis or emphysema. Symptoms can often include cough, mucus build up, fatigue, wheezing, and respiratory infection.

Chronic bronchitis and emphysema are diseases of the lungs in which the airways become narrowed. This leads to a limitation of the flow of air to and from the lungs, causing shortness of breath (dyspnea). In clinical practice, COPD is defined by its characteristically low airflow on lung function tests.

Lung damage and inflammation in the large airways results in chronic bronchitis. In the airways of the lung, the hallmark of chronic bronchitis is an increased number (hyperplasia) and increased size (hypertrophy) of the goblet cells and mucous glands of the airway. As a result, there is more mucus than usual in the airways, contributing to narrowing of the airways and causing a cough with sputum. Microscopically there is infiltration of the airway walls with inflammatory cells. Inflammation is followed by scarring and remodeling that thickens the walls and also results in narrowing of the airways. As chronic bronchitis progresses, there is squamous metaplasia (an abnormal change in the tissue lining the inside of the airway) and fibrosis (further thickening and scarring of the airway wall). The consequence of these changes is a limitation of airflow and difficulty breathing.

Asthma is a chronic lung disease characterized by inflammation and constriction of the airways. Asthma causes recurring periods of wheezing, tightness of the chest, shortness of breath, and coughing. Swelling and overproduction of mucus can cause further airway constriction and worsening of symptoms. There is evidence that increased matrix degradation may occur in asthma, and this may contribute to mechanical changes in the airways in asthma (Roberts et al (1995) Chest 107:111 S-117S, incorporated herein by reference in its entirety. Treatment of extracellular matrix degradation may ameliorate symptoms of asthma.

Cystic fibrosis is a recessive multi-system genetic disease characterized by abnormal transport of chloride and sodium across epithelium, leading to thick, viscous secretions in the lungs, pancreas, liver, intestine and reproductive tract. Cystic fibrosis is caused by a mutation in the gene for the protein cystic fibrosis transmembrane conductance regulator (CFTR). Lung disease results from clogging of the airways due to mucus build-up, decreased mucociliary clearance, and resulting inflammation, which can cause fibrotic injury and structural changes to the lungs. The fibrotic lung damage progresses over time leading some cystic fibrosis patients to require lung transplant.

Common symptoms of subjects suffering from cystic fibrosis include, but are not limited to, accumulation of thick mucus, copious phlegm production, frequent chest infections, frequent coughing, frequent shortness of breath, inflammation, decreased ability to exercise, opportunistic infections of the lung and sinus (including but not limited to *Staphylococcus aureus*, *Haemophilus influenzae*, *Mycobacterium aviium*, and *Pseudomonas aeruginosa*), pneumonia, tuberculosis, bronchiectasis, hemoptysis, pulmonary hypertension (and resulting heart failure), hypoxia, respiratory failure, allergic bronchopulmonary aspergillosis, mucus in the paranasal sinuses, sinus infection, facial pain, fever, excessive nasal drainage, development of nasal polyps, cardiorespiratory complications, CF-related diabetes, rectal prolapse, pancreatitis, malabsorption, intestinal blockage, exocrine pancreatic insufficiency, bile duct blockage, and liver cirrhosis.

In other embodiments, the 15-PGDH inhibitors can be used to treat or prevent fibrotic diseases, disorders or conditions caused by post-surgical adhesion formation. Post-surgical adhesion formation is a common complication of surgery. The formation of adhesions, from mechanical damage, ischemia, and infections, can increase morbidity and mortality following surgery. Although refined surgical procedures can reduce the magnitude of adhesion formation, adhesions are rarely eviscerated and an effective adjunctive therapy is needed. Reducing the fibrosis associated with this process could reduce pain, obstruction and other complications of surgery and promote healing and recovery.

Wounds (i.e., lacerations, openings) in mammalian tissue result in tissue disruption and coagulation of the microvasculature at the wound face. Repair of such tissue represents an orderly, controlled cellular response to injury. Soft tissue wounds, regardless of size, heal in a similar manner. Tissue growth and repair are biologic systems wherein cellular proliferation and angiogenesis occur in the presence of an oxygen gradient. The sequential morphological and structural changes which occur during tissue repair have been characterized in detail and have in some instances been quantified (see e.g., Hunt, T. K., et al., "Coagulation and macrophage stimulation of angiogenesis and wound healing," in The Surgical Wound, pp. 1-18, ed. F. Dineen & G. Hildrick-Smith (Lea & Febiger, Philadelphia: 1981)). The cellular morphology consists of three distinct zones. The central avascular wound space is oxygen deficient, acidotic and hypercarbic, and has high lactate levels. Adjacent to the wound space is a gradient zone of local anemia (ischemia) which is populated by dividing fibroblasts. Behind the leading zone is an area of active collagen synthesis characterized by mature fibroblasts and numerous newly-formed capillaries (i.e., neovascularization). U.S. Pat. Nos. 5,015, 629 and 7,022,675 (each incorporated by reference herein) disclose methods and compositions for increasing the rate of wound repair.

In some embodiments, the 15-PGDH inhibitors can used for reducing or preventing scar formation in a subject by administering to a subject in need of treatment. Scar formation is a natural part of the healing process. Disorderly collagen synthesis and deposition in a wound can result in excessive, thick, or raised scar formation. Generally, the larger the wound, the longer it takes to heal and the greater the chance of a problematic scar.

In other embodiments, the 15-PGDH inhibitors can be used to reduce or prevent scar formation on skin or scleroderma. There are several types of scars on skin. Hypertropic scars are raised, pinkish-red areas located inside the borders of the original injury. They are often described as itchy. In some cases, hypertropic scars shrink and fade on their own. Keloids are raised, deep-red areas that tend to cover much more area than that of the original injury. Even when surgically removed, keloids tend to recur. Atrophic scars are skin depressions, like those that sometimes form from severe acne. They are caused by inflammation that destroys the collagen during the rebuilding process, leaving an area of indentation.

In some embodiments, the 15-PGDH inhibitors can be used to treat or prevent systemic sclerosis. Systemic sclerosis is a systemic connective tissue disease characterized by alterations of the microvasculature, disturbances of the immune system and by massive deposition of collagen and other matrix substances in the connective tissue. Systemic sclerosis is a clinically heterogeneous generalized disorder which affects the connective tissue of the skin and internal organs such as gastrointestinal tract, lungs, heart and kidneys. Reduction of fibrosis resulting from systemic sclerosis may ameliorate symptoms and/or prevent further complications in affected tissues.

In other embodiments, the 15-PGDH inhibitors can be used to treat or prevent liver fibrosis. Liver fibrosis can result from a chronic liver disease, viral induced hepatic cirrhosis, hepatitis B virus infection, hepatitis C virus infection, hepatitis D virus infection, schistosomiasis, primary biliary cirrhosis, alcoholic liver disease or non-alcoholic steatohepatitis (NASH), NASH associated cirrhosis obesity, diabetes, protein malnutrition, coronary artery disease, auto-immune hepatitis, cystic fibrosis, alpha-1-antitrypsin deficiency, primary biliary cirrhosis, drug reaction and exposure to toxins.

Nonalcoholic steatohepatitis (NASH) is a common liver disease. It resembles alcoholic liver disease but occurs in people who drink little or no alcohol. The major feature in NASH is fat in the liver, along with inflammation and damage. Nevertheless, NASH can be severe and can lead to cirrhosis, in which the liver is permanently damaged and scarred and no longer able to work properly.

NASH is usually a silent disease with few or no symptoms. Patients generally feel well in the early stages and only begin to have symptoms—such as fatigue, weight loss, and weakness—once the disease is more advanced or cirrhosis develops. The progression of NASH can take years, even decades. The process can stop and, in some cases may even begin to reverse on its own without specific therapy. Or NASH can slowly worsen, causing scarring or fibrosis to appear and accumulate in the liver. As fibrosis worsens, cirrhosis develops in which the liver becomes seriously scarred, hardened, and unable to function normally. Not every person with NASH develops cirrhosis, but once serious scarring or cirrhosis is present, few treatments can halt the progression. A person with cirrhosis experiences fluid retention, muscle wasting, bleeding from the intestines, and liver failure. Liver transplantation is the only treatment for advanced cirrhosis with liver failure, and transplantation is increasingly performed in people with NASH. NASH ranks as one of the major causes of cirrhosis in America, behind hepatitis C and alcoholic liver disease.

In some embodiments, the 15-PGDH inhibitors can be used to treat or prevent kidney fibrosis. Kidney fibrosis can result from dialysis following kidney failure, catheter placement, a nephropathy, glomerulosclerosis, glomerulonephritis, chronic renal insufficiency, acute kidney injury, end stage renal disease or renal failure.

Kidney (renal) fibrosis results from excessive formation of fibrous connective tissue in the kidney. Kidney fibrosis causes significant morbidity and mortality and leads to a need for dialysis or kidney transplantation. Fibrosis can occur in either the filtering or reabsorptive component of the nephron, the functional unit of the kidney. A number of factors may contribute to kidney scarring, particularly derangements of physiology involved in the autoregulation of glomerular filtration. This in turn leads to replacement of normal structures with accumulated extracellular matrix. A spectrum of changes in the physiology of individual cells leads to the production of numerous peptide and non-peptide fibrogens that stimulate alterations in the balance between extracellular matrix synthesis and degradation to favor scarring.

In some embodiments, the symptoms of fibrosis of a tissue organ can comprise inflammation. In these embodiments, a therapeutically effective amount of the 15-PGDH inhibitor administered to the subject in need thereof can be an amount effective to decrease or reduce inflammatory cell count in the tissue or organ. A relevant sample can be obtained from the subject to determine the decrease or reduction in inflammatory cell count. In a non-limiting embodiment, the beneficial effect may be assessed by demonstrating a reduction in neutrophil count in BAL fluid from the subject with cystic fibrosis. The excessive recruitment of neutrophils into the airways of patients with CF is a significant predictor of lung disease severity in CF and therefore is an important therapeutic target. Methods for measuring such cell counts are well known in the art, including but not limited to FACS techniques. In some embodiments, the method may comprise reducing neutrophil cell count in BAL fluid from the subject compared to control. Any suitable control can be used for comparison, such as cystic fibrosis subjects not treated the 15-PGDH inhibitors. In some embodiments, a decrease in inflammatory cell count, such as neutrophil count, provides a clinical benefit to the subject. In various embodiments, the reduction in inflammatory cell count is at least 5%, 10%, 15%, 20%, 25%, 50%, or more compared to control.

In another embodiment, the beneficial effect of the 15-PGDH inhibitors may be assessed by a reduction in one or more inflammatory biomarkers in a relevant sample from the subject. In various non-limiting embodiments, the inflammatory biomarker may comprise or consist of one or more of cytokines or inflammatory cytokines associated with fibrosis. Such cytokines can include, for example, IL1β, MIP2 (e.g., CCL3 or CCL4), IFNδ, TGFβ, TNFα, IL-6, MCP-1, IL2, and IL-10 in BAL fluid. Methods for measuring the amount of such biomarkers are well known in the art, including but not limited to ELISAs. Thus, in this embodiment, the methods may further comprise the reducing an amount of one or more inflammatory biomarkers in a sample from the subject compared to control.

In other embodiments, the 15-PGDH inhibitors can be used in a method for decreasing or reducing collagen secretion or collagen deposition in a tissue or organ, such as the lung, the liver, the skin or the heart, of a subject. The method can include administering a therapeutically effective amount of the 15-PGDH inhibitors to the subject in need thereof. The subject can have or be at risk of an excessive collagen secretion or collagen deposition in the tissue or organ, such as the kidney, the lung, the liver, the intestines, the colon, the skin or the heart. Usually, the excessive collagen secretion or collagen deposition in an organ results from an injury or an insult. Such injury and insult are organ-specific. The 15-PGDH inhibitors can be administered over a sufficient period of time to decrease or reduce the level of collagen deposition in the tissue or organ, completely or partially. A sufficient period of time can be during one week, or between 1 week to 1 month, or between 1 to 2 months, or 2 months or more. For chronic condition, the 15-PGDH inhibitors can be advantageously administered for life time period.

15-PGDH inhibitors used to treat the fibrotic disease, disorder or condition and/or reduce collagen deposition can be identified using assays in which putative inhibitor compounds are applied to cells expressing 15-PGDH and then the functional effects on 15-PGDH activity are determined. Samples or assays comprising 15-PGDH that are treated with a potential inhibitor are compared to control samples without the inhibitor to examine the extent of effect. Control samples (untreated with modulators) are assigned a relative 15-PGDH activity value of 100%. Inhibition of 15-PGDH is achieved when the 15-PGDH activity value relative to the control is about 80%, optionally 50% or 25%, 10%, 5% or 1%.

Agents tested as inhibitors of SCD (e.g., 15-PGDH) can be any small chemical molecule or compound. Typically, test compounds will be small chemical molecules, natural products, or peptides. The assays are designed to screen large chemical libraries by automating the assay steps and providing compounds from any convenient source to assays, which are typically run in parallel (e.g., in microtiter formats on microtiter plates in robotic assays).

In some embodiments, the 15-PGDH inhibitor can include a compound having the following formula (I):

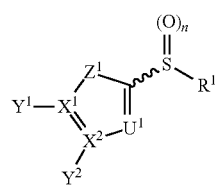

(I)

wherein n is 0-2;

$Y^1$, $Y^2$, and $R^1$ are the same or different and are each selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms (wherein from 1-3 of the ring atoms is independently selected from N, NH, N($C_1$-$C_6$ alkyl), NC(O) ($C_1$-$C_6$ alkyl), O, and S), $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—NH$_2$), carbamido (—NH—(CO)—NH$_2$), cyano(—CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N (aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), sulfonamide (—SO$_2$—NH$_2$, —SO$_2$NY$_2$ (wherein Y is independently H, arlyl or alkyl), phosphono (—P(O)(OH)$_2$), phosphonato (—P(O)(O$^-$)$_2$), phosphinato (—P(O)(O$^-$)), phospho (—PO$_2$), phosphino (—PH$_2$), polyalkylethers, phosphates, phosphate esters, groups incorporating amino acids or other moieties expected to bear positive or negative charge at physiological pH, combinations thereof, and wherein $Y^1$ and $Y^2$ may be linked to form a cyclic or polycyclic ring, wherein the ring is a substituted or unsubstituted aryl, a substituted or unsubstituted heteroaryl, a substituted or unsubstituted cycloalkyl, and a substituted or unsubstituted heterocyclyl;

$U^1$ is N, C—$R^2$, or C—NR$^3$R$^4$, wherein $R^2$ is selected from the group consisting of a H, a lower alkyl group, O, (CH$_2$)$_{n1}$OR' (wherein n1=1, 2, or 3), CF$_3$, CH$_2$—CH$_2$X, O—CH$_2$—CH$_2$X, CH$_2$—CH$_2$—CH$_2$X, O—CH$_2$—CH$_2$X, X, (wherein X=H, F, Cl, Br, or I), CN, (C=O)—R', (C=O)N(R')$_2$, O(CO)R', COOR' (wherein R' is H or a lower alkyl group), and wherein $R^1$ and $R^2$ may be linked to form a cyclic or polycyclic ring, wherein $R^3$ and $R^4$ are the same or different and are each selected from the group consisting of H, a lower alkyl group, O, (CH$_2$)$_{n1}$OR' (wherein n1=1, 2, or 3), CF$_3$, CH$_2$—CH$_2$X, CH$_2$—CH$_2$—CH$_2$X, (wherein X=H, F, Cl, Br, or I), CN, (C=O)—R', (C=O)N(R')$_2$, COOR' (wherein R' is H or a lower alkyl group), and $R^3$ or $R^4$ may be absent;

$X^1$ and $X^2$ are independently N or C, and wherein when $X^1$ and/or $X^2$ are N, $Y^1$ and/or $Y^2$, respectively, are absent;

$Z^1$ is O, S, CR$^a$R$^b$ or NR$^a$, wherein R$^a$ and R$^b$ are independently H or a $C_{1-8}$ alkyl, which is linear, branched, or cyclic, and which is unsubstituted or substituted;

and pharmaceutically acceptable salts thereof.

Examples of 15-PGDH inhibitors having formulas (I) include the following compounds:

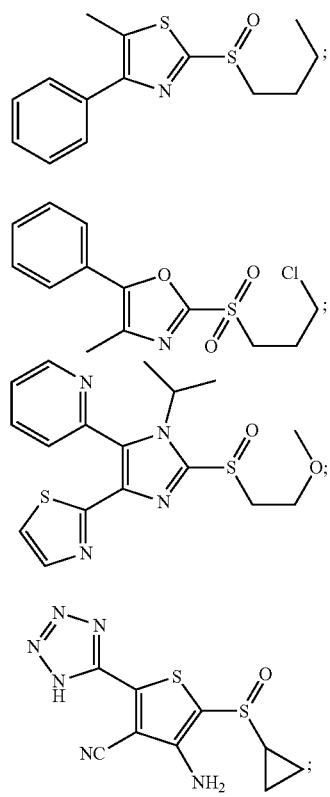

and pharmaceutically acceptable salts thereof.

In other embodiments, the 15-PGDH inhibitor can include a compound having the following formula (II):

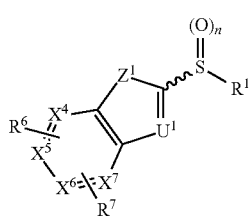
(II)

wherein n is 0-2

$X^4$, $X^5$, $X^6$, and $X^7$ are independently N or $CR^c$;

$R^1$, $R^6$, $R^7$, and $R^c$ are independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms (wherein from 1-3 of the ring atoms is independently selected from N, NH, N($C_1$-$C_6$ alkyl), NC(O)($C_1$-$C_6$ alkyl), O, and S), $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—NH$_2$), carbamido (—NH—(CO)—NH$_2$), cyano (—CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), sulfonamide (—SO$_2$—NH$_2$, —SO$_2$NY$_2$ (wherein Y is independently H, arlyl or alkyl), phosphono (—P(O)(OH)$_2$), phosphonato (—P(O)(O$^-$)$_2$), phosphinato (—P(O)(O$^-$)), phospho (—PO$_2$), phosphino (—PH$_2$), polyalkylethers, phosphates, phosphate esters, groups incoporating amino acids or other moieties expected to bear positive or negative charge at physiological pH, combinations thereof, and wherein $R^6$ and $R^7$ may be linked to form a cyclic or polycyclic ring, wherein the ring is a substituted or unsubstituted aryl, a substituted or unsubstituted heteroaryl, a substituted or unsubstituted cycloalkyl, and a substituted or unsubstituted heterocyclyl;

$U^1$ is N, C—$R^2$, or C—NR$^3$R$^4$, wherein $R^2$ is selected from the group consisting of a H, a lower alkyl group, O, (CH$_2$)$_{n1}$OR' (wherein n1=1, 2, or 3), CF$_3$, CH$_2$—CH$_2$X, O—CH$_2$—CH$_2$X, CH$_2$—CH$_2$—CH$_2$X, O—CH$_2$—CH$_2$X, X, (wherein X=H, F, Cl, Br, or I), CN, (C=O)—R', (C=O)N(R')$_2$, O(CO)R', COOR' (wherein R' is H or a lower alkyl group), and wherein $R^1$ and $R^2$ may be linked to form a cyclic or polycyclic ring, wherein $R^3$ and $R^4$ are the same or different and are each selected from the group consisting of H, a lower alkyl group, 0, (CH$_2$)$_{n1}$OR' (wherein n1=1, 2, or 3), CF$_3$, CH$_2$—CH$_2$X, CH$_2$—CH$_2$—CH$_2$X, (wherein X=H, F, Cl, Br, or I), CN, (C=O)—R', (C=O)N(R')$_2$, COOR' (wherein R' is H or a lower alkyl group), and $R^3$ or $R^4$ may be absent;

$Z^1$ is O, S, $CR^aR^b$ or $NR^a$, wherein $R^a$ and $R^b$ are independently H or a $C_{1-8}$ alkyl, which is linear, branched, or cyclic, and which is unsubstituted or substituted;

and pharmaceutically acceptable salts thereof.

Examples of 15-PGDH inhibitors having formulas (II) include the following compounds:

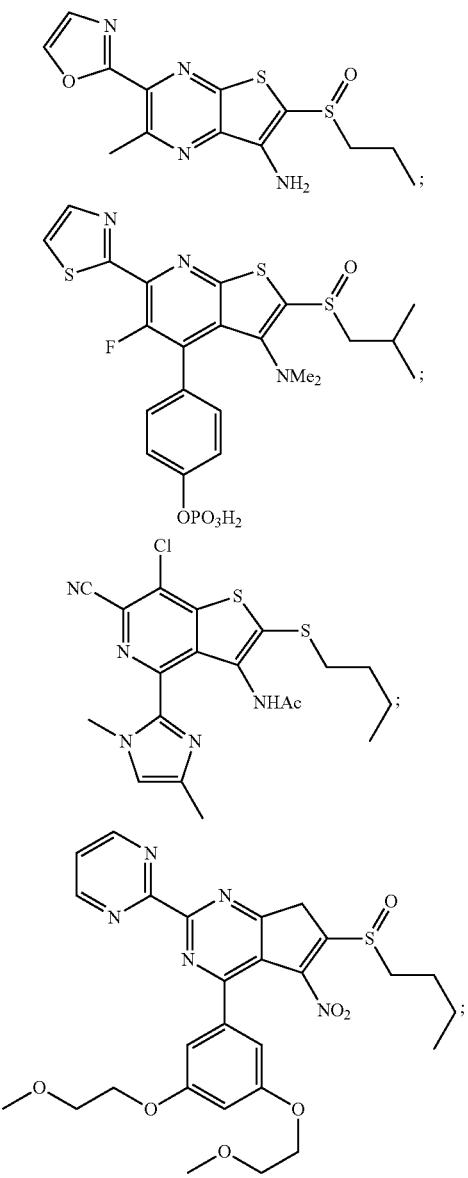

and pharmaceutically acceptable salts thereof.

In yet other embodiments, the 15-PGDH inhibitor can include a compound having the following formula (III) or (IV):

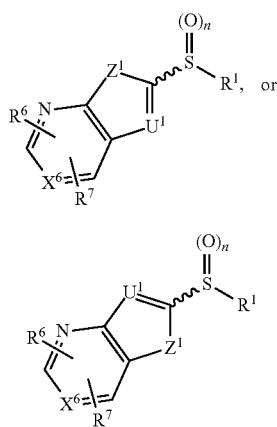

(III)

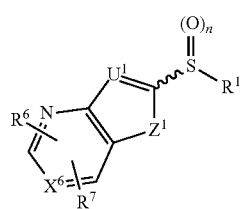

(IV)

wherein n is 0-2

$X^6$ is independently is N or $CR^c$;

$R^1$, $R^6$, $R^7$, and $R^c$ are independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms (wherein from 1-3 of the ring atoms is independently selected from N, NH, N($C_1$-$C_6$ alkyl), NC(O)($C_1$-$C_6$ alkyl), O, and S), $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—NH$_2$), carbamido (—NH—(CO)—NH$_2$), cyano (—CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), sulfonamide (—SO$_2$—NH$_2$, —SO$_2$NY$_2$ (wherein Y is independently H, arlyl or alkyl), phosphono (—P(O)(OH)$_2$), phosphonato (—P(O)(O$^-$)$_2$), phosphinato (—P(O)(O$^-$)), phospho (—PO$_2$), phosphino (—PH$_2$), polyalkyethers, phosphates, phosphate esters, groups incorporating amino acids or other moieties expected to bear positive or negative charge at physiological pH, combinations thereof, and wherein $R^6$ and $R^7$ may be linked to form a cyclic or polycyclic ring, wherein the ring is a substituted or unsubstituted aryl, a substituted or unsubstituted heteroaryl, a substituted or unsubstituted cycloalkyl, and a substituted or unsubstituted heterocyclyl;

$U^1$ is N, C—$R^2$, or C—$NR^3R^4$, wherein $R^2$ is selected from the group consisting of a H, a lower alkyl group, O, (CH$_2$)$_{n1}$OR' (wherein n1=1, 2, or 3), CF$_3$, CH$_2$—CH$_2$X, O—CH$_2$—CH$_2$X, CH$_2$—CH$_2$—CH$_2$X, O—CH$_2$—CH$_2$X, X, (wherein X=H, F, Cl, Br, or I), CN, (C=O)—R', (C=O)N(R')$_2$, O(CO)R', COOR' (wherein R' is H or a lower alkyl group), and wherein $R^1$ and $R^2$ may be linked to form a cyclic or polycyclic ring, wherein $R^3$ and $R^4$ are the same or different and are each selected from the group consisting of H, a lower alkyl group, O, (CH$_2$)$_{n1}$OR' (wherein n1=1, 2, or 3), CF$_3$, CH$_2$—CH$_2$X, CH$_2$—CH$_2$—CH$_2$X, (wherein X=H, F, Cl, Br, or I), CN, (C=O)—R', (C=O)N(R')$_2$, COOR' (wherein R' is H or a lower alkyl group), and $R^3$ or $R^4$ may be absent;

$Z^1$ is O, S, $CR^aR^b$ or $NR^a$, wherein $R^a$ and $R^b$ are independently H or a $C_{1-8}$ alkyl, which is linear, branched, or cyclic, and which is unsubstituted or substituted;

and pharmaceutically acceptable salts thereof.

In some embodiments, $R^1$ is selected from the group consisting of branched or linear alkyl including —(CH$_2$)$_{n_1}$CH$_3$ ($n_1$=0-7),

wherein $n_2$=0-6 and X is any of the following: $CF_yH_z$ (y+z=3), $CCl_yH_z$ (y+z=3), OH, OAc, OMe, $R^{71}$, $OR^{72}$, CN, $N(R^{73})_2$,

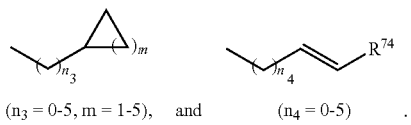

($n_3$ = 0-5, m = 1-5), and ($n_4$ = 0-5).

In other embodiments, $R^6$ and $R^7$ can each independently be one of the following:

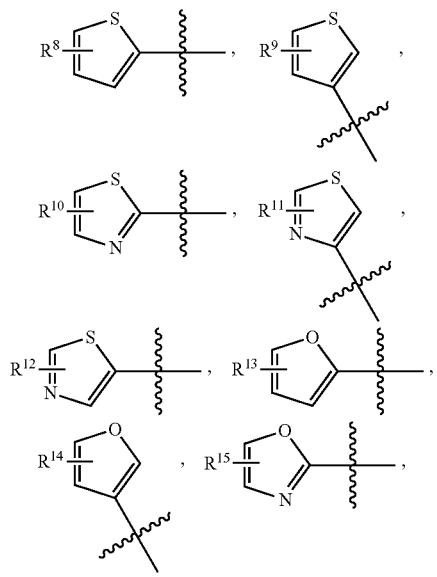

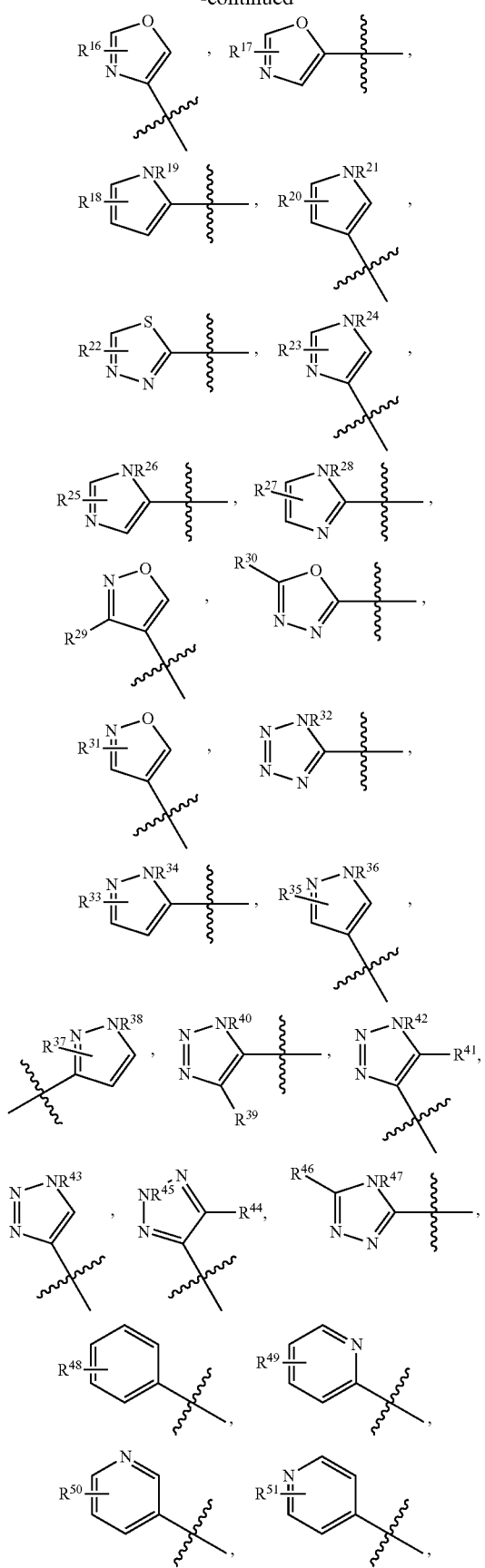
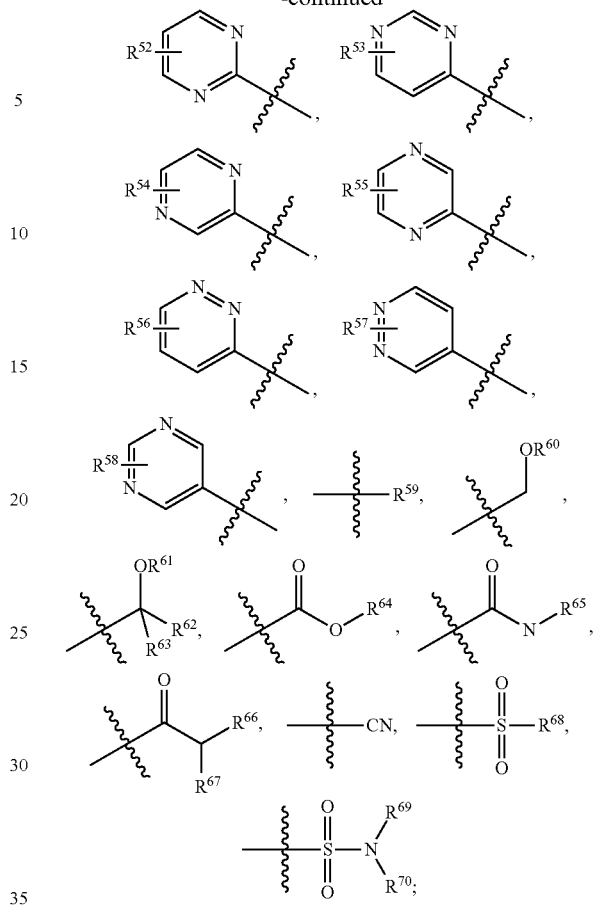

each $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, $R^{49}$, $R^{50}$, $R^{51}$, $R^{55}$, $R^{54}$, $R^{55}$, $R^{56}$, $R^{57}$, $R^{58}$, $R^{59}$, $R^{60}$, $R^{61}$, $R^{62}$, $R^{63}$, $R^{64}$, $R^{65}$, $R^{66}$, $R^{67}$, $R^{68}$, $R^{69}$, $R^{70}$, $R^{71}$, $R^{72}$, $R^{73}$, and $R^{74}$ are the same or different and are independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heterocycloalkenyl containing from 5-6 ring atoms, (wherein from 1-3 of the ring atoms is independently selected from N, NH, N($C_1$-$C_6$ alkyl), NC(O) ($C_1$-$C_6$ alkyl), O, and S), heteroaryl or heterocyclyl containing from 5-14 ring atoms, (wherein from 1-6 of the ring atoms is independently selected from N, NH, N($C_1$-$C_3$ alkyl), O, and S), $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO⁻), carbamoyl (—(CO)—NH$_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—NH$_2$), carbamido (—NH—(CO)—NH$_2$), cyano(—CN), isocyano (—N⁺C⁻), cyanato (—O—CN), isocyanato (—O—N⁺=C⁻), isothiocyanato (—S—CN), azido (—N=N⁺=N⁻), formyl (—(CO)—H), thioformyl (—(CS)—H), amino (—NH$_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), sulfanamido (—$SO_2$N(R)$_2$ where R is independently H, alkyl, aryl or heteroaryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—$NO_2$), nitroso (—NO), sulfo (—$SO_2$—OH), sulfonato (—$SO_2$—$O^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—$SO_2$-alkyl), $C_5$-$C_{20}$ arylsulfonyl (—$SO_2$-aryl), sulfonamide (—$SO_2$—$NH_2$, —$SO_2NY_2$ (wherein Y is independently H, arlyl or alkyl), phosphono (—P(O)(OH)$_2$), phosphonato (—P(O)($O^-$)$_2$), phosphinato (—P(O)($O^-$)), phospho (—$PO_2$), phosphino (—$PH_2$), polyalkyl ethers (—[($CH_2$)$_n$O]$_m$), phosphates, phosphate esters [—OP(O)(OR)$_2$ where R=H, methyl or other alkyl], groups incorporating amino acids or other moieties expected to bear positive or negative charge at physiological pH, and combinations thereof, and pharmaceutically acceptable salts thereof.

In still other embodiments, $R^6$ and $R^7$ can independently be a group that improves aqueous solubility, for example, a phosphate ester (—$OPO_3H_2$), a phenyl ring linked to a phosphate ester (—$OPO_3H_2$), a phenyl ring substituted with one or more methoxyethoxy groups, or a morpholine, or an aryl or heteroaryl ring substituted with such a group.

Examples of 15-PGDH inhibitors having formulas (III) or (IV) include the following compounds:

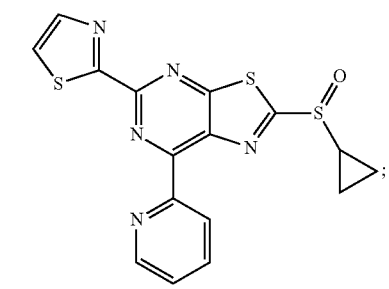

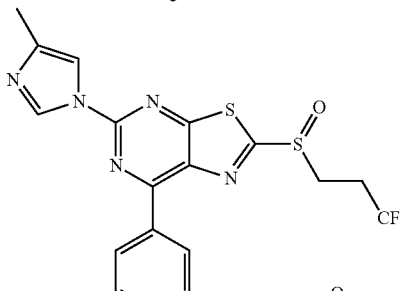

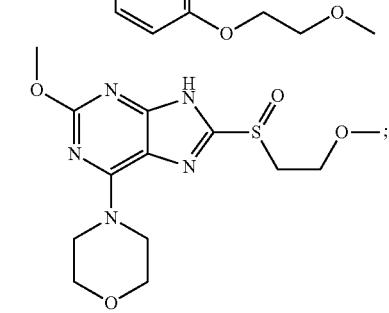

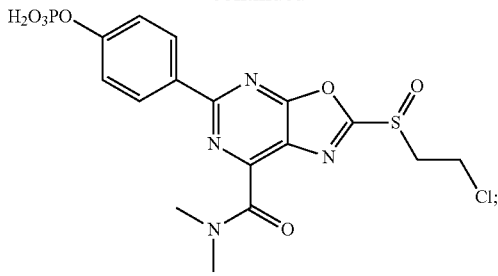

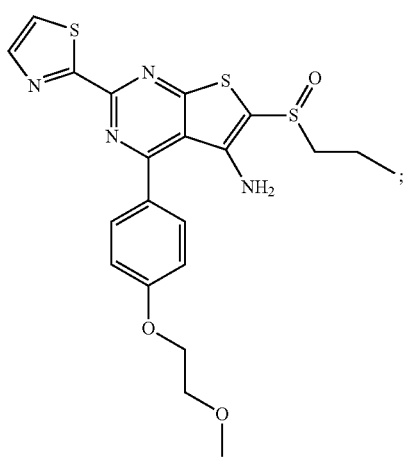

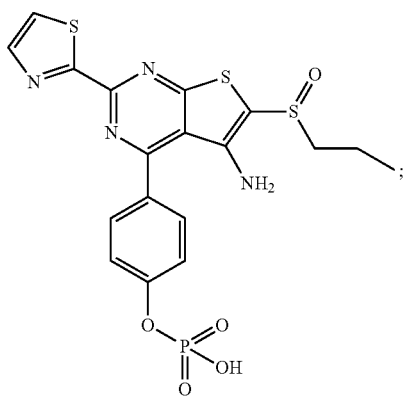

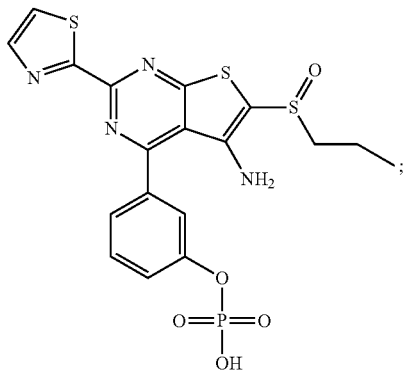

-continued

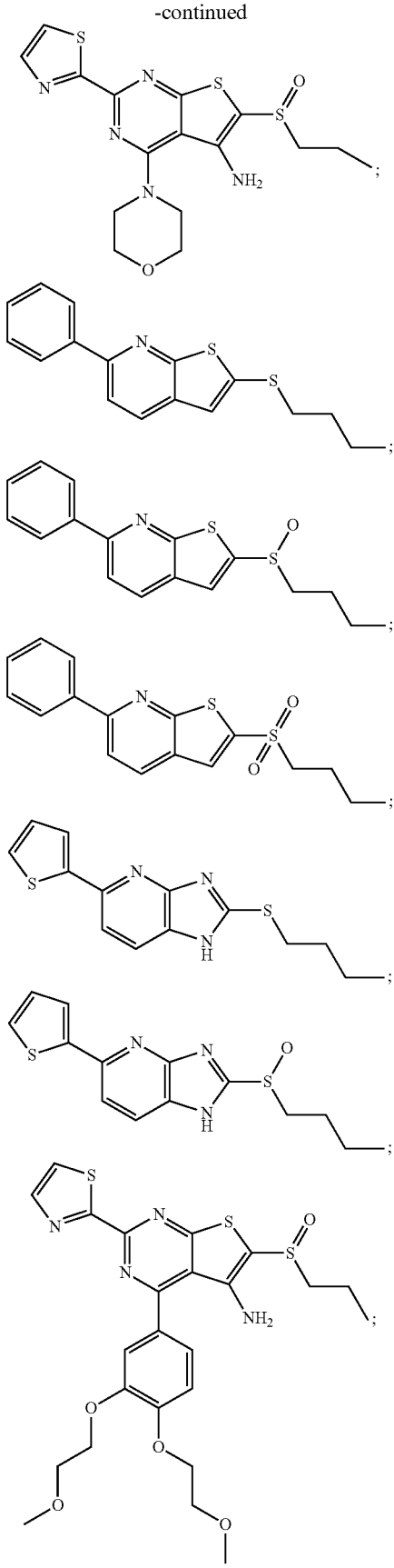

and pharmaceutically acceptable salts thereof.

In other embodiments, the 15-PGDH inhibitor can include a compound having the following formula (V):

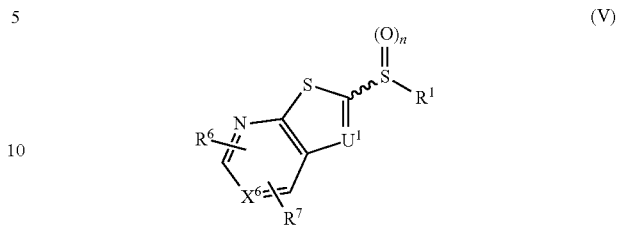

wherein n is 0-2

$X^6$ is independently is N or $CR^c$ $R^1$, $R^6$, $R^7$, and $R^c$ are each independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms (wherein from 1-3 of the ring atoms is independently selected from N, NH, N($C_1$-$C_6$ alkyl), NC(O)($C_1$-$C_6$ alkyl), 0, and S), $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—NH$_2$), carbamido (—NH—(CO)—NH$_2$), cyano(—CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), sulfonamide (—SO$_2$—NH$_2$, —SO$_2$NY$_2$ (wherein Y is independently H, arlyl or alkyl), phosphono (—P(O)(OH)$_2$), phosphonato (—P(O)(O$^-$)$_2$), phosphinato (—P(O)(O$^-$)), phospho (—PO$_2$), phosphino (—PH$_2$), polyalkylethers, phosphates, phosphate esters, groups incorporating amino acids or other moieties expected to bear positive or negative charge at physiological pH, combinations thereof, and wherein $R^6$ and $R^7$ may be linked to form a cyclic or polycyclic ring, wherein the ring is a substituted or unsubstituted aryl, a substituted or unsubstituted heteroaryl, a substituted or unsubstituted cycloalkyl, and a substituted or unsubstituted heterocyclyl;

$U^1$ is N, C—$R^2$, or C—$NR^3R^4$, wherein $R^2$ is selected from the group consisting of a H, a lower alkyl group, O, $(CH_2)_{n1}OR'$ (wherein n1=1, 2, or 3), $CF_3$, $CH_2$—$CH_2X$, O—$CH_2$—$CH_2$—$CH_2X$, $CH_2$—$CH_2$—$CH_2X$, O—$CH_2$—$CH_2X$, X, (wherein X=H, F, Cl, Br, or I), CN, (C=O)—R', (C=O)N(R')$_2$, O(CO)R', COOR' (wherein R' is H or a lower alkyl group), and wherein R$^1$ and R$^2$ may be linked to form a cyclic or polycyclic ring, wherein R$^3$ and R$^4$ are the same or different and are each selected from the group consisting of H, a lower alkyl group, O, (CH$_2$)$_{n_1}$OR' (wherein n1=1, 2, or 3), CF$_3$, CH$_2$—CH$_2$X, CH$_2$—CH$_2$—CH$_2$X, (wherein X=H, F, Cl, Br, or I), CN, (C=O)—R', (C=O)N(R')$_2$, COOR' (wherein R' is H or a lower alkyl group), and R$^3$ or R$^4$ may be absent;

and pharmaceutically acceptable salts thereof.

In some embodiments, R$^1$ is selected from the group consisting of branched or linear alkyl including —(CH$_2$)n$_1$CH$_3$ (n$_1$=0-7),

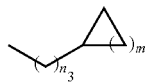

wherein n$_2$=0-6 and X is any of the following: CF$_y$H$_z$ (y+z=3), CCl$_y$H$_z$ (y+z=3), OH, OAc, OMe, R$^{71}$, OR$^{72}$, CN, N(R$^{73}$)$_2$,

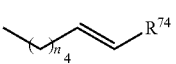

(n$_3$ = 0-5, m = 1-5), and (n$_4$ = 0-5).

In other embodiments, R$^6$ and R$^7$ can each independently be one of the following:

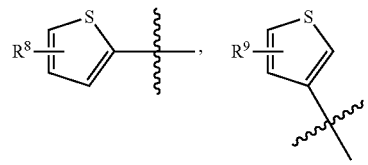

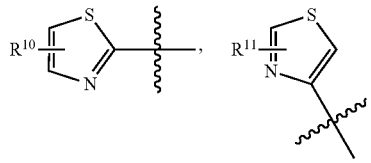

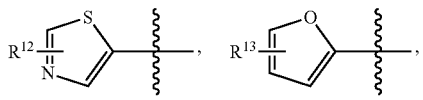

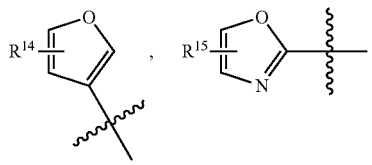

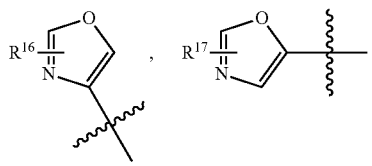

-continued

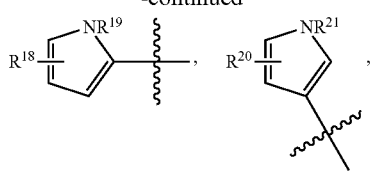

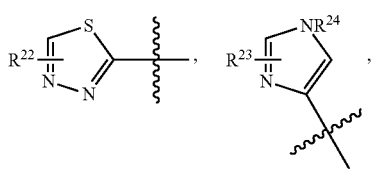

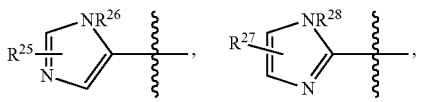

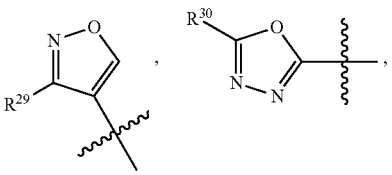

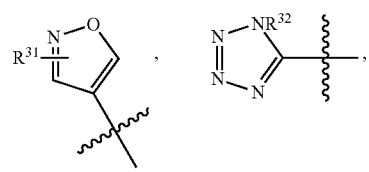

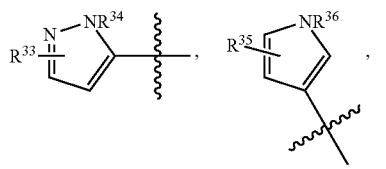

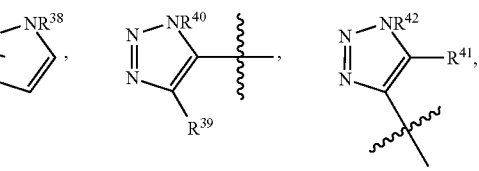

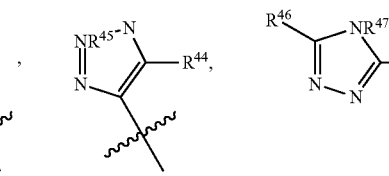

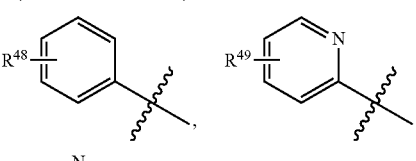

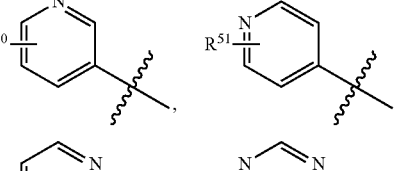

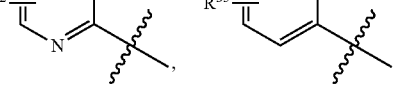

-continued

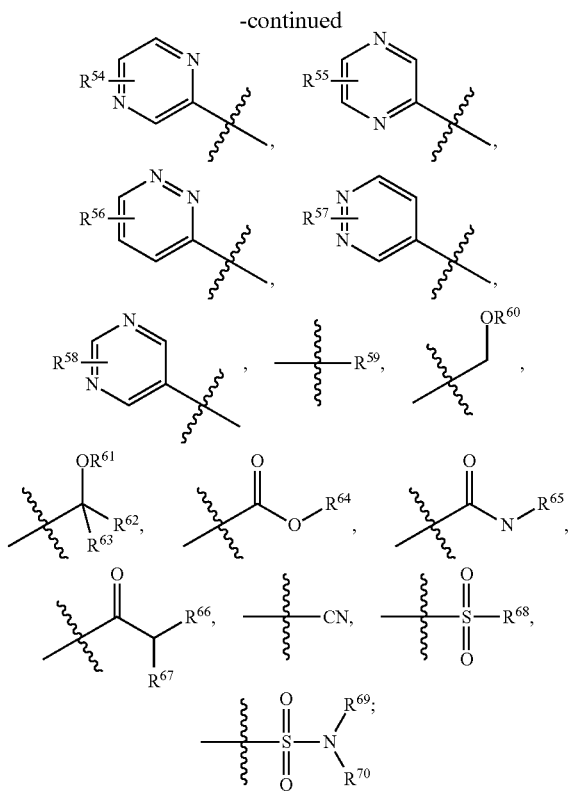

each each $R^8$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, $R^{49}$, $R^{50}$, $R^{51}$, $R^{52}$, $R^{53}$, $R^{54}$, $R^{55}$, $R^{56}$, $R^{57}$, $R^{58}$, $R^{59}$, $R^{60}$, $R^{61}$, $R^{62}$, $R^{63}$, $R^{64}$, $R^{65}$, $R^{66}$, $R^{67}$, $R^{68}$, $R^{69}$, $R^{70}$, $R^{71}$, $R^{72}$, $R^{73}$, and $R^{74}$, are the same or different and are independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heterocycloalkenyl containing from 5-6 ring atoms, (wherein from 1-3 of the ring atoms is independently selected from N, NH, N($C_1$-$C_6$ alkyl), NC(O)($C_1$-$C_6$ alkyl), O, and S), heteroaryl or heterocyclyl containing from 5-14 ring atoms, (wherein from 1-6 of the ring atoms is independently selected from N, NH, N($C_1$-$C_3$ alkyl), O, and S), $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO⁻), carbamoyl (—(CO)—NH$_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—NH$_2$), carbamido (—NH—(CO)—NH$_2$), cyano (—CN), isocyano (—N⁺C⁻), cyanato (—O—CN), isocyanato (—O—N⁺=C⁻), isothiocyanato (—S—CN), azido (—N=N⁺=N⁻), formyl (—(CO)—H), thioformyl (—(CS)—H), amino (—NH$_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), sulfanamido (—SO$_2$N(R)$_2$ where R is independently H, alkyl, aryl or heteroaryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O⁻), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), sulfonamide (—SO$_2$—NH$_2$, —SO$_2$NY$_2$ (wherein Y is independently H, arlyl or alkyl), phosphono (—P(O)(OH)$_2$), phosphonato (—P(O)(O⁻)$_2$), phosphinato (—P(O)(O⁻)), phospho (—PO$_2$), phosphino (—PH$_2$), polyalkyl ethers (—[(CH$_2$)$_n$O]$_m$), phosphates, phosphate esters [—OP(O)(OR)$_2$ where R=H, methyl or other alkyl], groups incorporating amino acids or other moieties expected to bear positive or negative charge at physiological pH, and combinations thereof, and pharmaceutically acceptable salts thereof.

In still other embodiments, $R^6$ and $R^7$ can independently be a group that improves aqueous solubility, for example, a phosphate ester (—OPO$_3$H$_2$), a phenyl ring linked to a phosphate ester (—OPO$_3$H$_2$), a phenyl ring substituted with one or more methoxyethoxy groups, or a morpholine, or an aryl or heteroaryl ring substituted with such a group.

In other embodiments, the 15-PGDH inhibitor can include a compound having the following formula (VI):

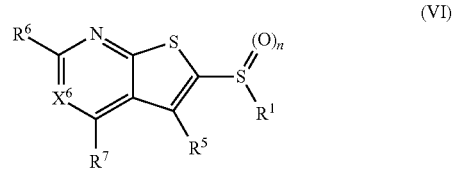

wherein n=0-2;

$X^6$ is N or $CR^c$;

$R^1$ is selected from the group consisting of branched or linear alkyl including —(CH$_2$)n$_1$CH$_3$ (n$_1$=0-7),

wherein n$_2$=0-6 and X is any of the following: $CF_yH_z$ (y+z=3), $CCl_yH_z$ (y+z=3), OH, OAc, OMe, $R^{71}$, $OR^{72}$, CN, $N(R^{73})_2$,

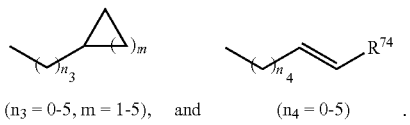

(n$_3$ = 0-5, m = 1-5), and (n$_4$ = 0-5).

$R^5$ is selected from the group consisting of H, Cl, F, NH$_2$, and $N(R^{76})_2$;

$R^6$ and $R^7$ can each independently be one of the following:

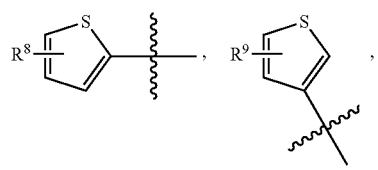

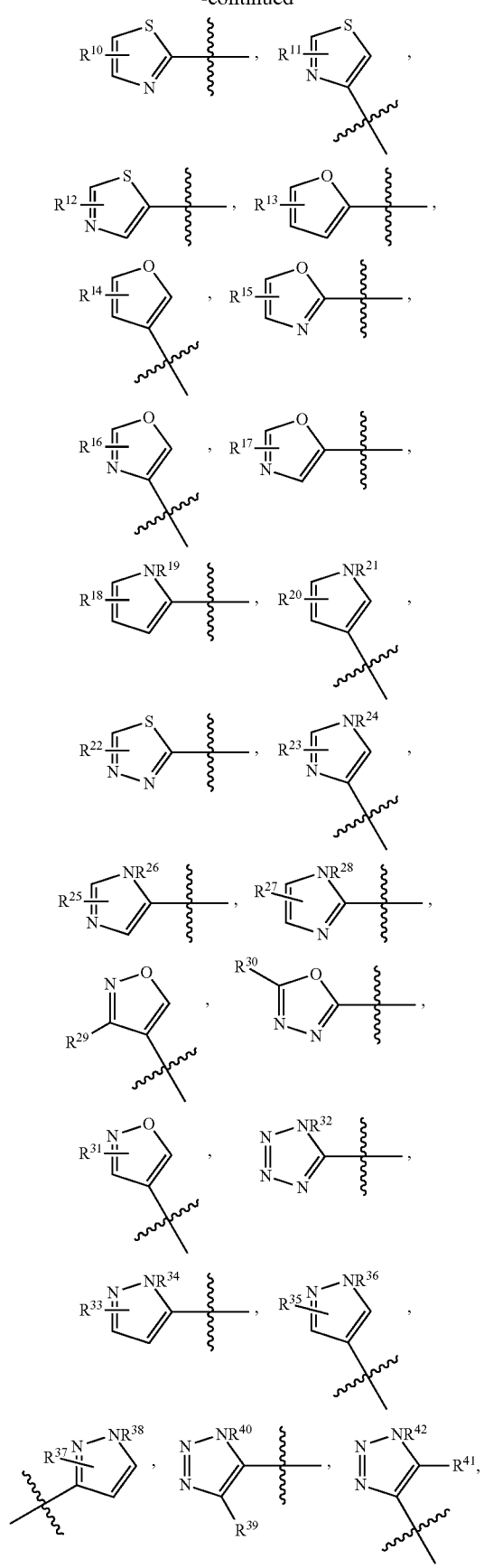
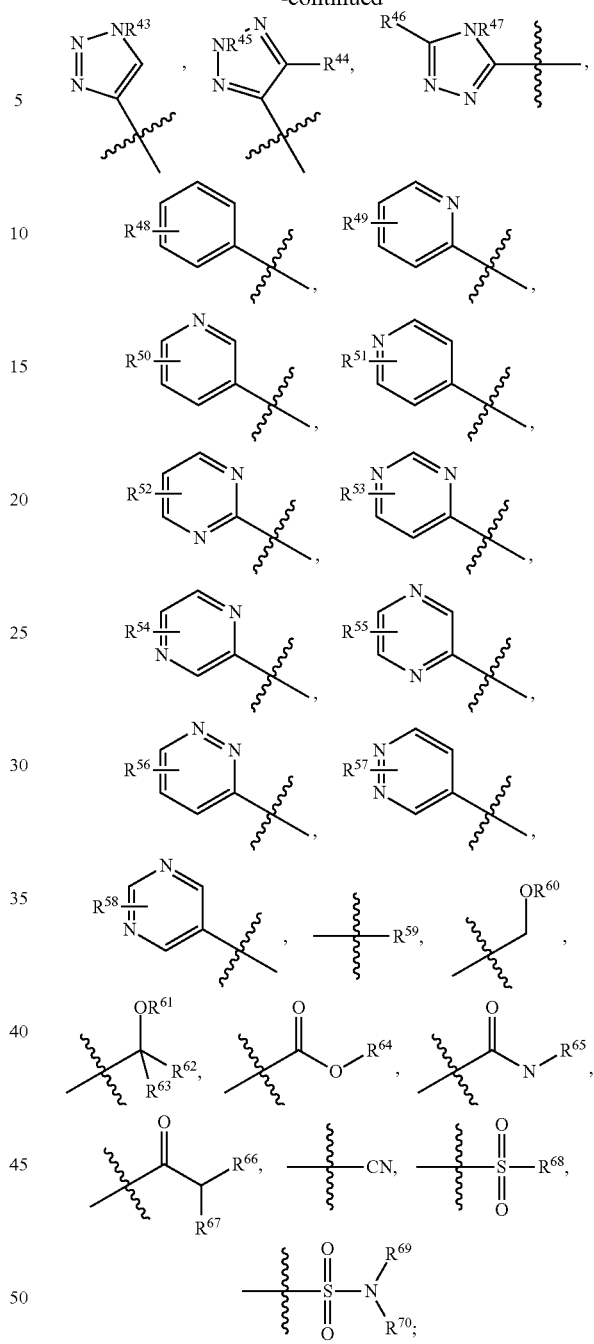

each $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, $R^{49}$, $R^{50}$, $R^{51}$, $R^{55}$, $R^{54}$, $R^{55}$, $R^{56}$, $R^{57}$, $R^{58}$, $R^{59}$, $R^{60}$, $R^{61}$, $R^{62}$, $R^{63}$, $R^{64}$, $R^{65}$, $R^{66}$, $R^{67}$, $R^{68}$, $R^{69}$, $R^{70}$, $R^{71}$, $R^{72}$, $R^{73}$, $R^{74}$, $R^{76}$, and $R^c$ are the same or different and are independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heterocycloalkenyl containing from 5-6 ring atoms, (wherein from 1-3 of the ring atoms is independently selected from N, NH, N($C_1$-$C_6$ alkyl), NC(O) ($C_1$-$C_6$ alkyl), O, and S), heteroaryl or heterocyclyl containing from 5-14 ring atoms, (wherein from 1-6 of the ring atoms is independently selected from N, NH, N($C_1$-$C_3$ alkyl), O, and S), $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—$NH_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—$NH_2$), carbamido (—NH—(CO)—$NH_2$), cyano (—CN), isocyano (—$N^+C^-$), cyanato (—O—CN), isocyanato (—O—$N^+$=$C^-$), isothiocyanato (—S—CN), azido (—N=$N^+$=$N^-$), formyl (—(CO)—H), thioformyl (—(CS)—H), amino (—$NH_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), sulfanamido (—$SO_2$N(R)$_2$ where R is independently H, alkyl, aryl or heteroaryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—$NO_2$), nitroso (—NO), sulfo (—$SO_2$—OH), sulfonato (—$SO_2$—$O^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—$SO_2$-alkyl), $C_5$-$C_{20}$ arylsulfonyl (—$SO_2$-aryl), sulfonamide (—$SO_2$—$NH_2$, —$SO_2NY_2$ (wherein Y is independently H, arlyl or alkyl), phosphono (—P(O)(OH)$_2$), phosphonato (—P(O)($O^-$)$_2$), phosphinato (—P(O)($O^-$)), phospho (—$PO_2$), phosphino (—$PH_2$), polyalkyl ethers (—[($CH_2$)$_n$O]$_m$), phosphates, phosphate esters [—OP(O)(OR)$_2$ where R=H, methyl or other alkyl], groups incorporating amino acids or other moieties expected to bear positive or negative charge at physiological pH, and combinations thereof, and pharmaceutically acceptable salts thereof.

In other embodiments, the 15-PGDH inhibitor can include a compound having the following formula (VII):

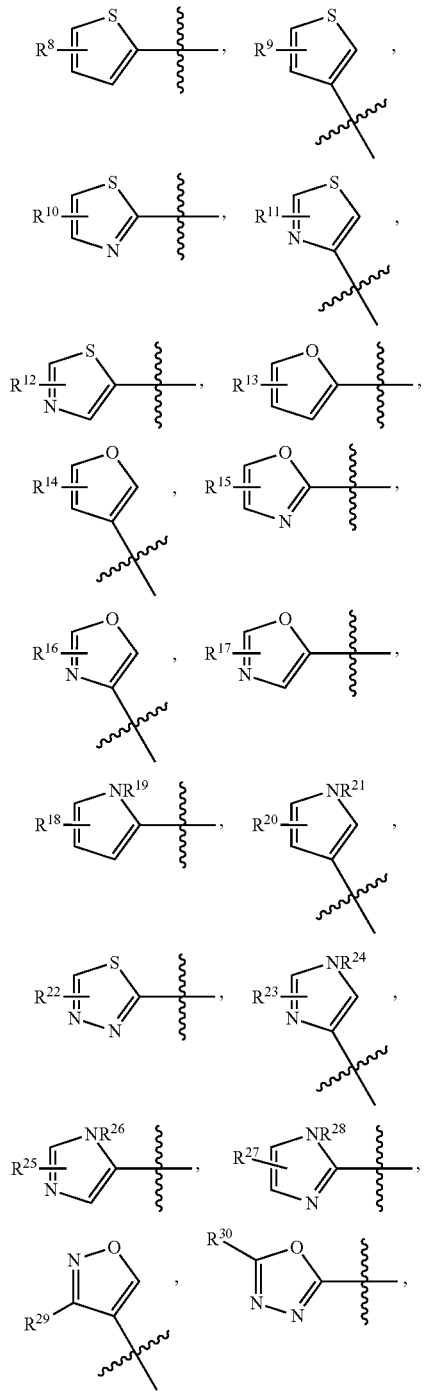

(VII)

wherein n=0-2;

$X^6$ is N or $CR^c$;

$R^1$ is selected from the group consisting of branched or linear alkyl including —($CH_2$)$n_1CH_3$ ($n_1$=0-7),

wherein $n_2$=0-6 and X is any of the following: $CF_yH_z$ (y+z=3), $CCl_yH_z$ (y+z=3), OH, OAc, OMe, $R^{71}$, $OR^{72}$, CN, $N(R^{73})_2$,

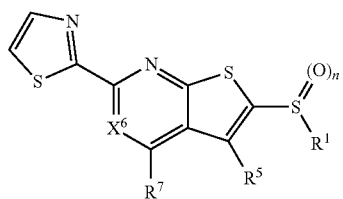

($n_3$ = 0-5, m = 1-5), and ($n_4$ = 0-5).

$R^5$ is selected from the group consisting of H, Cl, F, $NH_2$, and $N(R^{76})_2$;

$R^7$ can each independently be one of the following:

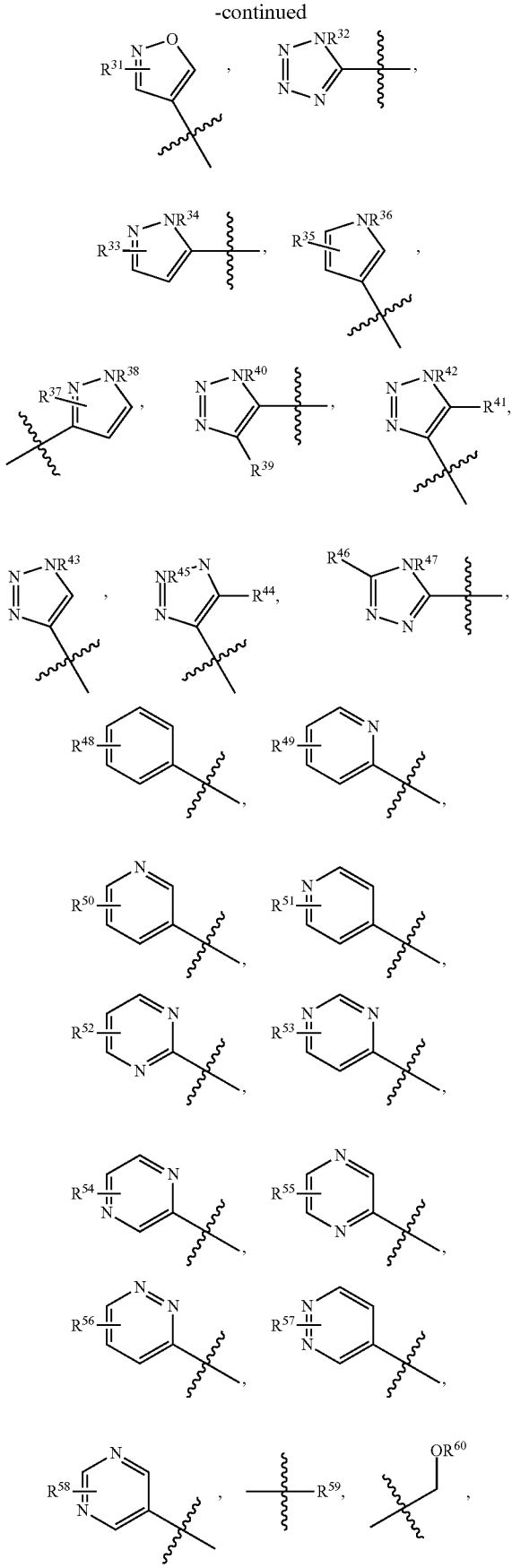

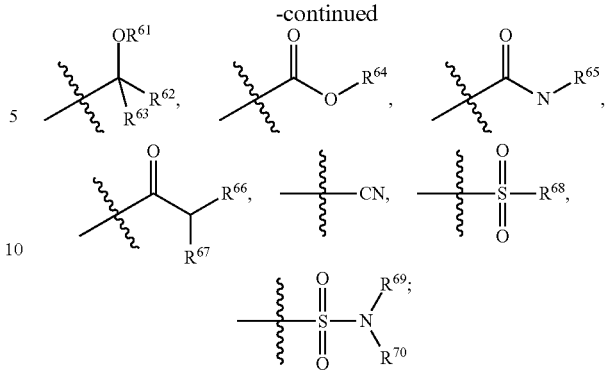

each $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, $R^{49}$, $R^{50}$, $R^{51}$, $R^{55}$, $R^{54}$, $R^{55}$, $R^{56}$, $R^{57}$, $R^{58}$, $R^{59}$, $R^{60}$, $R^{61}$, $R^{62}$, $R^{63}$, $R^{64}$, $R^{65}$, $R^{66}$, $R^{67}$, $R^{68}$, $R^{69}$, $R^{70}$, $R^{71}$, $R^{72}$, $R^{73}$, $R^{74}$, $R^{76}$, and $R^c$ are the same or different and are independently selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heterocycloalkenyl containing from 5-6 ring atoms, (wherein from 1-3 of the ring atoms is independently selected from N, NH, N($C_1$-$C_6$ alkyl), NC(O)($C_1$-$C_6$ alkyl), O, and S), heteroaryl or heterocyclyl containing from 5-14 ring atoms, (wherein from 1-6 of the ring atoms is independently selected from N, NH, N($C_1$-$C_3$ alkyl), O, and S), $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO⁻), carbamoyl (—(CO)—NH₂), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—NH₂), carbamido (—NH—(CO)—NH₂), cyano(—CN), isocyano (—N⁺C⁻), cyanato (—O—CN), isocyanato (—O—N⁺=C⁻), isothiocyanato (—S—CN), azido (—N=N⁺=N⁻), formyl (—(CO)—H), thioformyl (—(CS)—H), amino (—NH₂), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), sulfanamido (—SO₂N(R)₂ where R is independently H, alkyl, aryl or heteroaryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO₂), nitroso (—NO), sulfo (—SO₂—OH), sulfonato (—SO₂—O⁻), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO₂-alkyl), $C_5$-$C_{20}$ arylsulfonyl (—SO₂-aryl), sulfonamide (—SO₂—NH₂, —SO₂NY₂ (wherein Y is independently H, arlyl or alkyl), phosphono (—P(O)(OH)₂), phosphonato (—P(O)(O⁻)₂), phosphinato (—P(O)(O⁻)), phospho (—PO₂), phosphino (—PH₂), polyalkyl ethers (—[(CH₂)ₙO]ₘ), phosphates, phosphate esters [—OP(O)(OR)₂ where R=H, methyl or other alkyl], groups incorporating amino acids or other moieties expected to bear positive or negative charge at physiological pH, and combinations thereof, and pharmaceutically acceptable salts thereof.
Examples of compounds having formulas (V), (VI), or (VIII) are selected from the group consisting of:
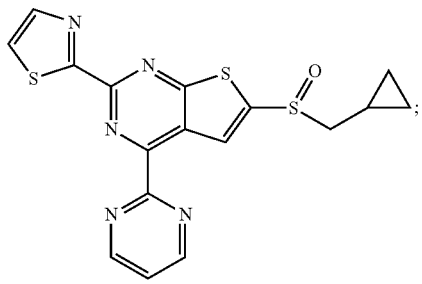
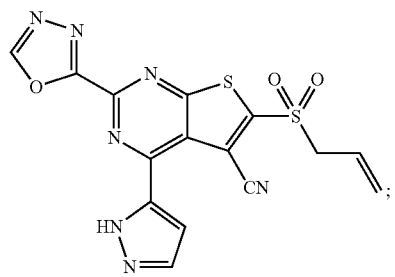
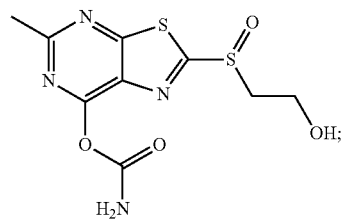
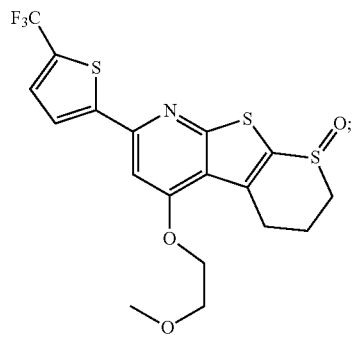
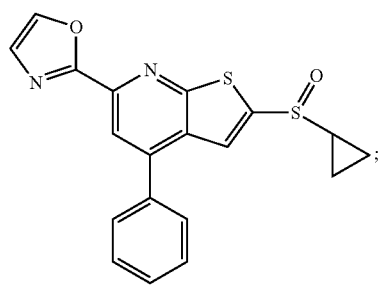
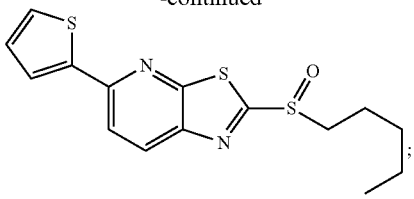
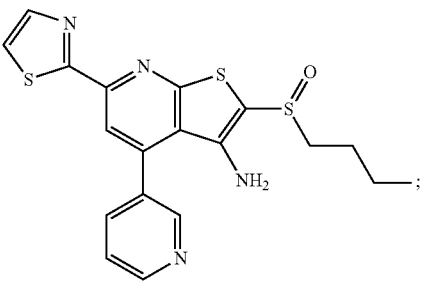
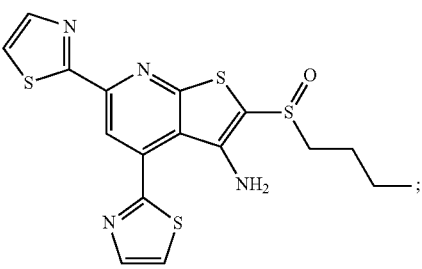
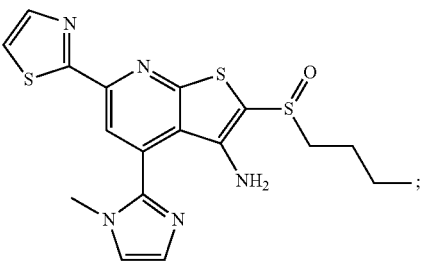
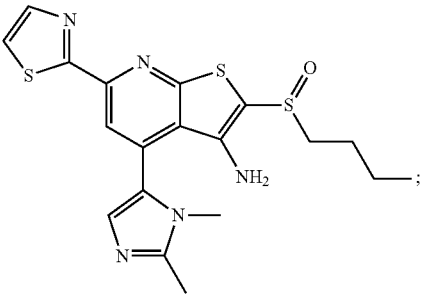
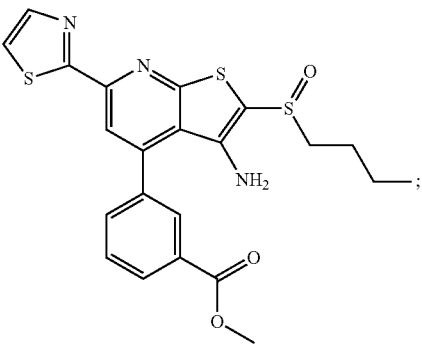

51
-continued
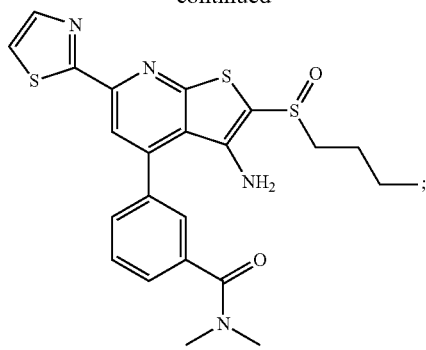
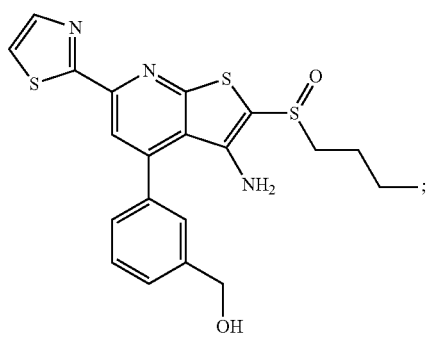
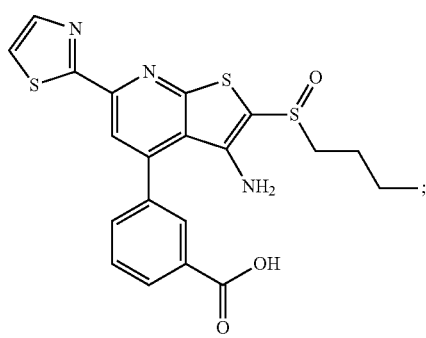
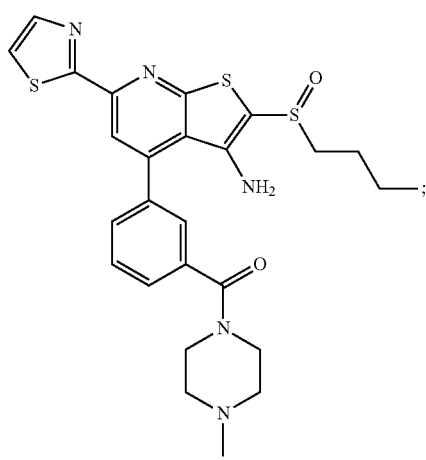
52
-continued
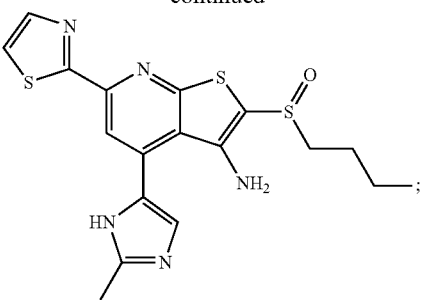
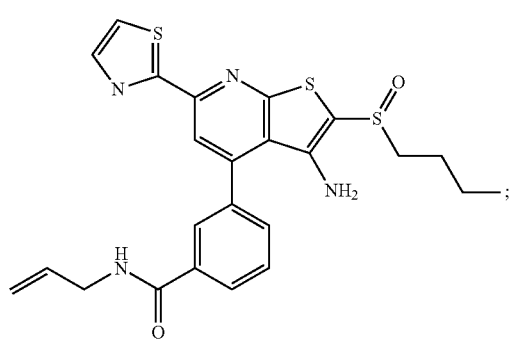
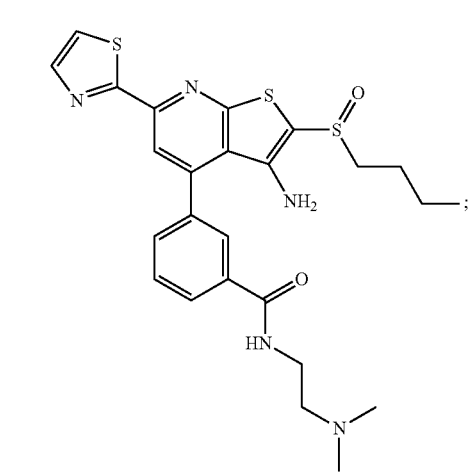
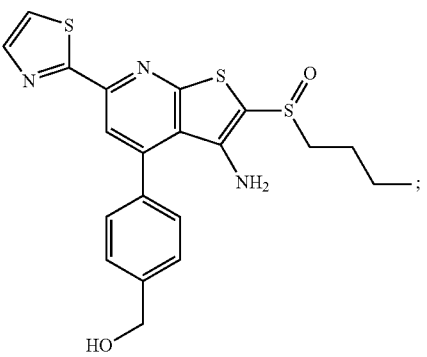

-continued
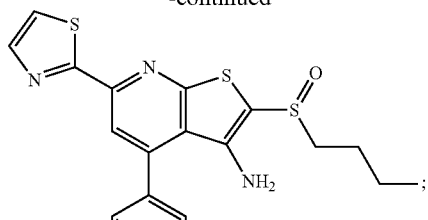
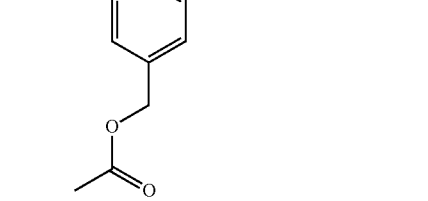
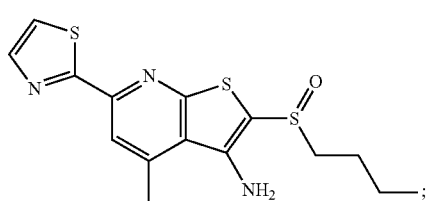
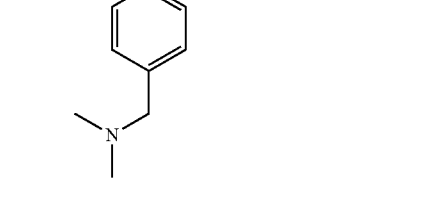
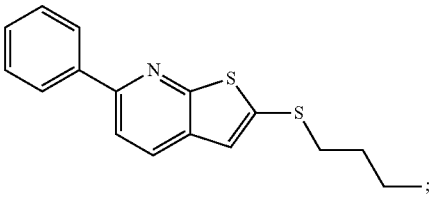
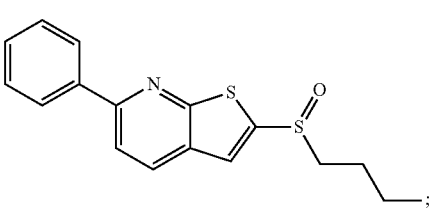
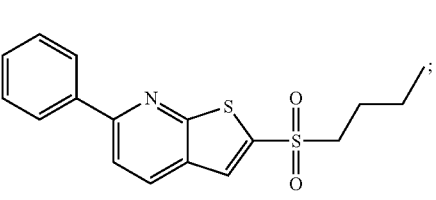
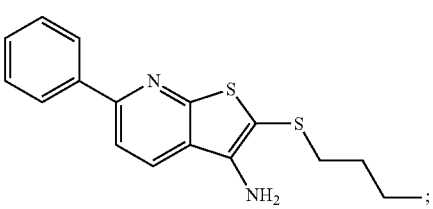
-continued
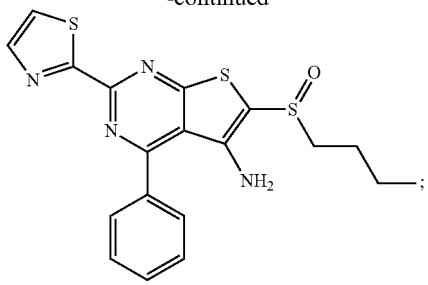
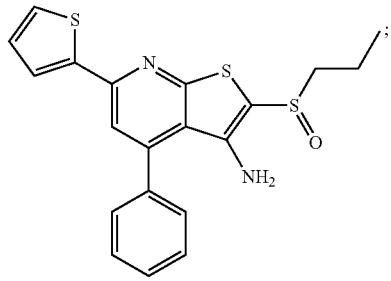
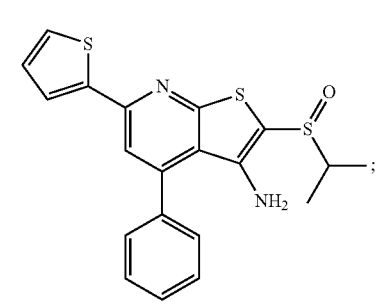
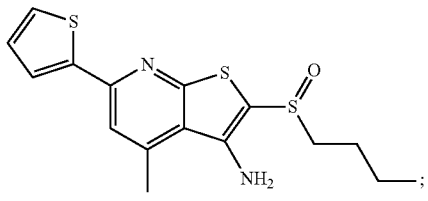
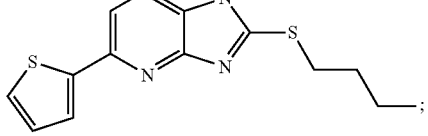
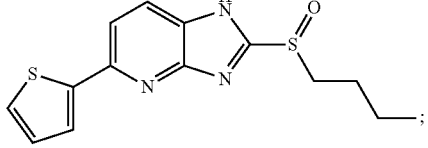
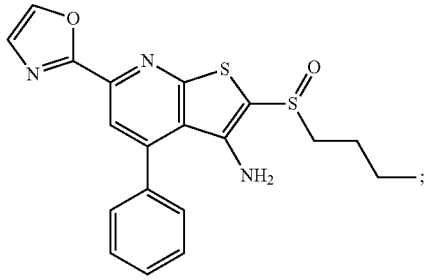

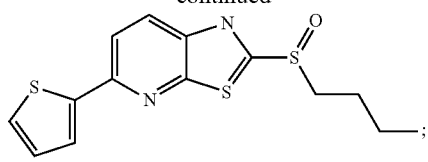
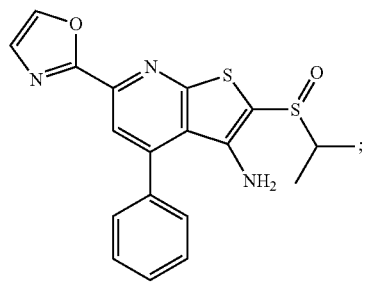
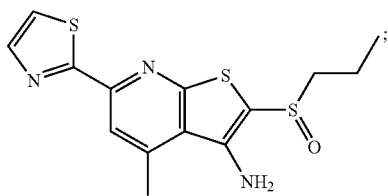
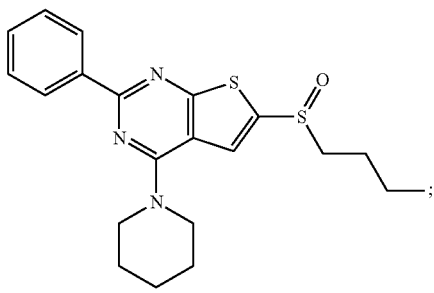
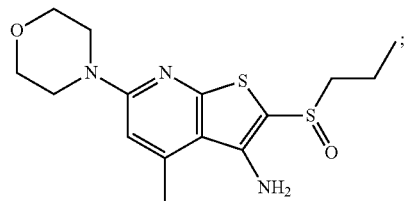
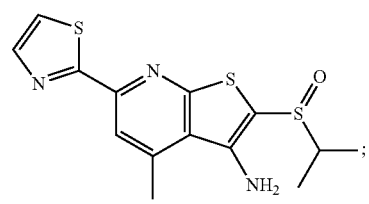
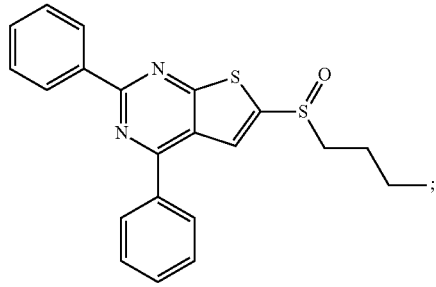
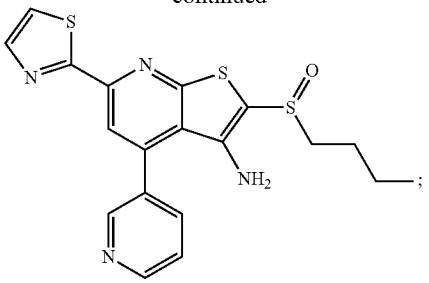
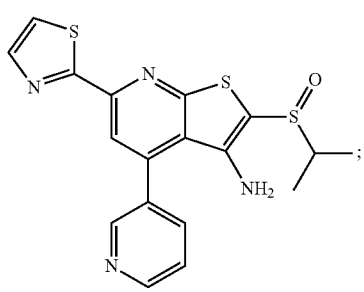
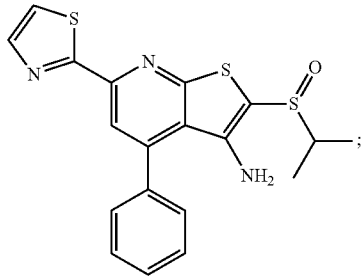
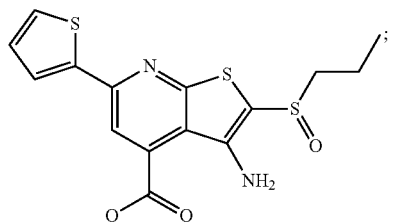
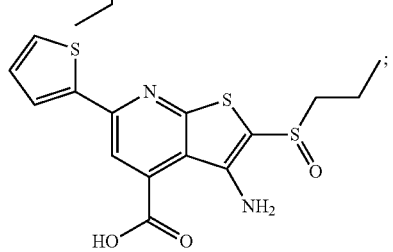
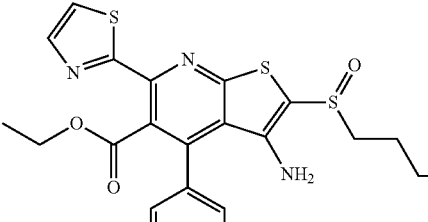
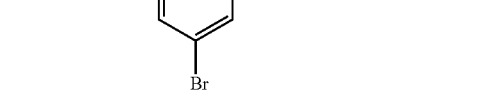

57
-continued
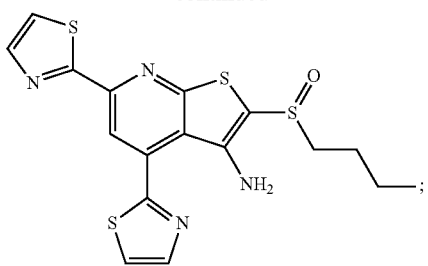
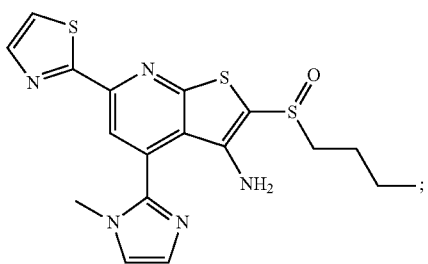
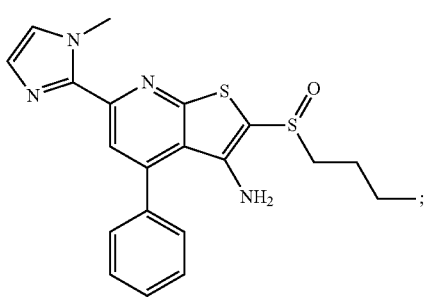
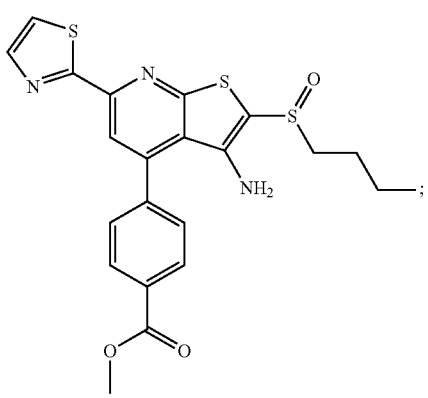
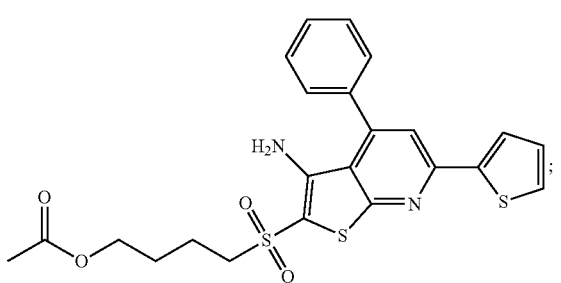
58
-continued
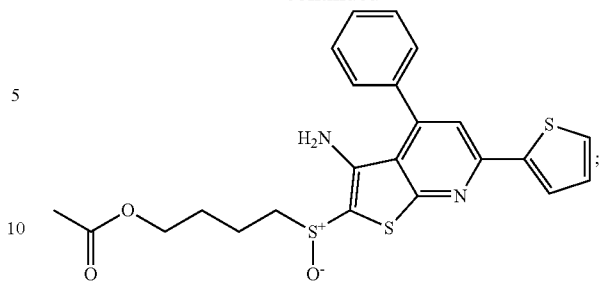
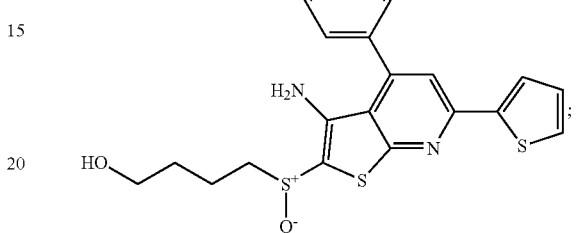
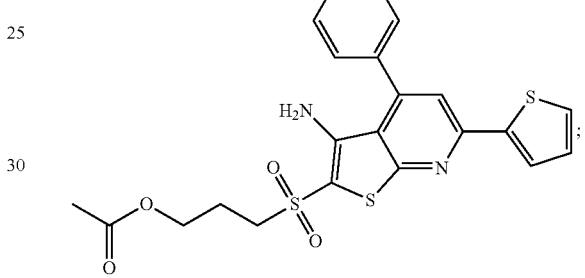
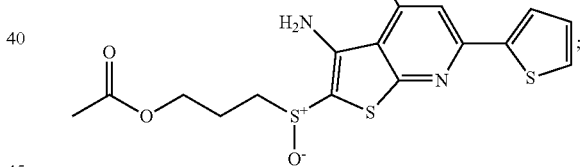
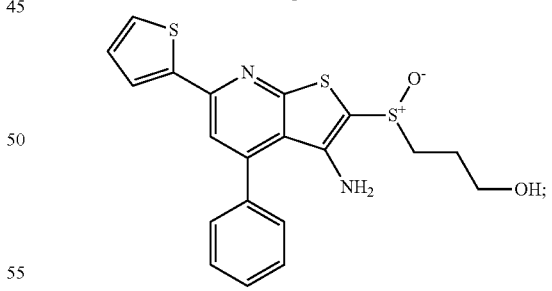
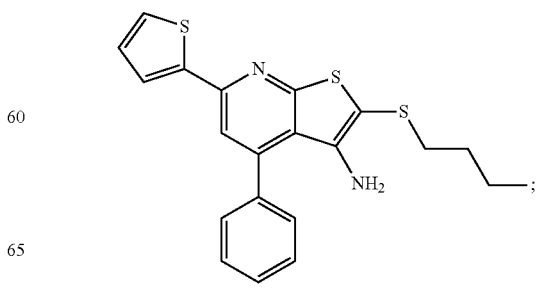

59
-continued
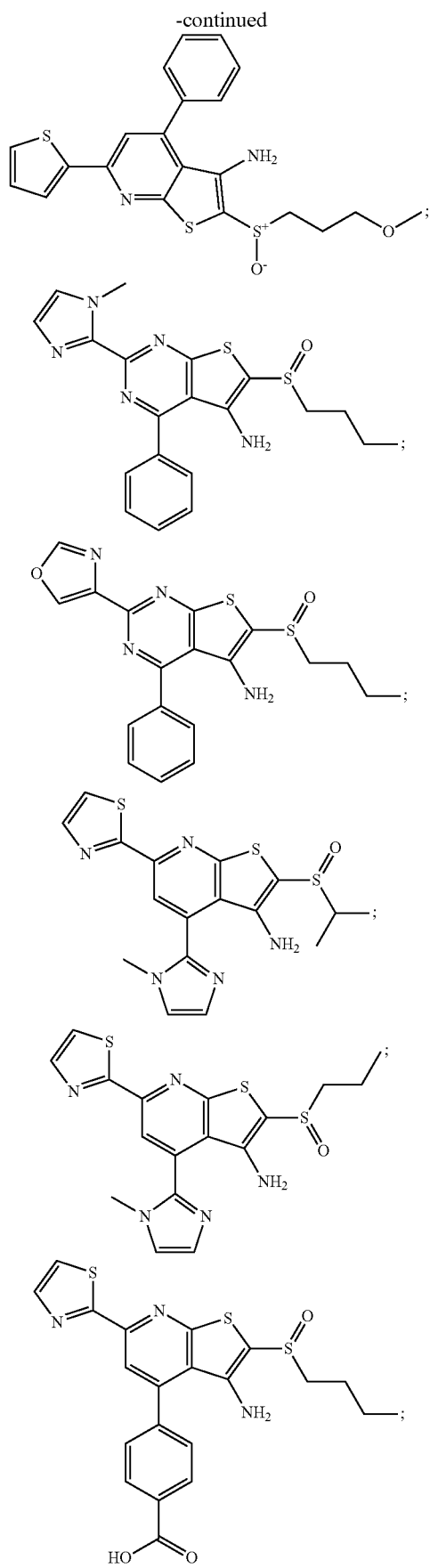
60
-continued
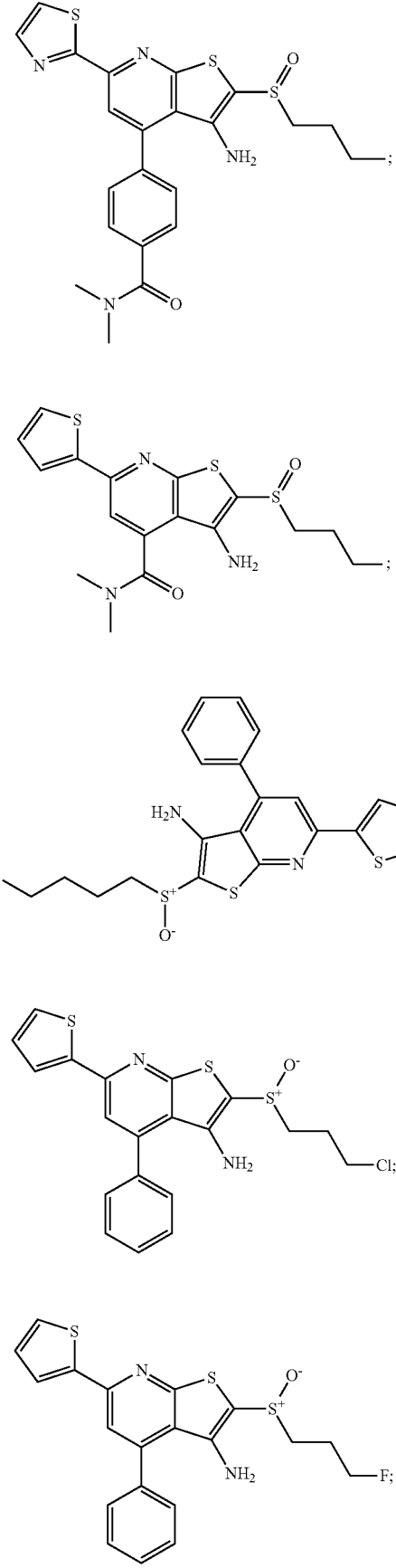

61
-continued
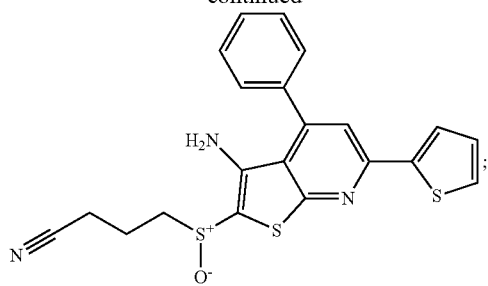
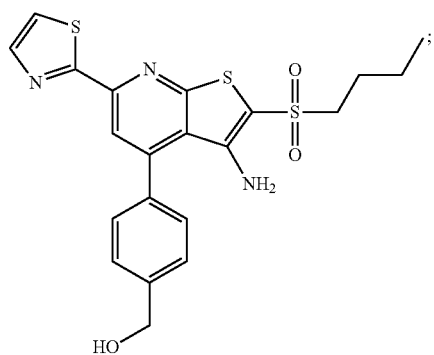
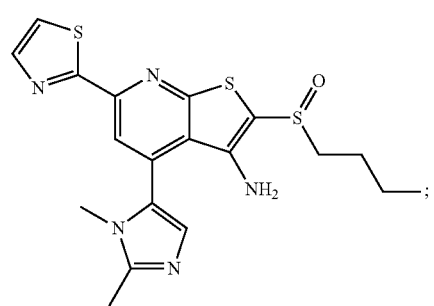
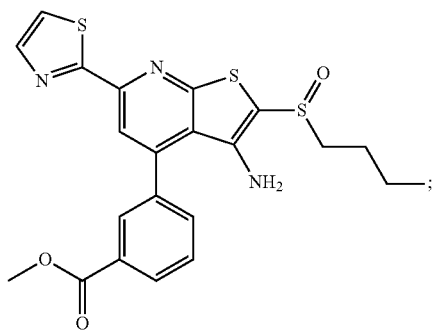
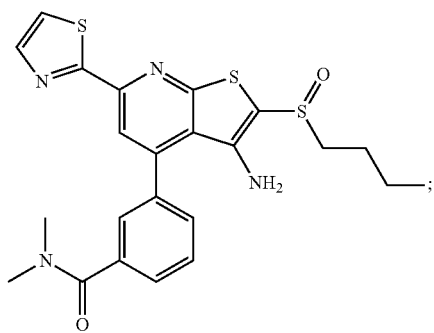
62
-continued
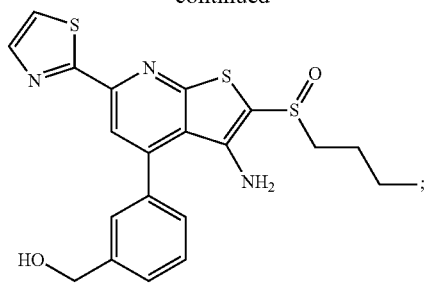
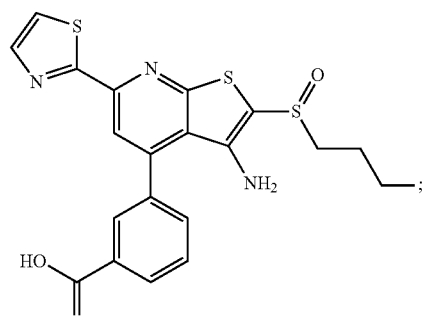
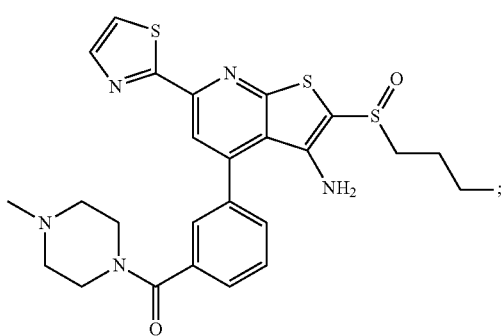
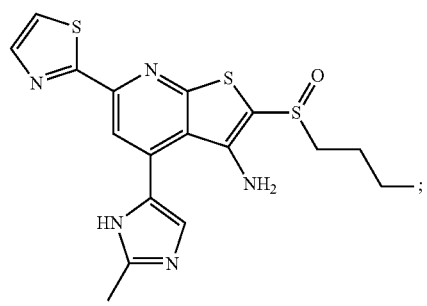
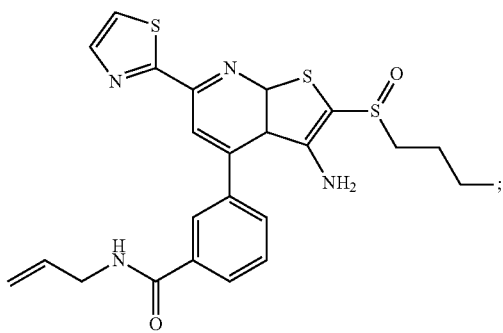

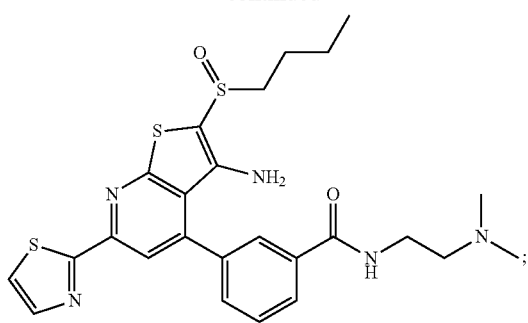
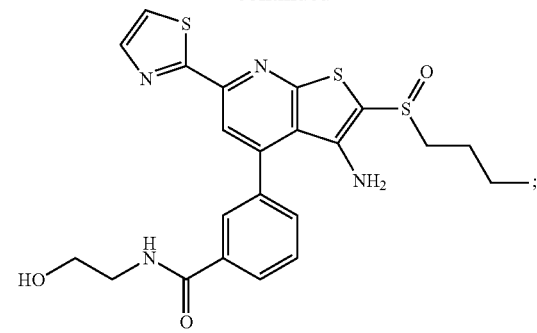
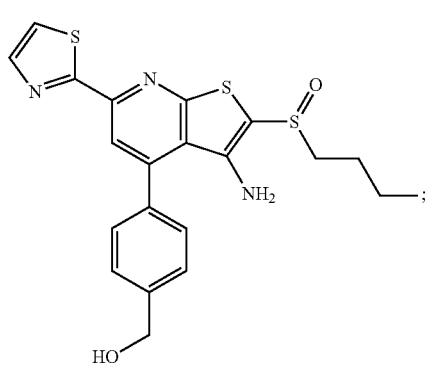
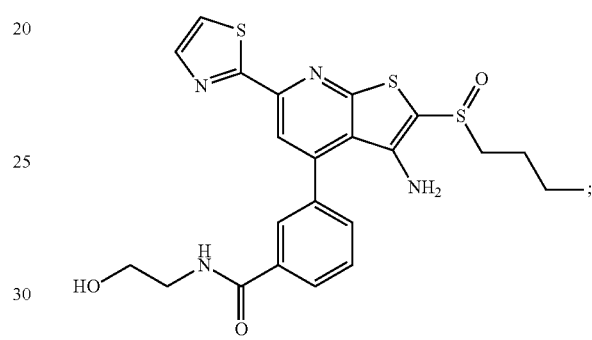
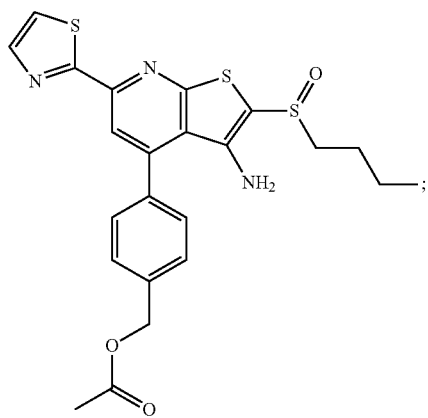
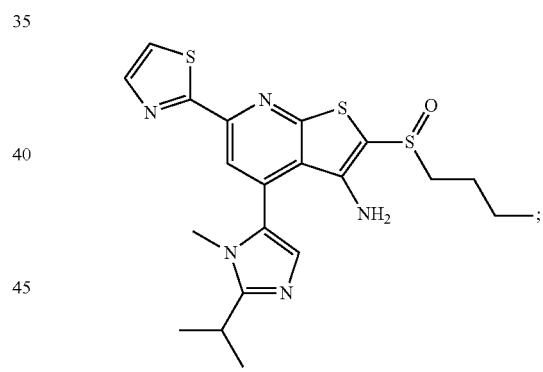
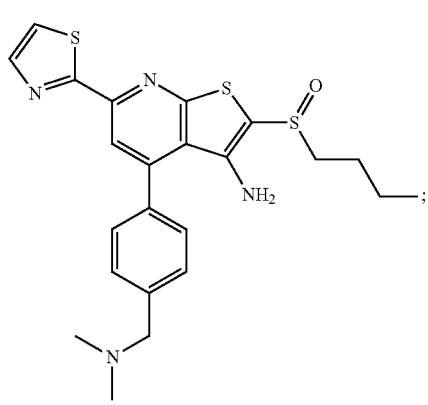
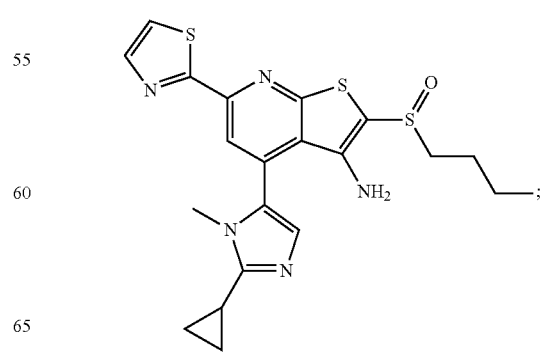

65
-continued
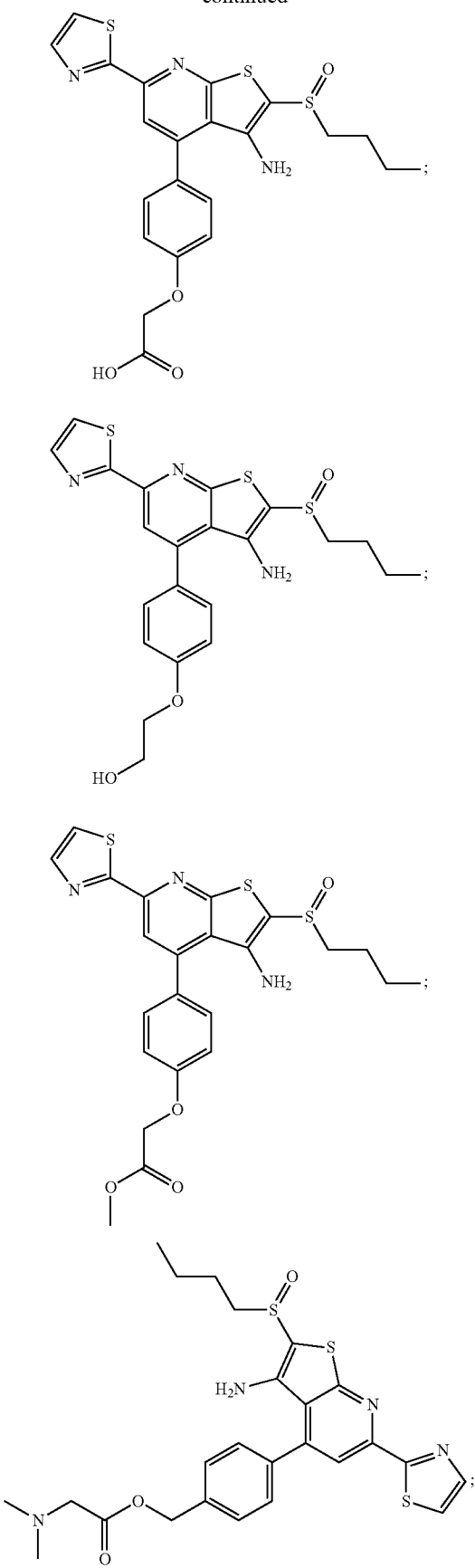
66
-continued
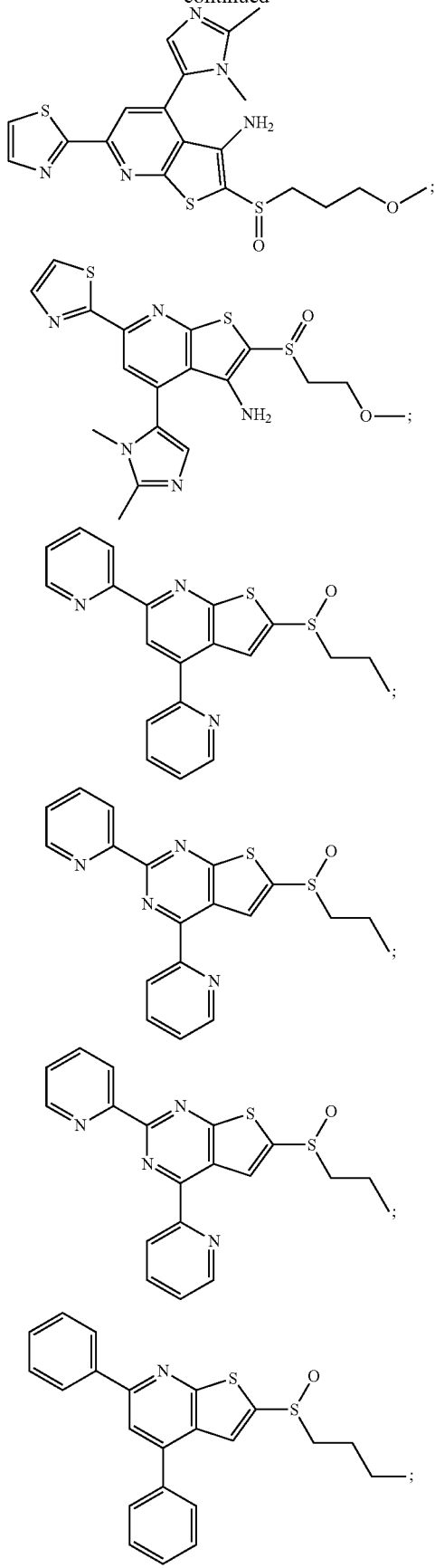

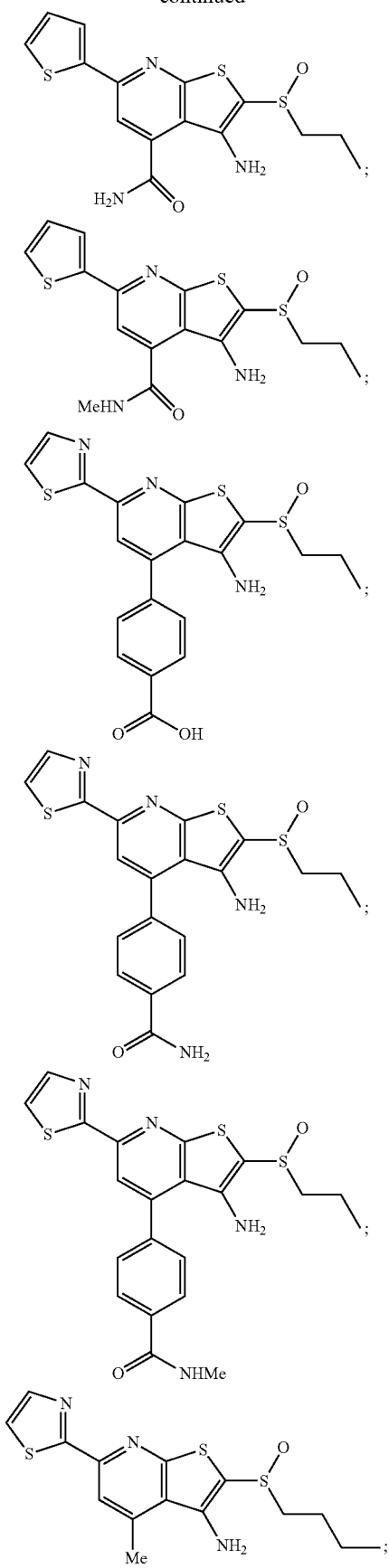
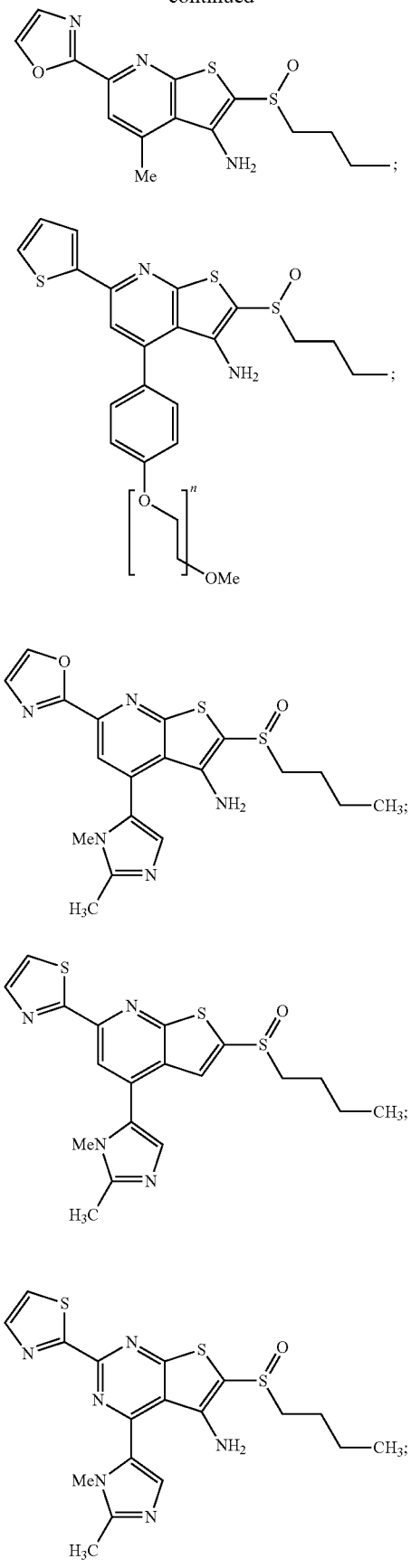

69
-continued
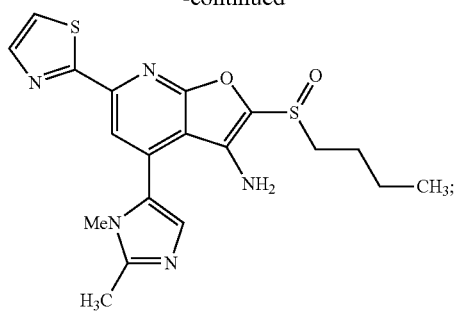
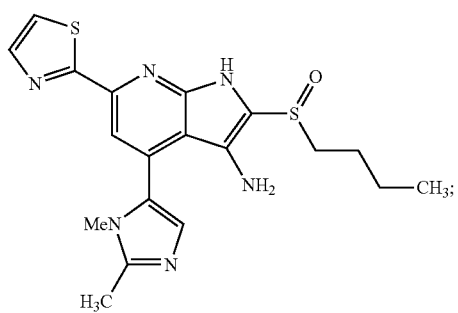
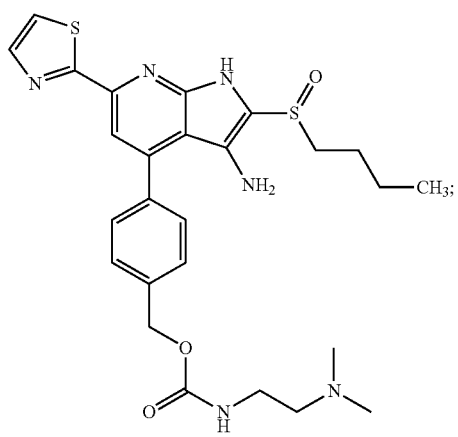
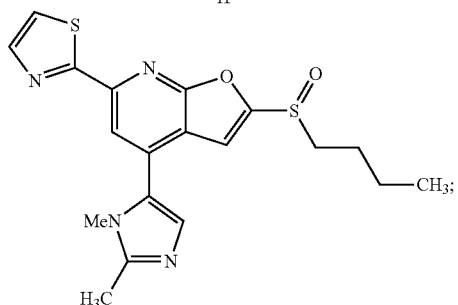
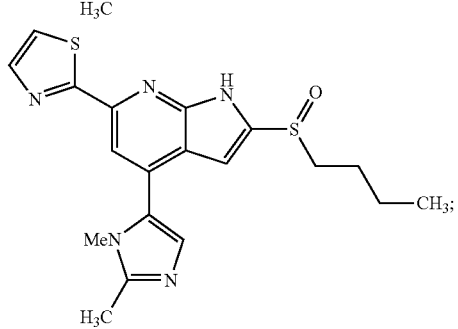
70
-continued
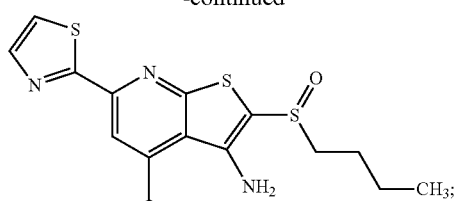
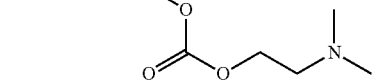
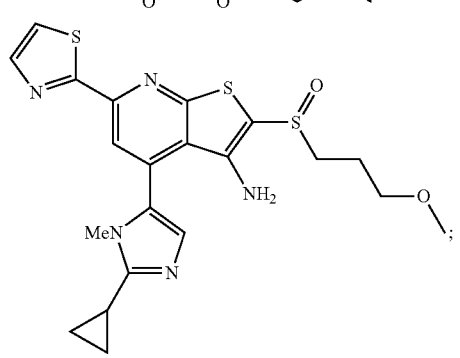
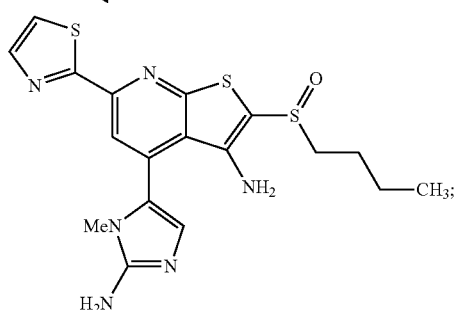
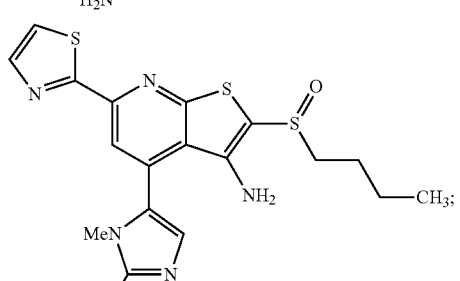
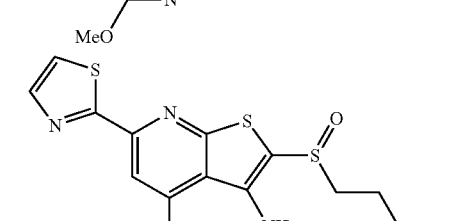
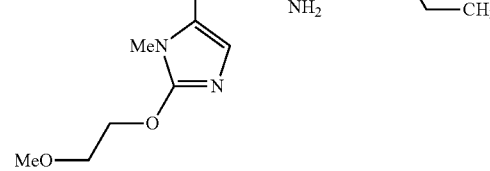

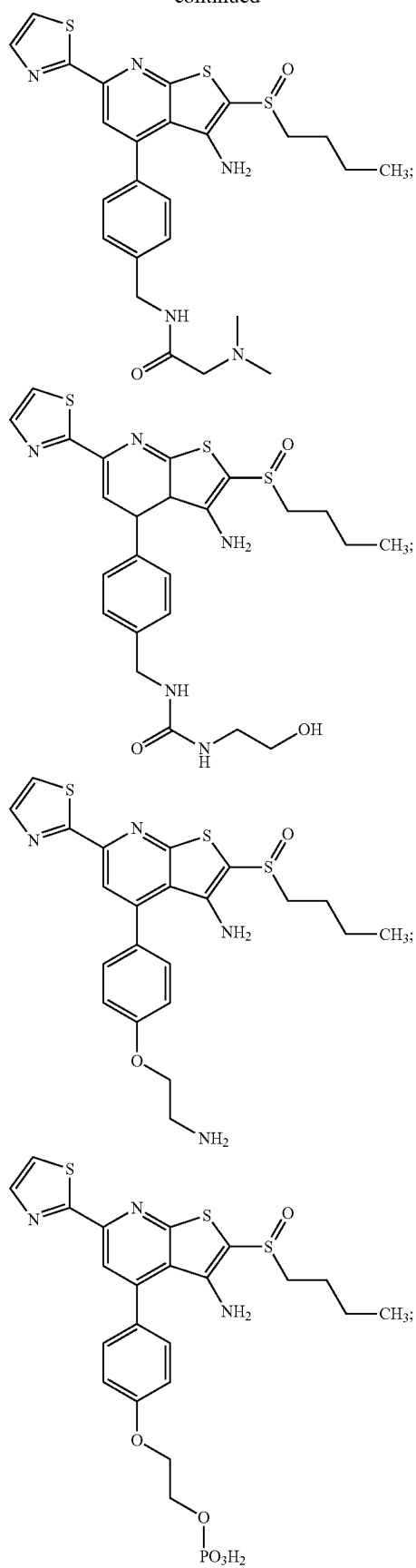
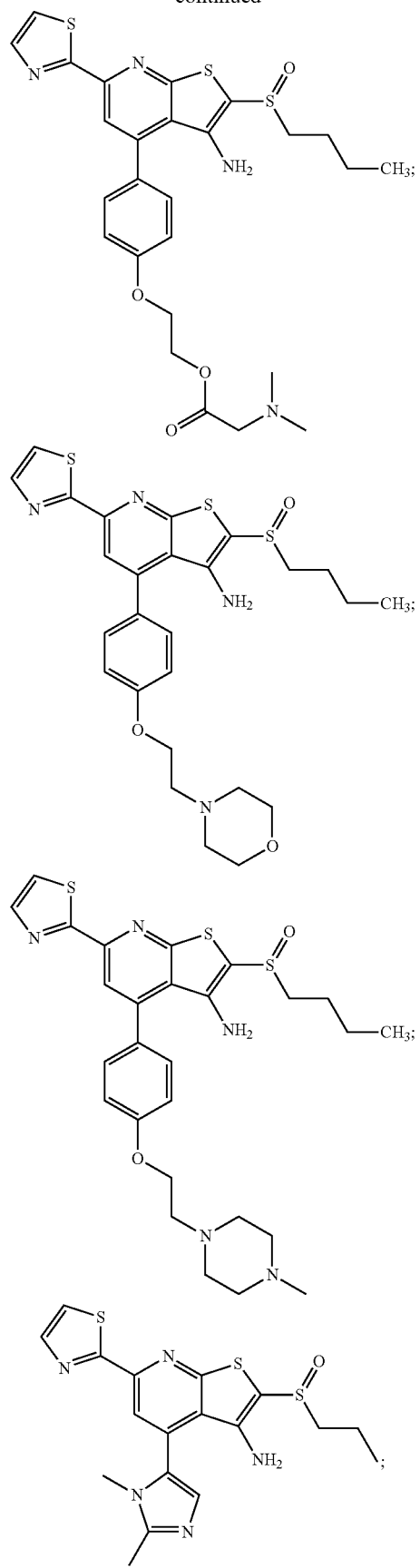

73
-continued
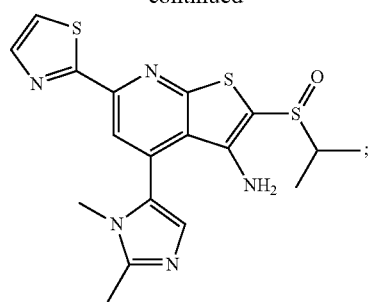
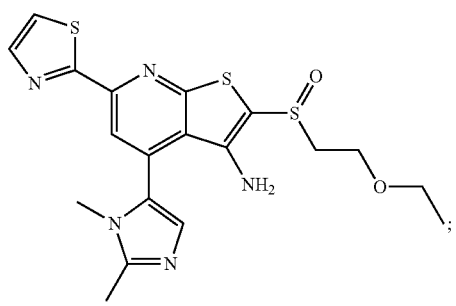
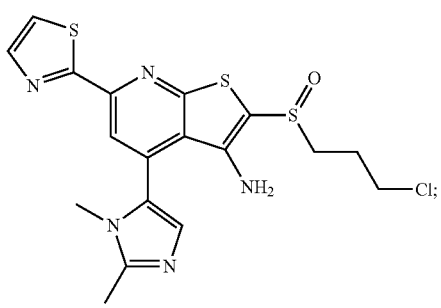
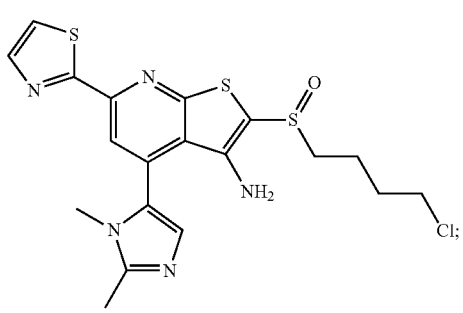
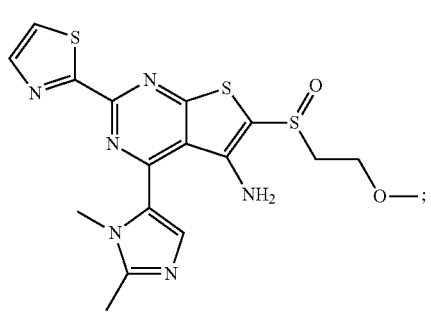
74
-continued
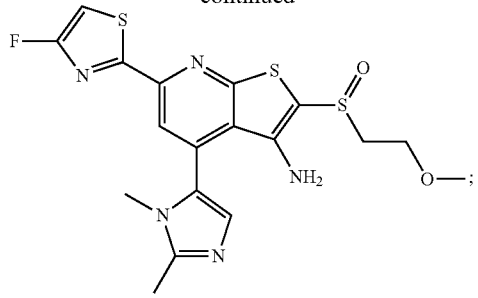
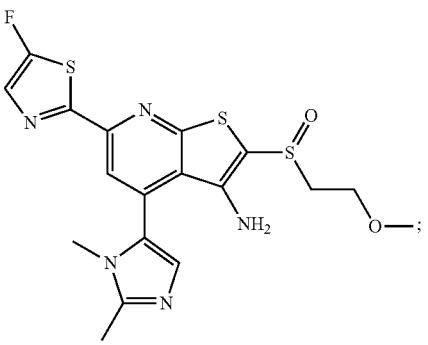
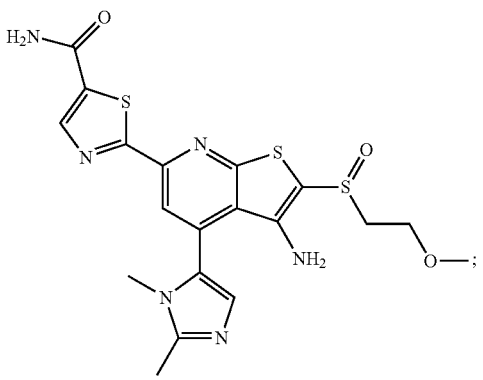
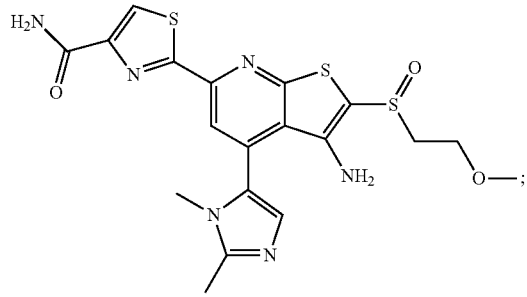
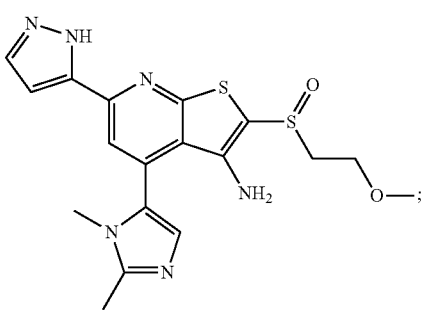

-continued
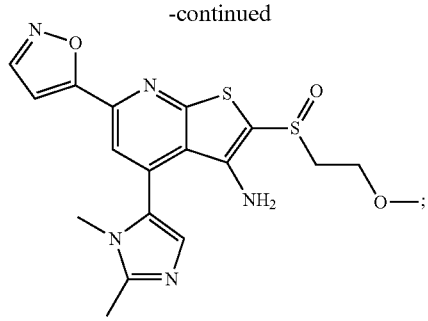
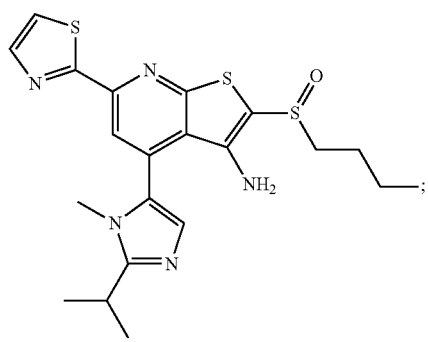
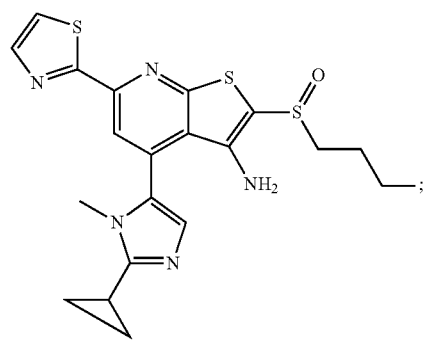
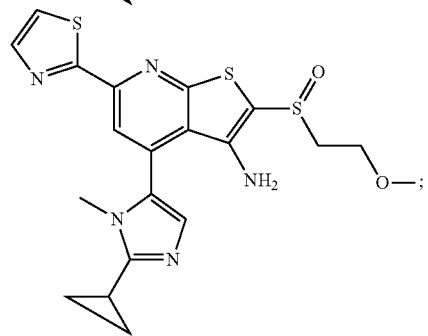
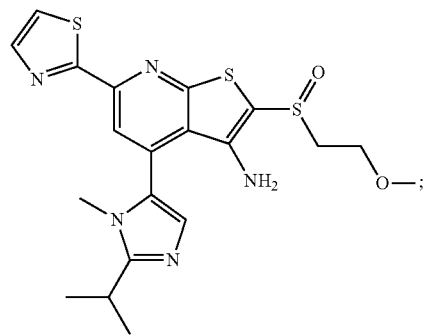
-continued
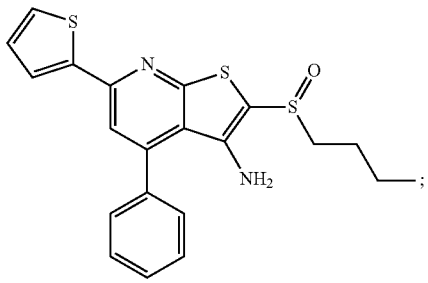
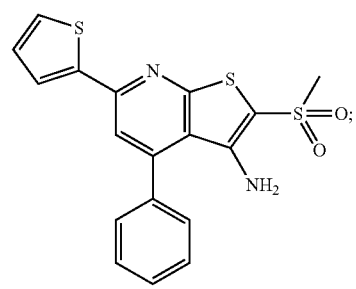
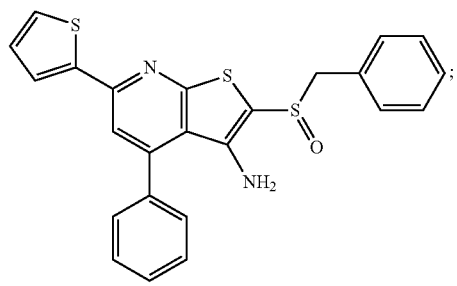
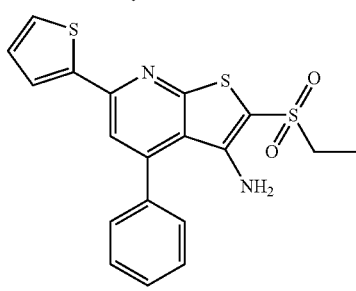
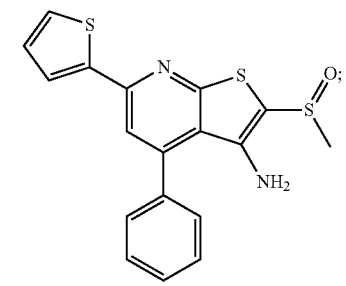
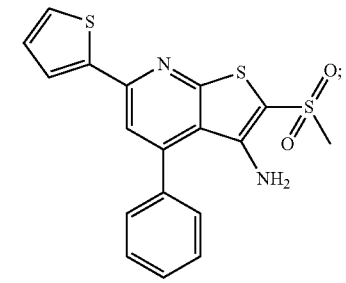

77
-continued
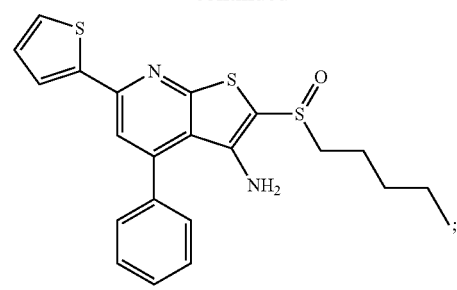
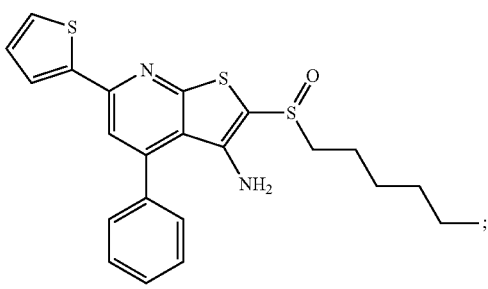
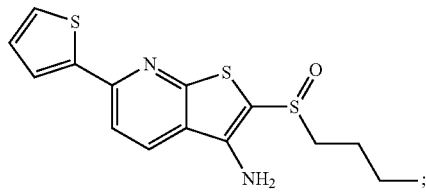
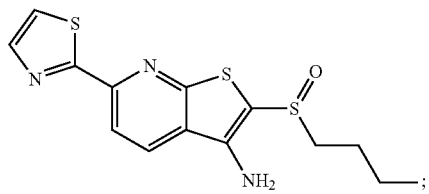
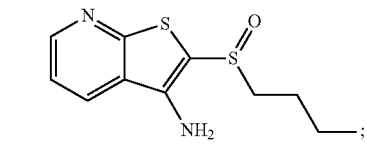
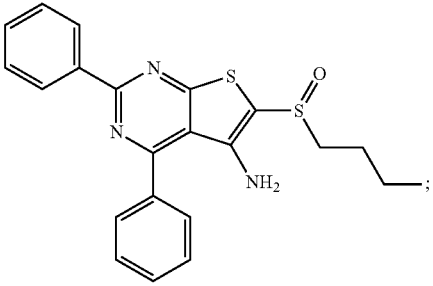
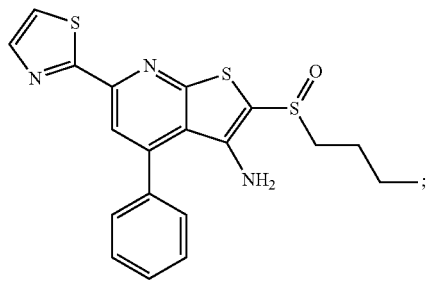
78
-continued
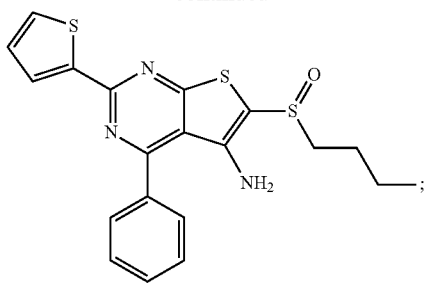
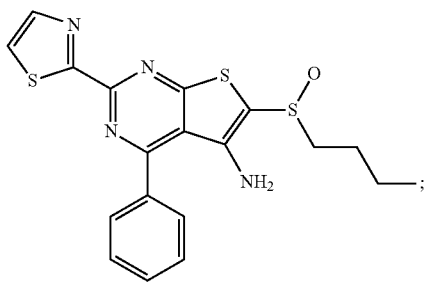
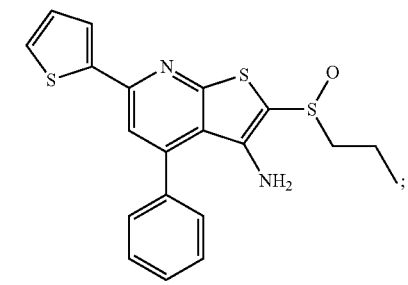
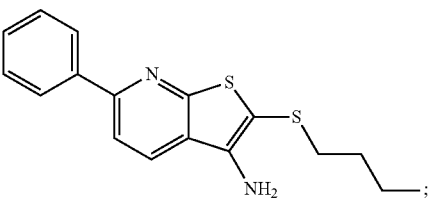
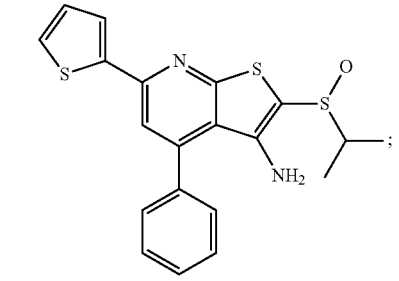
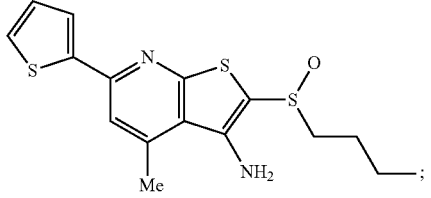

79
-continued
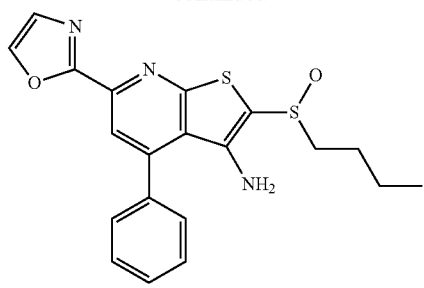
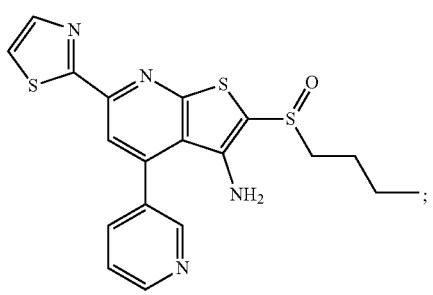
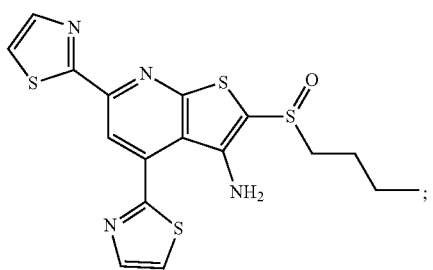
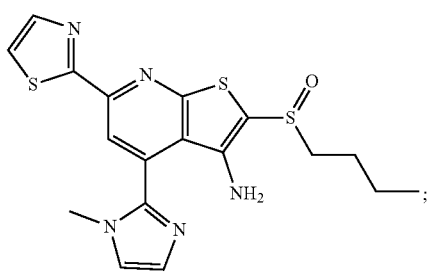
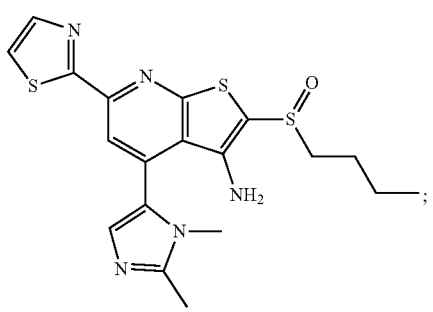
80
-continued
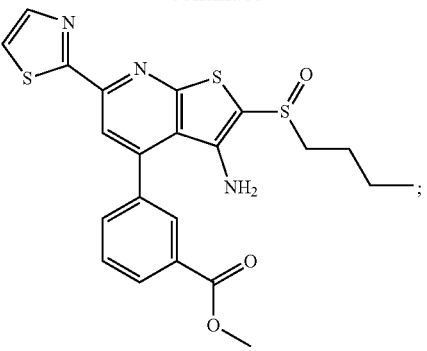
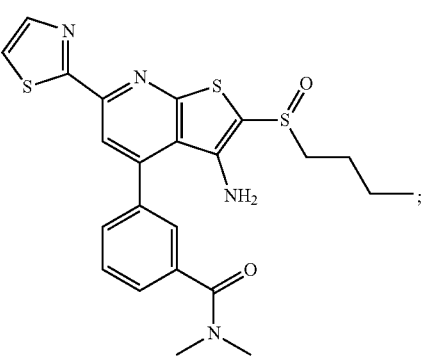
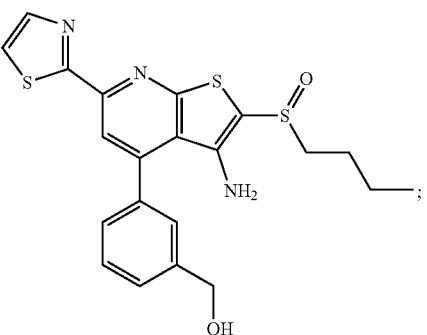
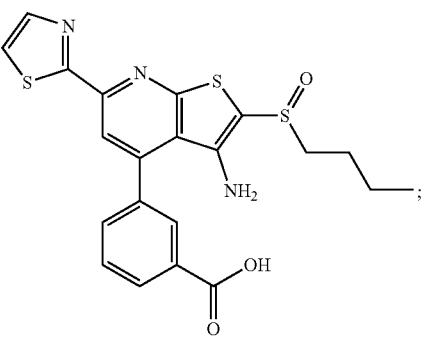

-continued

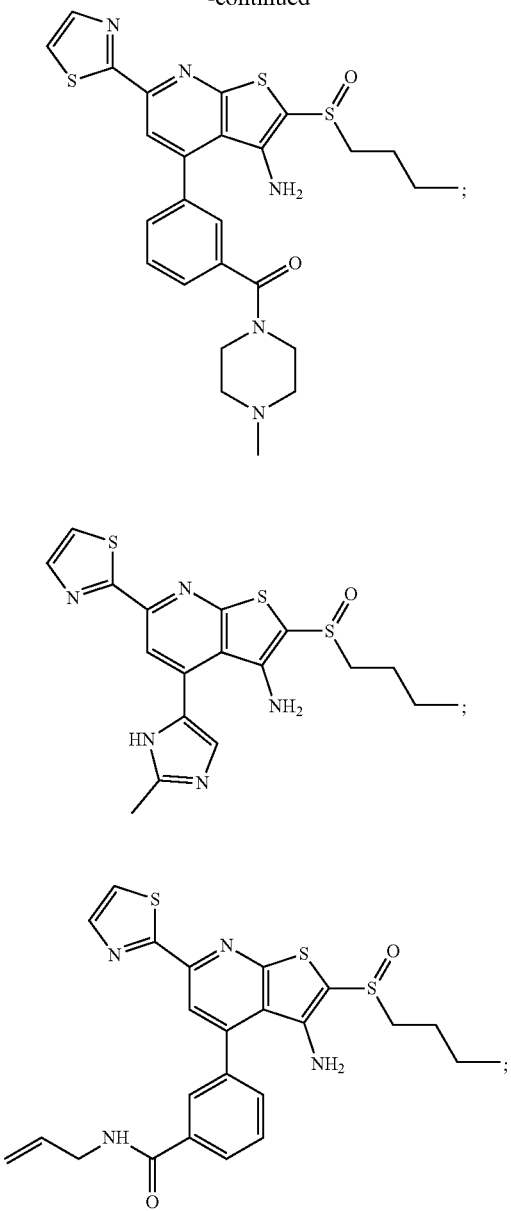

-continued

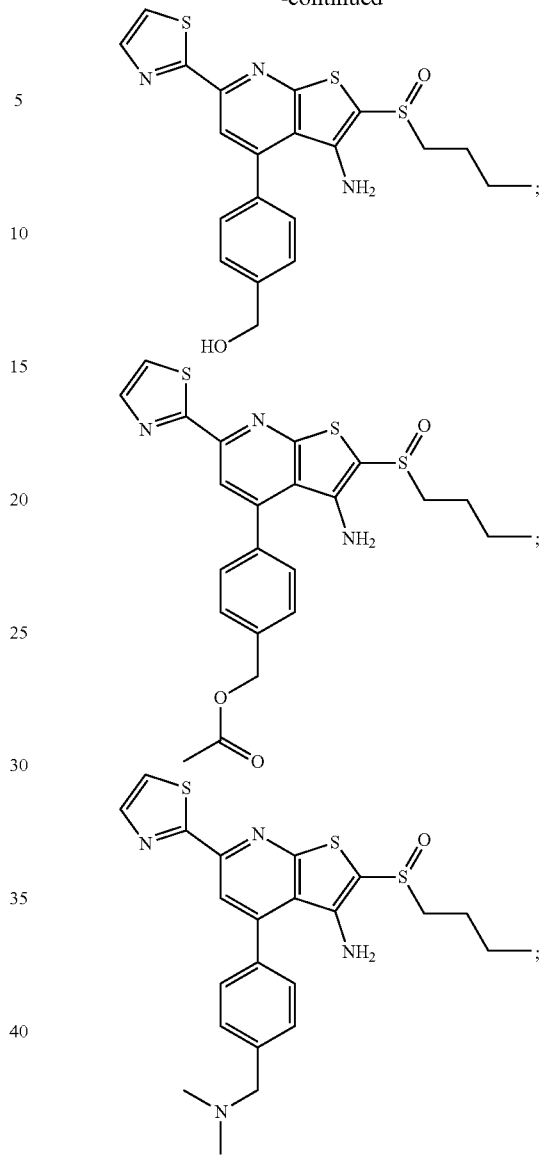

and pharmaceutically acceptable salts thereof.

In certain embodiments, the 15-PGDH inhibitor having formula (I), (II), (IV), (V), (VI), and (VII) can be selected that can ia) at 2.5 µM concentration, stimulate a Vaco503 reporter cell line expressing a 15-PGDH luciferase fusion construct to a luciferase output level of greater than 70 (using a scale on which a value of 100 indicates a doubling of reporter output over baseline); iia) at 2.5 µM concentration stimulate a V9m reporter cell line expressing a 15-PGDH luciferase fusion construct to a luciferase output level of greater than 75; iiia) at 7.5 µM concentration stimulate a LS174T reporter cell line expressing a 15-PGDH luciferase fusion construct to a luciferase output level of greater than 70; and iva) at 7.5 µM concentration, does not activate a negative control V9m cell line expressing TK-renilla luciferase reporter to a level greater than 20; and va) inhibits the enzymatic activity of recombinant 15-PGDH protein at an $IC_{50}$ of less than 1 µM.

In other embodiments, the 15-PGDH inhibitor can ib) at 2.5 µM concentration, stimulate a Vaco503 reporter cell line expressing a 15-PGDH luciferase fusion construct to

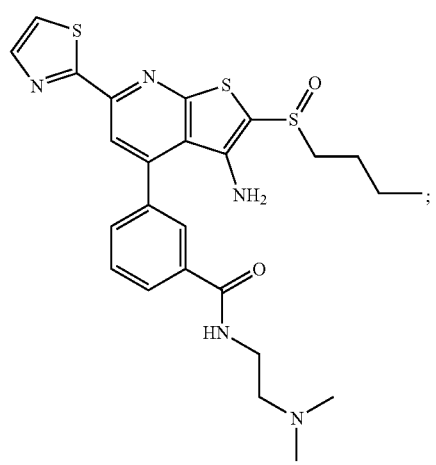

increase luciferase output; iib) at 2.5 µM concentration stimulate a V9m reporter cell line expressing a 15-PGDH luciferase fusion construct to increase luciferase output; iiib) at 7.5 µM concentration stimulate a LS174T reporter cell line expressing a 15-PGDH luciferase fusion construct to increase luciferase output; ivb) at 7.5 µM concentration, does not activate a negative control V9m cell line expressing TK-*renilla* luciferase reporter to a luciferase level greater than 20% above background; and vb) inhibits the enzymatic activity of recombinant 15-PGDH protein at an $IC_{50}$ of less than 1 µM.

In other embodiments, the 15-PGDH inhibitor can inhibit the enzymatic activity of recombinant 15-PGDH at an $IC_{50}$ of less than 1 µM, or preferably at an $IC_{50}$ of less than 250 nM, or more preferably at an $IC_{50}$ of less than 50 nM, or more preferably at an $IC_{50}$ of less than 10 nM, or more preferably at an $IC_{50}$ of less than 5 nM at a recombinant 15-PGDH concentration of about 5 nM to about 10 nM.

In other embodiments, the 15-PGDH inhibitor can increase the cellular levels of PGE-2 following stimulation of an A459 cell with an appropriate agent, for example IL1-beta.

In some embodiments, a 15-PGDH inhibitor can include a compound having the following formula (VIII):

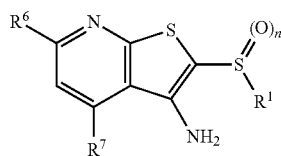

(VIII)

wherein n is 0-2;

$R^1$, $R^6$, and $R^7$ are the same or different and are each selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms (wherein from 1-3 of the ring atoms is independently selected from N, NH, N($C_1$-$C_6$ alkyl), NC(O) ($C_1$-$C_6$ alkyl), O, and S), $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—NH$_2$), carbamido (—NH—(CO)—NH$_2$), cyano(—CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N (aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), sulfonamide (—SO$_2$—NH$_2$, —SO$_2$NY$_2$ (wherein Y is independently H, arlyl or alkyl), phosphono (—P(O)(OH)$_2$), phosphonato (—P(O)(O$^-$)$_2$), phosphinato (—P(O)(O$^-$)), phospho (—PO$_2$), phosphino (—PH$_2$), polyalkylethers, phosphates, phosphate esters, groups incorporating amino acids or other moieties expected to bear positive or negative charge at physiological pH, combinations thereof, and wherein $R^6$ and $R^7$ may be linked to form a cyclic or polycyclic ring, wherein the ring is a substituted or unsubstituted aryl, a substituted or unsubstituted heteroaryl, a substituted or unsubstituted cycloalkyl, and a substituted or unsubstituted heterocyclyl; and pharmaceutically acceptable salts thereof.

15-PGDH inhibitors having formula (VIII) can be synthesized as shown:

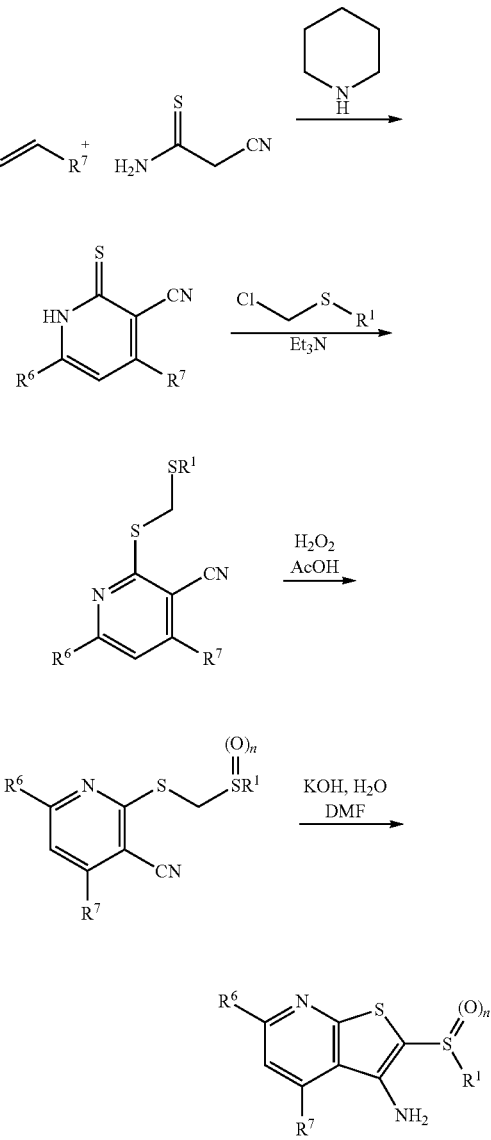

Any reaction solvent can be used in the above preparation process as long as it is not involved in the reaction. For example, the reaction solvent includes ethers such as diethyl ether, tetrahydrofuran and dioxane; halogenized hydrocarbons, such as dichloromethane and chloroform; amines such as pyridine, piperidine and triethylamine; alkylketones, such as acetone, methylethylketone and methylisobutyl; alcohols, such as methanol, ethanol and propanol; non-protonic polar solvent, such as N,N-dimethylformamide, N,N-dimethylacetamide, acetonitrile, dimethylsulfoxide and hexamethyl phosphoric acid triamide. Among non-reactive organic solvents that are ordinarily used in the organic synthesis, preferable solvents are those from which water generated in the reaction can be removed by a Dean-Stark trap. The examples of such solvents include, but are not limited to benzene, toluene, xylene and the like. The reaction product thus obtained may be isolated and purified by condensation, extraction and the like, which is ordinarily conducted in the field of the organic synthesis, if desired, by silica gel column chromatography. The individual enantiomers of PGDH inhibitors having the formula III can be separated by a preparative HPLC using chromatography columns containing chiral stationary phases.

Further, embodiments of this application include any modifications for the preparation method of the 15-PGDH inhibitors described above. In this connection, any intermediate product obtainable from any step of the preparation method can be used as a starting material in the other steps. Such starting material can be formed in situ under certain reaction conditions. Reaction reagents can also be used in the form of their salts or optical isomers.

Depending on the kinds of the substituents to be used in the preparation of the 15-PGDH inhibitors, and the intermediate product and the preparation method selected, novel 15-PGDH inhibitors can be in the form of any possible isomers such as substantially pure geometrical (cis or trans) isomers, optical isomers (enantiomers) and racemates.

In some embodiments, a 15-PGDH inhibitor having formula (VIII) can include a compound with the following formula (IX):

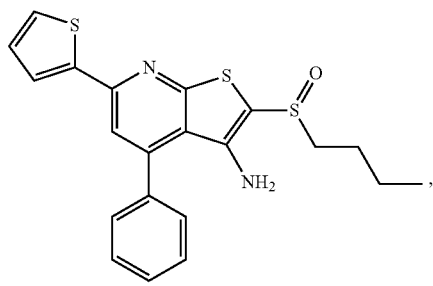

(IX)

and pharmaceutically acceptable salts thereof.

Advantageously, the 15-PDGH inhibitor having formula (IX) was found to: i) inhibit recombinant 15-PGDH at 1 nM concentration; ii) inhibit 15-PGDH in cell lines at 100 nM concentration, iii) increase $PGE_2$ production by cell lines; iv) is chemically stable in aqueous solutions over broad pH range; v) is chemically stable when incubated with hepatocyte extracts, vi) is chemically stable when incubated with hepatocyte cell lines; vii) shows 253 minutes plasma half-life when injected IP into mice; and viii) shows no immediate toxicity over 24 hours when injected IP into mice at 0.6 μmole/per mouse and at 1.2 μmole/per mouse and also no toxicity when injected IP into mice at 0.3 μmole/per mouse twice daily for 21 days.

In other embodiments, a 15-PGDH inhibitor having formula (IX) can include a compound with the following formula (IXa):

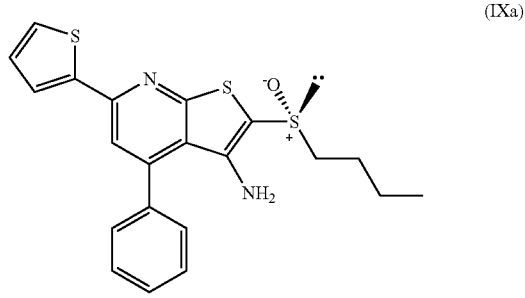

(IXa)

and pharmaceutically acceptable salts thereof.

In still other embodiments, a 15-PGDH inhibitor having formula (IX) can include a compound with the following formula (IXb):

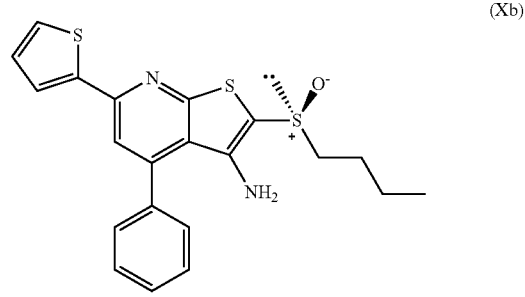

(Xb)

and pharmaceutically acceptable salts thereof.

In other embodiments, the 15-PDHG inhibitor can comprise a (+) or (−) optical isomer of a 15-PGDH inhibitor having formula (IX). In still other embodiments, the 15-PDHG inhibitor can comprise a mixture at least one of a (+) or (−) optical isomer of a 15-PGDH inhibitor having formula (IX). For example, the 15-PGDH inhibitor can comprise a mixture of: less than about 50% by weight of the (−) optical isomer of a 15-PGDH inhibitor having formula (IX) and greater than about 50% by weight of the (+) optical isomer of a 15-PGDH inhibitor having formula (IX), less than about 25% by weight of the (−) optical isomer of a 15-PGDH inhibitor having formula (IX) and greater than about 75% by weight of the (+) optical isomer of a 15-PGDH inhibitor having formula (IX), less than about 10% by weight of the (−) optical isomer of a 15-PGDH inhibitor having formula (IX) and greater than about 90% by weight of the (+) optical isomer of a 15-PGDH inhibitor having formula (IX), less than about 1% by weight of the (−) optical isomer of a 15-PGDH inhibitor having formula (IX) and greater than about 99% by weight of the (+) optical isomer of a 15-PGDH inhibitor having formula (IX), greater than about 50% by weight of the (−) optical isomer of a 15-PGDH inhibitor having formula (IX) and less than about 50% by weight of the (+) optical isomer of a 15-PGDH inhibitor having formula (IX), greater than about 75% by weight of the (−) optical isomer of a 15-PGDH inhibitor having formula (IX) and less than about 25% by weight of the (+) optical isomer of a 15-PGDH inhibitor having formula (IX), greater than about 90% by weight of the (−)

optical isomer of a 15-PGDH inhibitor having formula (IX) and less than about 10% by weight of the (+) optical isomer of a 15-PGDH inhibitor having formula (IX), or greater than about 99% by weight of the (−) optical isomer of a 15-PGDH inhibitor having formula (IX) and less than about 1% by weight of the (+) optical isomer of a 15-PGDH inhibitor having formula (IX).

In a still further embodiment, the 15-PDGH inhibitor can consist essentially of or consist of the (+) optical isomer of a 15-PGDH inhibitor having formula (IX). In yet another embodiment, the PDGH inhibitor can consist essentially of or consist of the (−) optical isomer of a 15-PGDH inhibitor having formula (IX).

In other embodiments, a 15-PGDH inhibitor having formula (VIII) can include a compound with the following formula (X):

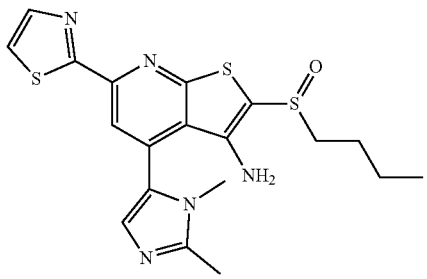

(X)

and pharmaceutically acceptable salts thereof.

Advantageously, the 15-PDGH inhibitor having formula (X) was found to: i) inhibit recombinant 15-PGDH at 3 nM concentration; ii) increase $PGE_2$ production by cell lines at 20 nM; iii) is chemically stable in aqueous solutions over broad pH range; iv) is chemically stable when incubated with mouse, rat and human liver extracts, v) shows 33 minutes plasma half-life when injected IP into mice; viii) shows no immediate toxicity over 24 hours when injected IP into mice at 50 mg/kg body weight, and ix) is soluble in water (pH=3) at 1 mg/mL.

In other embodiments, a 15-PGDH inhibitor having formula (X) can include a compound with the following formula (Xa):

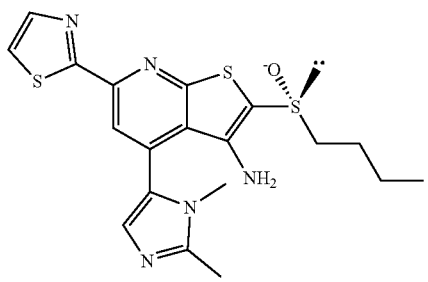

(Xa)

and pharmaceutically acceptable salts thereof.

In still other embodiments, a 15-PGDH inhibitor having formula (X) can include a compound with the following formula (Xb):

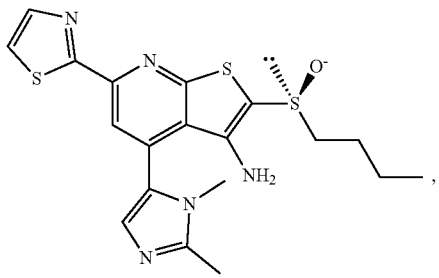

(Xb)

and pharmaceutically acceptable salts thereof.

In other embodiments, the 15-PDHG inhibitor can comprise a (+) or (−) optical isomer of a 15-PGDH inhibitor having formula (X). In still other embodiments, the 15-PDHG inhibitor can comprise a mixture at least one of a (+) or (−) optical isomer of a 15-PGDH inhibitor having formula (X). For example, the 15-PGDH inhibitor can comprise a mixture of: less than about 50% by weight of the (−) optical isomer of a 15-PGDH inhibitor having formula (X) and greater than about 50% by weight of the (+) optical isomer of a 15-PGDH inhibitor having formula (X), less than about 25% by weight of the (−) optical isomer of a 15-PGDH inhibitor having formula (X) and greater than about 75% by weight of the (+) optical isomer of a 15-PGDH inhibitor having formula (X), less than about 10% by weight of the (−) optical isomer of a 15-PGDH inhibitor having formula (X) and greater than about 90% by weight of the (+) optical isomer of a 15-PGDH inhibitor having formula (X), less than about 1% by weight of the (−) optical isomer of a 15-PGDH inhibitor having formula (X) and greater than about 99% by weight of the (+) optical isomer of a 15-PGDH inhibitor having formula (X), greater than about 50% by weight of the (−) optical isomer of a 15-PGDH inhibitor having formula (X) and less than about 50% by weight of the (+) optical isomer of a 15-PGDH inhibitor having formula (X), greater than about 75% by weight of the (−) optical isomer of a 15-PGDH inhibitor having formula (X) and less than about 25% by weight of the (+) optical isomer of a 15-PGDH inhibitor having formula (X), greater than about 90% by weight of the (−) optical isomer of a 15-PGDH inhibitor having formula (X) and less than about 10% by weight of the (+) optical isomer of a 15-PGDH inhibitor having formula (X), or greater than about 99% by weight of the (−) optical isomer of a 15-PGDH inhibitor having formula (X) and less than about 1% by weight of the (+) optical isomer of a 15-PGDH inhibitor having formula (X).

In a still further embodiment, the 15-PDGH inhibitor can consist essentially of or consist of the (+) optical isomer of a 15-PGDH inhibitor having formula (X). In yet another embodiment, the PDGH inhibitor can consist essentially of or consist of the (−) optical isomer of a 15-PGDH inhibitor having formula (X).

It will be appreciated that the other 15-PGDH inhibitors can be used in the methods described described herein. These other 15-PGDH inhibitors can include known 15-PGDH inhibitors including, for example, tetrazole compounds of formulas (I) and (II), 2-alkylideneaminooxyacet-amidecompounds of formula (I), heterocyclic compounds of fourmulas (VI) and (VII), and pyrazole compounds of formula (III) described in U.S. Patent Application Publication No. 2006/0034786 and U.S. Pat. No. 7,705,041; benzylidene-1,3-thiazolidine compounds of formula (I)

described in U.S. Patent Application Publication No. 2007/0071699; phenylfurylmethylthiazolidine-2,4-dione and phenylthienylmethylthiazolidine-2,4-dione compounds described in U.S. Patent Application Publication No. 2007/0078175; thiazolidenedione derivatives described in U.S. Patent Application Publication No. 2011/0269954; phenylfuran, phenylthiophene, or phenylpyrrazole compounds described in U.S. Pat. No. 7,294,641, 5-(3,5-disubstituted phenylazo)-2-hydroxybenzene-acetic acids and salts and lactones described in U.S. Pat. No. 4,725,676, and azo compounds described in U.S. Pat. No. 4,889,846.

The 15-PGDH inhibitors described herein can be provided in a pharmaceutical composition or cosmetic composition depending on the pathological or cosmetic condition or disorder being treated. A pharmaceutical composition containing the 15-PGDH inhibitors described herein as an active ingredient may be manufactured by mixing the derivative with a pharmaceutically acceptable carrier(s) or an excipient(s) or diluting the 15-PGDH inhibitors with a diluent in accordance with conventional methods. The pharmaceutical composition may further contain fillers, anticohesives, lubricants, wetting agents, flavoring agents, emulsifying agents, preservatives and the like. The pharmaceutical composition may be formulated into a suitable formulation in accordance with the methods known to those skilled in the art so that it can provide an immediate, controlled or sustained release of the 15-PGDH inhibitors after being administered into a mammal.

In some embodiments, the pharmaceutical composition may be formulated into a parenteral or oral dosage form. The solid dosage form for oral administration may be manufactured by adding excipient, if necessary, together with binder, disintegrants, lubricants, coloring agents, and/or flavoring agents, to the 15-PGDH inhibitors and shaping the resulting mixture into the form of tablets, sugar-coated pills, granules, powder or capsules. The additives that can be added in the composition may be ordinary ones in the art. For example, examples of the excipient include lactose, sucrose, sodium chloride, glucose, starch, calcium carbonate, kaolin, microcrystalline cellulose, silicate and the like. Exemplary binders include water, ethanol, propanol, sweet syrup, sucrose solution, starch solution, gelatin solution, carboxymethylcellulose, hydroxypropyl cellulose, hydroxypropyl starch, methylcellulose, ethylcellulose, shellac, calcium phosphonate and polypyrrolidone. Examples of the disintegrant include dry starch, sodium arginate, agar powder, sodium bicarbonate, calcium carbonate, sodium lauryl sulfate, stearic monoglyceride and lactose. Further, purified talc, stearates, sodium borate, and polyethylene glycol may be used as a lubricant; and sucrose, bitter orange peel, citric acid, tartaric acid, may be used as a flavoring agent. In some embodiments, the pharmaceutical composition can be made into aerosol formulations (e.g., they can be nebulized) to be administered via inhalation.

The 15-PGDH inhibitors described herein may be combined with flavoring agents, buffers, stabilizing agents, and the like and incorporated into oral liquid dosage forms such as solutions, syrups or elixirs in accordance with conventional methods. One example of the buffers may be sodium citrate. Examples of the stabilizing agents include tragacanth, acacia and gelatin.

In some embodiments, the 15-PGDH inhibitors described herein may be incorporated into an injection dosage form, for example, for a subcutaneous, intramuscular or intravenous route by adding thereto pH adjusters, buffers, stabilizing agents, relaxants, topical anesthetics. Examples of the pH adjusters and the buffers include sodium citrate, sodium acetate and sodium phosphate. Examples of the stabilizing agents include sodium pyrosulfite, EDTA, thioglycolic acid and thiolactic acid. The topical anesthetics may be procaine HCl, lidocaine HCl and the like. The relaxants may be sodium chloride, glucose and the like.

In other embodiments, the 15-PGDH inhibitors described herein may be incorporated into suppositories in accordance with conventional methods by adding thereto pharmaceutically acceptable carriers that are known in the art, for example, polyethylene glycol, lanolin, cacao butter or fatty acid triglycerides, if necessary, together with surfactants such as Tween.

The pharmaceutical composition may be formulated into various dosage forms as discussed above and then administered through various routes including an oral, inhalational, transdermal, subcutaneous, intravenous or intramuscular route. The dosage can be a pharmaceutically or therapeutically effective amount.

Therapeutically effective dosage amounts of the 15-PGDH inhibitor may be present in varying amounts in various embodiments. For example, in some embodiments, a therapeutically effective amount of the 15-PGDH inhibitor may be an amount ranging from about 10-1000 mg (e.g., about 20 mg-1,000 mg, 30 mg-1,000 mg, 40 mg-1,000 mg, 50 mg-1,000 mg, 60 mg-1,000 mg, 70 mg-1,000 mg, 80 mg-1,000 mg, 90 mg-1,000 mg, about 10-900 mg, 10-800 mg, 10-700 mg, 10-600 mg, 10-500 mg, 100-1000 mg, 100-900 mg, 100-800 mg, 100-700 mg, 100-600 mg, 100-500 mg, 100-400 mg, 100-300 mg, 200-1000 mg, 200-900 mg, 200-800 mg, 200-700 mg, 200-600 mg, 200-500 mg, 200-400 mg, 300-1000 mg, 300-900 mg, 300-800 mg, 300-700 mg, 300-600 mg, 300-500 mg, 400 mg-1,000 mg, 500 mg-1,000 mg, 100 mg-900 mg, 200 mg-800 mg, 300 mg-700 mg, 400 mg-700 mg, and 500 mg-600 mg). In some embodiments, the 15-PGDH inhibitor is present in an amount of or greater than about 10 mg, 50 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg. In some embodiments, the 15-PGDH inhibitor is present in an amount of or less than about 1000 mg, 950 mg, 900 mg, 850 mg, 800 mg, 750 mg, 700 mg, 650 mg, 600 mg, 550 mg, 500 mg, 450 mg, 400 mg, 350 mg, 300 mg, 250 mg, 200 mg, 150 mg, or 100 mg.

In other embodiments, a therapeutically effective dosage amount may be, for example, about 0.001 mg/kg weight to 500 mg/kg weight, e.g., from about 0.001 mg/kg weight to 400 mg/kg weight, from about 0.001 mg/kg weight to 300 mg/kg weight, from about 0.001 mg/kg weight to 200 mg/kg weight, from about 0.001 mg/kg weight to 100 mg/kg weight, from about 0.001 mg/kg weight to 90 mg/kg weight, from about 0.001 mg/kg weight to 80 mg/kg weight, from about 0.001 mg/kg weight to 70 mg/kg weight, from about 0.001 mg/kg weight to 60 mg/kg weight, from about 0.001 mg/kg weight to 50 mg/kg weight, from about 0.001 mg/kg weight to 40 mg/kg weight, from about 0.001 mg/kg weight to 30 mg/kg weight, from about 0.001 mg/kg weight to 25 mg/kg weight, from about 0.001 mg/kg weight to 20 mg/kg weight, from about 0.001 mg/kg weight to 15 mg/kg weight, from about 0.001 mg/kg weight to 10 mg/kg weight.

In still other embodiments, a therapeutically effective dosage amount may be, for example, about 0.0001 mg/kg weight to 0.1 mg/kg weight, e.g. from about 0.0001 mg/kg weight to 0.09 mg/kg weight, from about 0.0001 mg/kg weight to 0.08 mg/kg weight, from about 0.0001 mg/kg weight to 0.07 mg/kg weight, from about 0.0001 mg/kg weight to 0.06 mg/kg weight, from about 0.0001 mg/kg weight to 0.05 mg/kg weight, from about 0.0001 mg/kg weight to about 0.04 mg/kg weight, from about 0.0001 mg/kg weight to 0.03 mg/kg weight, from about 0.0001 mg/kg weight to 0.02 mg/kg weight, from about 0.0001 mg/kg weight to 0.019 mg/kg weight, from about 0.0001 mg/kg weight to 0.018 mg/kg weight, from about 0.0001 mg/kg weight to 0.017 mg/kg weight, from about 0.0001 mg/kg weight to 0.016 mg/kg weight, from about 0.0001 mg/kg weight to 0.015 mg/kg weight, from about 0.0001 mg/kg weight to 0.014 mg/kg weight, from about 0.0001 mg/kg weight to 0.013 mg/kg weight, from about 0.0001 mg/kg weight to 0.012 mg/kg weight, from about 0.0001 mg/kg weight to 0.011 mg/kg weight, from about 0.0001 mg/kg weight to 0.01 mg/kg weight, from about 0.0001 mg/kg weight to 0.009 mg/kg weight, from about 0.0001 mg/kg weight to 0.008 mg/kg weight, from about 0.0001 mg/kg weight to 0.007 mg/kg weight, from about 0.0001 mg/kg weight to 0.006 mg/kg weight, from about 0.0001 mg/kg weight to 0.005 mg/kg weight, from about 0.0001 mg/kg weight to 0.004 mg/kg weight, from about 0.0001 mg/kg weight to 0.003 mg/kg weight, from about 0.0001 mg/kg weight to 0.002 mg/kg weight. In some embodiments, the therapeutically effective dose may be 0.0001 mg/kg weight, 0.0002 mg/kg weight, 0.0003 mg/kg weight, 0.0004 mg/kg weight, 0.0005 mg/kg weight, 0.0006 mg/kg weight, 0.0007 mg/kg weight, 0.0008 mg/kg weight, 0.0009 mg/kg weight, 0.001 mg/kg weight, 0.002 mg/kg weight, 0.003 mg/kg weight, 0.004 mg/kg weight, 0.005 mg/kg weight, 0.006 mg/kg weight, 0.007 mg/kg weight, 0.008 mg/kg weight, 0.009 mg/kg weight, 0.01 mg/kg weight, 0.02 mg/kg weight, 0.03 mg/kg weight, 0.04 mg/kg weight, 0.05 mg/kg weight, 0.06 mg/kg weight, 0.07 mg/kg weight, 0.08 mg/kg weight, 0.09 mg/kg weight, or 0.1 mg/kg weight. The effective dose for a particular individual can be varied (e.g., increased or decreased) over time, depending on the needs of the individual.

In some embodiments, a therapeutically effective dosage may be a dosage of g/kg/day, 50 µg/kg/day, 100 µg/kg/day, 250 µg/kg/day, 500 µg/kg/day, 1000 µg/kg/day or more. In various embodiments, the amount of the 15-PGDH inhibitor or pharmaceutical salt thereof is sufficient to provide a dosage to a patient of between 0.01 µg/kg and 10 µg/kg; 0.1 µg/kg and 5 µg/kg; 0.1 µg/kg and 1000 µg/kg; 0.1 µg/kg and 900 µg/kg; 0.1 µg/kg and 900 µg/kg; 0.1 µg/kg and 800 µg/kg; 0.1 µg/kg and 700 µg/kg; 0.1 µg/kg and 600 µg/kg; 0.1 µg/kg and 500 µg/kg; or 0.1 µg/kg and 400 µg/kg.

Particular doses or amounts to be administered in accordance with the present invention may vary, for example, depending on the nature and/or extent of the desired outcome, on particulars of route and/or timing of administration, and/or on one or more characteristics (e.g., weight, age, personal history, genetic characteristic, lifestyle parameter, severity of cardiac defect and/or level of risk of cardiac defect, etc., or combinations thereof). Such doses or amounts can be determined by those of ordinary skill. In some embodiments, an appropriate dose or amount is determined in accordance with standard clinical techniques. For example, in some embodiments, an appropriate dose or amount is a dose or amount sufficient to reduce a disease severity index score by 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100% or more. For example, in some embodiments, an appropriate dose or amount is a dose or amount sufficient to reduce a disease severity index score by 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100%. Alternatively or additionally, in some embodiments, an appropriate dose or amount is determined through use of one or more in vitro or in vivo assays to help identify desirable or optimal dosage ranges or amounts to be administered.

Various embodiments may include differing dosing regimen. In some embodiments, the 15-PGDH inhibitor can be administered via continuous infusion. In some embodiments, the continuous infusion is intravenous. In other embodiments, the continuous infusion is subcutaneous. Alternatively or additionally, in some embodiments, the 15-PGDH inhibitor can be administered bimonthly, monthly, twice monthly, triweekly, biweekly, weekly, twice weekly, thrice weekly, daily, twice daily, or on another clinically desirable dosing schedule. The dosing regimen for a single subject need not be at a fixed interval, but can be varied over time, depending on the needs of the subject.

For topical application, the composition can be administered in the form of aqueous, alcoholic, aqueous-alcoholic or oily solutions or suspensions, or of a dispersion of the lotion or serum type, of emulsions that have a liquid or semi-liquid consistency or are pasty, obtained by dispersion of a fatty phase in an aqueous phase (O/W) or vice versa (W/O) or multiple emulsions, of a free or compacted powder to be used as it is or to be incorporated into a physiologically acceptable medium, or else of microcapsules or microparticles, or of vesicular dispersions of ionic and/or nonionic type. It may thus be in the form of a salve, a tincture, milks, a cream, an ointment, a powder, a patch, an impregnated pad, a solution, an emulsion or a vesicular dispersion, a lotion, aqueous or anhydrous gels, a spray, a suspension, a shampoo, an aerosol or a foam. It may be anhydrous or aqueous. It may also comprise solid preparations constituting soaps or cleansing cakes.

Pharmaceutical and/or cosmetic compositions including the 15-PGDH inhibitor described herein can additionally contain, for example, at least one compound chosen from prostaglandins, in particular prostaglandin $PGE_1$, $PGE_2$, their salts, their esters, their analogues and their derivatives, in particular those described in WO 98/33497, WO 95/11003, JP 97-100091, JP 96-134242, in particular agonists of the prostaglandin receptors. It may in particular contain at least one compound such as the agonists (in acid form or in the form of a precursor, in particular in ester form) of the prostaglandin $F_2\alpha$ receptor, such as for example latanoprost, fluprostenol, cloprostenol, bimatoprost, unoprostone, the agonists (and their precursors, in particular the esters such as travoprost) of the prostaglandin $E_2$ receptors such as 17-phenyl $PGE_2$, viprostol, butaprost, misoprostol, sulprostone, 16,16-dimethyl $PGE_2$, 11-deoxy $PGE_1$, 1-deoxy $PGE_1$, the agonists and their precursors, in particular esters, of the prostacycline (IP) receptor such as cicaprost, iloprost, isocarbacycline, beraprost, eprostenol, treprostinil, the agonists and their precursors, in particular the esters, of the prostaglandin $D_2$ receptor such as BW245C ((4S)-(3-[(3R,S)-3-cyclohexyl-3-isopropyl]-2,5-dioxo)-4-imidazolidinehept-anoic acid), BW246C ((4R)-(3-[(3R,S)-3-cyclohexyl-3-isopropyl]-2,5-dioxo)-4-imidazolidinehept-anoic acid), the agonists and their precursors, in particular the esters, of the receptor for the thromboxanes A2 (TP) such as I-BOP ([1S-[1a,2a(Z), 3b(1E,3S),4a]]-7-[3-[3-hydroxy-4-[4-(iodophenoxy)-1-butenyl]-7-oxabicyclo-[2.2.1]hept-2-yl]-5-heptenoic acid).

Advantageously, the composition can include at least one 15-PGDH inhibitor as defined above and at least one prostaglandin or one prostaglandin derivative such as for example the prostaglandins of series 2 including in particular $PGF_{2\alpha}$ and $PGE_2$ in saline form or in the form of precursors, in particular of the esters (example isopropyl esters), their derivatives such as 16,16-dimethyl $PGE_2$, 17-phenyl $PGE_2$ and 16,16-dimethyl $PGF_{2\alpha}$, 17-phenyl $PGF_{2\alpha}$, prostaglandins of series 1 such as 11-deoxyprostaglandin E1, 1-deoxyprostaglandin E1 in saline or ester form, is their analogues, in particular latanoprost, travoprost, fluprostenol, unoprostone, bimatoprost, cloprostenol, viprostol, butaprost, misoprostol, their salts or their esters.

The invention is further illustrated by the following examples, which is not intended to limit the scope of the claims.

Example 1

The following Example describes the synthesis of SW033291 and analogues thereof as well as provides mass spectrometry and NMR confirmation of the structures.

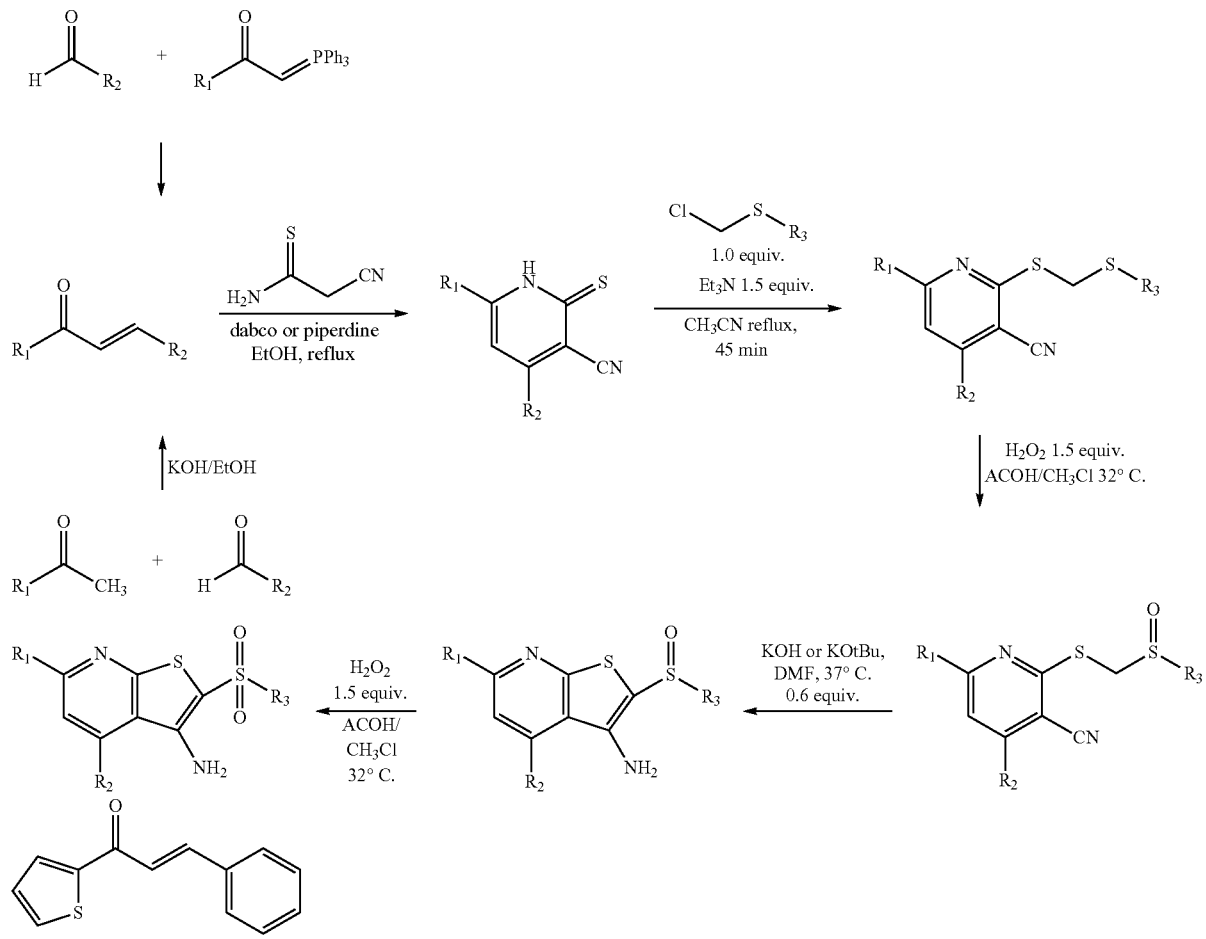

3-phenyl-1-(thiophen-2-yl)prop-2-en-1-one was prepared from benzaldehyde and 1-(thiophen-2-yl)ethanone via aldol condensation using procedure described by Azam (Parveen, H.; Iqbal, P. F.; Azam, A. *Synth. Commu.*, 2008, 38, 3973). $^1$H NMR (400 MHz, CDCl$_3$) δ 7.88-7.80 (m, 2H), 7.67 (dd, J=4.9, 1.1 Hz, 1H), 7.66-7.59 (m, 2H), 7.47-7.34 (m, 4H), 7.18 (dd, J=5.0, 3.8 Hz, 1H). ESI-MS (m/z): 215 [M+H]$^+$.

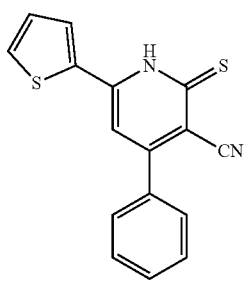 [SMILES: N#Cc1c(-c2ccccc2)cc(-c2cccs2)[nH]c1=S]

4-phenyl-6-(thiophen-2-yl)-2-thioxo-1,2-dihydropyridine-3-carbonitrile. To a solution of 3-phenyl-1-(thiophen-2-yl)prop-2-en-1-one (2.34 mmol, 500 mg) and cyanothioacetamide (7.0 mmol, 717 mg, 3.0 equiv.) in ethanol (7 mL), a few drops of piperidine were added. The reaction was refluxed for 3 h. The solid that formed was collected and recrystallized from acetic acid to give designed product in 46% isolated yield. $^1$H NMR (400 MHz, DMSO-d$_6$) δ 8.17 (d, J=3.8 Hz, 1H), 7.96 (d, J=5.0 Hz, 1H), 7.74-7.62 (m, 2H), 7.54 (dd, J=5.1, 2.0 Hz, 3H), 7.31-7.19 (m, 1H), 7.01 (s, 1H). ESI-MS (m/z): 295 [M+H]$^+$.

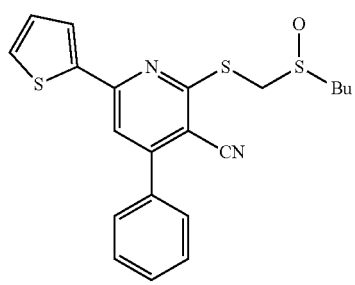

2-(((butylthio)methyl)sulfinyl)-4-phenyl-6-(thiophen-2-yl)nicotinonitrile. Acetic Acid (900 µL) and hydrogen peroxide (0.57 mmol, 1.5 equiv., 30% solution in water) were added to the solution of 2-(((butylthio)methyl)sulfinyl)-4-phenyl-6-(thiophen-2-yl)nicotinonitrile (0.38 mmol, 150 mg) in chloroform (900 µL). The reaction mixture was stirring at 32° C. for 45 min. The reaction was then diluted with EtOAc and washed with saturated NaHCO₃ solution, dried over magnesium sulfate, filtered and concentrated under reduced pressure to give 153 mg of designed product (98%). ¹H NMR (400 MHz, CDCl₃) δ 7.75 (dd, J=3.8, 1.1 Hz, 1H), 7.66-7.57 (m, 2H), 7.58-7.51 (m, 4H), 7.47 (s, 1H), 7.16 (dd, J=5.0, 3.8 Hz, 1H), 4.74 (d, J=13.0 Hz, 1H), 4.41 (d, J=13.0 Hz, 1H), 2.97 (dt, J=13.0, 8.2 Hz, 1H), 2.81 (dt, J=12.9, 7.3 Hz, 1H), 1.94-1.76 (m, 2H), 1.53-1.38 (m, 2H), 0.94 (t, J=7.4 Hz, 3H). ESI-MS (m/z): 413 [M+H]⁺.

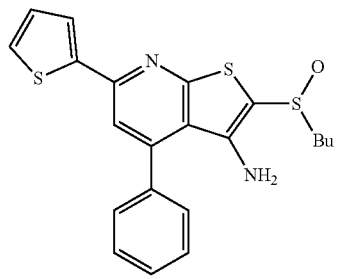

SW033291 2-(butylsulfinyl)-4-phenyl-6-(thiophen-2-yl)thieno[2,3-b]pyridin-3-amine was prepared using procedure describe by Kalugin (Kalugin V. E. *Russian. Chem. Bull., Int. Ed.,* 2006, 55, 529). To the solution of 4-(((butylthio)methyl)sulfinyl)-2,6-diphenylpyrimidine-5-carbonitrile (0.53 mmol, 220 mg) in DMF (0.25 M)/EtOH (0.5 M) was added KOH (0.32 mmol, 18 mg, 0.6 equiv., 0.1 M in water). The reaction mixture was stirred at 35° C. for 40 min. Once complete, the reaction was diluted with EtOAc and washed with 10% aq. solution of acidic acid, the organic phase was separated and aqueous layer was extracted twice with EtOAc, dried over magnesium sulfate, filtered and concentrated under reduced pressure to give 211 mg of SW033291 2-(butylsulfinyl)-4-phenyl-6-(thiophen-2-yl)thieno[2,3-b]pyridin-3-amine (96%). ¹H NMR (400 MHz, CDCl₃) δ 7.67-7.60 (m, 1H), 7.57-7.35 (m, 7H), 7.10 (dd, J=5.0, 3.7 Hz, 1H), 4.54 (s, 2H), 3.26 (ddd, J=12.8, 9.1, 6.0 Hz, 1H), 3.09 (ddd, J=12.8, 9.1, 6.6 Hz, 1H), 1.83-1.61 (m, 2H), 1.53-1.38 (m, 2H), 0.93 (t, J=7.3 Hz, 3H). ESI-MS (m/z): 413 [M+H]⁺.

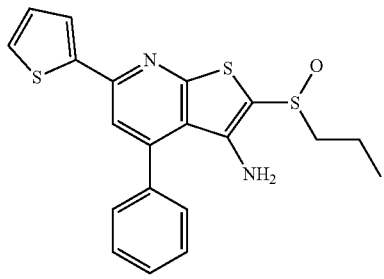

SW208437 4-phenyl-2-(propylsulfinyl)-6-(thiophen-2-yl)thieno[2,3-b]pyridin-3-amine was prepared in 56% isolated yield using synthetic procedures described for the preparation of analog SW033291. ¹H NMR (400 MHz, CDCl₃) δ 7.65 (dd, J=3.8, 1.1 Hz, 1H), 7.61-7.49 (m, 4H), 7.49-7.41 (m, 3H), 7.12 (dd, J=5.0, 3.7 Hz, 1H), 3.28 (ddd, J=12.7, 8.4, 6.3 Hz, 1H), 3.07 (ddd, J=12.7, 8.6, 7.0 Hz, 1H), 1.91-1.65 (m, 2H), 1.08 (t, J=7.4 Hz, 3H). APCI-MS (m/z): 399 [M+H]⁺.

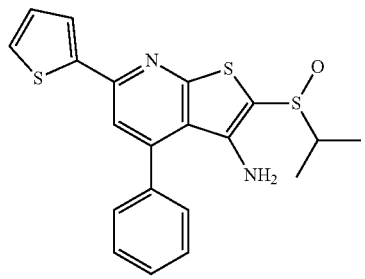

SW208438 2-(isopropylsulfinyl)-4-phenyl-6-(thiophen-2-yl)thieno[2,3-b]pyridin-3-amine was prepared in 48% isolated yield using synthetic procedures described for the preparation of analog SW033291. ¹H NMR (400 MHz, CDCl3) δ 7.64 (dd, J=3.7, 1.1 Hz, 1H), 7.58-7.47 (m, 5H), 7.47-7.39 (m, 2H), 7.10 (dd, J=5.0, 3.7 Hz, 1H), 4.59 (s, 2H), 3.38 (p, J=6.8 Hz, 1H), 1.43 (d, J=6.9 Hz, 3H), 1.25 (d, J=6.8 Hz, 3H). ESI-MS (m/z): 399 [M+H]⁺.

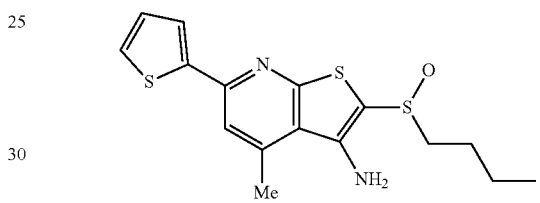

SW208488 2-(butylsulfinyl)-4-methyl-6-(thiophen-2-yl)thieno[2,3-b]pyridin-3-amine was prepared using synthetic procedures described for the preparation of analog SW033291. ¹H NMR (400 MHz, CDCl₃) δ 7.55 (dd, J=3.7, 1.2 Hz, 1H), 7.39 (dd, J=5.0, 1.1 Hz, 1H), 7.25-7.23 (m, 1H), 7.06 (dd, J=5.0, 3.7 Hz, 1H), 5.02 (s, 2H), 3.25 (ddd, J=12.7, 9.1, 6.0 Hz, 1H), 3.08 (ddd, J=12.8, 9.2, 6.4 Hz, 1H), 2.74 (s, 3H), 1.82-1.58 (m, 2H), 1.56-1.38 (m, 2H), 0.93 (t, J=7.3 Hz, 3H). ESI-MS (m/z): 351 [M+H]⁺.

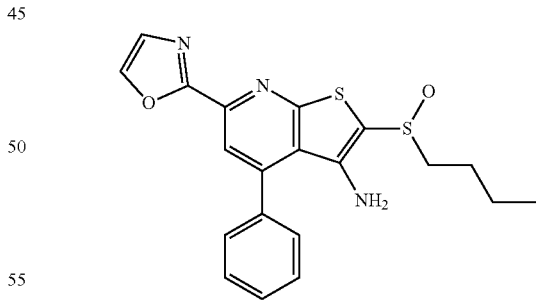

SW208496 2-(butylsulfinyl)-6-(oxazol-2-yl)-4-phenylthieno[2,3-b]pyridin-3-amine was prepared using synthetic procedures described for the preparation of analog SW033291. ¹H NMR (400 MHz, CDCl₃) δ 7.99 (s, 1H), 7.84 (d, J=0.8 Hz, 1H), 7.58-7.41 (m, 5H), 7.33 (d, J=0.8 Hz, 1H), 4.65 (s, 2H), 3.30 (ddd, J=12.9, 8.8, 6.2 Hz, 1H), 3.10 (ddd, J=12.8, 8.9, 6.9 Hz, 1H), 1.86-1.64 (m, 2H), 1.42-1.54 (m, 2H), 0.93 (t, J=7.4 Hz, 3H). ESI-MS (m/z): 398.1 [M+H]⁺.

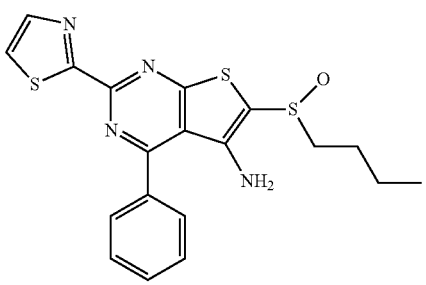

SW208436   6-(butylsulfinyl)-4-phenyl-2-(thiazol-2-yl)thieno [2,3-d]pyrimidin-5-amine was prepared by synthetic procedures described for the preparation of analog SW208065. ¹H NMR (400 MHz, CDCl₃) δ 8.06 (dd, J=3.1, 1H), 7.75-7.66 (m, 2H), 7.75-7.66 (m, 3H), 7.55 (dd, J=3.1, 1H), 4.87 (s, 2H), 3.30 (ddd, J=12.8, 8.4, 6.3 Hz, 1H), 3.12 (ddd, J=12.8, 8.6, 6.9 Hz, 1H), 1.85-1.65 (m, 2H), 1.55-1.40 (m, 2H), 0.95 (t, J=7.3 Hz, 3H). ESI-MS (m/z): 415.1 [M+H]⁺.

trated under reduced pressure to give designed product in 76% isolated yield. ¹H NMR (400 MHz, CDCl₃) δ 8.14 (d, J=8.4, 1H), 8.08 (d, J=8.2, 2H), 7.82 (d, J=8.4, 1H), 7.58-7.36 (m, 4H), 3.30-2.73 (m, 2H), 1.90-1.62 (m, 2H), 1.55-1.41 (m, 2H), 0.94 (t, J=7.3 Hz, 3H). ESI-MS (m/z): 316.1 [M+H]⁺.

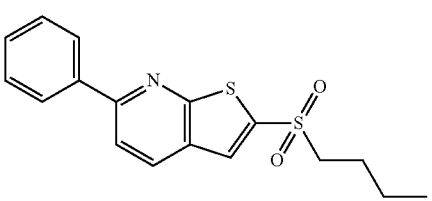 [SMILES: CCCCS(=O)(=O)c1cc2ccc(-c3ccccc3)nc2s1]

SW208434. Acetic Acid (200 μL) and hydrogen peroxide (0.15 mmol, 30% solution in water) were added to the solution of 2-(butylthio)-6-phenylthieno[2,3-b]pyridine (0.09 mmol, 27 mg) in chloroform (200 μL). The reaction mixture was stirring at 100° C. for 30 min. The reaction was then diluted with EtOAc and washed with saturated

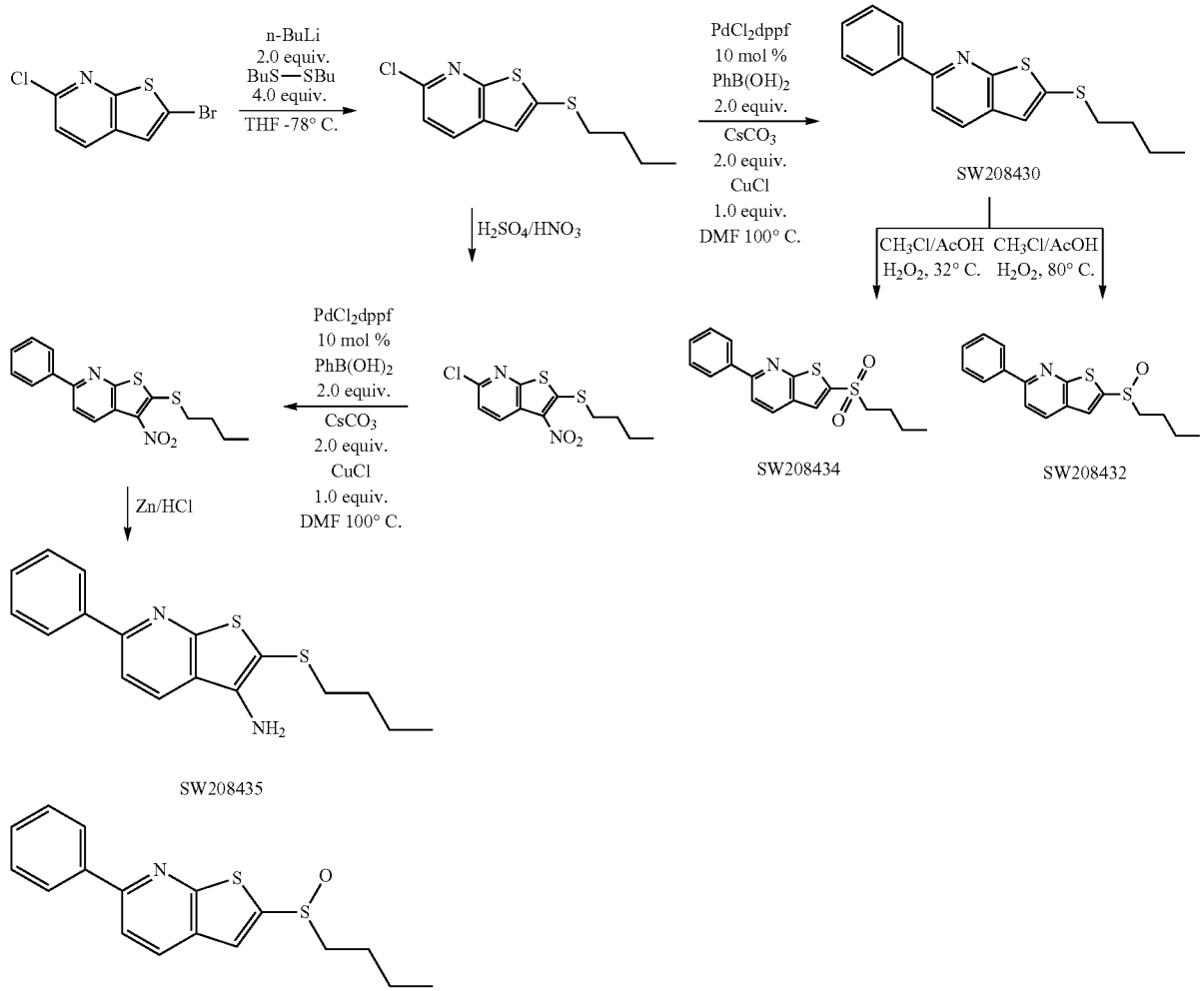

SW208432  2-(butylsulfinyl)-6-phenylthieno[2,3-b]pyridine. Acetic Acid (90 μL) and hydrogen peroxide (0.06 mmol, 1.5 equiv., 30% solution in water) were added to the solution of 2-(butylthio)-6-phenylthieno[2,3-b]pyridine (0.04 mmol, 12 mg) in chloroform (90 μL). The reaction mixture was stirring at 32° C. for 1 h. The reaction was then diluted with EtOAc and washed with saturated NaHCO₃ solution, dried over magnesium sulfate, filtered and concentrated under reduced pressure to give designed product in 81% isolated yield. ¹H NMR (400 MHz, CDCl₃) δ 8.23 (d, J=8.5 Hz, 1H), 8.09 (dd, J=8.2, 1.6 Hz, 2H), 7.89 (d, J=2.1 Hz, 1H), 7.59-7.39 (m, 4H), 3.39-3.10 (m, 2H), 1.92-1.68 (m, 2H), 1.54-1.27 (m, 2H), 0.91 (t, J=7.3 Hz, 3H). ESI-MS (m/z): 332.1 [M+H]⁺.

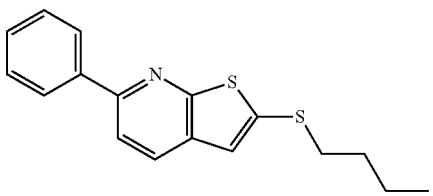 [SMILES: CCCCSc1cc2ccc(-c3ccccc3)nc2s1]

SW208430 2-(butylthio)-6-phenylthieno[2,3-b]pyridine. Phenylboronic acid (0.39 mmol, 2.0 equiv), 2-(butylthio)-6-chlorothieno[2,3-b]pyridine (50 mg, 0.195 mmol, 1.0 equiv), Cesium Carbonate (0.39 mmol, 2.0 equiv.), PdCl$_2$dppf (10 mol %), Copper Chloride (0.195 mmol, 1.0 equiv.) were heated in DMF at 100° C. for 12 h. After cooling to r.t. the reaction mixture was diluted with EtOAc and washed with water and next brine. The organic layer was dried over magnesium sulfate and the solvent was removed under reduced pressure. The crude product was purified by flash chromatography (Hexanes/EtOAc: 8/2) to afford designed product in 32% yield. $^1$H NMR (400 MHz, CDCl$_3$) δ 8.09-8.00 (m, 2H), 7.93 (d, J=8.3 Hz, 1H), 7.69 (d, J=8.3 Hz, 1H), 7.52-7.34 (m, 4H), 2.99 (t, J=7.9 Hz, 2H), 1.77-1.63 (m, 2H), 1.53-1.38 (m, 2H), 0.92 (t, J=7.3 Hz, 3H). ESI-MS (m/z): 300.1 [M+H]$^+$.

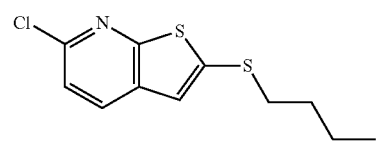

2-(butylthio)-6-chlorothieno[2,3-b]pyridine. To the solution of 2-bromo-6-chlorothieno[2,3-b]pyridine (40 mg, 0.16 mmol) in THF (2 mL) at −78° C. was added n-BuLi (0.32 mmol, 2.0 equiv.; 1.6 M solution in hexanes). The traction mixture was stirred for 5 min. and 1,2-dibutyldisulfane (0.48 mmol, 85.4 mg) was then added. The reaction mixture was stirred at −78° C. for additional 1 h, quenched with water and diluted with EtOAc. The organic layer was separated, dried over MgSO4, filtered and concentrated to give crude product, which was purified by flash column chromatography (95/5 Hexane/EtOAc) to give designed product in 91% isolated yield.

$^1$H NMR (400 MHz, CDCl3) δ 7.81 (d, J=8.3 Hz, 1H), 7.24 (d, J=8.3 Hz, 1H), 7.13 (s, 1H), 3.01-2.89 (m, 2H), 1.74-1.59 (m, 2H), 1.52-1.36 (m, 2H), 0.91 (t, J=7.4 Hz, 3H). ESI-MS (m/z): 258.0 [M+H]$^+$.

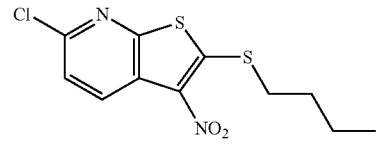 [SMILES: CCCCSc1sc2nc(Cl)ccc2c1[N+](=O)[O-]]

2-(butylthio)-6-chloro-3-nitrothieno[2,3-b]pyridine was prepared in 53% yield according procedure described by Nardine (Meth-Cohn, O.; Narine, B. *Tetrahedon Lett.* 1978, 23, 2045.). $^1$H NMR (400 MHz, CDCl$_3$) δ 8.68 (d, J=8.6 Hz, 1H), 7.45 (d, J=8.6 Hz, 1H), 3.15 (t, J=7.4 Hz, 2H), 1.95-1.73 (m, 2H), 1.68-1.41 (m, 2H), 0.99 (t, J=7.4 Hz, 3H). ESI-MS (m/z): 303.0 [M+H]$^+$.

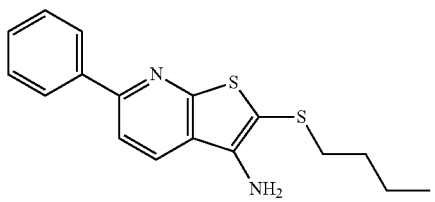 [SMILES: CCCCSc1sc2nc(-c3ccccc3)ccc2c1N]

SW208435 2-(butylthio)-6-phenylthieno[2,3-b]pyridin-3-amine. Phenylboronic acid (37 mg, 0.30 mmol, 2.0 equiv), 2-(butylthio)-6-chloro-3-nitrothieno[2,3-b]pyridine (46 mg, 0.15 mmol, 1.0 equiv), Cesium Carbonate (0.30 mmol, 2.0 equiv.), PdCl$_2$dppf (10 mol %), Copper Chloride (0.15 mmol, 15 mg, 1.0 equiv.) were heated in DMF at 100° C. for 12 h. After cooling to r.t. the reaction mixture was diluted with EtOAc and washed with water and next brine. The organic layer was dried over magnesium sulfate and the solvent was removed under reduced pressure. The crude product was purified by preparative TLC (AcOEt/Hexanes: 2/8) to afford 2-(butylthio)-3-nitro-6-phenylthieno[2,3-b] pyridine. ESI-MS (m/z): 345.1 [M+H]$^+$. 2-(butylthio)-3-nitro-6-phenylthieno[2,3-b]pyridine (0.017 mmol, 6 mg) was dissolved in a mixed solvent of acetic acid (0.12 mL) and conc. hydrochloric acid (one drop). Zinc (13 mg) was added at 0° C. After the mixture was stirred for 30 minutes, the reaction mixture was filtered, and the filtrate was neutralized with an aqueous solution of NaHCO$_3$, and extracted with DCM. The organic layer was washed with water and then with a saturated aqueous solution of sodium chloride, and dried over sodium sulfate. Subsequently, the solvent was evaporated to obtain designed product. $^1$H NMR (400 MHz, CDCl$_3$) δ 7.65-7.54 (m, 3H), 7.50-7.40 (m, 2H), 7.35-7.28 (m, 1H), 7.14 (d, J=8.4 Hz, 1H), 3.35-3.18 (m, 2H), 1.80-1.65 (m, 2H), 1.54-1.38 (m, 2H), 0.95 (t, J=7.3 Hz, 3H). ESI-MS (m/z): 315.1 [M+H]$^+$.

2-bromo-6-chlorothieno[2,3-b]pyridine was prepared according procedure described by Nardine. $^1$H NMR (400 MHz, CDCl$_3$) δ 7.87 (d, J=8.4 Hz, 1H), 7.28 (s, 1H), 7.27 (d, J=8.4 Hz, 1H). ESI-MS (m/z): 249 [M+H]$^+$.

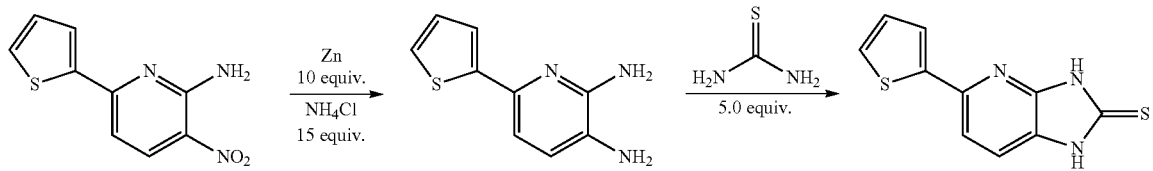

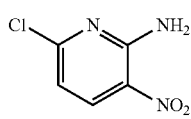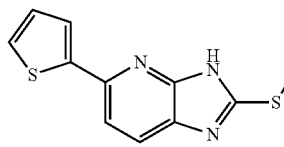

-continued

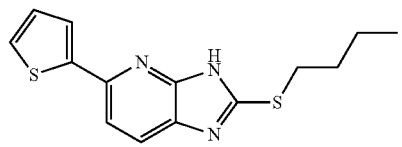

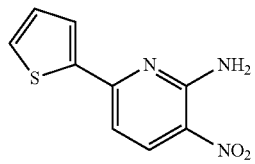

3-nitro-6-(thiophen-2-yl)pyridin-2-amine. Thiophene boronic acid (742 mg, 5.8 mmol, 2.0 equiv), 6-chloro-3-nitropyridin-2-amine (500 mg, 2.9 mmol, 1.0 equiv), Cesium Carbonate (5.8 mmol, 2.0 equiv.), PdCl$_2$dppf (10 mol %), Copper Chloride (2.9 mmol, 1.0 equiv.) in DMF were heated at 100° C. for 12 h. After cooling to r.t. the reaction mixture was diluted with EtOAc and washed with water and next brine. The organic layer was dried over magnesium sulfate and the solvent was removed under reduced pressure. The crude product was purified by column chromatography (hexanes/EtOAc: 8/2) to afford 3-nitro-6-(thiophen-2-yl)pyridin-2-amine in 63% yield. $^1$H NMR (400 MHzCDCl$_3$) δ 8.42 (d, J=8.7 Hz, 1H), 7.70 (dd, J=3.8, 1.1 Hz, 1H), 7.54 (dd, J=5.0, 1.1 Hz, 1H), 7.15 (dd, J=5.0, 3.8 Hz, 1H), 7.09 (d, J=8.7 Hz, 1H). ESI-MS (m/z): 222 [M+H]$^+$.

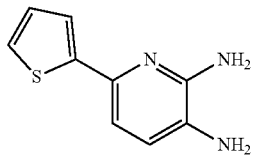 [SMILES: Nc1ccc(-c2cccs2)nc1N]

6-(thiophen-2-yl)pyridine-2,3-diamine. The starting material, 3-nitro-6-(thiophen-2-yl)pyridin-2-amine (1.20 mmol, 265.4 mg), was dissolved in a 5:1 acetone/water mixture. Zinc (12.0 mmol, 784 mg, 10 eq) and ammonium chloride (18 mmol, 962.5 mg, 15 eq) were added to the solution, which was stirred at room temperature for 1 hour. The solution was then filtered through a celite pad and washed with ethyl acetate. The filtrate was extracted twice with brine then the aqueous layer was back extracted with EtOAc. The combined organic layers were dried over magnesium sulfate, filtered, and concentrated under reduced pressure. Further purification by column chromatography gave 118.2 mg of 6-(thiophen-2-yl)pyridine-2,3-diamine (52%). $^1$H NMR (400 MHz, CD$_3$OD) δ 7.34 (dd, J=3.6, 1.1 Hz, 1H), 7.25 (dd, J=5.1, 1.1 Hz, 1H), 7.00 (dd, J=5.1, 3.6 Hz, 1H), 6.96-6.86 (m, 2H), 4.85 (s, 4H). ESI-MS (m/z): 192 [M+H]$^+$.

5-(thiophen-2-yl)-1,3-dihydro-2H-imidazo[4,5-b]pyridine-2-thione. Thiourea (16.97 mmol, 223.0 mg, 5 eq) was added to 6-(thiophen-2-yl)pyridine-2,3-diamine. The solution was heated at 170° C. for 2 hours. The addition of ethanol room temperature produced solid which was filtered to give 112.5 mg of 5-(thiophen-2-yl)-1,3-dihydro-2H-imidazo[4,5-b]pyridine-2-thione (82%). $^1$H NMR (400 MHz, (CD$_3$)$_2$SO) δ 7.69 (dd, J=3.7, 1.2 Hz, 1H), 7.66 (d, J=8.3 Hz, 1H), 7.56 (dd, J=5.1, 1.1 Hz, 1H), 7.47 (d, J=8.2 Hz, 1H), 7.15-7.09 (m, 1H). ESI-MS (m/z): 235 [M+2H]$^+$.

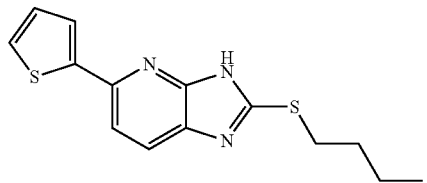 [SMILES: CCCCSc1nc2ccc(-c3cccs3)nc2[nH]1]

SW208494 2-(butylthio)-5-(thiophen-2-yl)-3H-imidazo[4,5-b]pyridine. A mixture of 5-(thiophen-2-yl)-1,3-dihydro-2H-imidazo[4,5-b]pyridine-2-thione (0.39 mmol, 92 mg), potassium carbonate (0.45 mmol, 61.9 mg, 1.1 eq), 1-bromobutane (0.39 mmol, 42.8 μL, 1 eq), 18-Crown-6 (0.039 mmol, 10.5 mg, 0.1 eq), and DMF (2.67 mL) was heated at 80° C. for 3 hours. This solution was then diluted with EtOAc and washed with water. The organic layer was dried over magnesium sulfate, filtered, and concentrated under high pressure to give 74.4 mg of SW208494 2-(butylthio)-5-(thiophen-2-yl)-3H-imidazo[4,5-b]pyridine (65%). $^1$H NMR (400 MHz, CDCl$_3$) δ 7.95-7.83 (m, 1H), 7.61-7.53 (m, 2H), 7.36 (d, J=5.1, 1H), 7.16-7.06 (m, 1H), 3.28 (t, J=7.3 Hz, 2H), 1.76-1.62 (m, 2H), 1.48-1.32 (m, 2H), 0.90 (t, J=7.4 Hz, 3H). ESI-MS (m/z): 290 [M+H]$^+$.

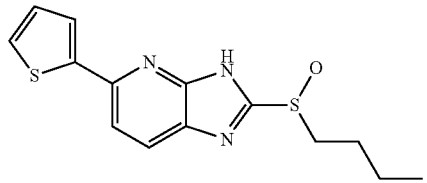

SW208495. 2-(butylsulfinyl)-5-(thiophen-2-yl)-3H-imidazo[4,5-b]pyridine. Chloroform (450 μL), acetic acid (450 μL), and hydrogen peroxide (0.376 mmol, 2.0 eq, 40 μL) were added to SW208494 2-(butylthio)-5-(thiophen-2-yl)-3H-imidazo[4,5-b]pyridine and heated at 45° C. for 2.5 hours. The solution was then diluted with EtOAc and washed with 10% acetic acid. The organic layer was separated, dried with magnesium sulfate, filtered, concentrated, and purified to give 16.8 mg of SW208495. $^1$H NMR (400 MHz, CDCl$_3$) δ 8.06 (d, J=8.5 Hz, 1H), 7.83-7.67 (m, 1H), 7.68-7.60 (m, 1H), 7.41 (d, J=5.3 Hz, 1H), 7.20-7.05 (m, 1H), 3.44-3.17 (m, 2H), 1.89-1.58 (m, 2H), 1.59-1.40 (m, 2H), 0.93 (t, J=7.3 Hz, 3H). ESI-MS (m/z): 306 [M+H]$^+$.

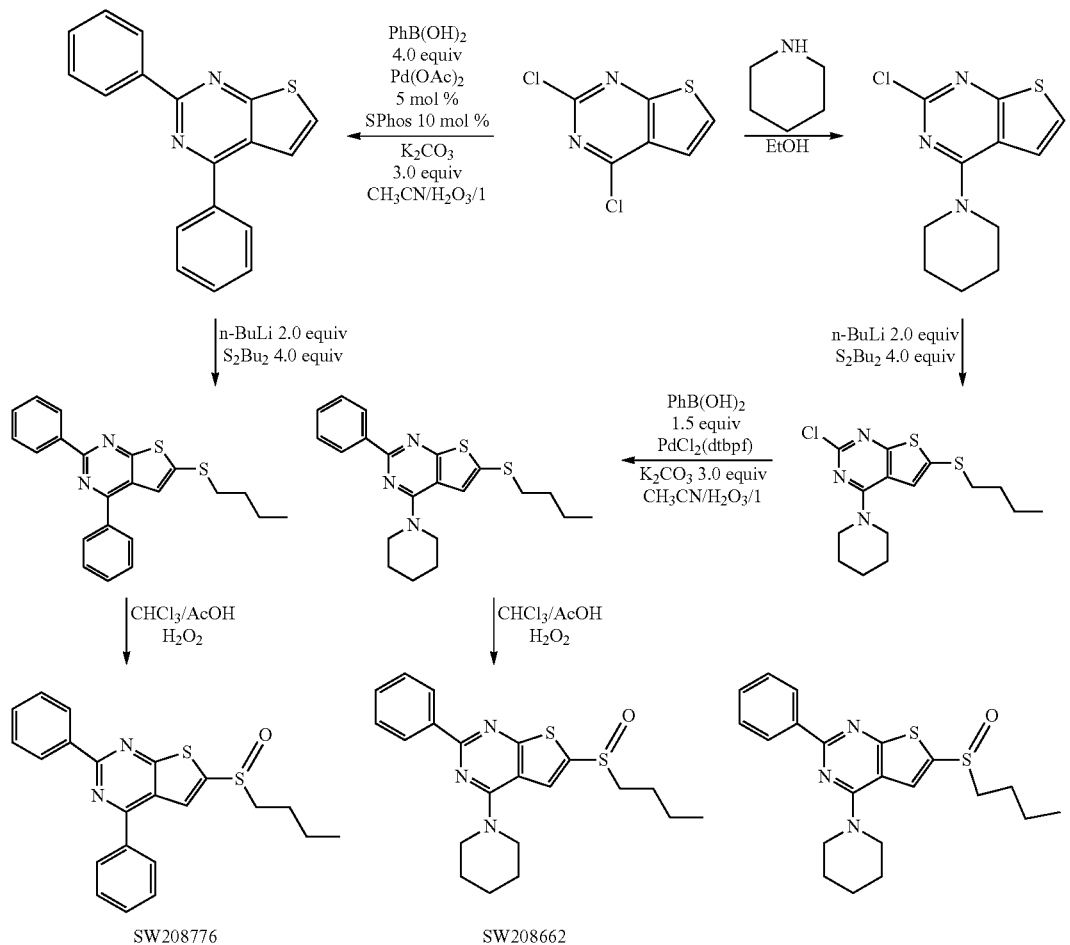

SW208662. 6-(butylsulfinyl)-2-phenyl-4-(piperidin-1-yl)thieno[2,3-d]pyrimidine. Acetic acid (50 μl) and hydrogen peroxide (5.0 μl, 30% solution in water) were added to the solution of 2-(butylthio)-6-phenyl-4-(piperidin-1-yl)thieno[2,3-b]pyrimidine (10 mg, 0.026 mmol) in chloroform (50 μl). The reaction mixture was stirred at 32° C. for 45 min. Once complete, the reaction was diluted with EtOAc and was washed with saturated NaHCO$_3$ solution, dried over magnesium sulfate, filtered and concentrated under reduce pressure to give designed product. $^1$H NMR (400 MHz, CDCl$_3$) δ 8.54-8.34 (m, 2H), 7.73 (s, 1H), 7.55-7.36 (m, 3H), 4.09-3.86 (m, 4H), 3.24-2.94 (m, 2H), 1.97-1.36 (m, 10H), 0.93 (t, J=7.3 Hz, 3H). ESI-MS (m/z): 400.1 [M+H]$^+$.

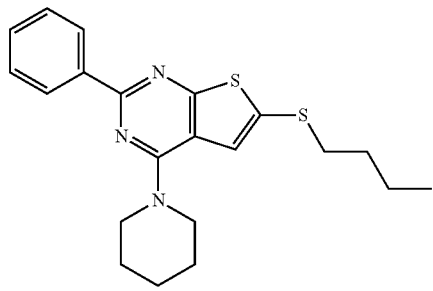 [SMILES: CCCCSc1cc2c(N3CCCCC3)nc(-c3ccccc3)nc2s1]

2-(butylthio)-6-phenyl-4-(piperidin-1-yl)thieno[2,3-b]pyrimidine. 2-(butylthio)-6-chloro-4-(piperidin-1-yl)thieno[2,3-b]pyrimidine (52 mg, 0.15 mmol), phenylboronic acid (27 mg, 0.22 mmol, 1.5 equiv), Potassium Carbonate (0.3 mmol, 2.0 equiv.), PdCl2dtbpf (10 mol mol %), in CH3CN:H2O (2:1) were heated at 100° C. overnight. After cooling to r.t. the reaction mixture was diluted with EtOAc and washed with water. The organic layer was dried over magnesium sulfate and the solvent was removed under reduced pressure. The crude product was purified by flash chromatography to afford designed product. 1H NMR (400 MHz, CHCl3) δ 8.49-8.36 (m, 2H), 7.51-7.36 (m, 3H), 7.29 (s, 1H), 3.95-3.85 (m, 4H), 2.90 (t, J=7.4 Hz, 2H), 1.76-1.73 (m, 6H), 1.70-1.59 (m, 2H), 1.48-1.39 (m, 2H), 0.91 (t, J=7.4 Hz, 3H). ESI-MS (m/z): 384.0 [M+H]+.

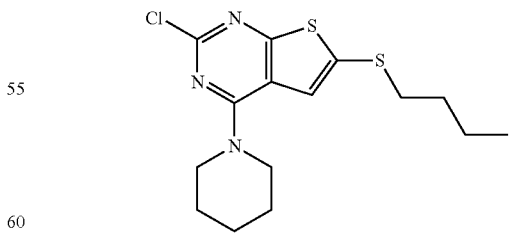

2-(butylthio)-6-chloro-4-(piperidin-1-yl)thieno[2,3-b]pyrimidine. To the solution of 6-chloro-4-(piperidin-1-yl)thieno[2,3-b]pyrimidine (52 mg, 0.20 mmol) in THF was added n-BuLi (0.4 mmol, 2.0 equiv., 1.6 M solution in hexanes) at −78° C. The reaction mixture was stirred for 5 min and 1,2-dibutyldisulfane (0.80 mmol, 4.0 equiv.) in THF was added. The reaction mixture was stirred for additional 1 h at −78° C. and then quenched. The crude product was purified by flash chromatography to afford designed product in 74% yield. $^1$H NMR (400 MHz, CHCl$_3$) δ 7.24 (s, 1H), 3.93-3.74 (m, 4H), 2.83 (t, J=7.3 Hz, 2H), 1.82-1.66 (m, 6H), 1.66-1.53 (m, 2H), 1.49-1.33 (m, 2H), 0.89 (t, J=7.3 Hz, 3H). ESI-MS (m/z): 342.1 [M+H]$^+$.

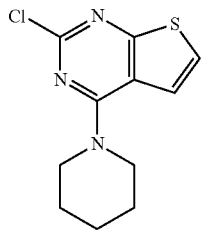 [SMILES: Clc1nc(N2CCCCC2)c2ccsc2n1]

6-chloro-4-(piperidin-1-yl)thieno[2,3-b]pyrimidine. 4,6-dichlorothieno[2,3-b]pyrimidine (50 mg, 0.24 mmol) and piperidine (0.36 mmol, 1.5 equiv.) in EtOH were stirred at room temperature overnight. The solvent was evaporated and crude compound purified by flash chromatography to give designed product in quantitative yield. $^1$H NMR (400 MHz, CDCl$_3$) δ 7.28 (d, J=6.1 Hz, 1H), 7.18 (d, J=6.2 Hz, 1H), 4.01-3.67 (m, 4H), 1.92-1.63 (m, 6H). ESI-MS (m/z): 254.0 [M+H]$^+$.

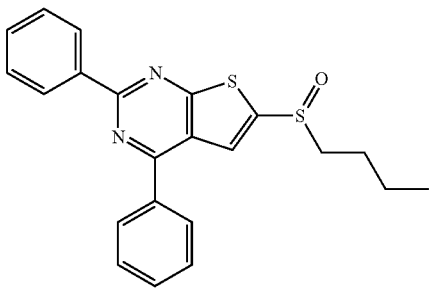 [SMILES: CCCCS(=O)c1cc2c(-c3ccccc3)nc(-c3ccccc3)nc2s1]

SW208776. 6-(butylsulfinyl)-2,4-diphenylthieno[2,3-d]pyrimidine. Acetic acid (250 μl) and hydrogen peroxide (20 μl, 30% solution in water) were added to the solution of 6-(butylthio)-2,4-diphenylthieno[2,3-d]pyrimidine (35 mg, 0.1 mmol) in chloroform (250 μl). The reaction mixture was stirred at 32° C. for 45 min. Once complete, the reaction was diluted with EtOAc and was washed with saturated NaHCO$_3$ solution, dried over magnesium sulfate, filtered and concentrated under reduce pressure to give designed product. $^1$H NMR (400 MHz, CDCl$_3$) δ 8.69-8.59 (m, 2H), 8.09-7.99 (m, 2H), 7.95 (s, 1H), 7.65-7.56 (m, 3H), 7.56-7.45 (m, 3H), 3.18-3.02 (m, 2H), 1.87-1.64 (m, 2H), 1.54-1.42 (m, 2H), 0.94 (t, J=7.3 Hz, 3H). ESI-MS (m/z): 393.1 [M+H]$^+$.

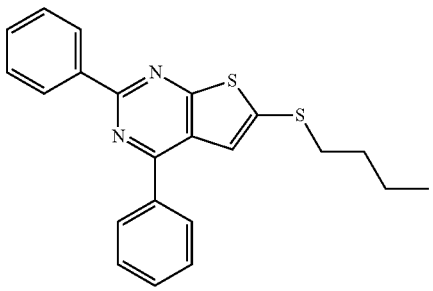 [SMILES: CCCCSc1cc2c(-c3ccccc3)nc(-c3ccccc3)nc2s1]

6-(butylthio)-2,4-diphenylthieno[2,3-d]pyrimidine. To the solution of 2,4-diphenylthieno[2,3-d]pyrimidine (53 mg, 0.28 mmol) in THF was added n-BuLi (0.56 mmol, 2.0 equiv., 225 μL, 2.5 M solution in hexanes) at −78° C. The reaction mixture was stirred for 5 min and 1,2-dibutyldisulfane (1.14 mmol, 4.0 equiv.) in THF was added. The reaction mixture was stirred for additional 1 h at −78° C. and then quenched. The crude product was purified by flash chromatography to afford designed product. $^1$H NMR (400 MHz, CDCl$_3$) δ 8.62-8.56 (m, 2H), 8.06-7.98 (m, 2H), 7.61-7.41 (m, 7H), 3.01 (t, J=7.3, 2H), 1.76-1.62 (m, 2H), 1.55-1.38 (m, 2H), 0.92 (t, J=7.4 Hz, 3H). ESI-MS (m/z): 377.1 [M+H]$^+$.

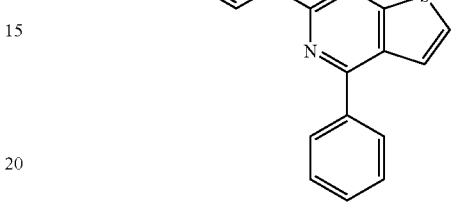

2,4-diphenylthieno[2,3-d]pyrimidine. 2,4-dichlorothieno[2,3-d]pyrimidine (100 mg, 0.50 mmol), phenylboronic acid (242 mg, 2.0 mmmol, 4.0 equiv), Potassium Carbonate (1.5 mmol, 3.0 equiv.), Pd(OAc)$_2$ (5 mol mol %), SPhos (10 mol %) in CH$_3$CN:H$_2$O (1.5:1) were heated at 100° C. overnight. After cooling to r.t. the reaction mixture was diluted with EtOAc and washed with water. The organic layer was dried over magnesium sulfate and the solvent was removed under reduced pressure. The crude product was purified by flash chromatography to afford designed product. $^1$H NMR (400 MHz, CDCl$_3$) δ 8.70-8.59 (m, 2H), 8.14-8.02 (m, 2H), 7.65-7.44 (m, 8H). ESI-MS (m/z): 289.0 [M+H]$^+$.

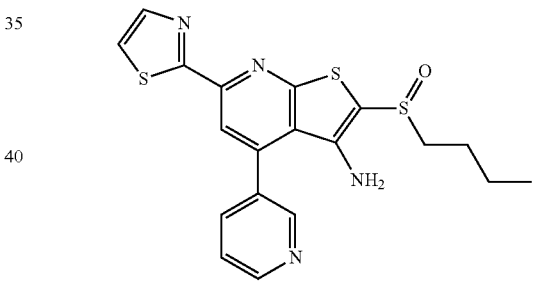

SW208777. 2-(butyl(λ$^1$-oxidanyl)-λ$^3$-sulfanyl)-4-(pyridin-3-yl)-6-(thiazol-2-yl)thieno[2,3-b]pyridin-3-amine was prepared using synthetic procedures described for the preparation of analog SW033291. $^1$H NMR (400 MHz, CDCl$_3$) δ 8.80 (s, 1H), 8.78 (dd, J=4.9, 1.7 Hz, 1H), 8.04 (s, 1H), 7.91 (d, J=3.2 Hz, 1H), 7.86 (d, J=6.4 Hz, 1H), 7.51 (d, J=3.1 Hz, 1H), 7.47 (dd, J=7.8, 4.8 Hz, 1H), 4.53 (s, 2H), 3.28 (ddd, J=12.8, 8.8, 6.3 Hz, 1H), 3.11 (ddd, J=12.8, 8.9, 6.9 Hz, 1H), 1.86-1.70 (m, 2H), 1.57-1.38 (m, 2H), 0.94 (t, J=7.3 Hz, 3H). ESI-MS (m/z): 415.0 [M+H]$^+$.

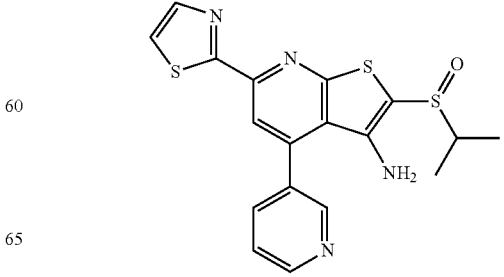

SW208780. 2-(isopropyl(λ¹-oxidanyl)-λ³-sulfanyl)-4-(pyridin-3-yl)-6-(thiazol-2-yl)thieno[2,3-b]pyridin-3-amine was prepared using synthetic procedures described for the preparation of analog SW033291. ¹H NMR (400 MHz, CDCl₃) δ 8.87-8.70 (m, 2H), 8.05 (s, 1H), 7.92 (d, J=3.1 Hz, 1H), 7.85 (dd, J=7.8, 2.4 Hz, 1H), 7.51 (d, J=3.2 Hz, 1H), 7.47 (dd, J=7.9, 4.9 Hz, 1H), 4.57 (s, 2H), 3.38 (p, J=6.8 Hz, 1H), 1.43 (d, J=6.8 Hz, 3H), 1.29 (d, J=6.8 Hz, 3H). ESI-MS (m/z): 400.1 [M+H]⁺.

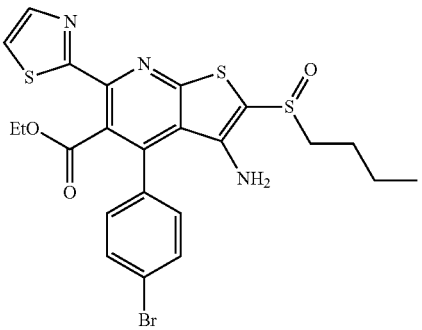 [SMILES: CCCCS(=O)c1sc2nc(-c3nccs3)c(C(=O)OCC)c(-c3ccc(Br)cc3)c2c1N]

SW209123. Ethyl 3-amino-4-(4-bromophenyl)-2-(butylsulfinyl)-6-(thiazol-2-yl)thieno[2,3-b]pyridine-5-carboxylate was prepared using synthetic procedures described for the preparation of analog SW033291. ¹H NMR (400 MHz, CDCl₃) δ 7.86 (d, J=3.2 Hz, 1H), 7.69-7.60 (m, 2H), 7.48 (d, J=3.2 Hz, 1H), 7.36-7.27 (m, 2H), 4.12 (q, J=7.2 Hz, 2H), 3.26 (ddd, J=12.9, 8.8, 6.3 Hz, 1H), 3.08 (ddd, J=12.9, 8.8, 6.3 Hz, 1H), 1.80-1.63 (m, 2H), 1.58-1.37 (m, 2H), 1.06 (t, J=7.2 Hz, 3H), 0.93 (t, J=7.3 Hz, 3H). ESI-MS (m/z): 564.0 [M+H]⁺.

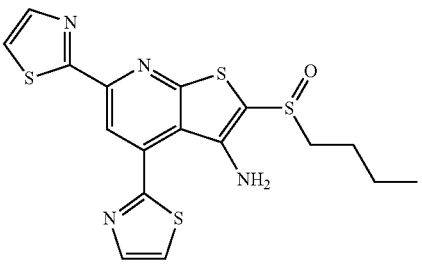 [SMILES: CCCCS(=O)c1sc2nc(-c3nccs3)cc(-c3nccs3)c2c1N]

SW209124. 2-(butylsulfinyl)-4,6-di(thiazol-2-yl)thieno[2,3-b]pyridin-3-amine was prepared using synthetic procedures described for the preparation of analog SW033291. ¹H NMR (400 MHz, CDCl₃) δ 8.48 (s, 1H), 8.01 (d, J=3.1 Hz, 1H), 7.96 (d, J=3.2 Hz, 1H), 7.61 (d, J=3.3 Hz, 1H), 7.52 (d, J=3.1 Hz, 1H), 6.69 (s, 2H), 3.30 (ddd, J=12.8, 9.2, 6.0 Hz, 1H), 3.14 (ddd, J=12.8, 9.2, 6.4 Hz, 1H), 1.83-1.60 (m, 2H), 1.43-1.53 (m, 2H), 0.93 (t, J=7.3 Hz, 3H). ESI-MS (m/z): 421.0 [M+H]⁺.

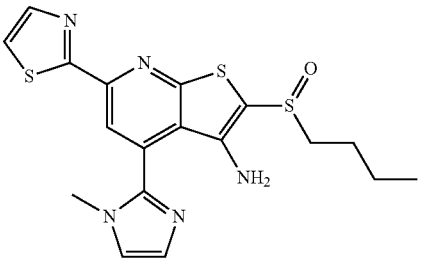 [SMILES: CCCCS(=O)c1sc2nc(-c3nccs3)cc(-c3nccn3C)c2c1N]

SW209125. 2-(butylsulfinyl)-4-(1-methyl-1H-imidazol-2-yl)-6-(thiazol-2-yl)thieno[2,3-b]pyridin-3-amine was prepared using synthetic procedures described for the preparation of analog SW033291. ¹H NMR (400 MHz, CDCl₃) δ 8.13 (s, 1H), 7.91 (d, J=3.2 Hz, 1H), 7.50 (d, J=3.1 Hz, 1H), 7.24 (d, J=1.2 Hz, 1H), 7.13 (d, J=1.2 Hz, 1H), 5.78 (s, 2H), 3.80 (s, 3H), 3.26 (ddd, J=12.8, 9.1, 6.0 Hz, 1H), 3.10 (ddd, J=12.8, 9.2, 6.5 Hz, 1H), 1.82-1.57 (m, 2H), 1.56-1.35 (m, 2H), 0.92 (t, J=7.3 Hz, 3H). ESI-MS (m/z): 418.1 [M+H]⁺.

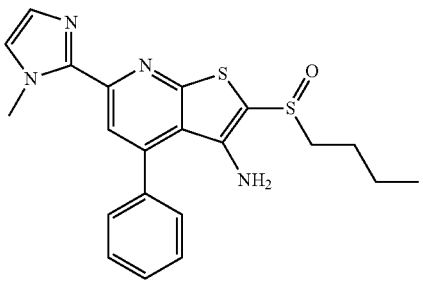 [SMILES: CCCCS(=O)c1sc2nc(-c3nccn3C)cc(-c3ccccc3)c2c1N]

SW209126. 2-(butylsulfinyl)-6-(1-methyl-1H-imidazol-2-yl)-4-phenylthieno[2,3-b]pyridin-3-amine was prepared using synthetic procedures described for the preparation of analog SW033291. ¹H NMR (400 MHz, CDCl₃) δ 8.08 (s, 1H), 7.58-7.32 (m, 5H), 7.11 (d, J=1.1 Hz, 1H), 7.00 (d, J=1.1 Hz, 1H), 4.58 (s, 2H), 4.19 (s, 3H), 3.27 (ddd, J=12.7, 9.0, 6.0 Hz, 1H), 3.08 (ddd, J=12.8, 9.1, 6.6 Hz, 1H), 1.79-1.60 (m, 2H), 1.56-1.37 (m, 2H), 0.92 (t, J=7.3 Hz, 3H). ESI-MS (m/z): 411.1 [M+H]⁺.

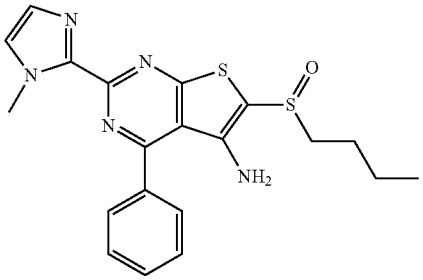 [SMILES: CCCCS(=O)c1sc2nc(-c3nccn3C)nc(-c3ccccc3)c2c1N]

SW209277. 6-(butylsulfinyl)-2-(1-methyl-1H-imidazol-2-yl)-4-phenylthieno[2,3-d]pyrimidin-5-amine was prepared using synthetic procedures described for the preparation of analog SW208065. ¹H NMR (400 MHz, CDCl₃) δ 7.71 (dd, J=6.9, 2.8 Hz, 2H), 7.63-7.49 (m, 3H), 7.29 (s, 1H), 7.07 (s, 1H), 4.85 (s, 2H), 4.18 (s, 3H), 3.29 (ddd, J=12.8, 8.6, 6.3 Hz, 1H), 3.11 (ddd, J=12.8, 8.7, 6.9 Hz, 1H), 1.83-1.65 (m, 2H), 1.59-1.39 (m, 2H), 0.94 (t, J=7.3 Hz, 3H). ESI-MS (m/z): 412.1 [M+H]⁺.

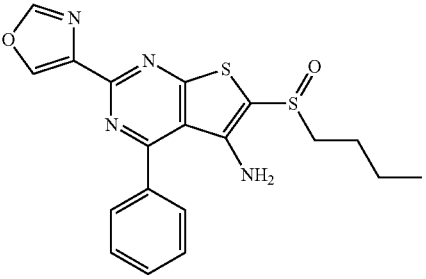 [SMILES: CCCCS(=O)c1sc2nc(-c3cocn3)nc(-c3ccccc3)c2c1N]

SW209278. 6-(butylsulfinyl)-2-(oxazol-4-yl)-4-phenylthieno[2,3-d]pyrimidin-5-amine was prepared using synthetic procedures described for the preparation of analog SW208065. ¹H NMR (400 MHz, CDCl₃) δ 8.51 (d, J=1.1 Hz, 1H), 8.01 (d, J=1.1 Hz, 1H), 7.75-7.61 (m, 2H), 7.62-7.48 (m, 3H), 4.56 (s, 2H), 3.29 (ddd, J=12.9, 8.8, 6.3 Hz, 1H), 3.09 (ddd, J=12.9, 8.9, 6.9 Hz, 1H), 1.81-1.64 (m, 2H), 1.56-1.39 (m, 2H), 0.93 (t, J=7.3 Hz, 3H). ESI-MS (m/z): 399.1 [M+H]⁺.

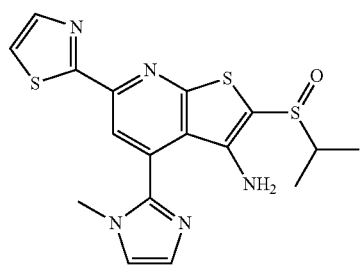 [SMILES: CC(C)S(=O)c1sc2nc(-c3nccs3)cc(-c3nccn3C)c2c1N]

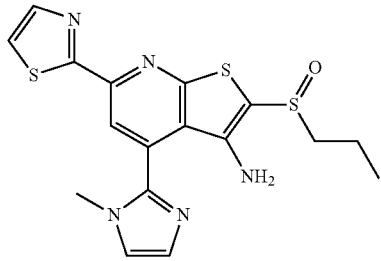 [SMILES: CCCS(=O)c1sc2nc(-c3nccs3)cc(-c3nccn3C)c2c1N]

SW209279. 2-(isopropylsulfinyl)-4-(1-methyl-1H-imidazol-2-yl)-6-(thiazol-2-yl)thieno[2,3-b]pyridin-3-amine was prepared using synthetic procedures described for the preparation of analog SW033291. $^1$H NMR (400 MHz, CDCl$_3$) δ 8.14 (s, 1H), 7.92 (d, J=3.2 Hz, 1H), 7.51 (d, J=3.2 Hz, 1H), 7.24 (s, 1H), 7.13 (d, J=1.2 Hz, 1H), 5.92 (s, 2H), 3.80 (s, 3H), 3.38 (p, J=6.8 Hz, 1H), 1.44 (d, J=6.8 Hz, 3H), 1.25 (d, J=6.8 Hz, 3H). ESI-MS (m/z): 404.1 [M+H]$^+$.

SW209280. 4-(1-methyl-1H-imidazol-2-yl)-2-(propylsulfinyl)-6-(thiazol-2-yl)thieno[2,3-b]pyridin-3-amine was prepared using synthetic procedures described for the preparation of analog SW033291. $^1$H NMR (400 MHz, CDCl$_3$) δ 8.14 (s, 1H), 7.92 (d, J=3.2 Hz, 1H), 7.51 (d, J=3.1, 1H), 7.25 (d, J=1.3 Hz, 1H), 7.14 (d, J=1.2 Hz, 1H), 5.97 (s, 2H), 3.80 (s, 3H), 3.27 (ddd, J=12.7, 8.3, 6.5 Hz, 1H), 3.07 (ddd, J=12.8, 8.4, 7.1 Hz, 1H), 1.85-1.69 (m, 2H), 1.07 (t, J=7.4 Hz, 3H). ESI-MS (m/z): 404.1 [M+H]$^+$.

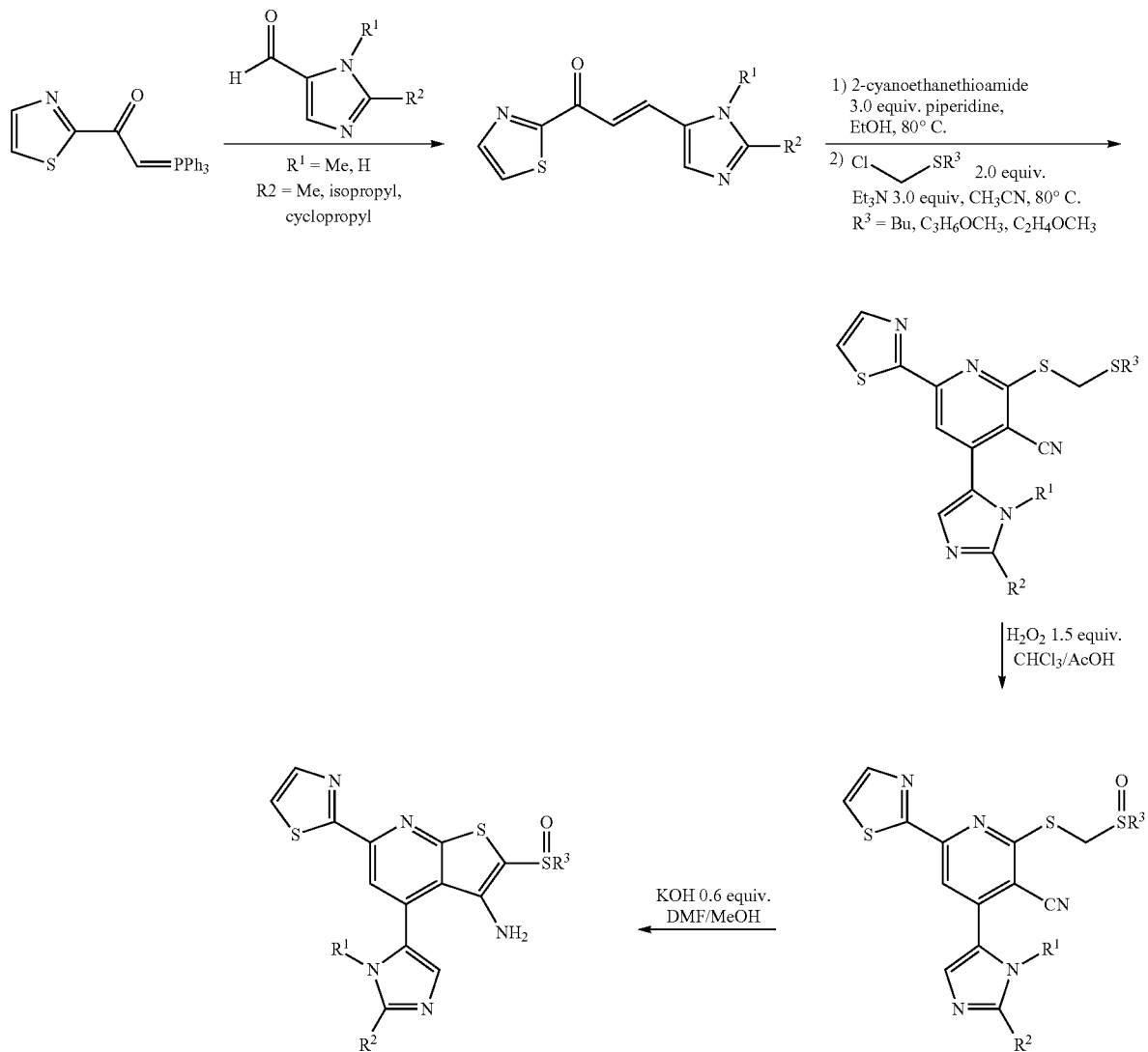

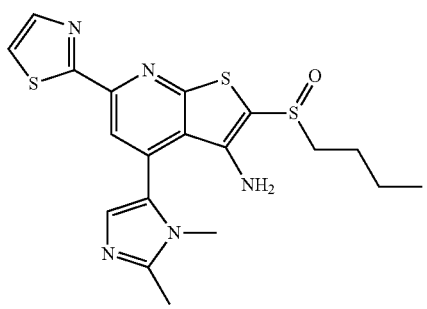

SW209415. 2-(butylsulfinyl)-4-(1,2-dimethyl-1H-imidazol-5-yl)-6-(thiazol-2-yl)thieno[2,3-b]pyridin-3-amine. To the solution of 2-(((butylsulfinyl)methyl)thio)-4-(1,2-dimethyl-1H-imidazol-5-yl)-6-(thiazol-2-yl)nicotinonitrile (0.14 mmol, 60 mg) in DMF (600 µl)/MeOH (300 µl) was added KOH (0.084 mmol, 4.70 mg, 0.6 equiv., 2.0 M in water). The reaction mixture was stirred at 32° C. for 20 min. Once complete, the reaction was diluted with EtOAc and acidified to pH 7 with 5% aq. solution of AcOH, the organic phase was separated and aqueous layer was extracted twice with EtOAc, dried over magnesium sulfate, filtered and concentrated under reduced pressure. The crude product was purified by flash chromatography to afford designed product in 97% isolated yield. $^1$H NMR (400 MHz, CDCl$_3$) δ 8.03 (s, 1H), 7.90 (d, J=3.1 Hz, 1H), 7.50 (d, J=3.2 Hz, 1H), 7.11 (s, 1H), 4.76 (s, 2H), 3.39 (s, 3H), 3.27 (ddd, J=12.9, 8.7, 6.4 Hz, 1H), 3.09 (ddd, J=12.8, 8.8, 6.9 Hz, 1H), 2.47 (s, 3H), 1.83-1.62 (m, 2H), 1.57-1.38 (m, 2H), 0.93 (t, J=7.3 Hz, 3H). ESI-MS (m/z): 432.1 [M+H]+. Two enantiomers of SW209415 can be separated by chiral HPLC: Chiralpak AD-H, 10×250 mm, 5 µM, 100% MeOH.

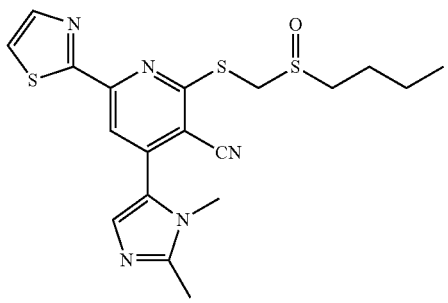 [SMILES: CCCCS(=O)CSc1nc(-c2nccs2)cc(-c2cnc(C)n2C)c1C#N]

2-(((butylsulfinyl)methyl)thio)-4-(1,2-dimethyl-1H-imidazol-5-yl)-6-(thiazol-2-yl)nicotinonitrile. To the solution of 2-(((butylthio)methyl)thio)-4-(1,2-dimethyl-1H-imidazol-5-yl)-6-(thiazol-2-yl)nicotinonitrile (85 mg, 0.205 mmol) in CHCl$_3$/AcOH (1:1, 0.15 M) was added H$_2$O$_2$ (0.31 mmol, 1.5 equiv. 30% solution in water). The reaction mixture was stirred at 32° C. for 40 min. Once complete, the reaction was diluted with EtOAc and was washed with saturated NaHCO$_3$ solution, dried over magnesium sulfate, filtered and concentrated under reduce pressure to give designed product in 92% yield. $^1$H NMR (400 MHz, CDCl$_3$) δ 7.98 (d, J=3.1 Hz, 1H), 7.94 (s, 1H), 7.60 (d, J=3.1 Hz, 1H), 7.43 (s, 1H), 4.72 (d, J=13.1 Hz, 1H), 4.41 (d, J=13.1 Hz, 1H), 3.63 (s, 3H), 2.96 (dt, J=12.9, 8.2 Hz, 1H), 2.84 (dt, J=12.9, 7.5 Hz, 1H), 2.51 (s, 3H), 1.94-1.74 (m, 2H), 1.63-1.38 (m, 2H), 0.95 (t, J=7.4 Hz, 3H). ESI-MS (m/z): 432.1 [M+H]+.

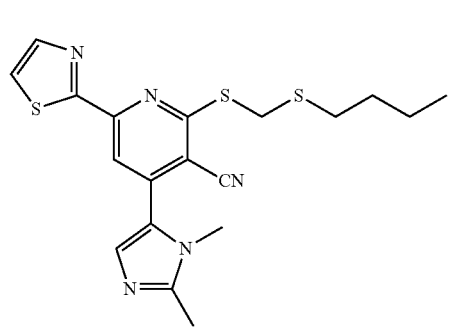 [SMILES: CCCCSCSc1nc(-c2nccs2)cc(-c2cnc(C)n2C)c1C#N]

2-(((butylthio)methyl)thio)-4-(1,2-dimethyl-1H-imidazol-5-yl)-6-(thiazol-2-yl)nicotinonitrile. To a suspension of 3-(1,2-dimethyl-1H-imidazol-5-yl)-1-(thiazol-2-yl)prop-2-en-1-one (0.31 mmol, 72 mg) and 2-cyanothioacetamide (0.93 mmol, 93 mg, 3.0 equiv.) in EtOH (1.5 mL), a few drops of piperidine were added. After being stirred at 80° C. for 2 h, EtOH was evaporated and crude product was redissolved in CH$_3$CN. Butyl(chloromethyl)sulfane (0.62 mmol, 85.5 mg) and Et$_3$N (0.93 mmol, 94.1 mg, 130 µL) were then added and the reaction mixture was stirred at 80° C. for 20 min. Once complete, the reaction was diluted with EtOAc and water. The organic phase was separated and aqueous layer was extracted twice with EtOAc. The combined extractions were washed with saturated NaCl solution, dried over magnesium sulfate, filtered and concentrated under reduced pressure. The residue was purified by flash chromatography to give 99 mg of designed product (77%). $^1$H NMR (400 MHz, CDCl$_3$) δ 7.96 (d, J=3.1 Hz, 1H), 7.85 (s, 1H), 7.56 (d, J=3.1 Hz, 1H), 7.37 (s, 1H), 4.49 (s, 2H), 3.60 (s, 3H), 2.72 (t, J=7.4 Hz, 2H), 2.48 (s, 3H), 1.62 (p, J=7.3 Hz, 2H), 1.40 (h, J=7.3 Hz, 2H), 0.90 (t, J=7.3 Hz, 3H). ESI-MS (m/z): 416.6 [M+H]$^+$.

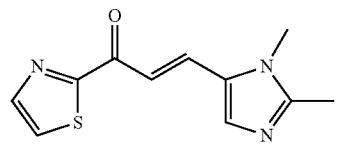 [SMILES: Cc1ncc(/C=C/C(=O)c2nccs2)n1C]

(E)-3-(1,2-dimethyl-1H-imidazol-5-yl)-1-(thiazol-2-yl)prop-2-en-1-one. To a solution of 1,5-dimethyl-1H-imidazole-2-carbaldehyde (2.0 mmol, 250 mg) in 6 ml of CH$_3$CN was added 1-(thiazol-2-yl)-2-(triphenyl-15-phosphanylidene)ethan-1-one (4.0 mmol, 1.55 g, 2.0 equiv.). The reaction mixture was stirred at 90° C. for 48 h. Once complete, solvent was evaporated and residue was purified by flash chromatography to give 331 mg of designed product (71%). ¹H NMR (400 MHz, Methanol-d4) δ 8.08 (d, J=3.0 Hz, 1H), 7.97 (d, J=3.0 Hz, 1H), 7.90 (d, J=15.9 Hz, 1H), 7.76 (d, J=15.9 Hz, 1H), 7.60 (s, 1H), 3.72 (s, 3H), 2.43 (s, 3H). ESI-MS (m/z): 234.3 [M+H]⁺.

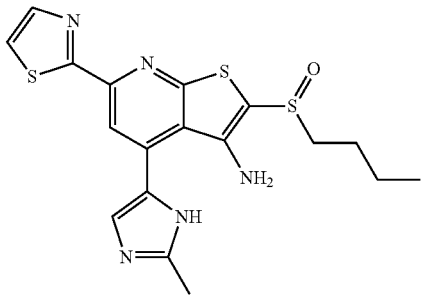 [SMILES: CCCCS(=O)c1sc2nc(-c3nccs3)cc(-c3cnc(C)[nH]3)c2c1N]

SW209428. 2-(butylsulfinyl)-4-(2-methyl-1H-imidazol-5-yl)-6-(thiazol-2-yl)thieno[2,3-b]pyridin-3-amine was prepared using synthetic procedures described for the preparation of analog SW209415. ¹H NMR (400 MHz, CDCl3) δ 10.51 (s, 1H), 8.10 (s, 1H), 7.89 (d, J=3.2 Hz, 1H), 7.46 (d, J=3.2 Hz, 1H), 7.40 (s, 1H), 3.31 (ddd, J=12.8, 9.3, 5.8 Hz, 1H), 3.15 (ddd, J=12.8, 9.3, 6.2 Hz, 1H), 2.42 (s, 3H), 1.79-1.58 (m, 2H), 1.57-1.38 (m, 2H), 0.93 (t, J=7.3 Hz, 3H). ESI-MS (m/z): 418.1 [M+H]⁺.

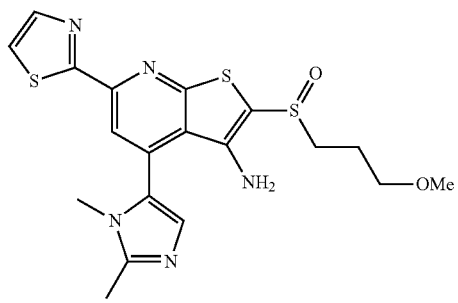 [SMILES: COCCCS(=O)c1sc2nc(-c3nccs3)cc(-c3cnc(C)n3C)c2c1N]

SW211688. 4-(1,2-dimethyl-1H-imidazol-5-yl)-2-((3-methoxypropyl) sulfinyl)-6-(thiazol-2-yl)thieno[2,3-b]pyridin-3-amine was prepared using synthetic procedures described for the preparation of analog SW209415. ¹H NMR (400 MHz, Acetone-d6) δ 8.03 (s, 1H), 7.99 (d, J=3.2 Hz, 1H), 7.82 (d, J=3.2 Hz, 1H), 7.09 (s, 1H), 5.06 (s, 2H), 3.51 (s, 3H), 3.48 (t, J=6.1 Hz, 2H), 3.26 (s, 3H), 3.26-3.18 (m, 1H), 3.18-3.12 (m, 1H), 2.43 (s, 3H), 2.00-1.89 (m, 2H). ESI-MS (m/z): 448.1 [M+H]⁺.

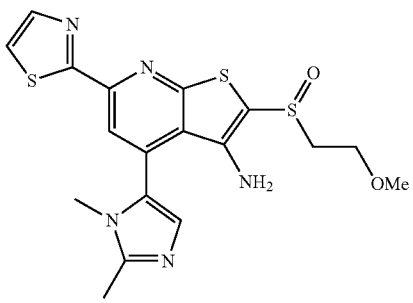 [SMILES: COCCS(=O)c1sc2nc(-c3nccs3)cc(-c3cnc(C)n3C)c2c1N]

SW211689. 4-(1,2-dimethyl-1H-imidazol-5-yl)-2-((2-methoxyethyl) sulfinyl)-6-(thiazol-2-yl)thieno[2,3-b]pyridin-3-amine was prepared using synthetic procedures described for the preparation of analog SW209415. ¹H NMR (400 MHz, CDCl3) δ 8.05 (s, 1H), 7.92 (d, J=3.2 Hz, 1H), 7.51 (d, J=3.2 Hz, 1H), 7.11 (s, 1H), 4.73 (s, 2H), 3.88-3.82 (m, 1H), 3.75-3.62 (m, 1H), 3.57 (ddd, J=13.1, 6.0, 3.9 Hz, 1H), 3.40 (s, 3H), 3.37 (s, 3H), 3.25 (ddd, J=12.8, 8.0, 4.4 Hz, 1H), 2.48 (s, 3H). ESI-MS (m/z): 434.1 [M+H]⁺.

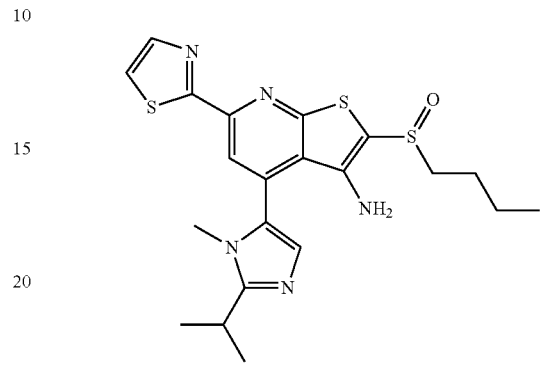

SW212344. 2-(butylsulfinyl)-4-(2-isopropyl-1-methyl-1H-imidazol-5-yl)-6-(thiazol-2-yl)thieno[2,3-b]pyridin-3-amine was prepared using synthetic procedures described for the preparation of analog SW209415. ¹H NMR (400 MHz, CDCl3) δ 8.06 (s, 1H), 7.92 (d, J=3.1 Hz, 1H), 7.51 (d, J=3.2 Hz, 1H), 7.15 (s, 1H), 4.71 (s, 2H), 3.41 (s, 3H), 3.27 (ddd, J=13.0, 8.5, 6.5 Hz, 1H), 3.19-2.98 (m, 2H), 1.83-1.59 (m, 2H), 1.58-1.41 (m, 2H), 1.39 (d, J=6.7 Hz, 6H), 0.94 (t, J=7.3 Hz, 3H). ESI-MS (m/z): 460.1 [M+H]⁺.

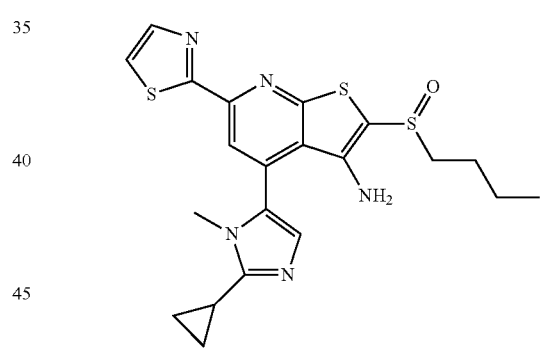

SW212345. 2-(butylsulfinyl)-4-(2-cyclopropyl-1-methyl-1H-imidazol-5-yl)-6-(thiazol-2-yl)thieno[2,3-b]pyridin-3-amine was prepared using synthetic procedures described for the preparation of analog SW209415. ¹H NMR (400 MHz, CDCl3) δ 8.04 (s, 1H), 7.91 (d, J=3.1 Hz, 1H), 7.50 (d, J=3.1 Hz, 1H), 7.07 (s, 1H), 4.77 (s, 2H), 3.51 (s, 3H), 3.27 (ddd, J=12.9, 8.7, 6.4 Hz, 1H), 3.10 (ddd, J=12.9, 8.8, 6.9 Hz, 1H), 1.95-1.78 (m, 1H), 1.81-1.62 (m, 2H), 1.58-1.37 (m, 2H), 1.17-0.98 (m, 4H), 0.93 (t, J=7.3 Hz, 3H). ESI-MS (m/z): 458.1 [M+H]⁺.

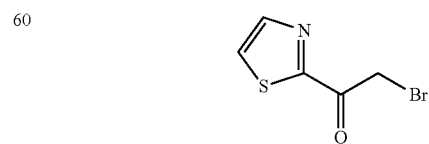

2-bromo-1-(thiazol-2-yl)ethan-1-one. n-Butyllithium (24.7 mL, 0.0617 mol, 2.5M in Hexane) was added dropwise to a solution of 2-thiazole (5.0 g, 0.059 mol) in anhydrous diethyl ether (48.8 mL) at −78° C. After 15 minutes, ethylbromoacetate (6.84 mL, 0.0617 mol) was added, the cold bath was removed and the solution was allowed to warm to room temperature. The reaction mixture was diluted with ether and water. The organic layer was separated, dried over Na2SO4, filtered and concetrated under reduced pressure. The crude product was suspended in hexanes and heated to reflux for 15 minutes then the product was decanted off leaving the impure oil. This was repeated 5 times to give a white solid with 88% yield. $^1$H NMR (400 MHz, CDCl3) δ 8.05 (d, J=3.0 Hz, 1H), 7.77 (d, J=3.0 Hz, 1H), 4.71 (s, 2H). ESI-MS (m/z): 207.8 [M+H]+.

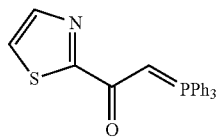

1-(thiazol-2-yl)-2-(triphenyl-15-phosphanylidene)ethan-1-one. To a solution of 2-bromo-1-(thiazol-2-yl)ethan-1-one (10.7 g, 0.0517 mol) in toluene (337.7 mL), triphenylphosphine (14.1 g, 0.0539 mol) was added portion wise. The mixture was stirred at room temperature for 3 hours. The yellowish precipitate was removed by filtration, and was washed several times with toluene and then petroleum ether. Water was added to the precipitate and was treated dropwise with 1N NaOH to pH 10 (at pH 7 there was a color change from yellow to orange). The mixture was stirred for 30 minutes at room temperature. The precipitate was removed by filtration and washed several times with water. The resulting orange solid, was heated at 50° C. under vacuum to remove any water, giving a 96% yield. $^1$H NMR (400 MHz, CDCl$_3$) δ 7.82 (d, J=3.1 Hz, 1H), 7.72 (ddd, J=12.8, 8.3, 1.4 Hz, 6H), 7.61-7.54 (m, 3H), 7.51-7.45 (m, 6H), 7.38 (dd, J=3.1, 1.3 Hz, 1H), 5.00 (d, J=23.3 Hz, 1H). ESI-MS (m/z): 387.9 [M+H]$^+$.

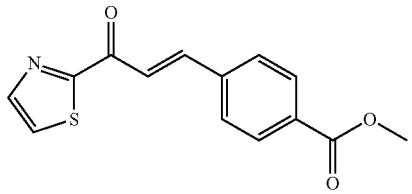 [SMILES: COC(=O)c1ccc(/C=C/C(=O)c2nccs2)cc1]

Methyl (E)-4-(3-oxo-3-(thiazol-2-yl)prop-1-en-1-yl)benzoate. In a dried flask, 1-(thiazol-2-yl)-2-(triphenyl-15-phosphanylidene)ethan-1-one (1.5 g, 3.9 mmol) and methyl 4-formyl benzoate (634 mg, 3.86 mmol) were dissolved in anhydrous chloroform (19.3 mL) and the solution stirred at 71° C. overnight. The solvent was evaporated under reduced pressure and the solid precipitate was purified using automated flash chromatography (100% DCM) to give a white solid in 76% yield. $^1$H NMR (400 MHz, CDC3) δ 8.10-8.05 (m, 3H), 8.01 (d, J=1.3 Hz, 2H), 7.76 (d, J=8.4 Hz, 2H), 7.72 (d, J=3.0 Hz, 1H), 3.93 (s, 3H). ESI-MS (m/z): 274.0 [M+H]+.

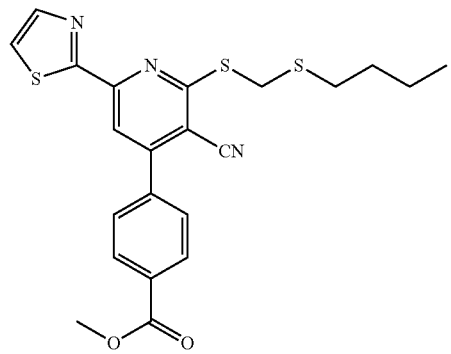 [SMILES: CCCCSCSc1nc(-c2nccs2)cc(-c2ccc(C(=O)OC)cc2)c1C#N]

Methyl 4-(2-(((butylthio)methyl)thio)-3-cyano-6-(thiazol-2-yl)pyridin-4-yl)benzoate. 2-cyanothioacetamide (274.8 mg, 2.744 mmol) and methyl (E)-4-(3-oxo-3-(thiazol-2-yl)prop-1-en-1-yl)benzoate (250.0 mg, 0.9147 mmol) were combined in a vial that was evacuated and backfilled with 02 then ethanol (2.75 mL) and piperdine (2 drops) were added. The solution was sparged for a few minutes then stirred at 80° C. for 4 hours. Once cooled, the solution was filtered, and the precipitate was rinsed with ethanol, and then washed in minimal amounts of acetic acid by heating at 80° C. for 45 minutes. When cooled, the washed solution was filtered leaving the crude brown/red solid product, which was carried forward to the next step. Standard alkylation procedure: Butyl(chloromethyl)sulfane (111.2 mg, 0.8059 mmol) in acetonitrile (1.32 mL), was added to the product from the first step, and Et3N (168.6 μL, 1.209 mmol) was added last. The solution was stirred at 80° C. for 20 minutes. The reaction mixture was diluted with EtOAc and washed with H2O, dried over Na2SO4, filtered, and concentrated under reduced pressure. The crude solid was purified using automated flash chromatography (80% hexane, 20% EtOAc). This produced a solid in 24% yield. $^1$H NMR (400 MHz, CDCl3) δ 8.18 (d, J=8.4 Hz, 2H), 8.02 (s, 1H), 7.98 (d, J=3.1 Hz, 1H), 7.71 (d, J=8.4 Hz, 2H), 7.58 (d, J=3.2 Hz, 1H), 4.52 (s, 2H), 3.95 (s, 3H), 2.76 (t, J=7.3 Hz, 2H), 1.64 (tt, J=7.7, 6.3 Hz, 2H), 1.42 (h, J=7.3 Hz, 2H), 0.91 (t, J=7.3 Hz, 3H). ESI-MS (m/z): 456.1 [M+H]+.

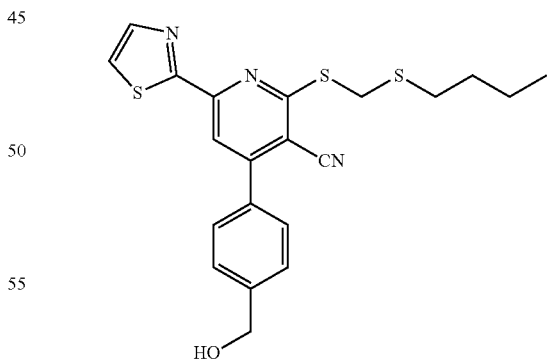

2-(((butylthio)methyl)thio)-4-(4-(hydroxymethyl)phenyl)-6-(thiazol-2-yl)nicotinonitrile. To the solution of methyl 4-(2-(((butylthio)methyl)thio)-3-cyano-6-(thiazol-2-yl)pyridin-4-yl)benzoate (336 mg, 0.737 mmol) in THF (8.41 mL) LiBH$_4$ (96.3 mg, 4.42 mmol) was added at 0° C. The reaction was stirred at room temperature for 36 hours, and the reaction was monitored by LC/MS. The reaction mixture was diluted with EtOAc and H$_2$O. The organic layer was dried over Na$_2$SO$_4$, filtered, and concentrated under reduced pressure, to give product in 96% yield. $^1$H NMR (400 MHz, CDCl$_3$) δ 8.02 (s, 1H), 7.98 (d, J=3.1 Hz, 1H), 7.69-7.62 (m, 2H), 7.56 (d, J=3.1 Hz, 1H), 7.56-7.49 (m, 2H), 4.79 (d, J=4.3 Hz, 2H), 4.52 (s, 2H), 2.82-2.60 (m, 2H), 1.71-1.58 (m, 2H), 1.49-1.33 (m, 2H), 0.91 (t, J=7.4 Hz, 3H). ESI-MS (m/z): 428.1 [M+H]$^+$.

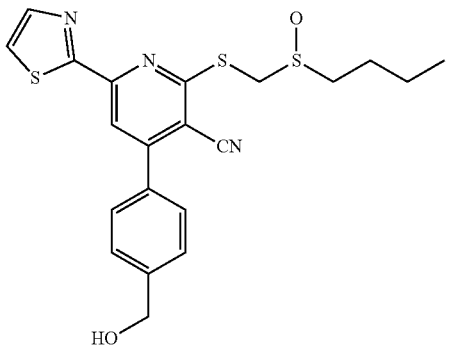

Standard oxidation procedure: 2-(((butyl(11-oxidanyl)-13-sulfanyl)methyl)thio)-4-(4-(hydroxymethyl)phenyl)-6-(thiazol-2-yl)nicotinonitrile. Chloroform (2.53 mL), acetic acid (1.39 mL), and hydrogen peroxide (108.0 µL, 1.057 mmol, 30% solution in water) were added to 2-(((butylthio)methyl)thio)-4-(4-(hydroxymethyl)phenyl)-6-(thiazol-2-yl)nicotinonitrile. The solution was stirred at 32° C. for 45 minutes. The reaction mixture was then diluted with EtOAc and washed with saturated NaHCO$_3$, and the organic layer was dried over Na2SO4, filtered, and concentrated under reduced pressure to give the desired product in 94% yield. $^1$H NMR (400 MHz, CDCl3) δ 8.03 (s, 1H), 7.93 (d, J=3.1 Hz, 1H), 7.59 (d, J=8.2 Hz, 2H), 7.55 (d, J=3.1 Hz, 1H), 7.48 (d, J=7.9 Hz, 2H), 4.73 (s, 2H), 4.66 (d, J=13.1 Hz, 1H), 4.38 (d, J=13.1 Hz, 1H), 2.93 (dt, J=13.0, 8.1 Hz, 1H), 2.79 (dt, J=13.0, 7.2 Hz, 1H), 1.84-1.72 (m, 2H), 1.55-1.33 (m, 2H), 0.91 (t, J=7.3 Hz, 3H).). ESI-MS (m/z): 444.1 [M+H]+.

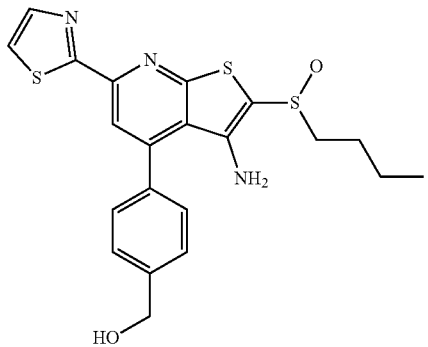

SW209510 (4-(3-amino-2-(butyl(11-oxidanyl)-13-sulfanyl)-6-(thiazol-2-yl)thieno[2,3-b]pyridin-4-yl)phenyl)methanol. t-BuOK (22.78 mg, 0.2028 mmol) was added to 2-(((butyl(11-oxidanyl)-13-sulfanyl)methyl)thio)-4-(4-(hydroxymethyl)phenyl)-6-(thiazol-2-yl)nicotinonitrile (150 mg, 0.338 mmol) and the vial was evacuated backfilled with N$_2$ three times before adding DMF (1.3 mL). The solution was sparged with N$_2$ for a few minutes before heating at 32° C. The reaction mixture was monitored every five minutes by TLC (80% EtOAc. 20% hexanes) and upon completion was diluted with EtOAc and washed with 10% AcOH. The organic layer was then dried over Na$_2$SO$_4$, filtered, and concentrated under reduced pressure. The product was purified using automated flash chromatography to give an isolated green solid/oil in 16% yield. $^1$H NMR (400 MHz, CDCl$_3$) δ 8.02 (s, 1H), 7.90 (d, J=3.2 Hz, 1H), 7.59-7.40 (m, 5H), 4.80 (s, 2H), 4.63 (s, 2H), 3.27 (ddd, J=12.8, 9.0, 6.1 Hz, 1H), 3.10 (ddd, J=12.8, 9.1, 6.6 Hz, 1H), 1.78-1.61 (m, 2H), 1.55-1.40 (m, 2H), 0.93 (t, J=7.3 Hz, 3H). ESI-MS (m/z): 444.1 [M+H]$^+$.

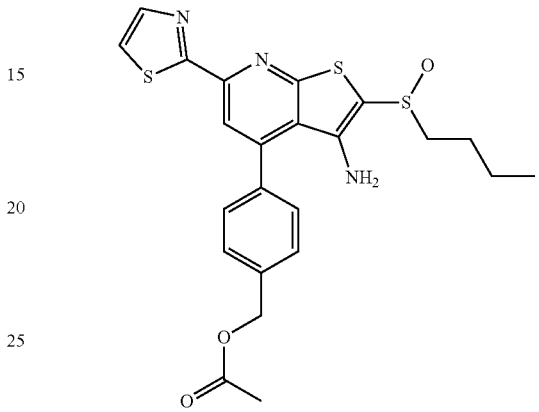

SW209511  4-(3-amino-2-(butyl(11-oxidanyl)-13-sulfanyl)-6-(thiazol-2-yl)thieno[2,3-b]pyridin-4-yl)benzyl acetate. This compound was formed during the workup of SW209510 in EtOAc (47% yield). $^1$H NMR (400 MHz, CDCl$_3$) δ 7.99 (s, 1H), 7.87 (d, J=3.2 Hz, 1H), 7.56-7.40 (m, 5H), 5.18 (s, 2H), 4.62 (s, 2H), 3.26 (ddd, J=12.8, 9.0, 6.1 Hz, 1H), 3.08 (ddd, J=12.8, 9.1, 6.6 Hz, 1H), 2.14 (s, 3H), 1.77-1.59 (m, 2H), 1.53-1.37 (m, 2H), 0.92 (t, J=7.3 Hz, 3H). ESI-MS (m/z): 486.1 [M+H]$^+$.

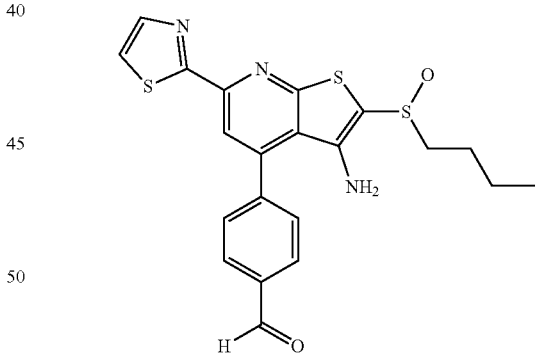

4-(3-amino-2-(butyl(11-oxidanyl)-13-sulfanyl)-6-(thiazol-2-yl)thieno[2,3-b]pyridin-4-yl)benzaldehyde. MnO$_2$ (111.3 mg, 1.28 mmol) was added to a solution of SW209510 (56.8 mg, 0.128 mmol) in DCM (2.3 mL) and stirred at room temperature overnight. LC/MS indicated that the reaction was incomplete. The reaction was filtered over celite, washed with DCM and the filtrate was concentrated under reduced pressure. The crude mixture was redissolved in DCM (2.3 mL) and MnO$_2$ (5 eq) was added. The solution was left to stir 24 hours at room temperature, was filtered over celite and washed with DCM. The filtrate was concentrated under reduced pressure and the resulting crude product was purified using automated flash chromatography (55% EtOAc, 45% hexanes) resulting in 24% isolated yield. $^1$H NMR (400 MHz, CDCl$_3$) δ 10.13 (s, 1H), 8.11-7.99 (m, 3H), 7.92 (d, J=3.1 Hz, 1H), 7.75-7.62 (m, 2H), 7.51 (d, J=3.2 Hz, 1H), 4.56 (s, 2H), 3.29 (ddd, J=12.8, 8.8, 6.3 Hz, 1H), 3.11 (ddd, J=12.8, 8.9, 6.9 Hz, 1H), 1.82-1.66 (m, 2H), 1.54-1.41 (m, 2H), 0.94 (t, J=7.3 Hz, 3H). ESI-MS (m/z): 442.1 [M+H]$^+$.

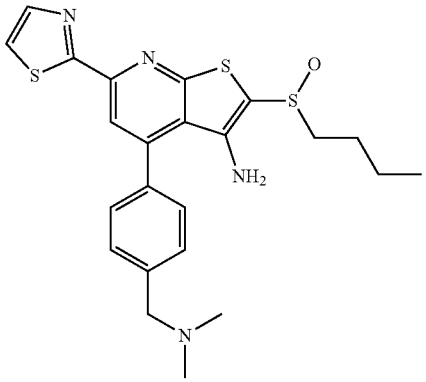

SW209513. 2-(butyl(11-oxidanyl)-13-sulfanyl)-4-(4-(((dimethylamino)methyl)phenyl)-6-(thiazol-2-yl)thieno[2,3-b]pyridin-3-amine. To a solution of 4-(3-amino-2-(butyl(11-oxidanyl)-13-sulfanyl)-6-(thiazol-2-yl)thieno[2,3-b]pyridin-4-yl)benzaldehyde (13.3 mg, 0.0301) in methanol (802.7 μL), dimethylamine (174 μL, 0.301 mmol, 2.0M in THF) and acetic acid (1.72 μL, 0.0301 mmol) were added and the reaction was stirred at room temperature for 90 minutes. The reaction was then cooled down to 0° C. and sodium cyanoborohydride (3.7 mg, 0.060 mmol) was added and the reaction stirred for 2 hours at this temperature before allowing to warm up to room temperature. After 24 hours, more sodium cyanoborohydride (2 eq) was added at 0° C. and left to stir at room temperature another 24 hours. Nitrogen was used to evaporate the solvent, giving a solid that was diluted with EtOAc and washed with saturated NaHCO$_3$. The organic layer was dried over Na$_2$SO$_4$, filtered, and concentrated under reduced pressure. The crude product was purified using flash chromatography (7% MeOH, 93% DCM) isolating the product in 13% yield. $^1$H NMR (400 MHz, CDCl$_3$) δ 8.07 (s, 1H), 7.93 (d, J=3.2 Hz, 1H), 7.51 (d, J=3.2 Hz, 1H), 7.49-7.41 (m, 4H), 4.67 (s, 2H), 3.55 (s, 2H), 3.36-3.25 (m, 1H), 3.13 (ddd, J=12.8, 9.0, 6.7 Hz, 1H), 2.30 (s, 6H), 1.78-1.68 (m, 2H), 1.55-1.44 (m, 2H), 0.95 (t, J=7.3 Hz, 3H). ESI-MS (m/z): 471.2 [M+H]$^+$.

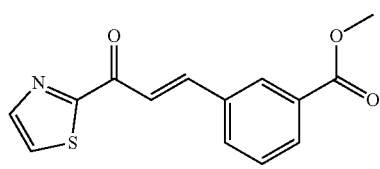 [SMILES: COC(=O)c1cccc(/C=C/C(=O)c2nccs2)c1]

Methyl (E)-3-(3-oxo-3-(thiazol-2-yl)prop-1-en-1-yl)benzoate. Followed procedure for methyl (E)-4-(3-oxo-3-(thiazol-2-yl)prop-1-en-1-yl)benzoate using methyl 3-formyl benzoate as the starting material. Purified the crude product using automated flash chromatography (50% EtOAc, 50% hexanes) isolating the product in 51% yield. $^1$H NMR (400 MHz, CDCl$_3$) δ 8.41-8.35 (m, 1H), 8.11-8.05 (m, 2H), 8.02 (d, J=1.3 Hz, 2H), 7.89-7.83 (m, 1H), 7.72 (d, J=3.0 Hz, 1H), 7.50 (t, J=7.8 Hz, 1H), 3.95 (s, 3H). ESI-MS (m/z): 274.1

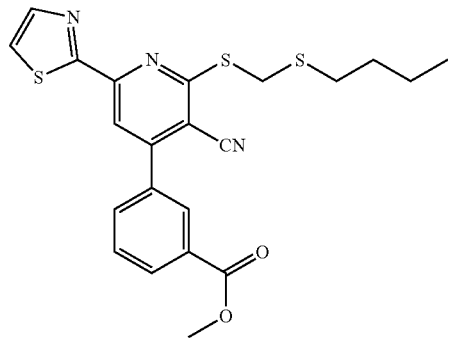 [SMILES: CCCCSCSc1nc(-c2nccs2)cc(-c2cccc(C(=O)OC)c2)c1C#N]

Methyl 3-(2-(((butylthio)methyl)thio)-3-cyano-6-(thiazol-2-yl)pyridin-4-yl)benzoate. Followed the procedure for methyl 4-(2-(((butylthio)methyl)thio)-3-cyano-6-(thiazol-2-yl)pyridin-4-yl)benzoate using methyl (E)-3-(3-oxo-3-(thiazol-2-yl)prop-1-en-1-yl)benzoate as the starting material. Isolated product in 87% yield. $^1$H NMR (400 MHz, CDCl$_3$) δ 8.32-8.26 (m, 1H), 8.20 (dt, J=7.9, 1.3 Hz, 1H), 8.04 (s, 1H), 7.99 (d, J=3.1 Hz, 1H), 7.85 (ddd, J=7.7, 2.0, 1.1 Hz, 1H), 7.62 (td, J=7.8, 0.6 Hz, 1H), 7.58 (d, J=3.1 Hz, 1H), 4.53 (s, 2H), 3.95 (s, 3H), 2.76 (t, J=7.3 Hz, 2H), 1.71-1.59 (m, 2H), 1.49-1.36 (m, 2H), 0.91 (t, J=7.3 Hz, 3H). ESI-MS (m/z): 456.1 [M+Z]$^+$.

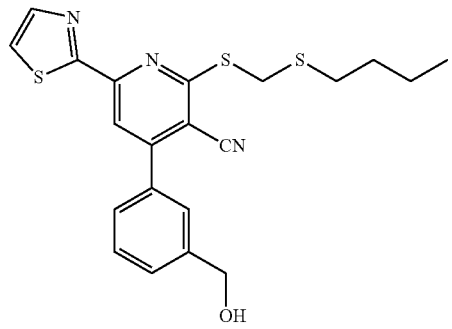 [SMILES: CCCCSCSc1nc(-c2nccs2)cc(-c2cccc(CO)c2)c1C#N]

2-(((butylthio)methyl)thio)-4-(3-(hydroxymethyl)phenyl)-6-(thiazol-2-yl)nicotinonitrile. Followed procedure for 2-(((butylthio)methyl)thio)-4-(4-(hydroxymethyl)phenyl)-6-(thiazol-2-yl)nicotinonitrile using methyl 3-(2-(((butylthio)methyl)thio)-3-cyano-6-(thiazol-2-yl)pyridin-4-yl)benzoate as the starting material. Isolated product in 84% yield. $^1$H NMR (400 MHz, CDCl$_3$) δ 8.00 (s, 1H), 7.95 (d, J=3.1 Hz, 1H), 7.64-7.61 (m, 1H), 7.58-7.52 (m, 2H), 7.52-7.46 (m, 2H), 4.76 (s, 2H), 4.50 (s, 2H), 2.74 (t, J=7.3 Hz, 2H), 1.69-1.54 (m, 2H), 1.46-1.37 (m, 2H), 0.90 (t, J=7.3 Hz, 3H). ESI-MS (m/z): 428.1 [M+H]$^+$.

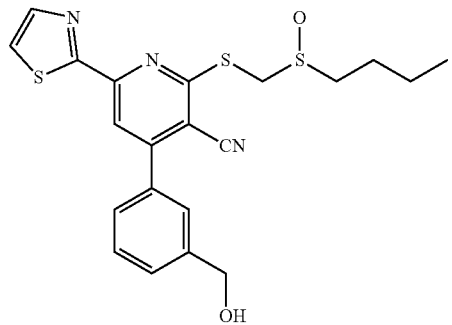

2-(((butyl(11-oxidanyl)-13-sulfanyl)methyl)thio)-4-(3-(hydroxymethyl)phenyl)-6-(thiazol-2-yl)nicotinonitrile. Followed standard oxidation procedure using 2-(((butylthio)methyl)thio)-4-(3-(hydroxymethyl)phenyl)-6-(thiazol-2-yl)nicotinonitrile as the starting material. Isolated product in 88% yield. $^1$H NMR (400 MHz, CDCl$_3$) δ 8.08 (s, 1H), 7.96 (d, J=3.1 Hz, 1H), 7.68-7.64 (m, 1H), 7.58-7.53 (m, 2H), 7.53-7.48 (m, 2H), 4.77 (s, 2H), 4.71 (d, J=13.1 Hz, 1H), 4.36 (d, J=13.1 Hz, 1H), 2.96 (dt, J=13.0, 8.2 Hz, 1H), 2.81 (dt, J=13.0, 7.3 Hz, 1H), 1.82 (p, J=7.7 Hz, 2H), 1.58-1.40 (m, 2H), 0.94 (t, J=7.3 Hz, 3H). ESI-MS (m/z): 444.1 [M+H]$^+$.

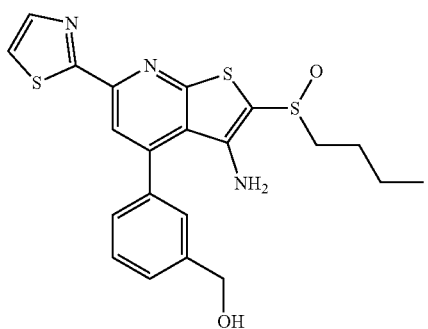

SW209418 (3-(3-amino-2-(butyl(11-oxidanyl)-13-sulfanyl)-6-(thiazol-2-yl)thieno[2,3-b]pyridin-4-yl)phenyl)methanol. Followed procedure for SW209510 using 2-(((butyl(11-oxidanyl)-13-sulfanyl)methyl)thio)-4-(3-(hydroxymethyl)phenyl)-6-(thiazol-2-yl)nicotinonitrile as the starting material to give an isolated product in 68% yield. $^1$H NMR (400 MHz, CDCl$_3$) δ 8.01 (s, 1H), 7.88 (d, J=3.1 Hz, 1H), 7.55-7.30 (m, 5H), 4.75 (s, 2H), 4.62 (s, 2H), 3.26 (ddd, J=12.8, 9.1, 6.0 Hz, 1H), 3.09 (ddd, J=12.8, 9.2, 6.5 Hz, 1H), 1.76-1.61 (m, 2H), 1.51-1.38 (m, 2H), 0.92 (t, J=7.3 Hz, 3H). ESI-MS (m/z): 444.1 [M+H]$^+$.

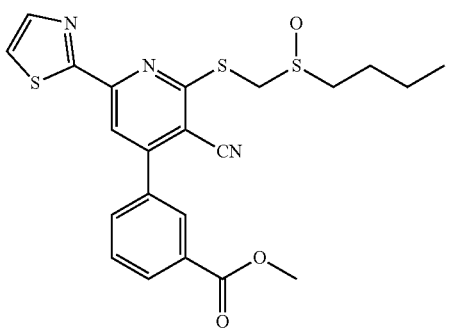

Methyl 3-(2-(((butyl(11-oxidanyl)-13-sulfanyl)methyl)thio)-3-cyano-6-(thiazol-2-yl)pyridin-4-yl)benzoate. Followed standard oxidation procedure, using methyl 3-(2-(((butylthio)methyl)thio)-3-cyano-6-(thiazol-2-yl)pyridin-4-yl)benzoate as the starting material. This gave an isolated product in 86% yield. $^1$H NMR (400 MHz, CDCl$_3$) δ 8.27 (t, J=1.6 Hz, 1H), 8.17 (dt, J=7.9, 1.4 Hz, 1H), 8.09 (s, 1H), 7.97 (d, J=3.1 Hz, 1H), 7.82 (ddd, J=7.7, 1.9, 1.1 Hz, 1H), 7.61 (m, 1H), 7.58 (d, J=3.1 Hz, 1H), 4.72 (d, J=13.1 Hz, 1H), 4.42 (d, J=13.1 Hz, 1H), 3.92 (s, 3H), 2.95 (dt, J=13.0, 8.1 Hz, 1H), 2.83 (dt, J=13.0, 7.3 Hz, 1H), 1.81 (p, J=7.7 Hz, 2H), 1.57-1.36 (m, 2H), 0.92 (t, J=7.3 Hz, 3H). ESI-MS (m/z): 472.1 [M+H]$^+$.

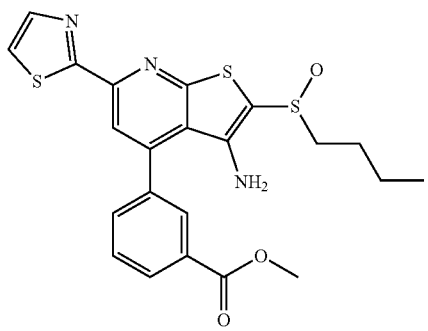

SW209416. Methyl 3-(3-amino-2-(butyl(11-oxidanyl)-13-sulfanyl)-6-(thiazol-2-yl)thieno[2,3-b]pyridin-4-yl)benzoate. Followed procedure for SW209510 using methyl 3-(2-(((butyl(11-oxidanyl)-13-sulfanyl)methyl)thio)-3-cyano-6-(thiazol-2-yl)pyridin-4-yl)benzoate as the starting material to give an isolated product in 68% yield. $^1$H NMR (400 MHz, CDCl$_3$) δ 8.26-8.11 (m, 2H), 8.02 (s, 1H), 7.89 (d, J=3.2 Hz, 1H), 7.76-7.56 (m, 2H), 7.49 (d, J=3.1 Hz, 1H), 4.54 (s, 2H), 3.93 (s, 3H), 3.27 (ddd, J=12.8, 9.0, 6.2 Hz, 1H), 3.09 (ddd, J=12.8, 9.0, 6.7 Hz, 1H), 1.79-1.61 (m, 2H), 1.55-1.39 (m, 2H), 0.92 (t, J=7.3 Hz, 3H). ESI-MS (m/z 472.1 [M+H]$^+$.

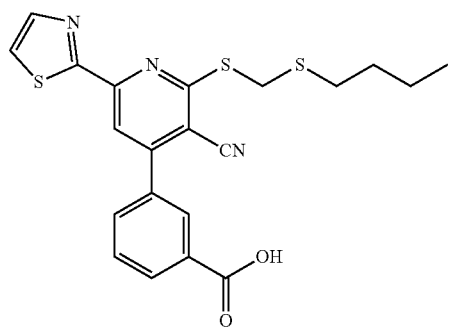 [SMILES: CCCCSCSc1nc(-c2nccs2)cc(-c2cccc(C(=O)O)c2)c1C#N]

Standard Hydrolysis Procedure of Ester to Carboxylic Acid: 3-(2-(((butylthio)methyl)thio)-3-cyano-6-(thiazol-2-yl)pyridin-4-yl)benzoic acid. THF (214.3 μL), MeOH (214.3 μL), and H$_2$O (71.4 μL) were added to methyl 3-(2-(((butylthio)methyl)thio)-3-cyano-6-(thiazol-2-yl)pyridin-4-yl)benzoate (50 mg, 0.110 mmol), and last LiOH (7.9 mg, 0.329 mmol) was added. The solution was stirred at room temperature for 3 hours. The reaction mixture was diluted with EtOAc and washed with 1M HCl. The organic layer was dried over Na$_2$SO$_4$, filtered, and concentrated under reduced pressure. The resulting product gave a 94% yield. $^1$H NMR (400 MHz, CDCl$_3$) δ 8.41 (t, J=1.7 Hz, 1H), 8.26 (dt, J=8.0, 1.3 Hz, 1H), 8.13 (s, 1H), 8.02 (d, J=3.1 Hz, 1H), 7.94-7.89 (m, 1H), 7.65 (t, J=7.8 Hz, 1H), 7.59 (d, J=3.1 Hz, 1H), 4.53 (s, 2H), 2.75 (t, J=7.3 Hz, 2H), 1.64 (p, J=7.5 Hz, 2H), 1.43 (m, 2H), 0.91 (t, J=7.3 Hz, 3H). ESI-MS (m/z): 442.1 [M+Z]+.

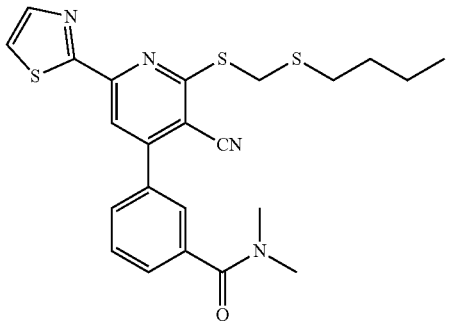 [SMILES: CCCCSCSc1nc(-c2nccs2)cc(-c2cccc(C(=O)N(C)C)c2)c1C#N]

Standard amide bond coupling procedure: 3-(2-(((butyl-thio)methyl)thio)-3-cyano-6-(thiazol-2-yl)pyridin-4-yl)-N,N-dimethylbenzamide. Dimethylamine hydrochloride (9.25 mg, 0.114 mmol) was added to a solution of 3-(2-(((butylthio)methyl)thio)-3-cyano-6-(thiazol-2-yl)pyridin-4-yl)benzoic acid (45.6 mg, 0.103 mmol), HATU (43.2 mg, 0.114 mmol), and DMF (266 µL) followed by DIPEA (36 µL, 0.21 mmol). The solution was stirred at room temperature for 3 hours, then diluted with EtOAc and washed with water. The organic layer was dried over Na₂SO₄, filtered, and concentrated under reduced pressure. The isolated solid gave an 86% yield. $^1$H NMR (400 MHz, CDCl₃) δ 7.99 (s, 1H), 7.97 (d, J=3.1 Hz, 1H), 7.69-7.61 (m, 2H), 7.58-7.51 (m, 3H), 4.50 (s, 2H), 3.11 (s, 3H), 3.03 (s, 3H), 2.73 (t, J=7.3 Hz, 2H), 1.62 (p, J=7.4 Hz, 2H), 1.40 (h, J=7.3 Hz, 2H), 0.89 (t, J=7.3 Hz, 3H). ESI-MS (m/z): 469.1 [M+H]+.

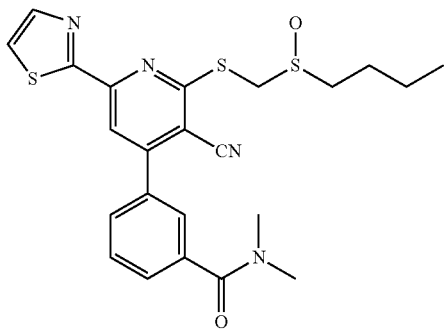

3-(2-(((butyl(11-oxidanyl)-13-sulfanyl)methyl)thio)-3-cyano-6-(thiazol-2-yl)pyridin-4-yl)-N,N-dimethylbenzamide. Followed standard oxidation procedure, using 3-(2-(((butylthio)methyl)thio)-3-cyano-6-(thiazol-2-yl)pyridin-4-yl)-N,N-dimethylbenzamide as the starting material to give the isolated product in 96% yield. $^1$H NMR (400 MHz, Chloroform-d) δ 8.08 (s, 1H), 7.98 (d, J=3.1 Hz, 1H), 7.70-7.64 (m, 2H), 7.61-7.54 (m, 3H), 4.70 (d, J=13.1 Hz, 1H), 4.42 (d, J=13.1 Hz, 1H), 3.11 (s, 3H), 3.03 (s, 3H), 2.95 (dt, J=12.9, 8.2 Hz, 1H), 2.81 (dt, J=12.9, 7.2 Hz, 1H), 1.82 (p, J=7.7 Hz, 2H), 1.56-1.36 (m, 2H), 0.93 (t, J=7.3 Hz, 3H). ESI-MS (m/z): 485.1 [M+H]+.

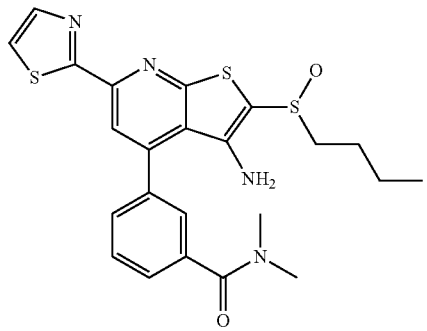

SW209417. 3-(3-amino-2-(butyl(11-oxidanyl)-13-sulfanyl)-6-(thiazol-2-yl)thieno[2,3-b]pyridin-4-yl)-N,N-dimethylbenzamide. Followed procedure for SW209510 using 3-(2-(((butyl(11-oxidanyl)-13-sulfanyl)methyl)thio)-3-cyano-6-(thiazol-2-yl)pyridin-4-yl)-N,N-dimethylbenzamide as the starting material to give the isolated product in 63% yield. $^1$H NMR (400 MHz, Chloroform-d) δ 8.02 (s, 1H), 7.90 (d, J=3.1 Hz, 1H), 7.62-7.51 (m, 4H), 7.49 (d, J=3.1 Hz, 1H), 4.59 (s, 2H), 3.27 (ddd, J=12.8, 9.0, 6.1 Hz, 1H), 3.15-2.97 (m, 7H), 1.78-1.64 (m, 2H), 1.55-1.39 (m, 2H), 0.93 (t, J=7.3 Hz, 3H).

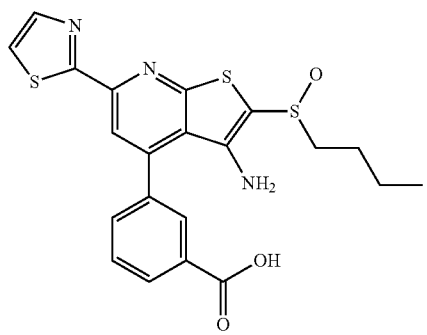

SW209419. 3-(3-amino-2-(butyl(11-oxidanyl)-13-sulfanyl)-6-(thiazol-2-yl)thieno[2,3-b]pyridin-4-yl)benzoic acid. Using SW209416 as the starting material, follow the standard hydrolysis procedure of ester to carboxylic acid. This gave an isolated yield of 98%. $^1$H NMR (400 MHz, (CD₃)₂CO)) δ 8.28-8.18 (m, 2H), 8.07 (s, 1H), 7.98 (d, J=3.2 Hz, 1H), 7.90 (d, J=7.6 Hz, 1H), 7.82 (d, J=3.2 Hz, 1H), 7.76 (t, J=7.6 Hz, 1H), 4.82 (s, 2H), 3.20 (ddd, J=12.8, 8.8, 6.3 Hz, 1H), 3.09 (ddd, J=12.9, 8.8, 6.8 Hz, 1H), 1.76-1.66 (m, 2H), 1.54-1.43 (m, 2H), 0.92 (t, J=7.3 Hz, 3H). ESI-MS (m/z): 458.1 [M+H]+.

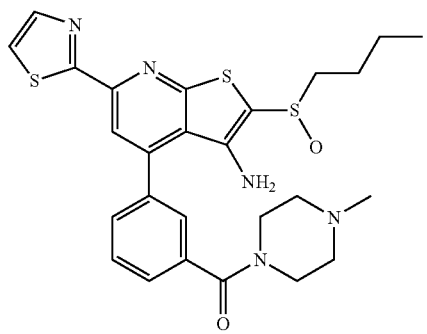

SW209420. (3-(3-amino-2-(butyl(11-oxidanyl)-13-sulfanyl)-6-(thiazol-2-yl)thieno[2,3-b]pyridin-4-yl)phenyl)(4-methylpiperazin-1-yl)methanone. Followed the standard amide bond coupling procedure, using SW209419 as the starting material and 1-methylpiperazine as the substrate. The product was purified using automated flash chromatography, recovering 38% isolated yield. $^1$H NMR (400 MHz, CDCl$_3$) δ 8.04 (s, 1H), 7.91 (d, J=3.2 Hz, 1H), 7.65-7.42 (m, 5H), 4.56 (s, 2H), 3.79 (m, 2H), 3.46 (m, 2H), 3.28 (ddd, J=12.9, 8.9, 6.1 Hz, 1H), 3.10 (ddd, J=12.9, 9.2, 7.0 Hz, 1H), 2.48 (m, 2H), 2.35 (m, 2H), 2.31 (s, 3H), 1.77-1.58 (m, 2H), 1.54-1.38 (m, 2H), 0.94 (t, J=7.3 Hz, 3H). ESI-MS (m/z): 540.2 [M+H]$^+$.

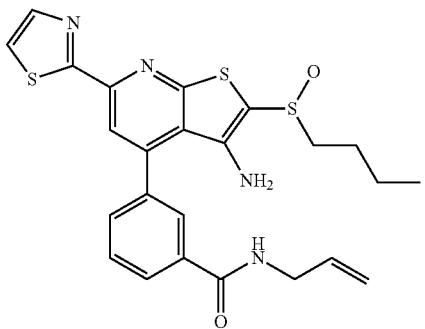

SW209508. N-allyl-3-(3-amino-2-(butyl(11-oxidanyl)-13-sulfanyl)-6-(thiazol-2-yl)thieno[2,3-b]pyridin-4-yl)benzamide. Followed the standard amide bond coupling procedure using SW209419 as the starting material and allylamine as the substrate. The isolated product gave a 92% yield. $^1$H NMR (400 MHz, CDCl$_3$) δ 8.05-7.91 (m, 3H), 7.88 (d, J=3.2 Hz, 1H), 7.68-7.53 (m, 2H), 7.48 (d, J=3.1 Hz, 1H), 6.01-5.82 (m, 1H), 5.25 (d, J=17.2 Hz, 1H), 5.16 (dd, J=10.2, 1.4 Hz, 1H), 4.52 (s, 2H), 4.19-3.98 (m, 2H), 3.24 (ddd, J=12.8, 9.0, 5.9 Hz, 1H), 3.16-2.98 (m, 1H), 1.78-1.56 (m, 2H), 1.57-1.38 (m, 2H), 0.92 (t, J=7.3 Hz, 3H). ESI-MS (m/z): 497.1 [M+H]$^+$.

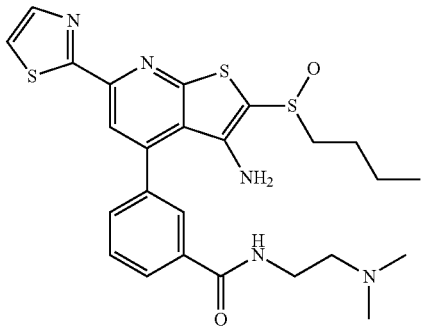

SW209509. 3-(3-amino-2-(butyl(11-oxidanyl)-13-sulfanyl)-6-(thiazol-2-yl)thieno[2,3-b]pyridin-4-yl)-N-(2-(dimethylamino)ethyl)benzamide. Followed the standard amide bond coupling procedure, using SW209419 as the starting material and N,n-dimethyl-ethane-1,2-diamine as the substrate. The reaction mixture was diluted with EtOAc and washed with water and NaOH was added to neutralize the pH. The organic layer was then dried over Na$_2$SO$_4$, filtered, and concentrated under reduced pressure. The crude product was purified using automated flash chromatography (93% DCM, 2% Et$_3$N, 5% MeOH) to give product in 70% isolated yield. $^1$H NMR (400 MHz, CDCl$_3$) δ 8.02 (s, 1H), 8.00-7.95 (m, 2H), 7.88 (d, J=3.2 Hz, 1H), 7.63-7.54 (m, 2H), 7.48 (d, J=3.2 Hz, 1H), 4.55 (s, 2H), 3.59-3.50 (m, 2H), 3.25 (ddd, J=12.8, 9.0, 6.0 Hz, 1H), 3.08 (ddd, J=12.8, 9.1, 6.6 Hz, 1H), 2.58 (t, J=5.9 Hz, 2H), 2.28 (s, 6H), 1.77-1.61 (m, 2H), 1.53-1.43 (m, 2H), 0.92 (t, J=7.3 Hz, 3H). ESI-MS (m/z): 528.2 [M+H]$^+$.

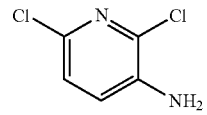

2,6-dichloropyridin-3-amine. The acetone/water mixture (297 mL, 5:1) was added to 2,6-dichloro-3-nitropyridine (3.0 g, 0.016 mol) followed by Zn (10.17 g, 0.1550 mol) and NH$_4$Cl (12.44 g, 0.2325 mol). The solution stirred at room temperature overnight. The reaction mixture was then filtered through celite and the filtrate was extracted with EtOAc. With the help of brine, the organic layer was separated, dried over MgSO$_4$ and concentrated under reduced pressure. $^1$H NMR (400 MHz, CDCl$_3$) δ 7.07 (d, J=8.2 Hz, 1H), 7.02 (d, J=8.3 Hz, 1H), 4.11 (s, 2H). ESI-MS (m/z): 163.0.

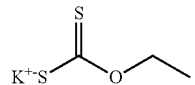

Potassium Ethyl Xanthate. A potassium ethoxide solution was prepared by dissolving KOH (6.5 g, 0.12 mol) in EtOH (63.4 mL). Carbon disulfide (7.14 mL, 0.118 mol) was added to the solution slowly with continuous stirring. The reaction mixture was cooled down to 5° C., filtered, and the precipitate was recrystallized twice from warm ethanol.

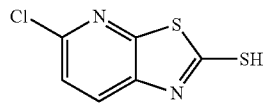 [SMILES: Sc1nc2ccc(Cl)nc2s1]

5-Chlorothiazolo[5,4-b]pyridine-2-thiol. Potassium ethyl xanthate (1.9 g, 0.012 mol) and anhydrous N-methyl-2-pyrrolidone (14.1 mL) were added to 2,6-dichloropyridin-3-amine (1.0 g, 0.0061 mol) under N$_2$. The solution was refluxed (170° C.) for 3.5 hours. The reaction mixture was cooled down to room temperature, acidified to pH 5 using AcOH, diluted in EtOAc, and washed several times with H$_2$O. The organic layer was separated, dried over MgSO$_4$, and concentrated under reduced pressure. This gave a red solid in 18% yield. $^1$H NMR (400 MHz, Chloroform-d) δ 7.41 (d, J=8.4 Hz, 1H), 7.30 (d, J=8.4 Hz, 1H). ESI-MS (m/z): 202.9.

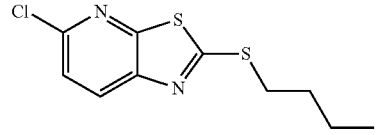

2-(Butylthio)-5-chlorothiazolo[5,4-b]pyridine. K$_2$CO$_3$ (75 mg, 0.54 mmol), 1-bromobutane (53.3 µL, 0.493 mmol), 18-Crown-6 (13.2 mg, 0.0493 mmol), and DMF (3.4 mL) were added to 5-chlorothiazolo[5,4-b]pyridine-2-thiol and the solution was heated at 80° C. for 3 hours. The solution was diluted with EtOAc, washed with H₂O, and the organic layer was separated, dried over MgSO₄, and concentrated under reduced pressure. The crude product was purified using flash chromatography to give 76% isolated yield. ¹H NMR (400 MHz, CDCl₃) δ 7.93 (d, J=8.5 Hz, 1H), 7.30 (d, J=8.5 Hz, 1H), 3.31 (t, J=7.3 Hz, 2H), 1.76 (p, J=7.5 Hz, 2H), 1.52-1.39 (m, 2H), 0.93 (t, J=7.3 Hz, 3H). ESI-MS (m/z): 259.0 [M+H]⁺.

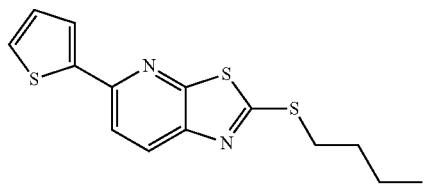 [SMILES: CCCCSc1nc2ccc(-c3cccs3)nc2s1]

2-(Butylthio)-5-(thiophen-2-yl)thiazolo[5'4-b]pyridine. 2-Thienylboronic acid (49.4 mg, 0.386 mmol), CsCO₃ (126 mg, 0.386 mmol), Pd(dppf)Cl₂ (15.8 mg, 0.0193 mmol), CuCl (19.1 mg, 0.193 mmol) and DMF (1 mL) were added to 2-(butylthio)-5-chlorothiazolo[5,4-b]pyridine (50 mg, 0.19 mmol) under N₂. The reaction mixture was heated to 100° C. for 30 minutes. Then the N₂ was disconnected and the vial was capped and sealed with teflon tape and allowed to stir overnight. The reaction mixture was diluted in EtOAc, washed with H₂O, and the organic layer was separated, dried over MgSO₄, filtered, and concentrated under reduced pressure to give the product in 31% isolated yield. ¹H NMR (400 MHz, CDCl₃) δ 7.98 (d, J=8.6 Hz, 1H), 7.63 (dd, J=3.8, 1.1 Hz, 1H), 7.51 (dd, J=5.1, 1.1 Hz, 1H), 7.23 (d, J=8.6 Hz, 1H), 7.14 (dd, J=5.0, 3.8 Hz, 1H), 3.24 (t, J=7.3 Hz, 2H), 1.78-1.66 (m, 2H), 1.57-1.41 (m, 2H), 0.96 (t, J=7.4 Hz, 3H). ESI-MS (m/z): 307.0 [M+H]⁺.

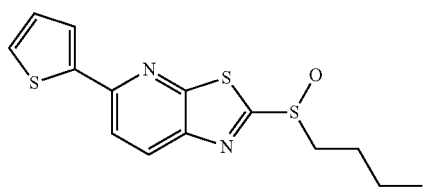

SW208599. 2-(butyl(11-oxidanyl)-13-sulfanyl)-5-(thiophen-2-yl)thiazolo[5,4-b]pyridine. CHCl₃ (142 μL), AcOH (142 μL), and H₂O₂ (12.0 μL, 0.118 mmol, 30% solution in H₂O) were added to 2-(butylthio)-5-(thiophen-2-yl)thiazolo[5,4-b]pyridine (18 mg. 0.059 mmol) and heated at 35° C. for 2.5 hours. The solution was diluted with EtOAc and washed with saturated NaHCO₃. The organic layer was separated, dried over MgSO₄, filtered, and concentrated under reduced pressure to give product in 60% isolated yield. ¹H NMR (400 MHz, CDCl₃) δ 8.39 (d, J=8.4 Hz, 1H), 8.06 (d, J=8.4 Hz, 1H), 7.74 (dd, J=3.8, 1.1 Hz, 1H), 7.61 (dd, J=5.0, 1.1 Hz, 1H), 7.19 (dd, J=5.0, 3.8 Hz, 1H), 3.15 (ddd, J=13.3, 9.8, 6.0 Hz, 1H), 2.96 (ddd, J=13.3, 9.9, 4.9 Hz, 1H), 1.98-1.80 (m, 1H), 1.60-1.52 (m, 1H), 1.52-1.37 (m, 2H), 0.93 (t, J=7.2 Hz, 3H). ESI-MS (m/z): 323.0 [M+H]⁺.

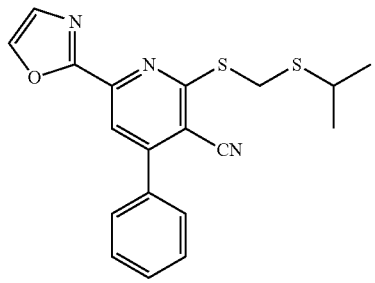 [SMILES: CC(C)SCSc1nc(-c2ncco2)cc(-c2ccccc2)c1C#N]

2-(((Isopropylthio)methyl)thio)-6-(oxazol-2-yl)-4-phenylnicotinonitrile. Follow the standard alkylation procedure, using (chloromethyl)(isopropyl)sulfane as the alkylating substrate, and 6-(oxazol-2-yl)-4-phenyl-2-thioxo-1,2-dihydropyridine-3-carbonitrile as the starting material. The crude product was purified using flash chromatography to give a solid in 62% isolated yield. ¹H NMR (400 MHz, CDCl₃) δ 7.97 (s, 1H), 7.88 (d, J=0.7 Hz, 1H), 7.67-7.61 (m, 2H), 7.56-7.50 (m, 3H), 7.37 (d, J=0.8 Hz, 1H), 4.63 (s, 2H), 3.24 (hept, J=6.7 Hz, 1H), 1.35 (d, J=6.7 Hz, 6H). ESI-MS (m/z): 368.0 [M+H]⁺.

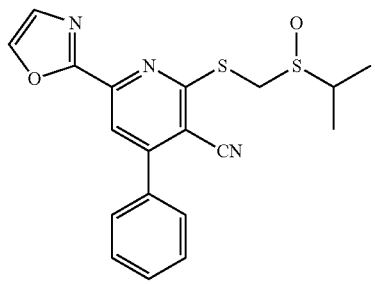

2-(((Isopropyl(11-oxidanyl)-13-sulfanyl)methyl)thio)-6-(oxazol-2-yl)-4-phenylnicotinonitrile. Follow the standard oxidation procedure using 2-(((isopropylthio)methyl)thio)-6-(oxazol-2-yl)-4-phenylnicotinonitrile as the starting material. Recovered quatitative isolated yield. ¹H NMR (400 MHz, CDCl₃) δ 8.03 (s, 1H), 7.88 (d, J=0.7 Hz, 1H), 7.67-7.61 (m, 2H), 7.58-7.50 (m, 3H), 7.39 (d, J=0.7 Hz, 1H), 4.79 (d, J=13.3 Hz, 1H), 4.55 (d, J=13.3 Hz, 1H), 3.18 (hept, J=6.9 Hz, 1H), 1.42 (d, J=1.5 Hz, 3H), 1.40 (d, J=1.3 Hz, 3H). ESI-MS (m/z): 384.1 [M+H]⁺.

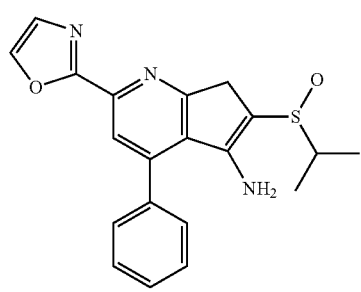

Standard Final Cyclization Procedure: SW208660. 2-(Isopropyl(11-oxidanyl)-13-sulfanyl)-6-(oxazol-2-yl)-4-phenylthieno[2,3-b]pyridin-3-amine. DMF (485 μL) and MeOH (244 μL) were added to 2-(((isopropyl(11-oxidanyl)-13-sulfanyl)methyl)thio)-6-(oxazol-2-yl)-4-phenylnicotinonitrile (47.2 mg, 0.123 mmol) dissolving it completely before KOH (4.1 mg in 100 μL of H₂O) was added to the solution. The reaction mixture was stirred at 35° C. for 40 minutes. The reaction mixture was diluted with EtOAc, washed with 10% AcOH and then washed with H₂O multiple times. The organic layer was separated, dried over MgSO₄, filtered, and concentrated under reduced pressure. The crude product was purified using flash chromatography to give product in 40% isolated yield ¹H NMR (400 MHz, CDCl₃) δ 7.99 (s, 1H), 7.85 (d, J=0.7 Hz, 1H), 7.56-7.44 (m, 5H), 7.34 (d, J=0.8 Hz, 1H), 4.69 (s, 2H), 3.41 (hept, J=6.8 Hz, 1H), 1.44 (d, J=6.8 Hz, 3H), 1.28 (d, J=6.9 Hz, 3H). ESI-MS (m/z): 384.1 [M+H]⁺.

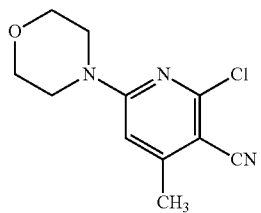 [SMILES: Cc1cc(N2CCOCC2)nc(Cl)c1C#N]

2-Chloro-4-methyl-6-morpholinonicotinonitrile. Anhydrous MeOH (3.97 mL) was added to 2,6-dichloro-4-methylnicotinonitrile (500 mg, 2.67 mmol) under N₂ and the mixture was cooled down to 0° C. Morpholine (473.7 μL, 5.493 mmol) was added dropwise to the solution and the solution stirred at room temperature overnight. The reaction mixture was filtered, washing the precipitate with MeOH (500 μL) and H₂O (3-4 mL). DCM was added to the precipitate, followed by MgSO₄, and the solution was filtered, then concentrated under reduced pressure. The crude producte was purified using automated flash chromatography to give product in 85% isolated yield. ¹H NMR (400 MHz, CDCl₃) δ 7.26 (s, 1H), 3.81-3.73 (m, 4H), 3.68-3.58 (m, 4H), 2.42 (d, J=0.8 Hz, 3H). ESI-MS (m/z): 238.1 [M+H]⁺.

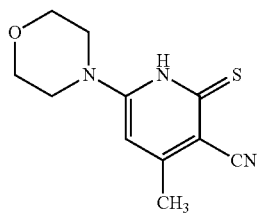 [SMILES: Cc1cc(N2CCOCC2)[nH]c(=S)c1C#N]

4-Methyl-6-morpholino-2-thioxo-1,2-dihydropyridine-3-carbonitrile. NaOME (73.6 mg, 1.36 mmol) and methyl 3-mercapiopropionate (151 μL, 1.363 mmol) were added to a solution of 2-chloro-4-methyl-6morpholinonicotinonitrile (324 mg, 1.36 mmol) in DMF (4.10 mL) and the reaction mixture was stirred at 80° C. for 1 hour. Once cooled down, the reaction mixture was diluted with EtOAc and washed with H₂O. The organic layer was separated, dried over MgSO4, filtered, and concentrated under reduced pressure to give a crude mixture of 1:1 starting material to product, which was carried forward to the next step. ESI (m/z): 322.1 [M+H]+. NaH (150.8 mg, 3.769 mmol, 60% in mineral oil) and THF (10 mL) were added to a flame dried flask under N2, followed by the crude product from the previous step dissolved in THF (10 mL). The reaction mixture was refluxed for 6 hours and addition NaH (2 eq) was and left refluxing overnight. EtOH (1.5 mL) was added then the reaction mixture was concentrated down under reduced pressure. H₂O (8 mL) was added and the solution was adjusted to pH 6 with concentrated HCl before filtering to leave a crude solid that was carried forward. ESI (m/z): 236.1 [M+H]+.

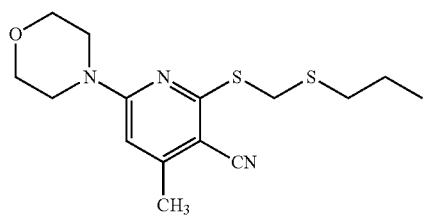 [SMILES: CCCSCSc1nc(N2CCOCC2)cc(C)c1C#N]

4-Methyl-6-morpholino-2-(((propylthio)methyl)thio) nicotinonitrile. Followed the standard alkylating procedure, using 4-methyl-6-morpholino-2-thioxo-1,2-dihydropyridine-3-carbonitrile as the starting material and (chloromethyl)(propyl)sulfane as the alkylating substrate. The crude product was carried forward. ESI (m/z): 324.1 [M+H]+.

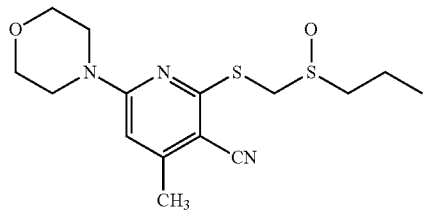

2-((((11-oxidanyl)(propyl)-13-sulfanyl)methyl)thio)-4-methyl-6-morpholinonicotinonitrile. Followed the standard oxidation procedure using 4-methyl-6-morpholino-2-(((propylthio)methyl)thio)nicotinonitrile as the starting material. The crude product was carried forward. ESI (m/z): 340.1 [M+H]⁺.

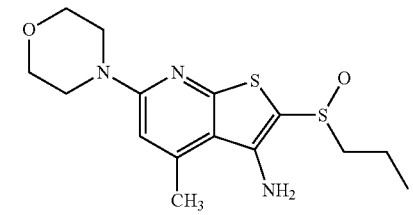

SW208663. 2-((11-oxidanyl)(propyl)-13-sulfanyl)-4-methyl-6-morpholinothieno[2,3-b]pyridin-3-amine. Followed the standard final cyclization procedure using 2-((((11-oxidanyl)(propyl)-13-sulfanyl)methyl)thio)-4-methyl-6-morpholinonicotinonitrile as the starting material. The crude product was purified by flash chromatography, and PTLC to give isolated product in 10% yield. ¹H NMR (400 MHz, CDCl₃) δ 6.36 (s, 1H), 4.91 (s, 2H), 3.85-3.76 (m, 4H), 3.63-3.58 (m, 4H), 3.32-3.18 (m, 1H), 3.09-2.99 (m, 1H), 2.65 (s, 3H), 1.81-1.66 (m, 2H), 1.07 (t, J=7.4 Hz, 3H). ESI (m/z): 340.1 [M+H]⁺.

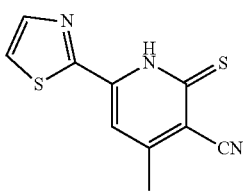

4-Methyl-6-(thiazol-2-yl)-2-thioxo-1,2-dihydropyridine-3-carbonitrile. Followed same procedure as 4-Methyl-6-morpholino-2-thioxo-1,2-dihydropyridine-3-carbonitrile, using methyl 3-((3-cyano-4-methyl-6-(thiazol-2-yl)pyridin-2-yl)thio)propanoate as the starting material. The crude product was carried forward. ESI-MS (m/z): 234.0 [M+H]⁺.

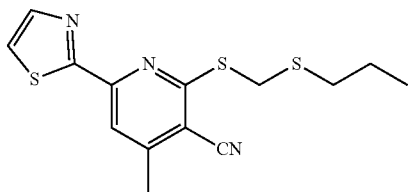 [SMILES: CCCSCSc1nc(-c2nccs2)cc(C)c1C#N]

4-Methyl-2-(((propylthio)methyl)thio)-6-(thiazol-2-yl)nicotinonitrile. Followed the standard alkylation procedure using 4-Methyl-6-(thiazol-2-yl)-2-thioxo-1,2-dihydropyridine-3-carbonitrile as the starting material, and (chloromethyl)(propyl)sulfane as the alkylating substrate. The crude product was purified using automated flash chromatography to give product in 23% isolated yield. $^1$H NMR (400 MHz, Chloroform-d) δ 7.96 (d, J=3.1 Hz, 1H), 7.83 (s, 1H), 7.54 (d, J=3.1 Hz, 1H), 4.47 (s, 2H), 2.70 (t, J=7.2 Hz, 2H), 2.55 (s, 3H), 1.67 (h, J=7.3 Hz, 2H), 0.99 (t, J=7.3 Hz, 3H). ESI-MS (m/z): 322.0 {M+H]⁺.

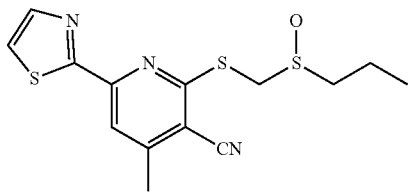

2-((((11-oxidanyl)(propyl)-13-sulfanyl)methyl)thio)-4-methyl-6-(thiazol-2-yl)nicotinonitrile. Followed the standard oxidation procedure using 4-methyl-2-(((propylthio)methyl)thio)-6-(thiazol-2-yl)nicotinonitrile as the starting material to give white solid in 91% isolated yield. $^1$H NMR (400 MHz, CDCl₃) δ 7.97 (d, J=3.1 Hz, 1H), 7.92 (s, 1H), 7.56 (d, J=3.2 Hz, 1H), 4.74 (d, J=13.2 Hz, 1H), 4.44 (d, J=13.1 Hz, 1H), 2.89 (m, 2H), 2.57 (s, 3H), 1.93-1.79 (m, 2H), 1.06 (t, J=7.4 Hz, 3H). ESI-MS (m/z): 338.0 [M+H]⁺.

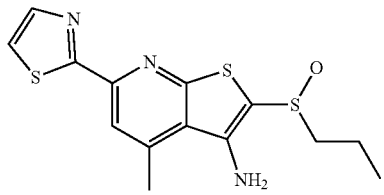

SW208661. 2-((11-oxidanyl)(propyl)-13-sulfanyl)-4-methyl-6-(thiazol-2-yl)thieno[2,3-b]pyridin-3-amine. Followed standard final cyclization procedure using 2-((((11-oxidanyl)(propyl)-13-sulfanyl)methyl)thio)-4-methyl-6-(thiazol-2-yl)nicotinonitrile as the starting material. Purified the crude product using flash chromatography to give 61% bright green isolated product. $^1$H NMR (400 MHz, CDCl₃) δ 7.95 (s, 1H), 7.93 (d, J=3.2 Hz, 1H), 7.48 (d, J=3.2 Hz, 1H), 5.16 (s, 2H), 3.37-3.23 (m, 1H), 3.16-3.05 (m, 1H), 2.85 (s, 3H), 1.83 (h, J=7.5 Hz, 2H), 1.11 (t, J=7.4 Hz, 3H). ESI-MS (m/z): 338.0 [M+H]⁺.

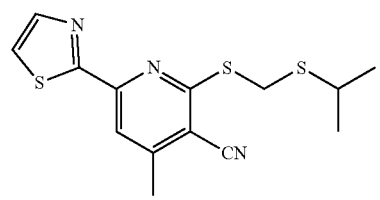 [SMILES: Cc1cc(-c2nccs2)nc(SCSC(C)C)c1C#N]

2-(((isopropylthio)methyl)thio)-4-methyl-6-(thiazol-2-yl)nicotinonitrile. Followed standard alkylating procedure using (chloromethyl)(isopropyl)sulfane as the alkylating substrate and 4-methyl-6-(thiazol-2-yl)-2-thioxo-1,2-dihydropyridine-3-carbonitrile as the starting material. Purified using automated flash chromatography to give product in 32% isolated yield. $^1$H NMR (400 MHz, CDCl3) δ 7.94 (d, J=3.2 Hz, 1H), 7.82 (s, 1H), 7.52 (d, J=3.2 Hz, 1H), 4.48 (s, 2H), 3.18 (hept, J=6.6 Hz, 1H), 2.54 (s, 3H), 1.31 (d, J=6.7 Hz, 6H). ESI-MS (m/z): 322.0 [M+H]+.

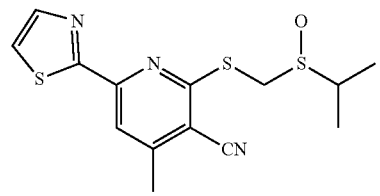

2-(((isopropyl(11-oxidanyl)-13-sulfanyl)methyl)thio)-4-methyl-6-(thiazol-2-yl)nicotinonitrile. Followed standard oxidation procedure using 2-(((isopropylthio)methyl)thio)-4-methyl-6-(thiazol-2-yl)nicotinonitrile as the starting material to give a solid product in 84% yield. $^1$H NMR (400 MHz, CDCl₃) δ 7.97 (d, J=3.1 Hz, 1H), 7.91 (s, 1H), 7.56 (d, J=3.1 Hz, 1H), 4.57 (d, J=13.3 Hz, 1H), 4.46 (d, J=13.3 Hz, 1H), 3.05 (hept, J=6.9 Hz, 1H), 2.57 (s, 3H), 1.38 (d, J=7.1 Hz, 3H), 1.36 (d, J=6.7 Hz, 3H). ESI-MS (m/z): 338.0 [M+H]⁺.

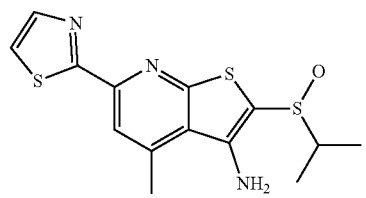

SW208664. 2-(Isopropyl(11-oxidanyl)-13-sulfanyl)-4-methyl-6-(thiazol-2-yl)thieno[2,3-b]pyridin-3-amine. Followed standard final cyclization procedure using 2-(((isopropyl(11-oxidanyl)-13-sulfanyl)methyl)thio)-4-methyl-6-(thiazol-2-yl)nicotinonitrile as the starting material. The crude product was purified using flash chromatography to give bright green oil/solid in 48% isolated yield. ¹H NMR (400 MHz, Chloroform-d) δ 7.93 (s, 1H), 7.92 (d, J=3.2 Hz, 1H), 7.46 (d, J=3.2 Hz, 1H), 3.38 (hept, J=6.9 Hz, 1H), 2.84 (s, 3H), 1.46 (d, J=6.8 Hz, 3H), 1.29 (d, J=6.8 Hz, 3H). ESI-MS (m/z): 338.0 [M+H]⁺.

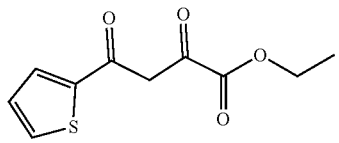

Ethyl 2,4-dioxo-4-(thiophen-2-yl)butanoate. 2-Acetylthiophene (1.71 mL, 0.0159 mol) was added to a solution of NaOEt (730 mg Na cubes in 50 mL of EtOH) and the solution was cooled to 0° C. for 1-2 hours then diethyl oxylate (3.2 ᵐL) was added to the solution. This was left to stir at room temperature overnight. The reaction mixture was diluted with EtOAc and H₂O with a little brine to assist the separation. The organic layer was collected, dried with MgSO₄, filtered, and concentrated under reduced pressure. The crude product was purified using automated flash chromatography giving an oil product with 23% yield. ESI-MS (m/z): 227.0 [M+H]⁺.

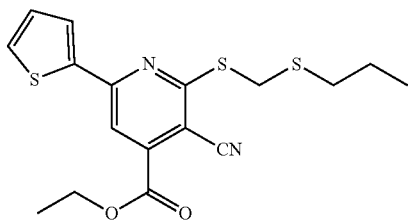 [SMILES: CCCSCSc1nc(-c2cccs2)cc(C(=O)OCC)c1C#N]

Ethyl 3-cyano-2-(((propylthio)methyl)thio)-6-(thiophen-2-yl)isonicotinate. 2-Cyanothioacetamide (250.6 mg, 2.503 mmol) and ethyl 2,4-dioxo-4-(thiophen-2-yl)butanoate (565.7 mg, 2.503 mmol) were dissolved in EtOH (7.46 mL) under gentle heating (40° C.), then Et₃N (174.5 μL, 1.251 mmol) was added drop wise to the stirring solution. The reaction mixture was heated at 60° C. and after 3 hours was concentrated down under reduced pressure and the crude product was carried forward to the next step. Followed standard alkylating procedure using ethyl 3-cyano-6-(thiophen-2-yl)-2-thioxo-1,2-dihydropyridine-4-carboxylate as the starting material and (chloromethyl)(propyl)sulfane as the alkylating reagent. The crude product was purified twice using automated flash chromatography (20% EtOAc, 80% hexanes) to give 34% isolated product. ¹H NMR (400 MHz, CDCl₃) δ 7.70 (s, 1H), 7.60 (dd, J=3.8, 1.1 Hz, 1H), 7.44 (dd, J=5.1, 1.1 Hz, 1H), 7.04 (dd, J=5.0, 3.8 Hz, 1H), 4.38 (q, J=7.2 Hz, 2H), 4.32 (s, 2H), 2.59 (t, J=7.2 Hz, 2H), 1.57 (h, J=7.4 Hz, 2H), 1.36 (t, J=7.1 Hz, 3H), 0.89 (t, J=7.3 Hz, 3H). ESI-MS (m/z): 378.9 [M+H]⁺.

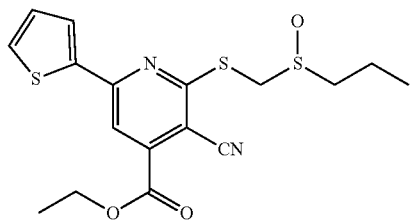

Ethyl 2-((((11-oxidanyl)(propyl)-13-sulfanyl)methyl)thio)-3-cyano-6-(thiophen-2-yl)isonicotinate. Followed standard oxidation procedure using ethyl 3-cyano-2-(((propylthio)methyl)thio)-6-(thiophen-2-yl)isonicotinate as the starting material to give a solid with quantitative yield. ¹H NMR (400 MHz, CDCl₃) δ 7.86 (s, 1H), 7.72 (dd, J=3.8, 1.1 Hz, 1H), 7.53 (dd, J=5.0, 1.1 Hz, 1H), 7.11 (dd, J=5.0, 3.8 Hz, 1H), 4.68 (d, J=13.2 Hz, 1H), 4.49 (d, J=13.2 Hz, 1H), 4.43 (q, J=7.1 Hz, 2H), 2.96-2.82 (m, 2H), 1.87-1.75 (m, 2H), 1.40 (t, J=7.2 Hz, 3H), 1.02 (t, J=7.4 Hz, 3H). ESI-MS (m/z): 394.9 [M+H]⁺.

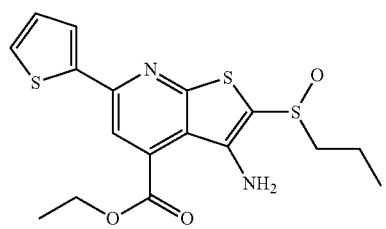

SW208781. Ethyl 2-((11-oxidanyl)(propyl)-13-sulfanyl)-3-amino-6-(thiophen-2-yl)thieno[2,3-b]pyridine-4-carboxylate. t-BuOK (74.1 mg, 0.661 mmol) was added to a solution of ethyl 2-((((11-oxidanyl)(propyl)-13-sulfanyl)methyl)thio)-3-cyano-6-(thiophen-2-yl)isonicotinate (433.7 mg, 1.101 mmol) in DMF (4.3 mL) and the solution stirred for 40 minutes at 35° C. More t-BuOK (74.1 mg, 0.661 mmol) was added and allowed to stir at 35° C. for an hour. The reaction mixture was diluted with EtOAc and washed with 10% AcOH, and then multiple times with H₂O. The organic layer was separated, dried over MgSO₄, filtered, and concentrated under reduced pressure. The crude product was purified using flash chromatography to give product in 30% isolated yield. ¹H NMR (400 MHz, CDCl₃) δ 8.01 (s, 1H), 7.69 (dd, J=3.8, 1.1 Hz, 1H), 7.46 (dd, J=5.0, 1.1 Hz, 1H), 7.11 (dd, J=5.0, 3.8 Hz, 1H), 6.09 (s, 2H), 4.49 (q, J=7.1 Hz, 2H), 3.36-3.22 (m, 1H), 3.15-3.00 (m, 1H), 1.87-1.68 (m, 2H), 1.47 (t, J=7.1 Hz, 3H), 1.07 (t, J=7.4 Hz, 3H). ESI-MS (m/z): 394.9 [M+H]⁺.

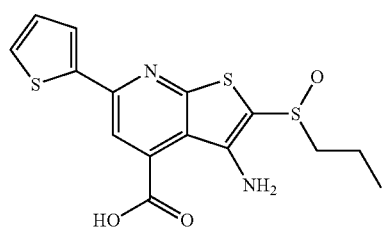

SW208782. 2-((11-oxidanyl)(propyl)-13-sulfanyl)-3-amino-6-(thiophen-2-yl)thieno[2,3-b]pyridine-4-carboxylic acid. Followed the standard hydrolysis procedure using SW208781 as the starting material which gave product in 40% isolated yield. ¹H NMR (400 MHz, C₃D7NO) δ 8.56 (s, 1H), 8.29 (d, J=3.7 Hz, 1H), 8.19 (s, 1H), 7.99 (d, J=5.0 Hz, 1H), 7.47-7.41 (m, 1H), 3.36 (ddd, J=12.8, 8.4, 6.1 Hz, 1H), 3.24 (ddd, J=12.8, 8.6, 6.8 Hz, 1H), 1.98-1.85 (m, 2H), 1.23 (t, J=7.4 Hz, 3H). ESI-MS (m/z): 366.8.

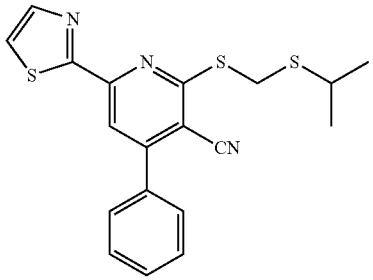 [SMILES: CC(C)SCSc1nc(-c2nccs2)cc(-c2ccccc2)c1C#N]

2-(((isopropylthio)methyl)thio)-4-phenyl-6-(thiazol-2-yl)nicotinonitrile. Followed the standard alkylation procedure using 4-phenyl-6-(thiazol-2-yl)-2-thioxo-1,2-dihydropyridine-3-carbonitrile as the starting material and (chloromethyl)(isopropyl)sulfane as the alkylating reagent. This was purified using automated flash chromatography to give product in 72% isolated yield. ¹H NMR (400 MHz, CDCl₃) δ 8.03 (s, 1H), 7.98 (d, J=3.1 Hz, 1H), 7.70-7.62 (m, 2H), 7.57 (d, J=3.1 Hz, 1H), 7.56-7.48 (m, 3H), 4.56 (s, 2H), 3.24 (hept, J=6.7 Hz, 1H), 1.36 (d, J=6.7 Hz, 6H). ESI-MS (m/z): 383.9.

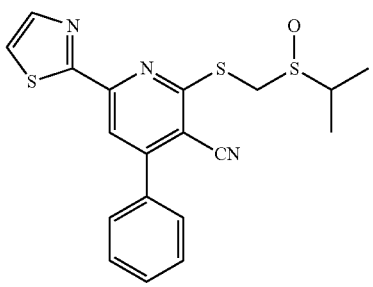

2-(((isopropyl(11-oxidanyl)-13-sulfanyl)methyl)thio)-4-phenyl-6-(thiazol-2-yl)nicotinonitrile. Followed the standard oxidation procedure using 2-(((isopropylthio)methyl)thio)-4-phenyl-6-(thiazol-2-yl)nicotinonitrile as the starting material. This gave white solid product in 91% yield. ¹H NMR (400 MHz, CDCl₃) δ 8.12 (s, 1H), 8.00 (d, J=3.1 Hz, 1H), 7.70-7.63 (m, 2H), 7.60 (d, J=3.1 Hz, 1H), 7.58-7.51 (m, 3H), 4.63 (d, J=13.2 Hz, 1H), 4.48 (d, J=13.2 Hz, 1H), 3.09 (hept, J=6.9 Hz, 1H), 1.42 (d, J=10.5 Hz, 3H), 1.39 (d, J=10.5 Hz, 3H). ESI-MS (m/z): 399.9.

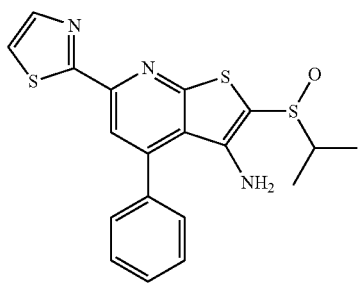

SW208780. 2-(isopropyl(11-oxidanyl)-13-sulfanyl)-4-phenyl-6-(thiazol-2-yl)thieno[2,3-b]pyridin-3-amine.
t-BuOK (2.5 mg, 0.023 mmol) was added to a solution of 2-(((isopropyl(11-oxidanyl)-13-sulfanyl)methyl)thio)-4-phenyl-6-(thiazol-2-yl)nicotinonitrile (15 mg, 0.038 mmol) in DMF (148 µL), and stirred at 35° C. for 40 minutes. The reaction mixture was diluted with EtOAc and washed with 10% AcOH, then several times with H₂O. The organic layer was dried over NaSO₄, filtered, and concentrated under reduced pressure. The crude product was purified using flash chromatography to give product in 75% yield. ¹H NMR (400 MHz, CDCl₃) δ 8.05 (s, 1H), 7.91 (d, J=3.2 Hz, 1H), 7.57-7.42 (m, 6H), 4.68 (s, 2H), 3.47-3.33 (m, 1H), 1.44 (d, J=6.8 Hz, 3H), 1.27 (d, J=6.8 Hz, 3H). ESI-MS (m/z): 399.9.

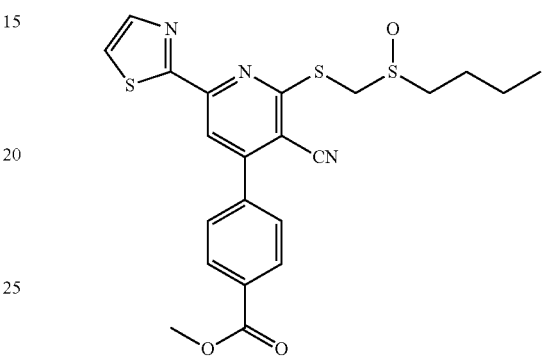

Methyl 4-(2-(((butyl(11-oxidanyl)-13-sulfanyl)methyl)thio)-3-cyano-6-(thiazol-2-yl)pyridin-4-yl)benzoate. Followed standard oxidation procedure using methyl 4-(2-(((butylthio)methyl)thio)-3-cyano-6-(thiazol-2-yl)pyridin-4-yl)benzoate as the starting material to give white solid in 98% isolated yield. ¹H NMR (400 MHz, CDCl₃) δ 8.15 (d, J=8.3 Hz, 2H), 8.05 (s, 1H), 7.95 (d, J=3.1 Hz, 1H), 7.68 (d, J=8.3 Hz, 2H), 7.57 (d, J=3.1 Hz, 1H), 4.68 (d, J=13.1 Hz, 1H), 4.42 (d, J=13.1 Hz, 1H), 3.91 (s, 3H), 3.01-2.86 (m, 1H), 2.87-2.74 (m, 1H), 1.88-1.72 (m, 2H), 1.55-1.35 (m, 2H), 0.91 (t, J=7.3 Hz, 3H). ESI-MS (m/z): 472.1 [M+H]⁺.

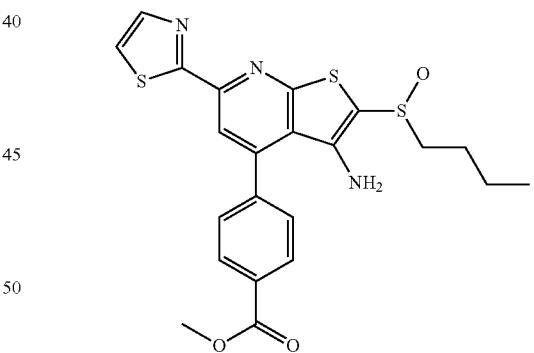

SW209127. Methyl 4-(3-amino-2-(butyl(11-oxidanyl)-13-sulfanyl)-6-(thiazol-2-yl)thieno[2,3-b]pyridin-4-yl)benzoate. t-BuOK (21.8 mg, 0.194 mmol) was added to methyl 4-(2-(((butyl(11-oxidanyl)-13-sulfanyl)methyl)thio)-3-cyano-6-(thiazol-2-yl)pyridin-4-yl)benzoate (152.8 mg, 0.3239 mmol) in DMF (1.30 mL) and the solution stirred at 35° C. for 40 minutes. The reaction mixture was diluted with EtOAc and washed with 10% AcOH, and several times with H₂O. The organic layer was separated, dried over Na₂SO₄, filtered, and concentrated under reduced pressure. The crude product was purified using automated flash chromatography to give the bright green product in 66% isolated yield. ¹H NMR (400 MHz, CDCl₃) δ 8.19 (d, J=7.5 Hz, 2H), 8.04 (s, 1H), 7.91 (d, J=3.2 Hz, 1H), 7.67-7.54 (m, 2H), 7.50 (d, J=3.2 Hz, 1H), 3.9₇ (s, 3H), 3.27 (ddd, J=12.8, 8.9, 6.2 Hz, 1H), 3.10 (ddd, J=12.8, 9.0, 6.8 Hz, 1H), 1.81-1.63 (m, 2H), 1.54-1.39 (m, 2H), 0.93 (t, J=7.3 Hz, 3H). ESI-MS (m/z): 472.1 [M+H]+.

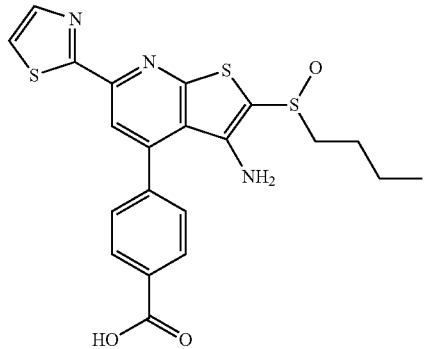

SW209281. 4-(3-amino-2-(butyl(11-oxidanyl)-13-sulfanyl)-6-(thiazol-2-yl)thieno[2,3-b]pyridin-4-yl)benzoic acid. Followed standard hydrolysis procedure using SW209127 as the starting material to give bright green solid in 84% isolated yield. ¹H NMR (400 MHz, CDCl₃) δ 8.16 (d, J=8.4 Hz, 2H), 8.05 (s, 1H), 7.95 (d, J=3.2 Hz, 1H), 7.68-7.55 (m, 2H), 7.52 (d, J=3.2 Hz, 1H), 3.40-3.24 (m, 1H), 3.24-3.04 (m, 1H), 1.83-1.65 (m, 2H), 1.55-1.37 (m, 2H), 0.93 (t, J=7.3 Hz, 3H). ESI-MS (m/z): 458.1 [M+H]+.

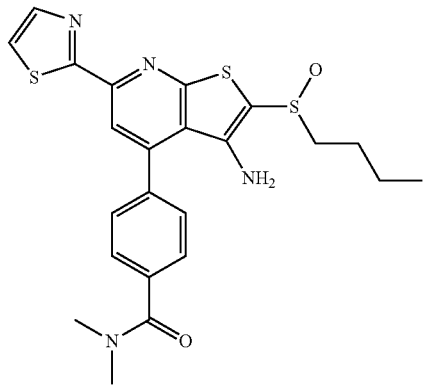

SW209282. 4-(3-amino-2-(butyl(11-oxidanyl)-13-sulfanyl)-6-(thiazol-2-yl)thieno[2,3-b]pyridin-4-yl)-N,N-dimethylbenzamide. Followed standard amide bond coupling procedure using SW209281 as the starting material and dimethylamine hydrochloride as the coupling reagent. The product was purified using automated flash chromatography (20% hexane, 80% EtOAc) to give bright green solid in 59% isolated yield ¹H NMR (400 MHz, CDCl₃) δ 8.03 (s, 1H), 7.91 (d, J=3.2 Hz, 1H), 7.66-7.44 (m, 5H), 3.36-3.21 (m, 1H), 3.14 (s, 3H), 3.13-3.06 (m, 1H), 3.02 (s, 3H), 1.81-1.64 (m, 2H), 1.55-1.41 (m, 2H), 0.93 (t, J=7.3 Hz, 3H). ESI-MS (m/z): 485.1 [M+H]+.

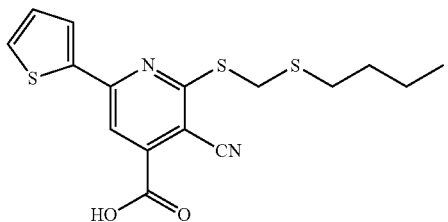 [SMILES: CCCCSCSc1nc(-c2cccs2)cc(C(=O)O)c1C#N]

2-(((butylthio)methyl)thio)-3-cyano-6-(thiophen-2-yl)isonicotinic acid. Followed standard hydrolysis procedure using ethyl 2-(((butylthio)methyl)thio)-3-cyano-6-(thiophen-2-yl)isonicotinate as the starting material to give isolated product in 94% yield. ¹H NMR (400 MHz, CDCl₃) δ 10.65 (s, 1H), 7.95 (s, 1H), 7.76 (dd, J=3.8, 1.1 Hz, 1H), 7.57 (dd, J=5.0, 1.0 Hz, 1H), 7.17 (dd, J=5.0, 3.7 Hz, 1H), 4.46 (s, 2H), 2.72 (t, J=7.2 Hz, 2H), 1.67-1.55 (m, 2H), 1.40 (h, J=7.4 Hz, 2H), 0.90 (t, J=7.3 Hz, 3H). ESI-MS (m/z): 365.0 [M+H]+.

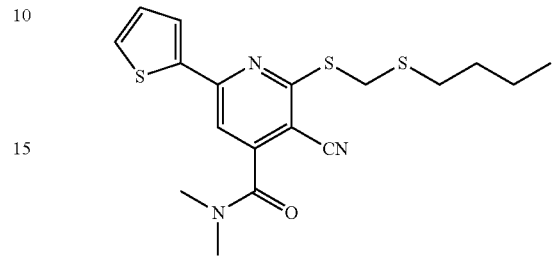

2-(((butylthio)methyl)thio)-3-cyano-N,N-dimethyl-6-(thiophen-2-yl)isonicotinamide. Followed standard amide bond coupling procedure using 2-(((butylthio)methyl)thio)-3-cyano-6-(thiophen-2-yl)isonicotinic acid as the starting material and dimethylamine as the coupling reagent. The crude material was purified using automated flash chromatography (20% EtOAc, 80% hexanes) to give product in 53% isolated yield. ¹H NMR (400 MHz, Chloroform-d) δ 7.67 (d, J=3.8 Hz, 1H), 7.54 (d, J=5.0 Hz, 1H), 7.34 (s, 1H), 7.15 (t, J=4.8, 3.9, 0.7 Hz, 1H), 4.49 (s, 2H), 3.16 (s, 3H), 2.98 (s, 3H), 2.72 (t, 2H), 1.62 (p, J=7.7 Hz, 2H), 1.41 (h, J=7.3 Hz, 2H), 0.90 (t, J=7.7, 7.0 Hz, 3H). ESI-MS (m/z): 392.1 [M+H]+.

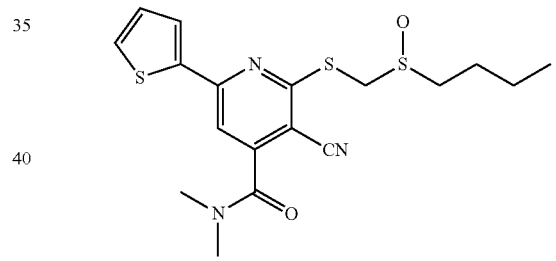

2-(((butyl(11-oxidanyl)-13-sulfanyl)methyl)thio)-3-cyano-N,N-dimethyl-6-(thiophen-2-yl)isonicotinamide. Followed standard oxidation procedure using 2-(((butylthio)methyl)thio)-3-cyano-N,N-dimethyl-6-(thiophen-2-yl)isonicotinamide as the starting material to give solid product in 85% isolated yield. ¹H NMR (400 MHz, CDCl₃) δ 7.67 (d, J=3.8 Hz, 1H), 7.54 (d, J=5.0 Hz, 1H), 7.34 (s, 1H), 7.20-7.06 (m, 1H), 4.49 (s, 2H), 3.16 (s, 3H), 2.98 (s, 3H), 2.72 (t, 2H), 1.62 (p, J=7.7 Hz, 2H), 1.41 (h, J=7.3 Hz, 2H), 0.90 (t, J=7.7, 7.0 Hz, 3H). ESI-MS (m/z): 408.1 [M+H]+.

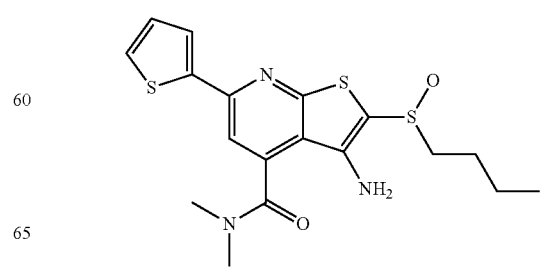

SW209283. 3-amino-2-(butyl(11-oxidanyl)-13-sulfanyl)-N,N-dimethyl-6-(thiophen-2-yl)thieno[2,3-b]pyridine-4-carboxamide. t-BuOK (6.5 mg, 0.058 mmol) was added to a solution of 2-(((butyl(11-oxidanyl)-13-sulfanyl)methyl)thio)-3-cyano-N,N-dimethyl-6-(thiophen-2-yl)isonicotinamide (39.2 mg, 0.962 mmol) in DMF (380 µL) and the solution was heated at 35° C. for 40 minutes. The reaction mixture was diluted with EtOAc and washed with 10% AcOH, then several times with H₂O. The organic layer was separated and dried over Na₂SO₄, filtered, and concentrated under reduced pressure. The crude material was isolated using automated flash chromatography (20% hexanes, 80% EtOAc) to give the final product in 20% isolated yield. $^1$H NMR (400 MHz, Chloroform-d) δ 7.66 (dd, J=3.8, 1.1 Hz, 1H), 7.52-7.42 (m, 2H), 7.13 (dd, J=5.0, 3.7 Hz, 1H), 3.34-3.23 (m, 1H), 3.21 (s, 3H), 3.15-3.02 (m, 1H), 2.96 (s, 3H), 1.79-1.62 (m, 2H), 1.55-1.36 (m, 2H), 0.93 (t, J=7.3 Hz, 3H). ESI-MS (m/z): 408.1 [M+H]⁺.

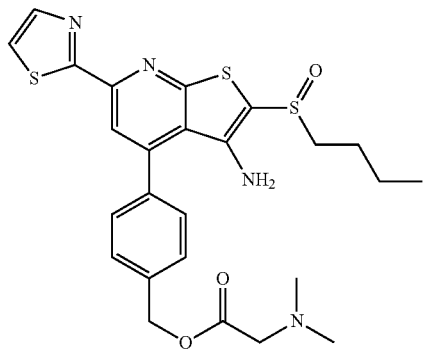 [SMILES: CCCCS(=O)c1sc2nc(-c3nccs3)cc(-c3ccc(COC(=O)CN(C)C)cc3)c2c1N]

SW212366. 4-(3-amino-2-(butylsulfinyl)-6-(thiazol-2-yl)thieno[2,3-b]pyridin-4-yl)benzyl dimethylglycinate. N,N-Dimethylglycine (3.5 mg, 0.034 mmol), 1-ethyl-3-(3-dimethylaminopropyl)carbodiimide (6.5 mg, 0.034 mmol), and DMAP (4.1 mg, 0.0334 mmol) were added to SW209510 (10 mg, 0.023 mmol) and dissolved in DMF (270 µL). The reaction mixture stirred at room temperature overnight, then neutralized with 1M NaOH, washed with H₂O and extracted with EtOAc. The organic layer was dried over Na₂SO₄, filtered and concentrated under reduced pressure. The crude product was purified using flash chromatography (7% MeOH, 93% DCM) to give a quantitative yield of green solid product $^1$H NMR (400 MHz, CDCl₃) δ 8.02 (s, 1H), 7.90 (d, J=3.2 Hz, 1H), 7.56-7.43 (m, 5H), 5.25 (s, 2H), 4.61 (s, 2H), 3.35-3.27 (m, 1H), 3.26 (s, 2H), 3.16-3.04 (m, 1H), 2.37 (s, 6H), 1.78-1.63 (m, 2H), 1.55-1.39 (m, 2H), 0.93 (t, J=7.3 Hz, 3H). ESI-MS (m/z): 529.1 [M+H]⁺.

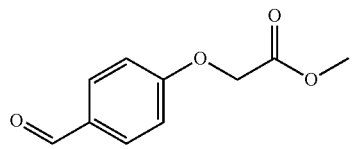

Methyl 2-(4-formylphenoxy)acetate. To a solution of 4-hydroxybenzaldehyde (3.0 g, 25 mmol) in acetone (61.4 mL), K₂CO₃ (5.43 g, 39.3 mmol) was added and the mixture was stirred vigorously. Methylbromoacetate (2.8 mL, 29 mmol) was added and the mixture was stirred for 3.5 hrs at room temperature. The reaction mixture was concentrated down under reduced pressure then washed with H₂O and extracted with EtOAc. The organic layer was separated, dried over Na₂SO₄, filtered, and concentrated to give a colorless oil that solidified under vacuum in 82% isolated yield. $^1$H NMR (400 MHz, CDCl₃) δ 9.87 (s, 1H), 7.82 (d, J=8.8 Hz, 2H), 6.98 (d, J=8.7 Hz, 2H), 4.70 (s, 2H), 3.79 (s, 3H). ESI-MS (m/z): 195.1 [M+H]⁺.

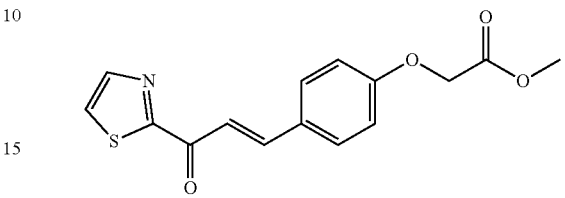

Methyl (E)-2-(4-(3-oxo-3-(thiazol-2-yl)prop-1-en-1-yl)phenoxy)acetate. 2-acetylthiazole (534 µL, 5.15 mmol) was added to a solution of methyl 2-(4-formylphenoxy)acetate (1.0 g, 5.2 mmol) in MeOH (11 mL) under N₂. NaOMe (279 mg, 5.15 mmol) was added last and the reaction mixture stirred at room temperature overnight. The reaction mixture was filtered, and the precipitate was washed with small amount of MeOH then diluted with DCM and washed with H₂O. The organic layer was separated, dried over Na₂SO₄, filtered, and concentrated under reduced pressure. This gave solid product in 21% isolated yield. $^1$H NMR (400 MHz, Chloroform-d) δ 8.03 (d, J=3.0 Hz, 1H), 7.95 (d, J=15.9 Hz, 1H), 7.82 (d, J=16.0 Hz, 1H), 7.70-7.61 (m, 3H), 6.92 (d, J=8.8 Hz, 2H), 4.67 (s, 2H), 3.80 (s, 3H). ESI-MS (m/z): 304.1 [M+H]⁺.

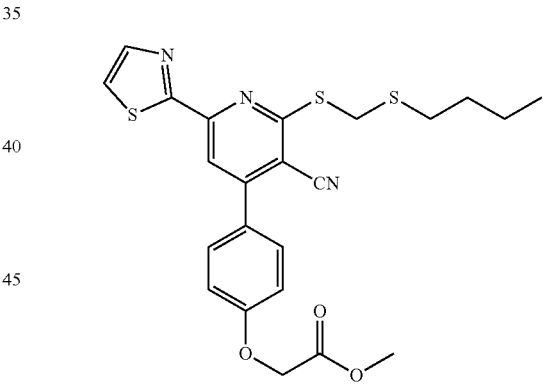

Methyl 2-(4-(2-(((butylthio)methyl)thio)-3-cyano-6-(thiazol-2-yl)pyridin-4-yl)phenoxy)acetate. EtOH (495 µL) was added to 2-cyanothioacetamide (49.5 mg, 0.494 mmol) and methyl(E)-2-(4-(3-oxo-3-(thiazol-2-yl)prop-1-en-1-yl)phenoxy)acetate (50 mg, 0.16 mmol), followed by 1 drop of piperidine. The reaction mixture stirred at 80° C. for 4 hours then was concentrated under reduced pressure and the crude was carried forward to the next step. Followed the standard alkylation procedure, using methyl 2-(4-(3-cyano-6-(thiazol-2-yl)-2-thioxo-1,2-dihydropyridin-4-yl)phenoxy)acetate as the starting material and butyl(chloromethyl)sulfane as the alkylating reagent. The crude product was purified using automated flash chromatography (20% EtOAc, 80% hexanes) to give solid product in 70% isolated yield. $^1$H NMR (400 MHz, CDCl₃) δ 7.96 (s, 1H), 7.95 (d, J=3.1 Hz, 1H), 7.62 (d, J=8.8 Hz, 2H), 7.54 (d, J=3.1 Hz, 1H), 7.02 (d, J=8.8 Hz, 2H), 4.69 (s, 2H), 4.49 (s, 2H), 3.81 (s, 3H), 2.73

(t, J=7.3 Hz, 2H), 1.68-1.56 (m, 2H), 1.46-1.34 (m, 2H), 0.89 (t, J=7.3 Hz, 3H). ESI-MS (m/z): 486.1 [M+H]⁺.

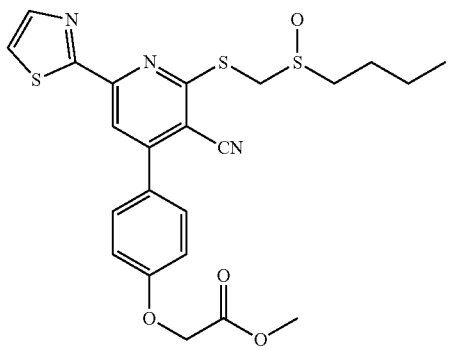

Methyl 2-(4-(2-(((butyl(11-oxidanyl)-13-sulfanyl)methyl)thio)-3-cyano-6-(thiazol-2-yl)pyridin-4-yl)phenoxy)acetate. Followed the standard oxidation procedure using methyl 2-(4-(2-(((butylthio)methyl)thio)-3-cyano-6-(thiazol-2-yl)pyridin-4-yl)phenoxy)acetate as the starting material. The crude product was purified using automated flash chromatography (50% EtOAc, 50% hexanes). ¹H NMR (400 MHz, CDCl₃) δ 7.97 (s, 1H), 7.90 (d, J=3.1 Hz, 1H), 7.57 (d, J=8.8 Hz, 2H), 7.52 (d, J=3.1 Hz, 1H), 6.98 (d, J=8.8 Hz, 2H), 4.65 (s, 2H), 4.62 (d, J=13.1 Hz, 1H), 4.37 (d, J=13.1 Hz, 1H), 3.75 (s, 3H), 2.96-2.84 (m, 1H), 2.81-2.71 (m, 1H), 1.76 (p, J=7.6 Hz, 2H), 1.51-1.33 (m, 2H), 0.88 (t, J=7.3 Hz, 3H). ESI-MS (m/z): 502.1 [M+H]⁺.

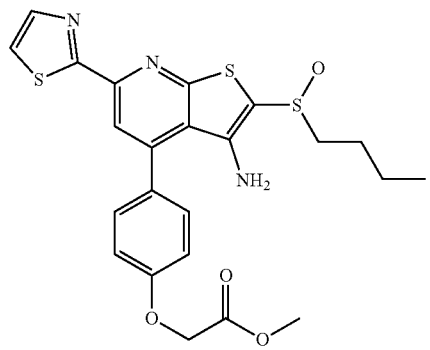

SW212365. Methyl 2-(4-(3-amino-2-(butyl(1 11-oxidanyl)-13-sulfanyl)-6-(thiazol-2-yl)thieno[2,3-b]pyridin-4-yl)phenoxy)acetate. Methyl 2-(4-(2-(((butyl(11-oxidanyl)-13-sulfanyl)methyl)thio)-3-cyano-6-(thiazol-2-yl)pyridin-4-yl)phenoxy)acetate (80 mg, 0.16 mmol) and t-BuOK (10.7 mg, 0.0954 mmol) were combined in a vial that was evacuated and backfilled with N₂ three times, then DMF (627 μL) was added and N₂ was bubbled through the solution. The reaction mixture was stirred at room temperature for about 10 minutes and then was diluted with EtOAc and washed with 10% AcOH. The organic layer was washed several times with water, dried over Na₂SO₄, filtered, and concentrated. The crude product was purified using automated flash chromatography (30% EtOAc, 70% hexanes) to give green solid with 56% isolated yield. ¹H NMR (400 MHz, CDCl₃) δ 7.97 (s, 1H), 7.89-7.86 (m, 1H), 7.47 (d, J=3.1 Hz, 1H), 7.46-7.37 (m, 2H), 7.02 (d, J=8.5 Hz, 2H), 4.70 (s, 2H), 4.66 (s, 2H), 3.82 (s, 3H), 3.34-3.18 (m, 1H), 3.16-3.01 (m, 1H), 1.77-1.64 (m, 2H), 1.51-1.38 (m, 2H), 0.92 (t, J=7.3 Hz, 3H). ESI-MS (m/z): 502.1 [M+H]⁺

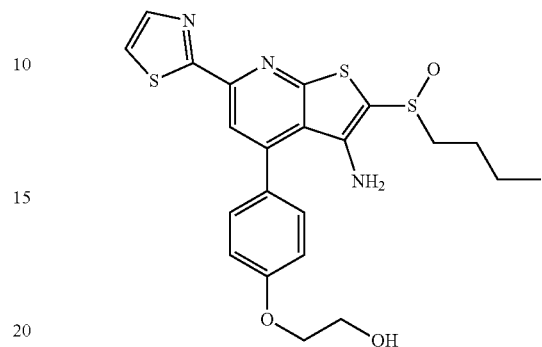

SW212364. 2-(4-(3-amino-2-(butyl(11-oxidanyl)-13-sulfanyl)-6-(thiazol-2-yl)thieno[2,3-b]pyridin-4-yl)phenoxy)ethan-1-ol. Followed the same procedure as for 2-(((butylthio)methyl)thio)-4-(4-(hydroxymethyl)phenyl)-6-(thiazol-2-yl)nicotinonitrile using SW212365 as the starting material to give a quantitative yield of desired product ¹H NMR (400 MHz, CDCl₃) δ 8.01 (s, 1H), 7.90 (d, J=3.2 Hz, 1H), 7.48 (d, J=3.1 Hz, 1H), 7.46-7.35 (m, 2H), 7.07-6.99 (m, 2H), 4.69 (s, 2H), 4.18-4.11 (m, 2H), 4.04-3.96 (m, 2H), 3.34-3.23 (m, 1H), 3.17-3.04 (m, 1H), 1.80-1.61 (m, 2H), 1.53-1.40 (m, 2H), 0.93 (t, J=7.3 Hz, 3H). ESI-MS (m/z): 474.1 [M+H]⁺.

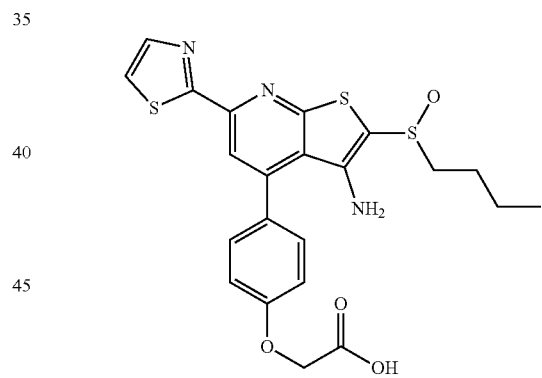

SW212363. 2-(4-(3-amino-2-(butyl(11-oxidanyl)-13-sulfanyl)-6-(thiazol-2-yl)thieno[2,3-b]pyridin-4-yl)phenoxy)acetic acid. Followed the standard hydrolysis procedure using SW212365 as the starting material to give a quantitative yield. ¹H NMR (400 MHz, MeOD) δ 7.98 (s, 1H), 7.94 (d, J=3.2 Hz, 1H), 7.74 (d, J=3.2 Hz, 1H), 7.46 (d, J=8.4 Hz, 2H), 7.14 (d, J=8.9 Hz, 2H), 4.67 (s, 2H), 3.35-3.24 (m, 1H), 3.16-3.04 (m, 1H), 1.78-1.57 (m, 2H), 1.55-1.43 (m, 2H), 0.95 (t, J=7.3 Hz, 3H). ESI-MS (m/z): 488.1 [M+H]⁺.

Synthesis of Chloromethyl Thio Ethers

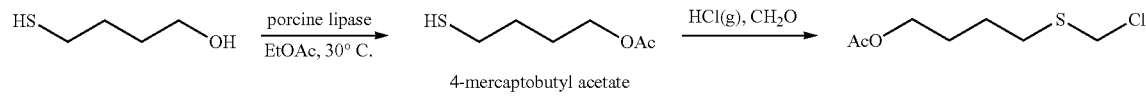

4-mercaptobutyl acetate

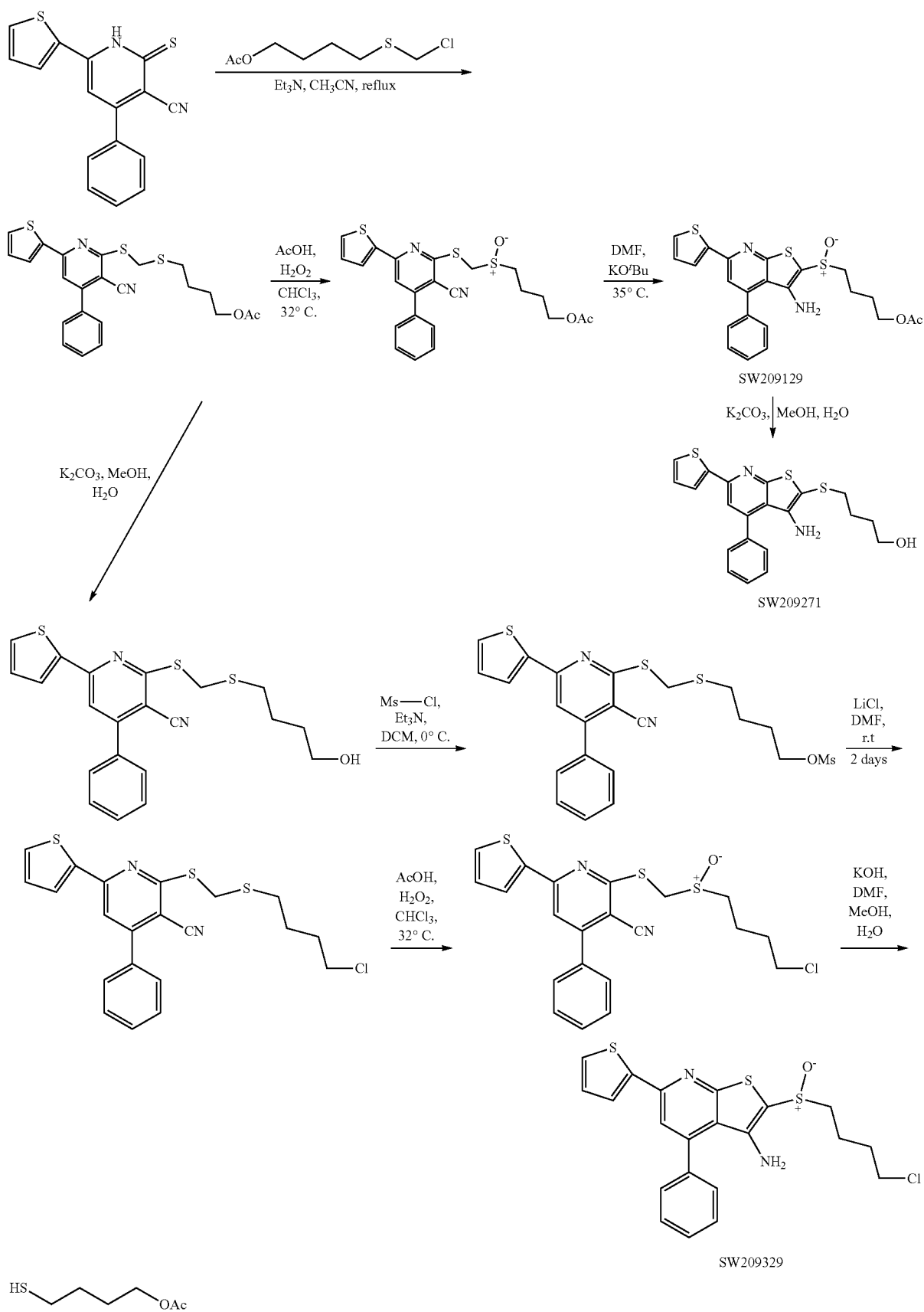

4-mercaptobutyl acetate. Porcine lipase (2.35 g) was added to a solution of 4-mercapto-1-butanol (2.45 g, 23.10 mmol) in ethyl acetate (42.0 ml). The reaction was heated at 30° C. for 6 days. Despite incomplete conversion the mixture was filtered and condensed. Purification was carried out on an automated flash chromatography system in 100% DCM to give oil in 84% yield. $^1$H NMR (400 MHz, CHCl$_3$) δ 4.08 (t, J=6.2 Hz, 2H), 2.57 (q, J=7.1 Hz, 2H), 2.05 (s, 3H), 1.85), 1.59 (m, 4H), 1.36 (t, J=7.9 Hz, 1H).

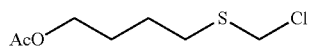 [SMILES: CC(=O)OCCCCSCCl]

4-((chloromethyl)thio)butyl acetate. Hydrogen chloride gas was bubbled for 40 minutes into 4-mercaptobutyl acetate (2.84 g, 19.2 mmol) which had been cooled in a dry ice/acetone bath and until the internal temperature stabilized before paraformaldehyde (0.815 g, 27.17 mmol) was slowly added using a solid addition funnel. The reaction was stirred cold for 3 hours during which hydrogen chloride bubbling was continued and then ceased as the reaction was warmed gently to ambient temperature and stirred overnight. The crude mixture was diluted with minimal DCM. The aqueous phase was removed and the organic layer was washed with brine and dried over Na$_2$SO$_4$, filtered and condensed to give an oil in 62% yield. $^1$H NMR (400 MHz, CHCl$_3$) 4.75 (s, 2H), 4.10 (t, J=6.0 Hz, 2H), 2.95-2.66 (m, 2H), 2.06 (s, 3H), 1.85-1.67 (m, 4H).

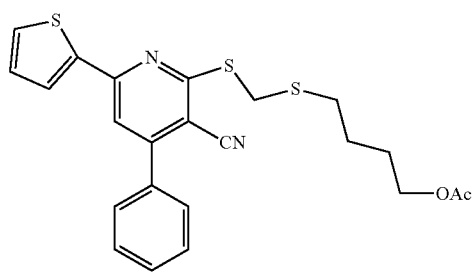 [SMILES: CC(=O)OCCCCSCSc1nc(-c2cccs2)cc(-c2ccccc2)c1C#N]

4-((((3-cyano-4-phenyl-6-(thiophen-2-yl)pyridin-2-yl)thio)methyl)thio)butyl acetate. A mixture of 4-((chloromethyl)thio)butyl acetate (602.3 mg, 3.1 mmol), 4-phenyl-6-(thiophen-2-yl)-2-thioxo-1,2-dihydropyridine-3-carbonitrile (352.2 mg, 1.2 mmol) and triethylamine (250 ml, 1.8 mmol) in acetonitrile (1.2 ml) was refluxed for three hours. The crude mixture was then condensed and purified on an automated flash chromatography system in 0-40% EtOAc/hexanes. Fractions containing the desired product were further purified on an automated flash chromatography in 0-30% EtOAc/hexanes to give a clear oil in 41% yield. $^1$H NMR (400 MHz, CHCl$_3$) δ 7.72 (dd, J=3.7, 1.1 Hz, 1H), 7.64-7.59 (m, 2H), 7.55 (dt, J=5.6, 2.3 Hz, 4H), 7.44 (s, 1H), 7.17 (dd, J=5.0, 3.8 Hz, 1H), 4.55 (s, 2H), 4.11-4.02 (m, 2H), 2.86-2.63 (m, 2H), 2.05 (s, 3H), 1.77 (t, J=3.4 Hz, 4H). ESI-MS (m/z): 455.1 [M+H]$^+$.

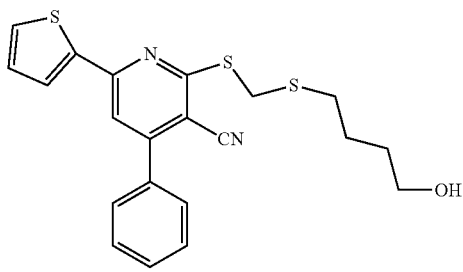 [SMILES: N#Cc1c(-c2ccccc2)cc(-c2cccs2)nc1SCSCCCCO]

2-((((4-hydroxybutyl)thio)methyl)thio)-4-phenyl-6-(thiophen-2-yl)nicotinonitrile. K$_2$CO$_3$ (157.7 mg, 1.14 mmol) was added to a solution of 4-((((3-cyano-4-phenyl-6-(thiophen-2-yl)pyridin-2-yl)thio)methyl)thio)butyl acetate. (245.4 mg, 0.54 mmol) in methanol (8.0 ml) and water (2.0 ml) and the reaction was stirred for 2 hours. The mixture was dried then diluted with EtOAc and washed twice with water and then brine. The organic layer was dried over Na$_2$SO$_4$, filtered and concentrated under reduce pressure to give desired product in 71% yield. $^1$H NMR (400 MHz, CDCl$_3$) δ 7.72 (dd, J=3.7, 1.1 Hz, 1H), 7.61 (dd, J=6.6, 3.0 Hz, 2H), 7.54 (dd, J=5.1, 2.2 Hz, 4H), 7.43 (s, 1H), 7.16 (dd, J=5.0, 3.8 Hz, 1H), 4.55 (s, 2H), 3.67 (t, J=6.2 Hz, 2H), 2.80 (t, J=7.1 Hz, 2H), 1.84-1.63 (m, 4H). ESI-MS (m/z): 413.1 [M+H]$^+$.

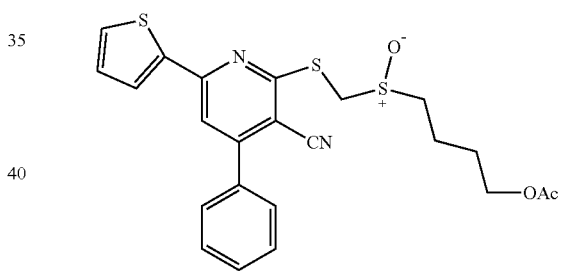

4-((((3-cyano-4-phenyl-6-(thiophen-2-yl)pyridin-2-yl)thio)methyl)sulfinyl)butyl acetate. Acetic acid (370 µl) and hydrogen peroxide (29 µl, 30% solution in water) were added to the solution of 4-((((3-cyano-4-phenyl-6-(thiophen-2-yl)pyridin-2-yl)thio)methyl)thio)butyl acetate (85.2 mg, 0.19 mmol) in chloroform (370 µl). The reaction mixture was stirred at 32° C. for 90 min. Once complete, the reaction was diluted with chloroform and washed with saturated NaHCO$_3$ solution, and extracted three times with chloroform. The combined organic layers was dried over Na$_2$SO$_4$, filtered and concentrated under reduce pressure to give designed product in 94% yield. $^1$H NMR (400 MHz, CDCl$_3$) δ 7.77 (d, J=3.8 Hz, 1H), 7.62 (dd, J=4.1, 2.3 Hz, 2H), 7.60-7.54 (m, 4H), 7.51 (s, 1H), 7.19 (dd, J=5.0, 3.8 Hz, 1H), 4.78 (d, J=13.0 Hz, 1H), 4.44 (d, J=13.0 Hz, 1H), 4.11 (t, J=6.4 Hz, 2H), 3.03 (dt, J=12.9, 8.0 Hz, 1H), 2.87 (dt, J=12.8, 7.3 Hz, 1H), 2.05 (s, 3H), 2.03-1.77 (m, 4H). ESI-MS (m/z): 471.1 [M+H]$^+$.

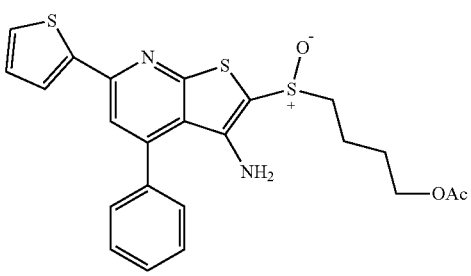

SW209129. 4-((3-amino-4-phenyl-6-(thiophen-2-yl)thieno[2,3-b]pyridin-2-yl)sulfinyl)butyl acetate. Potassium tert-butoxide (9.7 mg, 0.086 mmol) was added to a solution of 4-((((3-cyano-4-phenyl-6-(thiophen-2-yl)pyridin-2-yl)thio)methyl)sulfinyl)butyl acetate (58.2 mg, 0.12 mmol) in DMF (490 μl). The reaction mixture was stirred at 35° C. for 45 minutes, then diluted with EtOAc and washed several times with water. The aqueous layer was also back-extracted. The combined organic layer was washed with brine, dried over Na$_2$SO$_4$, filtered and concentrated under reduce pressure. Purification was carried out using automated flash chromatography in 0-90% EtOAc/hexanes to give the desired product in 44% yield. $^1$H NMR (400 MHz, CDCl$_3$) δ7.63-7.49 (m, 5H), 7.45 (dd, J=4.9, 1.1 Hz, 2H), 7.41 (s, 1H), 7.10 (dd, J=5.0, 3.7 Hz, 1H), 4.59 (bs, 2H), 4.08 (t, J=5.8 Hz, 2H), 3.39-3.23 (m, 1H), 3.10 (ddd, J=12.8, 8.4, 6.2 Hz, 1H), 2.03 (s, 3H), 1.96-1.72 (m, 4H). ESI-MS (m/z): 471.1 [M+H]$^+$.

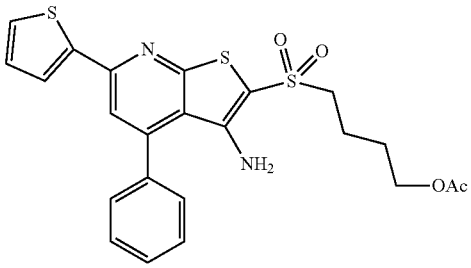 [SMILES: CC(=O)OCCCCS(=O)(=O)c1sc2nc(-c3cccs3)cc(-c3ccccc3)c2c1N]

SW209128. 4-((3-amino-4-phenyl-6-(thiophen-2-yl)thieno[2,3-b]pyridin-2-yl)sulfonyl)butyl acetate. Isolated as the over oxidation product from 4-((3-amino-4-phenyl-6-(thiophen-2-yl)thieno[2,3-b]pyridin-2-yl)sulfinyl)butyl acetate in 13.5% yield.

$^1$H NMR (400 MHz, CDCl$_3$) δ 7.71 (dd, J=3.7, 1.1 Hz, 1H), 7.61-7.55 (m, 3H), 7.53-7.44 (m, 4H), 7.15 (dd, J=5.0, 3.7 Hz, 1H), 5.10 (s, 2H), 4.06 (t, J=6.3 Hz, 2H), 3.32-3.18 (m, 2H), 2.02 (s, 3H), 1.98-1.87 (m, 2H), 1.77 (dt, J=8.6, 6.4 Hz, 2H). ESI-MS (m/z): 487.1 [M+H]$^+$.

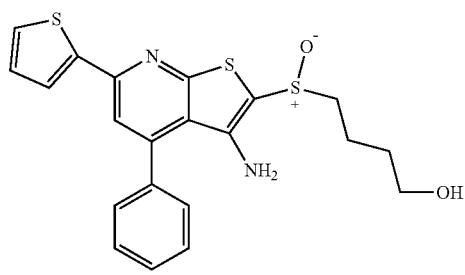

SW209271. 4-((3-amino-4-phenyl-6-(thiophen-2-yl)thieno[2,3-b]pyridin-2-yl)sulfinyl)butan-1-ol. K$_2$CO$_3$ (12.5 mg, 0.09 mmol) was added to a solution of SW209129 (18.7 mg, 0.04 mmol) in methanol (470 μl) and water (100 μl) and the reaction was stirred for 2.5 hours. The mixture was dried then diluted with EtOAc and washed twice with water and then brine. The organic layer was dried over Na$_2$SO$_4$, filtered and concentrated under reduce pressure to give desired product in 80% yield. $^1$H NMR (400 MHz, CDCl$_3$) δ 7.62 (d, J=1.1 Hz, 1H), 7.60-7.50 (m, 4H), 7.49-7.41 (m, 3H), 7.11 (dd, J=5.0, 3.7 Hz, 1H), 4.68-4.44 (s, 2H), 3.67 (t, J=6.1 Hz, 2H), 3.42-3.27 (m, 1H), 3.13 (ddd, J=12.9, 8.4, 6.9 Hz, 1H), 1.93-1.65 (m, 4H). ESI-MS (m/z): 429.0 [M+H]$^+$.

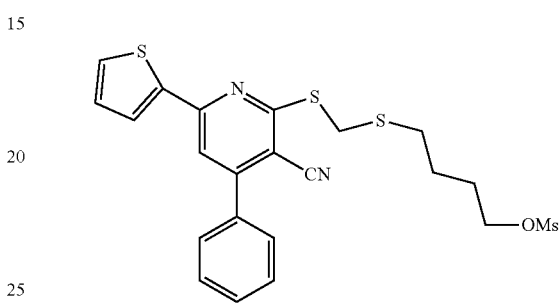

4-((((3-cyano-4-phenyl-6-(thiophen-2-yl)pyridin-2-yl)thio)methyl)thio)butyl methanesulfonate. A solution of triethylamine (38 μl, 0.28 mmol) in anhydrous DCM (1.0 ml) is cooled in an ice bath before the addition of 2-((((4-hydroxybutyl)thio)methyl)thio)-4-phenyl-6-(thiophen-2-yl)nicotinonitrile (40.6 mg, 0.098 mmol) followed by dropwise addition of methanesulfonyl chloride (17.5 μl, 0.23 mmol). After 30 minutes the crude mixture was washed with brine and dried over Na$_2$SO$_4$, filtered and condensed to give desired product in 98% yield. $^1$H NMR (400 MHz, CDCl$_3$) δ 7.74 (dd, J=3.9, 1.1 Hz, 1H), 7.64-7.50 (m, 7H), 7.17 (dd, J=5.1, 3.8 Hz, 1H), 5.46 (s, 2H), 4.01-3.78 (m, 2H), 2.65 (ddd, J=10.1, 5.3, 1.9 Hz, 2H), 2.52-2.37 (m, 4H). ESI-MS (m/z): 491.1 [M+H]$^+$.

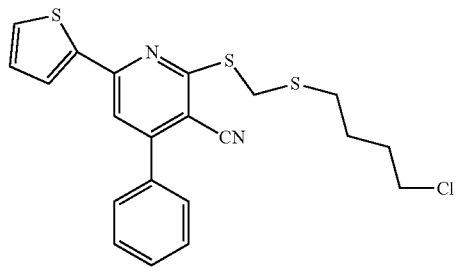 [SMILES: N#Cc1c(-c2ccccc2)cc(-c2cccs2)nc1SCSCCCCCl]

2-((((4-chlorobutyl)thio)methyl)thio)-4-phenyl-6-(thiophen-2-yl)nicotinonitrile. Lithium chloride (32.0 mg, 0.75 mmol) was added to a solution of 4-((((3-cyano-4-phenyl-6-(thiophen-2-yl)pyridin-2-yl)thio)methyl)thio)butyl methanesulfonate (21.8 mg, 0.044 mmol) in DMF (0.4 ml). The reaction went to completion within two days. The mixture was diluted with EtOAc and washed several times with water and then brine. The organic layer was dried over Na$_2$SO$_4$, filtered and condensed. Purification was performed on an automated chromatography system in 0-40% EtOAc/hexanes and gave the desired product in 76% yield. $^1$H NMR (400 MHz, CDCl$_3$) δ 7.72 (dd, J=3.7, 1.1 Hz, 1H), 7.62 (dd, J=6.5, 3.0 Hz, 2H), 7.59-7.52 (m, 4H), 7.44 (s, 1H), 7.17 (dd, J=5.0, 3.8 Hz, 1H), 4.56 (s, 2H), 3.56 (t, J=6.3 Hz, 2H), 2.80 (t, J=7.0 Hz, 2H), 1.95-1.79 (m, 4H). ESI-MS (m/z): 431.0 [M+H]⁺.

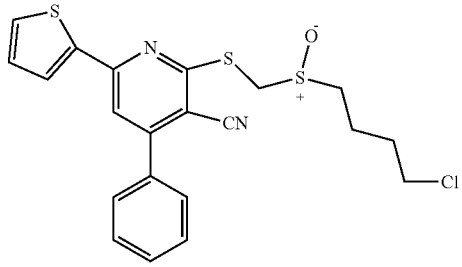

2-((((4-chlorobutyl)sulfinyl)methyl)thio)-4-phenyl-6-(thiophen-2-yl)nicotinonitrile. Acetic acid (70 µl) and hydrogen peroxide (5.2 µl, 30% solution in water) were added to the solution of 2-((((4-chlorobutyl)thio)methyl)thio)-4-phenyl-6-(thiophen-2-yl)nicotinonitrile (14.6 mg, 0.034 mmol) in chloroform (70 al). The reaction mixture was stirred at 32° C. for 40 min and then diluted with chloroform and was washed with saturated NaHCO₃ solution and extracted three times with chloroform. The combined organic layers was dried over Na₂SO₄, filtered and concentrated under reduce pressure to give designed product. ¹H NMR (400 MHz, CDCl₃) δ 7.77 (d, J=3.8 Hz, 1H), 7.62 (dd, J=6.6, 2.9 Hz, 2H), 7.57 (q, J=4.5, 3.1 Hz, 4H), 7.51 (s, 1H), 7.19 (t, J=4.4 Hz, 1H), 4.77 (d, J=13.0 Hz, 1H), 4.47 (d, J=13.0 Hz, 1H), 3.58 (t, J=6.2 Hz, 2H), 3.03 (dt, J=13.2, 7.7 Hz, 1H), 2.87 (dt, J=13.4, 7.0 Hz, 1H), 2.16-1.87 (m, 4H). ESI-MS (m/z): 447.1 [M+H]⁺.

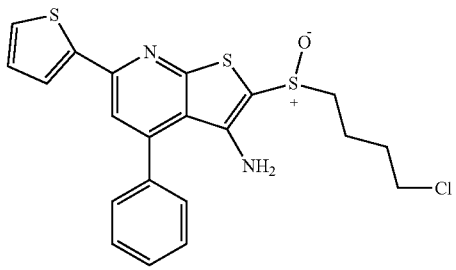

SW209329. 2-((4-chlorobutyl)sulfinyl)-4-phenyl-6-(thiophen-2-yl)thieno[2,3-b]pyridin-3-amine. A basic methanolic solution (1.0 mg, 0.018 mmol of potassium hydroxide in 12.0 µl water and 57.5 µl methanol) was transferred to a vial containing a solution of 2-((((4-chlorobutyl)sulfinyl)methyl)thio)-4-phenyl-6-(thiophen-2-yl)nicotinonitrile (12.4 mg, 0.028 mmol) in dimethylformamide (91.5 µl). The reaction was heated at 38° C. for 30 minutes, before being cooled, diluted with EtOAc and washed several times with water, then brine. The organic layer was dried over Na₂SO₄, filtered and condensed. The crude mixture was purified using an automated chromatography system in 0-60% EtOAc/hexanes. Isolated yield=65%. ¹H NMR (400 MHz, CDCl₃) δ 7.64 (d, J=3.7 Hz, 1H), 7.61-7.50 (m, 4H), 7.50-7.43 (m, 3H), 7.12 (t, J=4.4 Hz, 1H), 4.59 (s, 2H), 3.66-3.47 (m, 2H), 3.40-3.24 (m, 1H), 3.20-3.06 (m, 1H), 1.95 (q, J=5.6 Hz, 4H). ESI-MS (m/z): 447.0 [M+H]⁺.

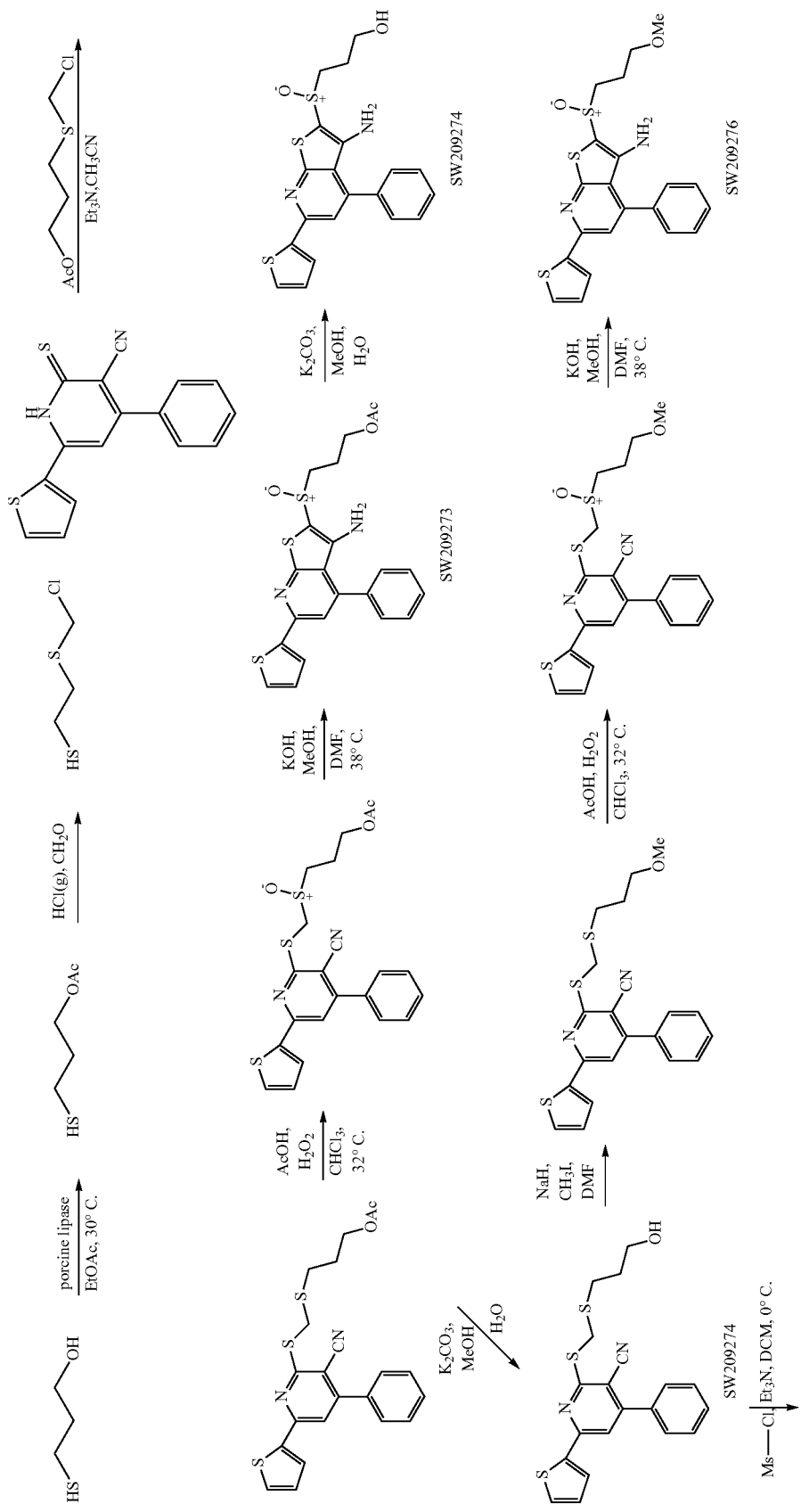

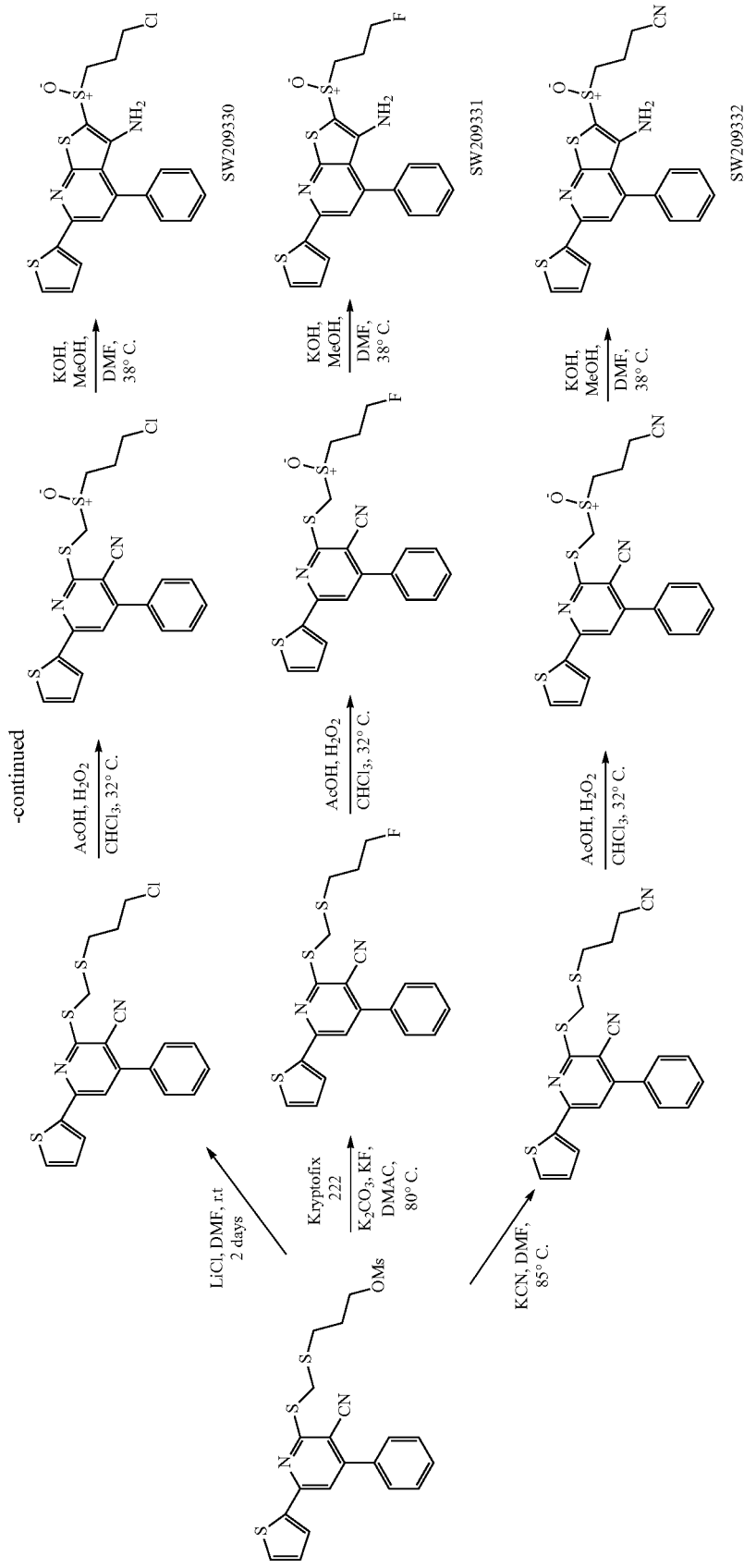

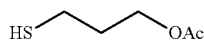

3-mercaptopropyl acetate. Porcine lipase (5.52 g) was added to a solution of 3-mercapto-1-propanol (5.03 g, 54.6 mmol) in ethyl acetate (70 ml). The reaction was heated at 28° C. for 12 days. Despite incomplete conversion the mixture was filtered and condensed. Purification was carried out on an automated flash chromatography system in 100% DCM to give oil in 66% yield. $^1$H NMR (400 MHz, CHCl$_3$) δ 4.17 (t, J=6.2 Hz, 2H), 2.60 (q, J=7.4 Hz, 2H), 2.05 (s, 3H), 1.93 (p, J=6.6 Hz, 2H), 1.39 (t, J=8.1 Hz, 2H).

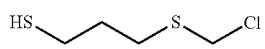

3-((chloromethyl)thio)propane-1-thiol. Hydrogen chloride gas was bubbled for 60 minutes into 3-((chloromethyl)thio)propane-1-thiol (4.80 g, 35.7 mmol) which had been cooled in a dry ice/acetone bath and until the internal temperature stabilized before paraformaldehyde (1.59 g, 53.3 mmol) was slowly added using a solid addition funnel. The reaction was stirred cold for 1.5 hours during which hydrogen chloride bubbling was continued and then ceased as the reaction was warmed gently to ambient temperature and stirred overnight. The crude mixture was diluted with minimal DCM. The aqueous phase was removed and the organic layer was washed with brine and dried over Na$_2$SO$_4$, filtered and condensed to give an oil in 80% yield of a mixture of 2.4:1 desired monomer chloride to diacetate dimer. $^1$H NMR (400 MHz, CHCl$_3$) δ 4.74 (s, 2H), 4.17 (t, J=6.4 Hz, 2H), 2.91-2.77 (m, 2H), 2.06 (d, J=1.0 Hz, 3H), 2.03-1.94 (m, 2H).

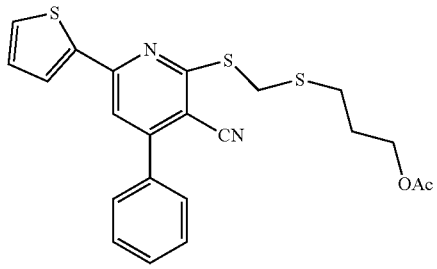 [SMILES: CC(=O)OCCCSCSc1nc(-c2cccs2)cc(-c2ccccc2)c1C#N]

3-((((3-cyano-4-phenyl-6-(thiophen-2-yl)pyridin-2-yl)thio)methyl)thio)propyl acetate. Prepared analogously to 4-((((3-cyano-4-phenyl-6-(thiophen-2-yl)pyridin-2-yl)thio)methyl)thio)butyl acetate in 26% yield (isolated). $^1$H NMR (400 MHz, CHCl$_3$) δ 7.72 (dd, J=3.8, 1.1 Hz, 1H), 7.66-7.58 (m, 2H), 7.54 (dd, J=4.2, 2.9 Hz, 4H), 7.44 (d, J=1.3 Hz, 1H), 7.17 (dd, J=5.0, 3.8 Hz, 1H), 4.55 (s, 2H), 4.18 (t, J=6.3 Hz, 2H), 2.84 (t, J=7.3 Hz, 2H), 2.05 (s, 3H), 2.05-1.97 (m, 2H). ESI-MS (m/z): 441.0 [M+H]$^+$.

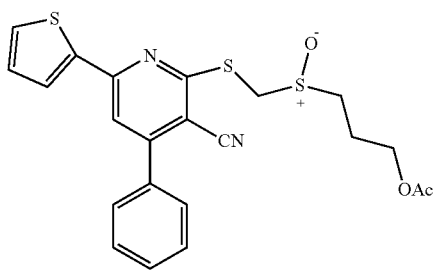

3-((((3-cyano-4-phenyl-6-(thiophen-2-yl)pyridin-2-yl)thio)methyl)sulfinyl)propyl acetate. Prepared analogously to 4-((((3-cyano-4-phenyl-6-(thiophen-2-yl)pyridin-2-yl)thio)methyl)sulfinyl)butyl acetate in 90% yield. $^1$H NMR (400 MHz, CHCl$_3$) δ 7.77 (dd, J=3.7, 1.1 Hz, 1H), 7.68-7.60 (m, 2H), 7.57 (ddd, J=6.9, 4.5, 2.0 Hz, 4H), 7.51 (s, 1H), 7.19 (dd, J=5.0, 3.8 Hz, 1H), 4.81 (d, J=13.1 Hz, 1H), 4.44 (d, J=13.1 Hz, 1H), 4.22 (td, J=6.3, 1.3 Hz, 2H), 3.09 (dt, J=13.0, 8.1 Hz, 1H), 2.89 (dt, J=13.1, 7.1 Hz, 1H), 2.28-2.17 (m, 2H), 2.04 (s, 3H). ESI-MS (m/z): 457.1 [M+H]$^+$.

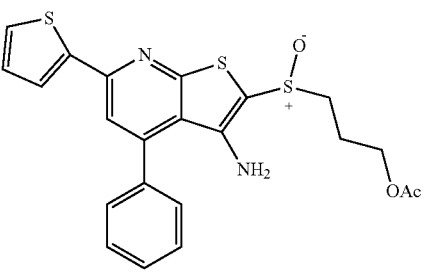

SW209273. 3-((3-amino-4-phenyl-6-(thiophen-2-yl)thieno[2,3-b]pyridin-2-yl)sulfinyl)propyl acetate. Prepared analogously to 4-((3-amino-4-phenyl-6-(thiophen-2-yl)thieno[2,3-b]pyridin-2-yl)sulfinyl)butyl acetate in 37% yield. $^1$H NMR (400 MHz, CHCl$_3$) δ 7.62-7.52 (m, 5H), 7.45 (dd, J=5.0, 1.1 Hz, 2H), 7.41 (s, 1H), 7.10 (dd, J=5.0, 3.7 Hz, 1H), 4.65-4.56 (s, 2H), 4.27-4.14 (m, 2H), 3.42-3.25 (m, 1H), 3.15 (dt, J=12.9, 7.7 Hz, 1H), 2.09 (ddd, J=7.5, 6.2, 1.3 Hz, 2H), 2.05 (s, 3H). ESI-MS (m/z): 457.1 [M+H]$^+$.

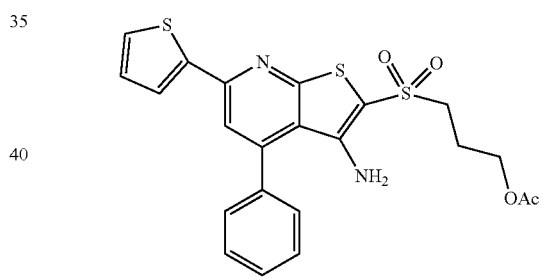

SW209272. 3-((3-amino-4-phenyl-6-(thiophen-2-yl)thieno[2,3-b]pyridin-2-yl)sulfonyl)propyl acetate. Isolated as the over oxidation product from 3-((3-amino-4-phenyl-6-(thiophen-2-yl)thieno[2,3-b]pyridin-2-yl)sulfinyl)propyl acetate in 7% yield. $^1$H NMR (400 MHz, CHCl$_3$) δ 7.72 (d, J=3.8 Hz, 1H), 7.62-7.53 (m, 3H), 7.54-7.45 (m, 4H), 7.15 (dd, J=5.0, 3.8 Hz, 1H), 5.12 (s, 2H), 4.15 (t, J=6.2 Hz, 2H), 3.39-3.19 (m, 2H), 2.25-2.12 (m, 2H), 2.03 (s, 3H). ESI-MS (m/z): 457.1 [M+H]$^+$.

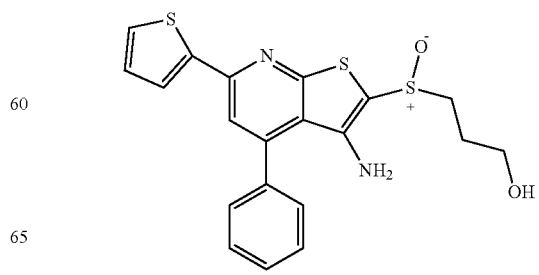

SW209274. 3-((3-amino-4-phenyl-6-(thiophen-2-yl)thieno[2,3-b]pyridin-2-yl)sulfinyl)propan-1-ol. Was prepared analogously to SW209271. 4-((3-amino-4-phenyl-6-(thiophen-2-yl)thieno[2,3-b]pyridin-2-yl)sulfinyl)butan-1-ol in 84% yield. $^1$H NMR (400 MHz, CHCl$_3$) δ 7.63 (dd, J=3.7, 1.1 Hz, 1H), 7.55 (p, J=4.6, 3.2 Hz, 4H), 7.46 (dd, J=5.0, 1.1 Hz, 2H), 7.43 (s, 1H), 7.11 (dd, J=5.0, 3.7 Hz, 1H), 4.60 (s, 2H), 3.77 (t, J=5.8 Hz, 2H), 3.49-3.33 (m, 1H), 3.21 (dt, J=13.5, 6.9 Hz, 1H), 2.13-1.98 (m, 2H). ESI-MS (m/z): 415.1 [M+H]$^+$.

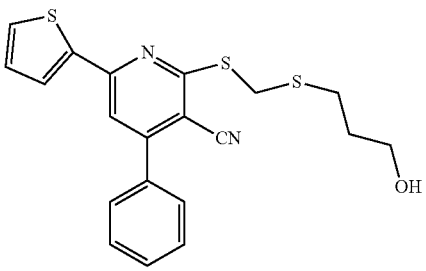 [SMILES: N#Cc1c(-c2ccccc2)cc(-c2cccs2)nc1SCSCCCO]

2-((((3-hydroxypropyl)thio)methyl)thio)-4-phenyl-6-(thiophen-2-yl)nicotinonitrile. Prepared analogously to 2-((((4-hydroxybutyl)thio)methyl)thio)-4-phenyl-6-(thiophen-2-yl)nicotinonitrile in 98% yield. $^1$H NMR (400 MHz, CHCl$_3$) 7.71 (dd, J=3.8, 1.1 Hz, 1H), 7.63-7.57 (m, 2H), 7.55-7.50 (m, 4H), 7.41 (s, 1H), 7.15 (dd, J=5.0, 3.8 Hz, 1H), 4.54 (s, 2H), 3.76 (t, J=6.1 Hz, 2H), 2.88 (t, J=7.1 Hz, 2H), 1.93 (ddd, J=13.2, 7.1, 6.1 Hz, 2H), 1.88-1.80 (m, 1H). ESI-MS (m/z): 399.1 [M+H]$^+$.

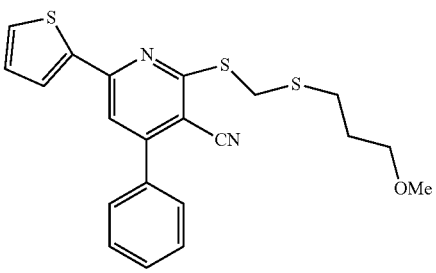 [SMILES: COCCCSCSc1nc(-c2cccs2)cc(-c2ccccc2)c1C#N]

2-((((3-methoxypropyl)thio)methyl)thio)-4-phenyl-6-(thiophen-2-yl)nicotinonitrile. Sodium hydride (micro spatula tipful) was added to an ice-cooled solution of 2-((((3-hydroxypropyl)thio)methyl)thio)-4-phenyl-6-(thiophen-2-yl)nicotinonitrile (41.6 mg, 0.10 mmol) in DMF (1.0 ml). The mixture was stirred cold for 15 minutes before the addition of methyl iodide (34 ml, 0.55 mmol). The mixture was stirred cold in the melting ice-bath for 2 hours, then diluted with EtOAc and washed several times with water and then brine. The organic layer was dried over Na$_2$SO$_4$, filtered and condensed. Purification was carried out on an automated flash chromatography system in 0-40% EtOAc/hexanes with an isolated yield of 56%. $^1$H NMR (400 MHz, CHCl$_3$) δ 7.72 (dd, J=3.8, 1.1 Hz, 1H), 7.61 (dd, J=6.6, 3.1 Hz, 2H), 7.57-7.51 (m, 4H), 7.43 (s, 1H), 7.17 (dd, J=5.0, 3.8 Hz, 1H), 4.55 (s, 2H), 3.49 (t, J=6.1 Hz, 2H), 3.34 (s, 3H), 2.85 (t, J=7.3 Hz, 2H), 1.95 (ddd, J=13.4, 7.3, 6.1 Hz, 2H). ESI-MS (m/z): 413.1 [M+H]$^+$.

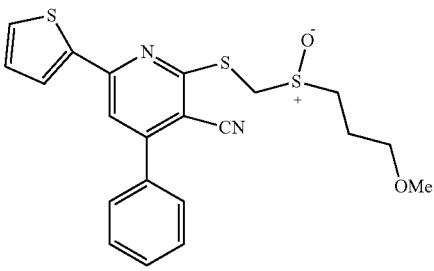

2-((((3-methoxypropyl)sulfinyl)methyl)thio)-4-phenyl-6-(thiophen-2-yl)nicotinonitrile. Prepared analogously to 4-((((3-cyano-4-phenyl-6-(thiophen-2-yl)pyridin-2-yl)thio)methyl)sulfinyl)butyl acetate in 71% yield. $^1$H NMR (400 MHz, CHCl$_3$) δ 7.76 (dd, J=3.8, 1.1 Hz, 1H), 7.65-7.58 (m, 2H), 7.56 (td, J=4.6, 2.0 Hz, 4H), 7.49 (s, 1H), 7.18 (dd, J=5.0, 3.8 Hz, 1H), 4.73 (d, J=13.1 Hz, 1H), 4.47 (d, J=13.0 Hz, 1H), 3.54 (qt, J=9.5, 5.8 Hz, 2H), 3.34 (s, 3H), 3.14 (dt, J=13.1, 7.9 Hz, 1H), 2.89 (ddd, J=13.1, 8.0, 6.4 Hz, 1H), 2.20-2.08 (m, 2H). ESI-MS (m/z): 429.1 [M+H]$^+$.

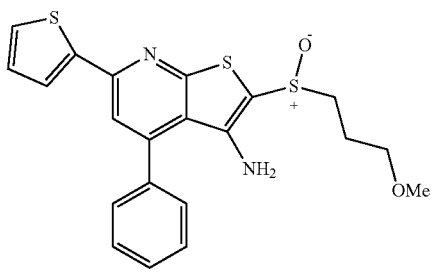

SW209276. 2-((3-methoxypropyl)sulfinyl)-4-phenyl-6-(thiophen-2-yl)thieno[2,3-b]pyridin-3-amine. Was prepared analogously to SW209329. 2-((4-chlorobutyl)sulfinyl)-4-phenyl-6-(thiophen-2-yl)thieno[2,3-b]pyridin-3-amine. Isolated yield=48%. $^1$H NMR (400 MHz, CHCl$_3$) δ 7.64 (ddd, J=7.2, 3.8, 1.7 Hz, 2H), 7.58-7.52 (m, 4H), 7.48-7.42 (m, 2H), 7.12 (qd, J=3.7, 1.8 Hz, 1H), 4.57 (s, 2H), 3.50 (td, J=6.1, 1.6 Hz, 2H), 3.40-3.29 (m, 4H), 3.26-3.13 (m, 1H), 2.09-1.95 (m, 2H). ESI-MS (m/z): 429.1 [M+H]$^+$.

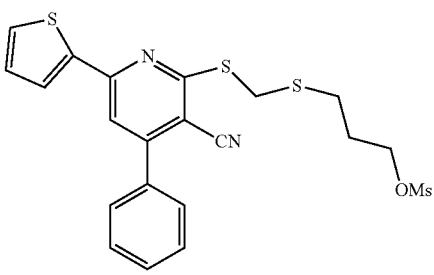

3-((((3-cyano-4-phenyl-6-(thiophen-2-yl)pyridin-2-yl)thio)methyl)thio)propyl methanesulfonate. Prepared analogously to 4-((((3-cyano-4-phenyl-6-(thiophen-2-yl)pyridin-2-yl)thio)methyl)thio)butyl methanesulfonate in quantitative yield. $^1$H NMR (400 MHz, CHCl$_3$) δ 7.69 (t, J=3.3 Hz, 1H), 7.63-7.55 (m, 2H), 7.52 (p, J=3.6, 3.0 Hz, 4H), 7.41 (q, J=2.6, 2.2 Hz, 1H), 7.14 (p, J=3.4, 2.5 Hz, 1H), 4.52 (q, J=2.2 Hz, 2H), 4.40-4.22 (m, 2H), 2.99 (s, 3H), 2.86 (td, J=7.2, 4.8 Hz, 2H), 2.10 (qt, J=6.4, 2.3 Hz, 2H). ESI-MS (m/z): 477.0 [M+H]$^+$.

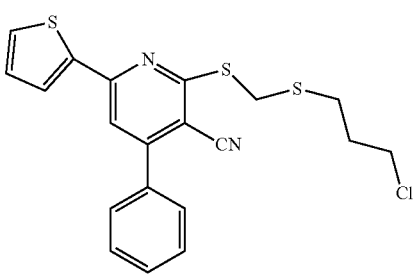 [SMILES: N#Cc1c(-c2ccccc2)cc(-c2cccs2)nc1SCSCCCCl]

2-((((3-chloropropyl)thio)methyl)thio)-4-phenyl-6-(thiophen-2-yl)nicotinonitrile. Prepared analogously to 2-((((4-chlorobutyl)thio)methyl)thio)-4-phenyl-6-(thiophen-2-yl)nicotinonitrile. Purification was performed using an automated flash chromatography system in 0-50% EtOAc/hexanes with an isolated yield of 69%. ¹H NMR (400 MHz, CHCl₃) δ 7.72 (dd, J=3.7, 1.1 Hz, 1H), 7.64-7.59 (m, 2H), 7.57-7.53 (m, 4H), 7.44 (s, 1H), 7.17 (dd, J=5.0, 3.8 Hz, 1H), 4.56 (s, 2H), 3.68 (t, J=6.3 Hz, 2H), 2.93 (t, J=7.0 Hz, 2H), 2.15 (p, J=6.7 Hz, 2H). ESI-MS (m/z): 417.0 [M+H]⁺.

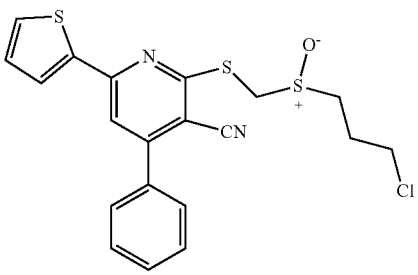

2-((((3-chloropropyl)sulfinyl)methyl)thio)-4-phenyl-6-(thiophen-2-yl)nicotinonitrile. Prepared analogously to 2-((((4-chlorobutyl)sulfinyl)methyl)thio)-4-phenyl-6-(thiophen-2-yl)nicotinonitrile in 90% yield. ¹H NMR (400 MHz, CHCl₃) δ 7.76 (dd, J=3.8, 1.1 Hz, 1H), 7.62 (dq, J=7.1, 2.6, 2.2 Hz, 2H), 7.59-7.53 (m, 4H), 7.51 (s, 1H), 7.18 (dd, J=5.0, 3.8 Hz, 1H), 4.74 (d, J=13.1 Hz, 1H), 4.51 (d, J=13.1 Hz, 1H), 3.79-3.63 (m, 2H), 3.28-3.16 (m, 1H), 3.04-2.88 (m, 1H), 2.43-2.31 (m, 2H). ESI-MS (m/z): 433.0 [M+H]⁺.

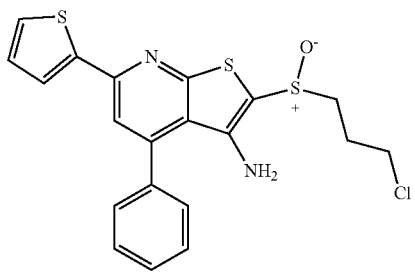

SW209330. 2-((3-chloropropyl)sulfinyl)-4-phenyl-6-(thiophen-2-yl)thieno[2,3-b]pyridin-3-amine. Prepared analogously to SW209329. 2-((4-chlorobutyl)sulfinyl)-4-phenyl-6-(thiophen-2-yl)thieno[2,3-b]pyridin-3-amine. Purification on an automated chromatography system in 0-60% EtOAc/hexanes gave the desired in 88% yield. ¹H NMR (400 MHz, CHCl₃) δ 7.57 (h, J=5.7, 5.3 Hz, 1H), 7.45 (t, J=6.0 Hz, 0H), 7.40 (s, 0H), 7.09 (t, J=4.4 Hz, 0H), 4.61 (s, 0H), 3.67 (td, J=6.4, 3.2 Hz, 0H), 3.40 (dt, J=14.1, 7.3 Hz, 0H), 3.24 (dt, J=13.1, 7.6 Hz, 0H), 2.25 (p, J=7.0 Hz, 0H).

ESI-MS (m/z): 433.0 [M+H]⁺.

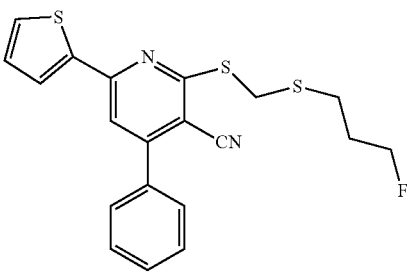 [SMILES: N#Cc1c(-c2ccccc2)cc(-c2cccs2)nc1SCSCCCF]

2-((((3-fluoropropyl)thio)methyl)thio)-4-phenyl-6-(thiophen-2-yl)nicotinonitrile. Kryptofix 222 (44.4 mg, 0.012 mmol), KF (6.1 mg, 0.10 mmol) and K₂CO₃ (3.0 mg, 0.022 mmol) were charged to a vial containing 3-((((3-cyano-4-phenyl-6-(thiophen-2-yl)pyridin-2-yl)thio)methyl)thio)propyl methanesulfonate (54.2 mg, 0.11 mmol). DMF (1.1 ml) was added and the reaction was heated at 85° C. for 65 minutes. The cooled mixture was diluted with EtOAc and washed several times with water and then brine. The organic layer was dried over Na₂SO₄, filtered and condensed. Yield=96%. Crude product was carried forward. ¹H NMR (400 MHz, CHCl₃) δ 7.72 (dd, J=3.7, 1.1 Hz, 1H), 7.64-7.59 (m, 2H), 7.54 (dd, J=4.9, 2.2 Hz, 4H), 7.43 (s, 1H), 7.17 (dd, J=5.1, 3.7 Hz, 1H), 4.63 (t, J=5.7 Hz, 1H), 4.55 (s, 2H), 4.51 (t, J=5.8 Hz, 1H), 3.67 (t, J=6.3 Hz, 2H), 2.91 (dt, J=11.2, 7.1 Hz, 1H), 2.14 (p, J=6.7 Hz, 1H). ESI-MS (m/z): 401.1 [M+H]⁺.

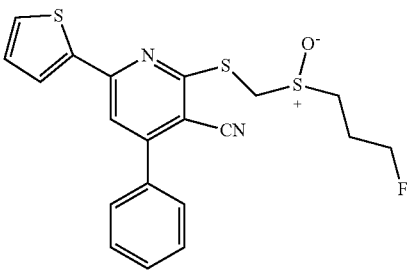

2-((((3-fluoropropyl)sulfinyl)methyl)thio)-4-phenyl-6-(thiophen-2-yl)nicotinonitrile. Acetic acid (215 μl) and hydrogen peroxide (16.75 μl, 30% solution in water) were added to the solution of 2-((((3-fluoropropyl)thio)methyl)thio)-4-phenyl-6-(thiophen-2-yl)nicotinonitrile (43.3 mg, 0.034 mmol) in chloroform (215 al). The reaction mixture was stirred at 32° C. for 50 min and then diluted with chloroform and was washed with saturated NaHCO₃ solution and extracted three times with chloroform. The combined organic layers was dried over Na₂SO₄, filtered and concentrated under reduce pressure in 94% yield. ESI-MS (m/z): 417.1 [M+H]⁺.

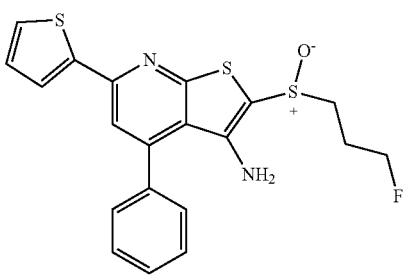

SW209331. 2-((3-fluoropropyl)sulfinyl)-4-phenyl-6-(thiophen-2-yl)thieno[2,3-b]pyridin-3-amine. Prepared analogously to SW209329. 2-((4-chlorobutyl)sulfinyl)-4-phenyl-6-(thiophen-2-yl)thieno[2,3-b]pyridin-3-amine. The crude mixture was purified preparatively in 4% MeOH/DCM. Isolated yield=32%. $^1$H NMR (400 MHz, CHCl$_3$) δ 7.68 (dd, J=3.8, 1.1 Hz, 1H), 7.56 (q, J=2.7 Hz, 4H), 7.53-7.44 (m, 3H), 7.14 (dd, J=5.1, 3.7 Hz, 1H), 4.65 (td, J=5.8, 3.2 Hz, 1H), 4.60 (s, 2H), 4.53 (td, J=5.8, 3.1 Hz, 1H), 3.40 (dt, J=13.0, 7.3 Hz, 1H), 3.24 (dt, J=13.1, 7.6 Hz, 1H), 2.19 (dtt, J=26.4, 7.5, 5.7 Hz, 2H). ESI-MS (m/z): 417.1 [M+H]$^+$.

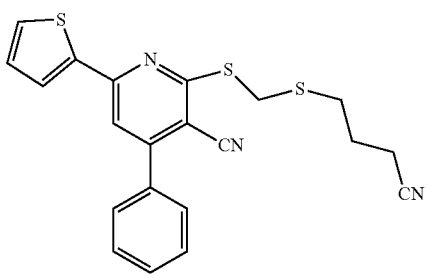 [SMILES: N#CCCCSCSc1nc(-c2cccs2)cc(-c2ccccc2)c1C#N]

2-((((3-cyanopropyl)thio)methyl)thio)-4-phenyl-6-(thiophen-2-yl)nicotinonitrile. A solution of 3-((((3-cyano-4-phenyl-6-(thiophen-2-yl)pyridin-2-yl)thio)methyl)thio)propyl methanesulfonate (54.6 mg, 0.11 mmol) and KCN (76.9 mg, 1.18 mmol) in DMF (1.14 ml) was heated at 85° C. for 4 hours. The cooled mixture was diluted with EtOAc and washed several times with water and then brine. The organic phase was dried over Na$_2$SO$_4$, filtered and condensed. Yield=89%. $^1$H NMR (400 MHz, CHCl$_3$) δ 7.71 (d, J=3.5 Hz, 1H), 7.60 (dt, J=6.4, 2.0 Hz, 3H), 7.54 (qt, J=5.6, 2.5 Hz, 4H), 7.44 (d, J=1.4 Hz, 1H), 7.16 (ddd, J=5.2, 3.8, 1.5 Hz, 1H), 4.53 (d, J=1.7 Hz, 2H), 2.93-2.82 (m, 2H), 2.52 (td, J=7.1, 1.4 Hz, 2H), 2.09-1.92 (m, 2H). ESI-MS (m/z): 408.1 [M+H]$^+$.

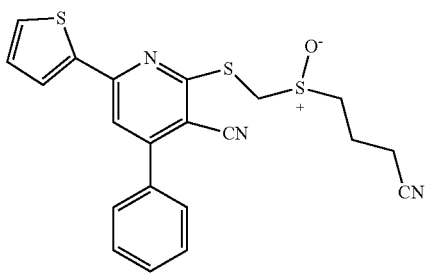

2-((((3-cyanopropyl)sulfinyl)methyl)thio)-4-phenyl-6-(thiophen-2-yl)nicotinonitrile. Acetic acid (205 μl) and hydrogen peroxide (15.6 μl, 30% solution in water) were added to the solution of 2-((((3-cyanopropyl)thio)methyl)thio)-4-phenyl-6-(thiophen-2-yl)nicotinonitrile (41.1 mg, 0.10 mmol) in chloroform (205 μl). The reaction mixture was stirred at 32° C. for 70 min and then diluted with chloroform and was washed with saturated NaHCO$_3$ solution and extracted three times with chloroform. The combined organic layers was dried over Na$_2$SO$_4$, filtered and concentrated under reduce pressure in 91% yield. ESI-MS (m/z): 424.1 [M+H]$^+$.

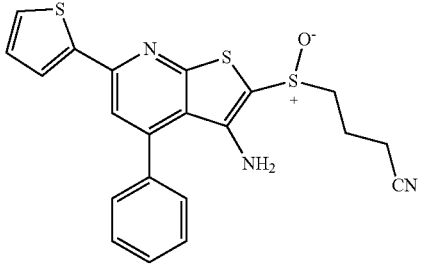

SW209332. 4-((3-amino-4-phenyl-6-(thiophen-2-yl)thieno[2,3-b]pyridin-2-yl)sulfinyl)butanenitrile. Prepared analogously to SW209329. 2-((4-chlorobutyl)sulfinyl)-4-phenyl-6-(thiophen-2-yl)thieno[2,3-b]pyridin-3-amine. The crude mixture was purified preparatively in 4% MeOH/DCM. Isolated yield=45%. $^1$H NMR (400 MHz, CHCl$_3$) δ 7.65 (d, J=3.7 Hz, 1H), 7.60-7.51 (m, 4H), 7.51-7.44 (m, 3H), 7.13 (t, J=4.4 Hz, 1H), 4.64 (s, 2H), 3.41 (dt, J=14.0, 7.3 Hz, 1H), 3.19 (dt, J=13.3, 7.5 Hz, 1H), 2.59 (t, J=7.1 Hz, 2H), 2.20 (p, J=7.3 Hz, 2H). ESI-MS (m/z): 424.0 [M+H]$^+$.

Example 2

Methods

Mice 8 week old female C57/BL6J mice were purchased from Jackson Labs (stock #000664). All mouse studies were approved by the institutional animal care and use committee at Case Western Reserve University.

Bleomycin Instillation

To induce disease onset, mice were anesthetized with ketamine/xylazine and the trachea exposed by cervical excision. Bleomycin sulfate (Enzo-BML-AP302-0010) was dissolved in H$_2$O and administered intratracheally as a single dose of 2 mg/kg in 50 μl solution per animal.

IP Injections

Following bleomycin instillation, mice were injected in the intraperitoneal cavity with either Vehicle (10% EtOH, 5% Cremaphor, D5 H2O), or 5.0 mg/kg SW033291 (+) 2× daily for 35 days.

Animal Mortality and Body Weight

Mortality was observed daily over the duration of the study. Body weights were measured prior to instillation and twice weekly post-bleomycin instillation.

Hydroxyproline Assay

Hydroxyproline was used to measure collagen content in mouse lungs (Sigma-MAK008-1KT). Briefly, mice were sacrificed and the right lung dissected for collagen quantitation. Experiments were performed according to the manufacturer's protocol. 10 mg of total lung was weighed, homogenized in sterile water and hydrolyzed in 12N HCl on 120° C. heat block for 3 h. The hydrolyzed samples were incubated with 4-(Dimethylamino) benzaldehyde (DMAB)

for 90 min at 60° C., and the absorbance of oxidized hydroxyproline was measured at 560 nm.

Gene Expression Studies

To measure expression of inflammatory cytokines at Day 35 post bleomycin instillation, mice were sacrificed and the left lung dissected for RNA isolation. Tissue samples were homogenized on ice and the RNAqueous kit (Ambion-AM1912) was used to isolate total RNA. cDNA was synthesized (Invitrogen Superscript III-18080044) and real-time PCR performed using the following Taqman primers (Applied Biosystems):

Mouse B2M (endogenous control)-Mm00437762_m1
Mouse CCL4-Mm00443111_m1
Mouse TNF-Mm00443258_m1
Mouse TGFB-Mm01178820_m1
Mouse IFNG-Mm01168134_m1
Mouse IL2-Mm99999222_m1
Mouse CCL3-Mm00441259_g1.

FIG. 1 illustrates a schematic diagram of an assay for measuring the effects of SW033291 on weight maintenance and survival in a mouse model of idiopathic pulmonary fibrosis.

FIGS. 2(A-B) illustrate plots showing (A) weight change and (B) survival of vehicle and SW033291 treated mouse models of idiopathic pulmonary fibrosis. SW033291 treated mice exhibited enhanced maintenance of weight and improved survival compared to vehicle treated mice.

FIG. 3 illustrates a schematic diagram of an assay for measuring the effects of SW033291 on collagen deposition in a mouse model of idiopathic pulmonary fibrosis.

Figure 4:
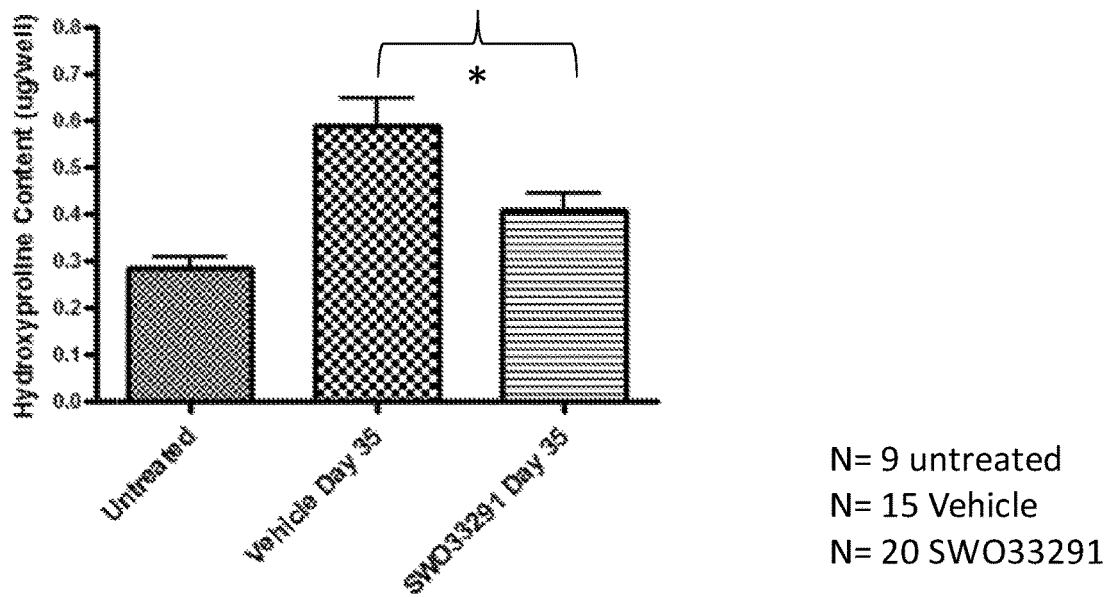
FIG. 4 illustrates a graph showing collagen deposition in vehicle and SW033291 treated mouse models of idiopathic pulmonary fibrosis.

FIG. 4 illustrates a graph showing collagen deposition in vehicle and SW033291 treated mouse models of idiopathic pulmonary fibrosis. SW033291 treated mice exhibited reduced collagen deposition compared to vehicle treated mice, as assayed by tissue hydroxyproline content.

Figure 5:
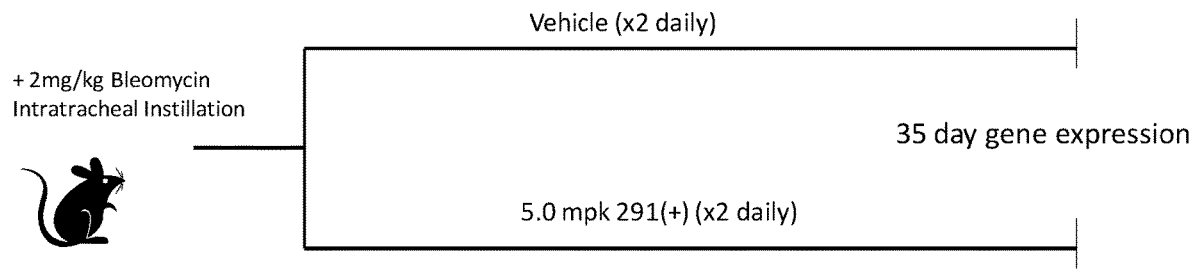
FIG. 5 illustrates a schematic diagram of an assay for measuring the effects of SW033291 on inflammatory cytokine expression in a mouse model of idiopathic pulmonary fibrosis.
Figure 6A:
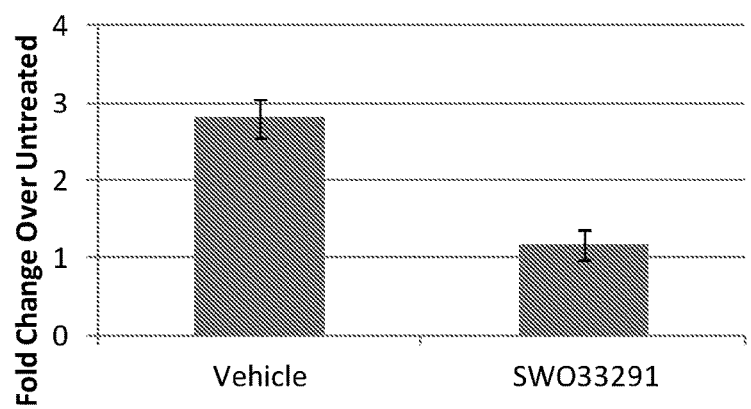
FIGS. 6(A-F) illustrate graphs showing inflammatory cytokine expression in vehicle and SW033291 treated mice models of idiopathic pulmonary fibrosis.
Figure 6B:
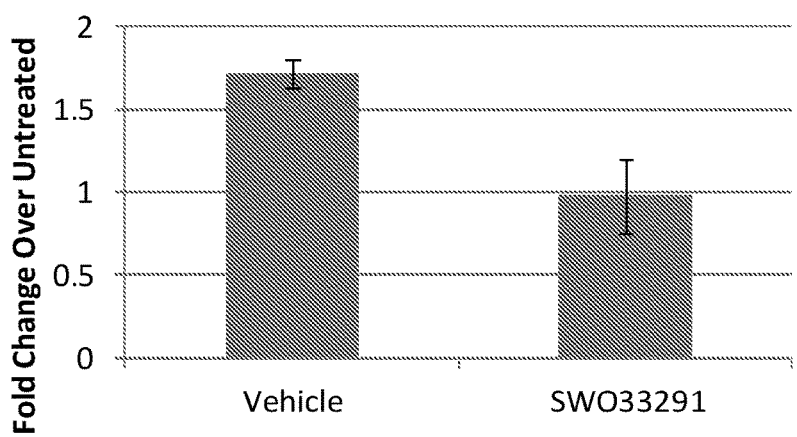
Figure 6C:
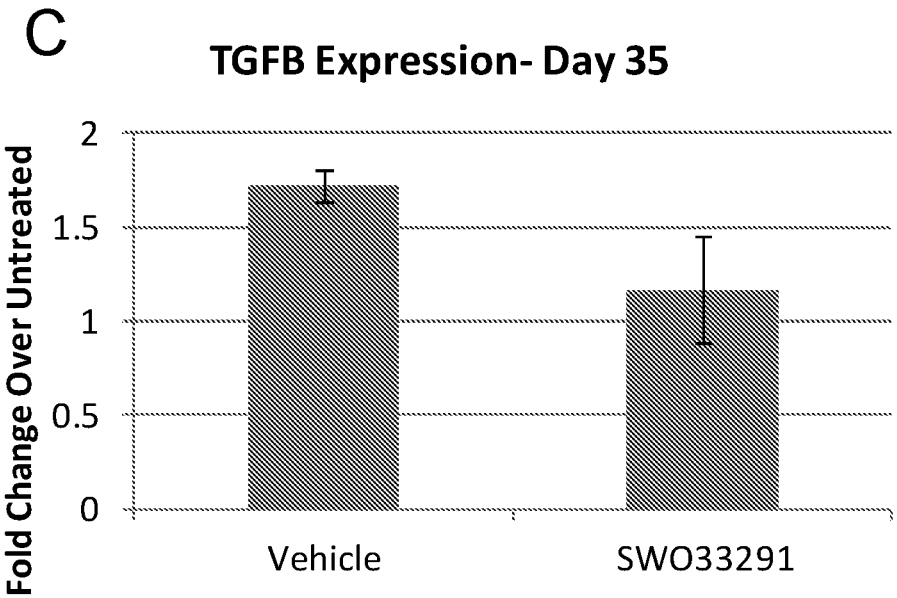
Figure 6D:
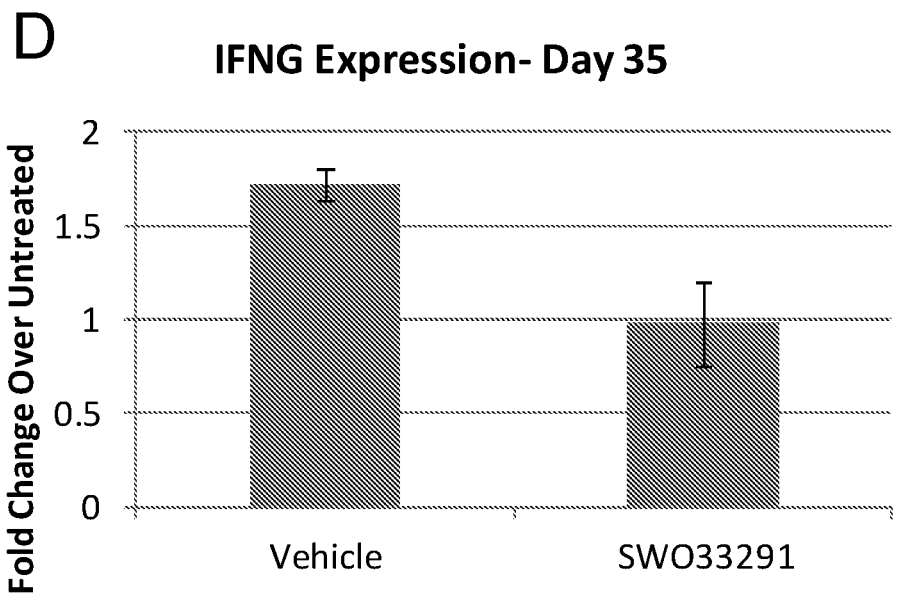
Figure 6E:
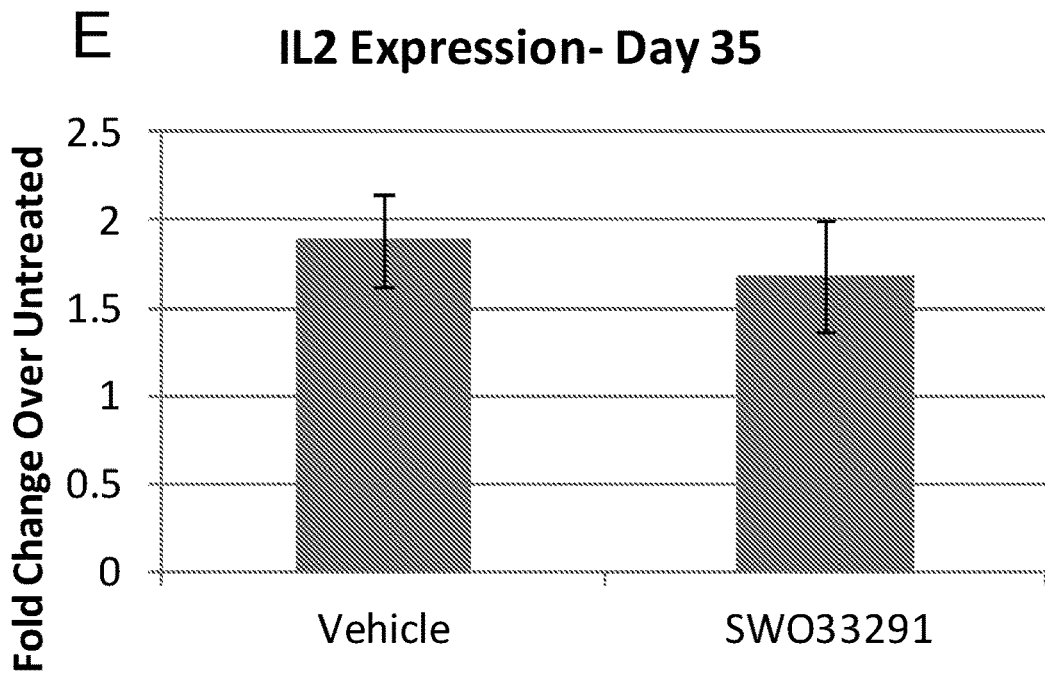
Figure 6F:
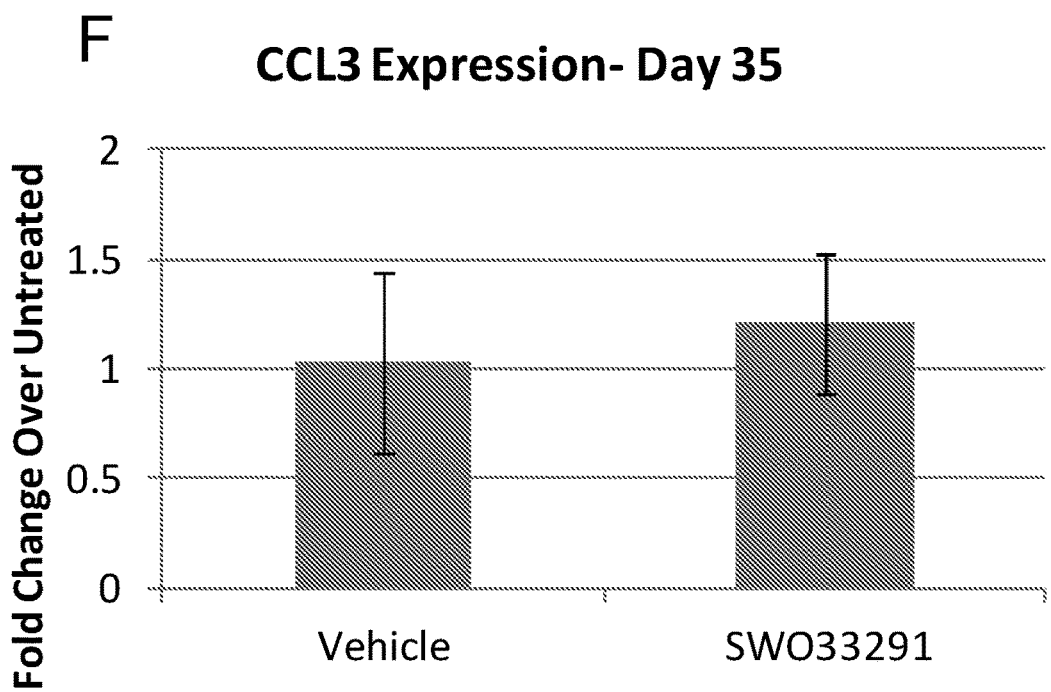
Figure 7A:
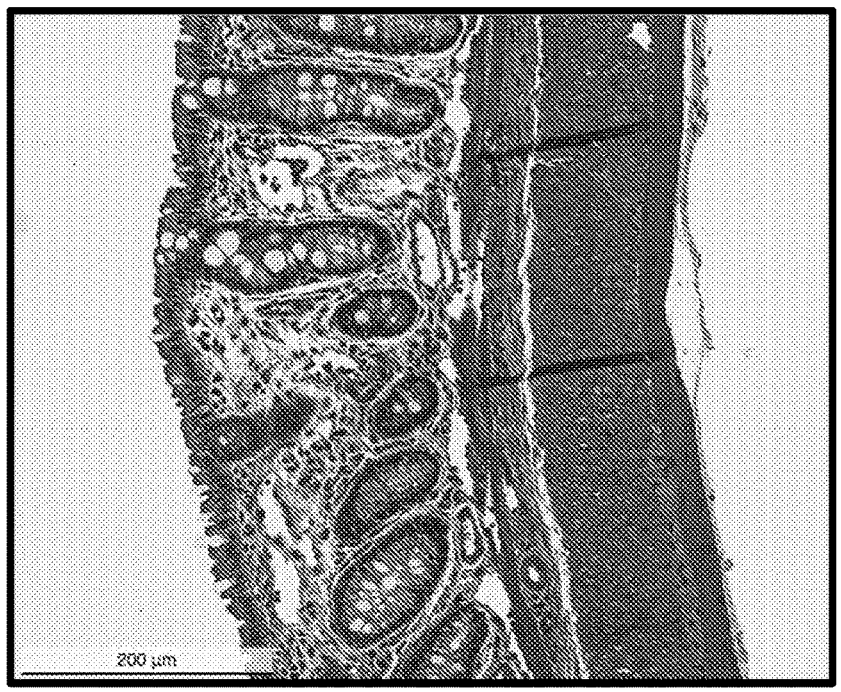
FIGS. 7(A-D) illustrate images of vehicle and (+)SW033291 treated mouse models of intestinal fibrosis.
Figure 7B:
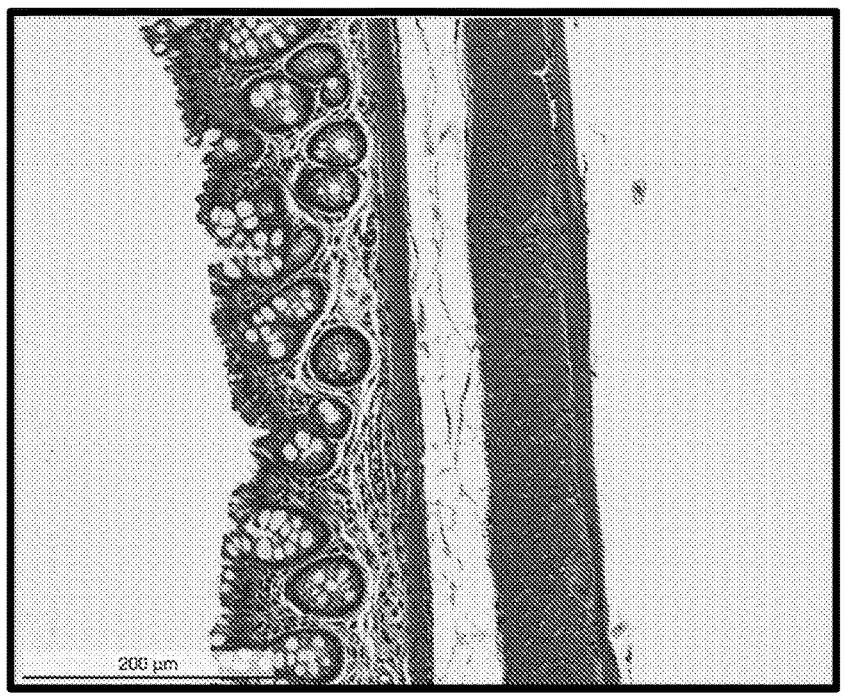
Figure 7C:
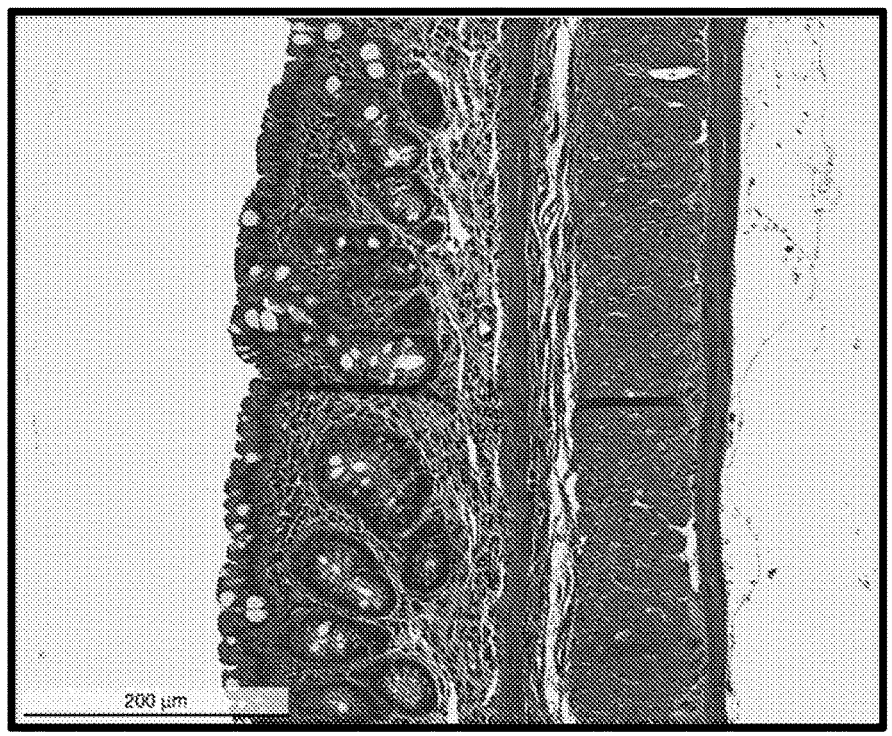
Figure 7D:
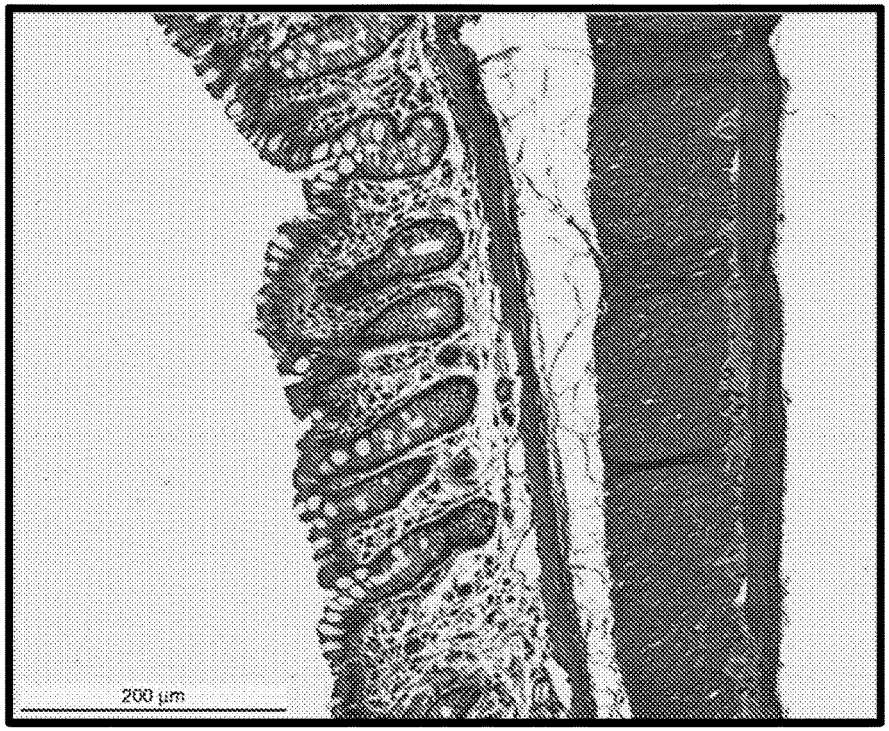

FIG. 5 illustrates a schematic diagram of an assay for measuring the effects of SW033291 on inflammatory cytokine expression in a mouse model of idiopathic pulmonary fibrosis.

FIGS. 6(A-F) illustrate graphs showing inflammatory cytokine expression in vehicle and SW033291 treated mice models of idiopathic pulmonary fibrosis.

Example 3

Figure 8:
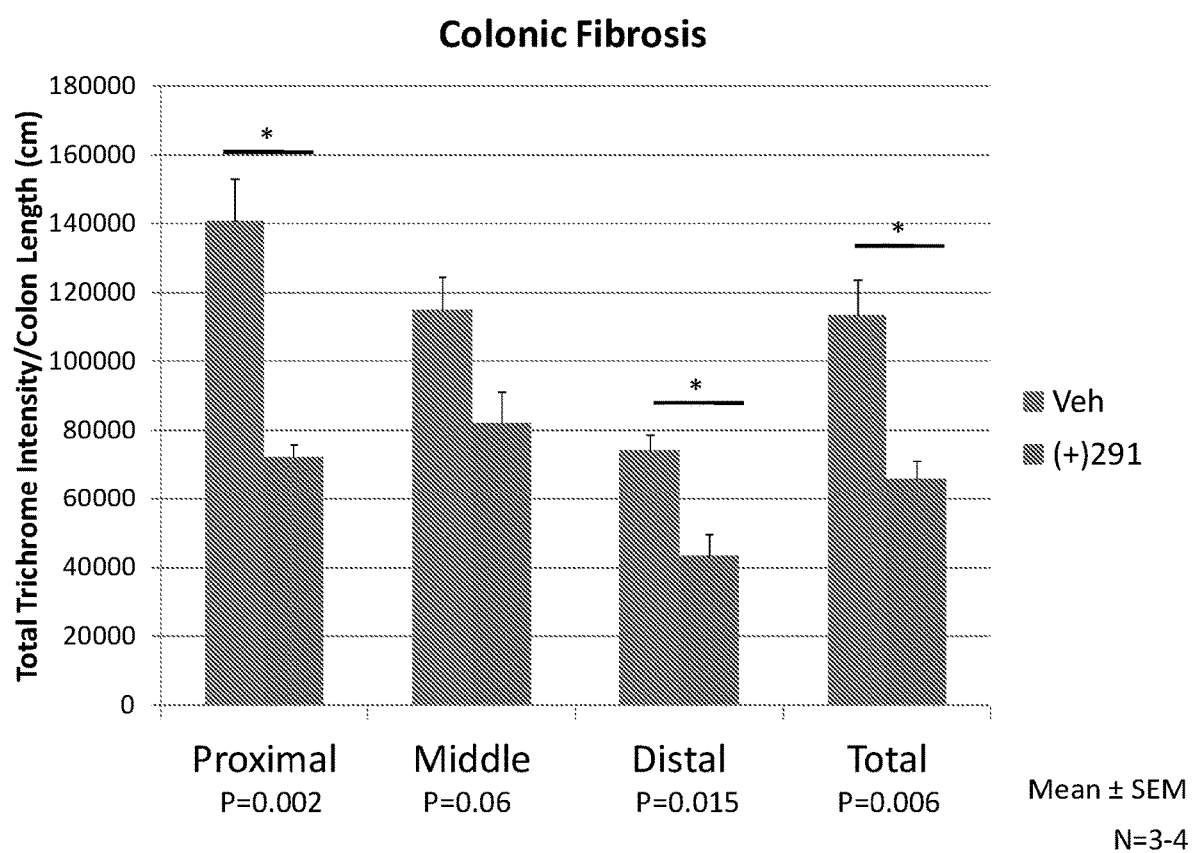
FIG. 8 illustrates a graph showing colonic fibrosis in vehicle and (+)SW033291 treated mouse models of intestinal fibrosis.

To establish a model of intestinal fibrosis due to chronic colitis, 8-week male FVB/N mice were subjected to three cycles of dextran sodium sulfate (DSS; 2% w/v) in sterile drinking water. Each cycle consisted of 7 days of DSS followed by 10 days of recovery without DSS. To explore the effects of 15-PGDH inhibition on intestinal fibrosis, mice were administered either (+)SW033291 5 mg/kg IP injections twice a day or vehicle injections from the end of the third DSS exposure (day 41) for a total of 28 days. On day 69, colons were harvested from mice, longitudinally open, and embedded in agar for orientation, and fixed in formalin overnight. Slides were prepared from paraffin-embedded formalin-fixed samples according to standard procedures. The degree of fibrosis in the mouse colon in the two groups were compared by Masson's Trichrome staining. The intensity of positive trichrome staining was quantified using ImageJ software in the following manner. 10 evenly spaced images were captured at 20× from each third of the colon from each mouse. (FIGS. 7(A-D)) Significant lymphovascular compartments or extracolonic connective tissue attachments seen on slides were excluded during the image capture. RGB channels were split from the images, and the blue channel from each image was divided by the red channel. After generating an intensity histogram of all pixels in the resultant image, the area under the curve (AUC) was calculated for intensities above 1.3 (blue/red) cutoff. The sum of AUC (total trichrome intensity) was normalized by the colon length. FIG. 8 shows colonic fibrosis (+)SW033291 treated mice was substantially reduced compared to vehicle treated mice.

While this invention has been particularly shown and described with references to preferred embodiments thereof, it will be understood by those skilled in the art that various changes in form and details may be made therein without departing from the scope of the invention encompassed by the appended claims. All patents, publications and references cited in the foregoing specification are herein incorporated by reference in their entirety.

The following is claimed:

1. A method of treating lung fibrosis in a subject in need thereof, the method comprising administering to the subject a therapeutically effective amount of a 15-PGDH inhibitor, wherein the 15-PGDH inhibitor includes a compound having formula (VI):

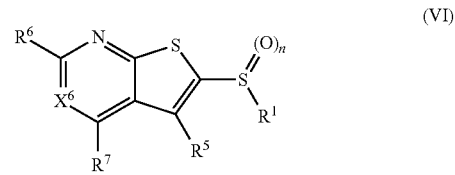

wherein: n=1;
$X^6$ is N or $CR^c$;
$R^1$ is selected from the group consisting of branched or linear alkyl and

wherein $n_2$=0-6 and X is any of the following: $CF_yH_z$ (y+z=3), $CCl_yH_z$ (y+z=3), OH, OAc, OMe, $R^{71}$, $OR^{72}$, CN, $N(R^{73})_2$,

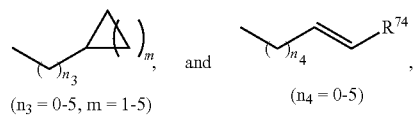

$R^5$ is selected from the group consisting of H, Cl, F, $NH_2$, and $N(R^{76})_2$,
$R^6$ and $R^7$ are the same or different and are each independently one of the following:

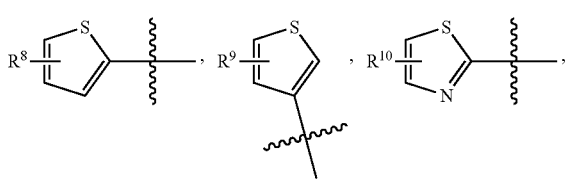

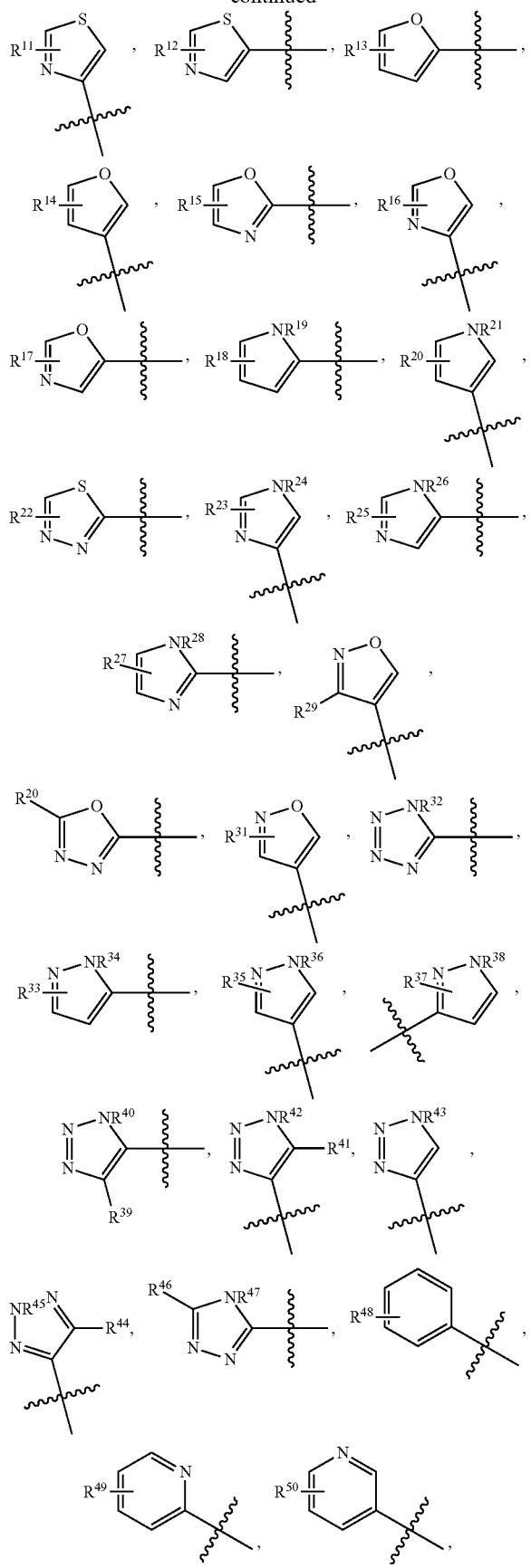
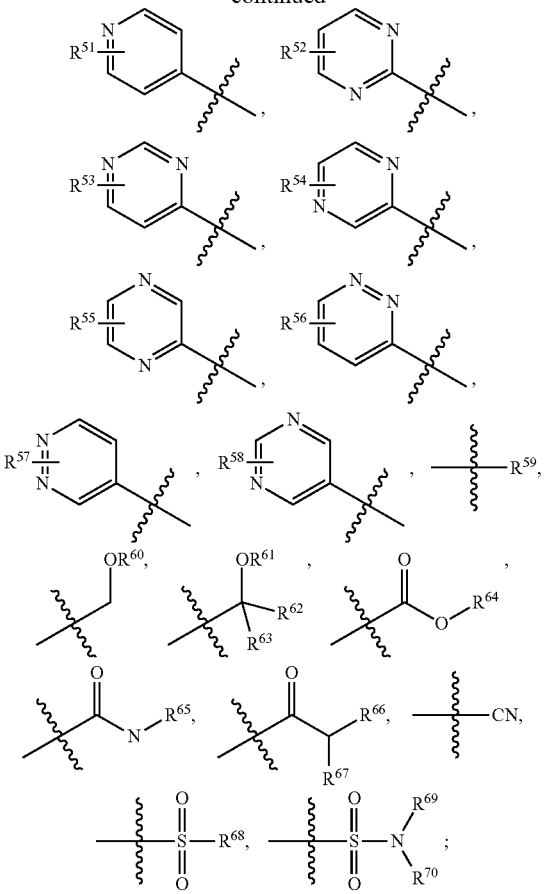

and each $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, $R^{49}$, $R^{50}$, $R^{51}$, $R^{52}$, $R^{53}$, $R^{54}$, $R^{55}$, $R^{56}$, $R^{57}$, $R^{58}$, $R^{59}$, $R^{60}$, $R^{61}$, $R^{62}$, $R^{63}$, $R^{64}$, $R^{65}$, $R^{66}$, $R^{67}$, $R^{68}$, $R^{69}$, $R^{70}$, $R^{71}$, $R^{72}$, $R^{73}$, $R^{74}$, $R^{76}$, and $R^c$ are the same or different and are independently selected from the group consisting of hydrogen, substituted or unsubstituted $C_1$-$C_{24}$ alkyl, $C_2$-$C_{24}$ alkenyl, $C_2$-$C_{24}$ alkynyl, $C_6$-$C_{20}$ aryl, heterocycloalkenyl containing from 5-6 ring atoms, (wherein from 1-3 of the ring atoms is independently selected from N, NH, N($C_1$-$C_6$ alkyl), NC(O)($C_1$-$C_6$ alkyl), O, and S), heteroaryl or heterocyclyl containing from 5-14 ring atoms, (wherein from 1-6 of the ring atoms is independently selected from N, NH, N($C_1$-$C_3$ alkyl), O, and S), $C_6$-$C_{24}$ alkaryl, $C_6$-$C_{24}$ aralkyl, halo, silyl, hydroxyl, sulfhydryl, $C_1$-$C_{24}$ alkoxy that is optionally substituted with at least one hydroxyl, amino, or mono- or di-($C_1$-$C_{24}$ alkyl)-amino, $C_2$-$C_{24}$ alkenyloxy, $C_2$-$C_{24}$ alkynyloxy, $C_5$-$C_{20}$ aryloxy, acyl, acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO—), carbamoyl (—(CO)—NH$_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—NH$_2$), carbamido (—NH—(CO)—NH$_2$), cyano (—CN), isocyano (—N+C—), cyanato (—O—

CN), isocyanato (—O—N+=C—), isothiocyanato (—S—CN), azido (—N=N+=N—), formyl (—(CO)—H), thioformyl (—(CS)—H), amino (—NH$_2$), mono- or di-(C$_1$-C$_{24}$ alkyl)-amino that is optionally substituted with at least one hydroxyl, amino, or mono- or di-(C$_1$-C$_{24}$ alkyl)-amino, C$_6$-C$_{20}$ aryl amino, C$_2$-C$_{24}$ alkylamido (—NH—(CO)-alkyl), C$_6$-C$_{20}$ arylamido (—NH—(CO)-aryl), sulfanamido (—SO$_2$N(R)$_2$ where R is independently H, alkyl, aryl or heteroaryl), imino, alkylimino, arylimino, nitro (—NO$_2$), nitroso (—NO), sulfo (—SO$_2$—OH), sulfonato (—SO$_2$—O—), C$_1$-C$_{24}$ alkylsulfanyl, arylsulfanyl, C$_1$-C$_{24}$ alkylsulfinyl (—(SO)-alkyl), C$_5$-C$_{20}$ arylsulfinyl (—(SO)-aryl), C$_1$-C$_{24}$ alkylsulfonyl (—SO$_2$-alkyl), C$_5$-C$_{20}$ arylsulfonyl (—SO$_2$-aryl), sulfonamide (—SO$_2$—NH$_2$, —SO$_2$NY$_2$ (wherein Y is independently H, arlyl or alkyl), phosphono (—P(O)(OH)$_2$), phosphonato (—P(O)(O—)$_2$), phosphinato (—P(O)(O—)), phospho (—PO$_2$), phosphino (—PH$_2$), polyalkyl ethers (—[(CH$_2$)$_n$O]$_m$), phosphates, phosphate esters [—OP(O)(OR)$_2$ where R=H, methyl or other alkyl], and combinations thereof, or pharmaceutically acceptable salts thereof.

2. The method of claim 1, wherein the lung fibrosis is characterized, in whole or in part, by the excess production of fibrous material, including excess production of fibrotic material within the extracellular matrix, or the replacement of normal tissue elements by abnormal, non-functional, and/or excessive accumulation of matrix-associated components.

3. The method of claim 1, wherein the lung fibrosis is selected from the group consisting of pulmonary fibrosis, pulmonary hypertension, chronic obstructive pulmonary disease (COPD), asthma, idiopathic pulmonary fibrosis, sarcoidosis, cystic fibrosis, familial pulmonary fibrosis, silicosis, asbestosis, coal worker's pneumoconiosis, carbon pneumoconiosis, hypersensitivity pneumonitides, pulmonary fibrosis caused by inhalation of inorganic dust, pulmonary fibrosis caused by an infectious agent, pulmonary fibrosis caused by inhalation of noxious gases, aerosols, chemical dusts, fumes or vapors, induced interstitial lung disease, chemotherapy/radiation induced pulmonary fibrosis, pulmonary hypertension, and combinations there.

4. The method of claim 3, wherein the lung fibrosis is cystic fibrosis.

5. The method of claim 1, wherein the 15-PGDH inhibitor is administered at an amount effective to reduce or inhibit any of collagen deposition, collagen accumulation, collagen fiber accumulation, inflammatory cytokine expression, and/or inflammatory cell infiltration in a tissue or organ of the subject being treated.

6. The method of claim 1, wherein the compound is selected from the group consisting of:

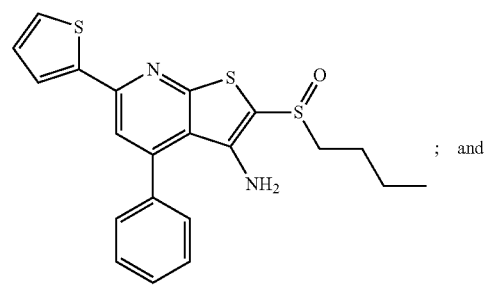

; and

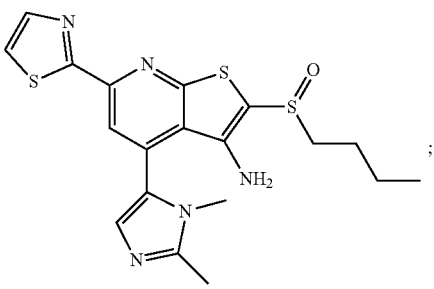

or pharmaceutically acceptable salts thereof.

7. The method of claim 1, wherein the 15-PGDH inhibitor is selected from the group consisting of:

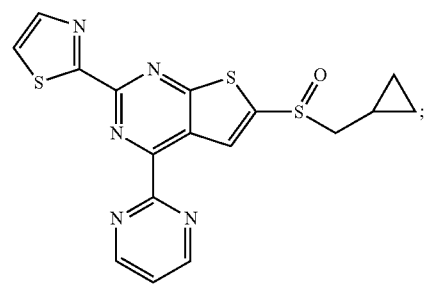

;

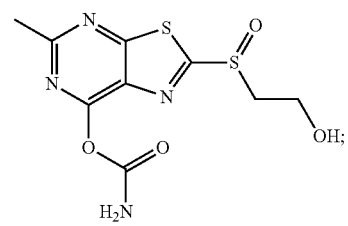

;

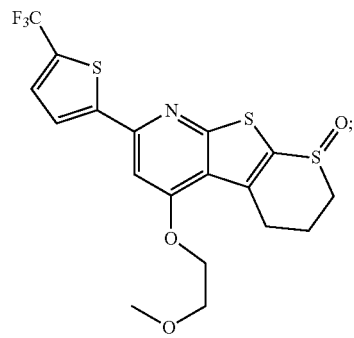

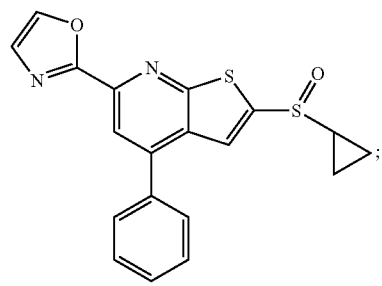

;

169
-continued
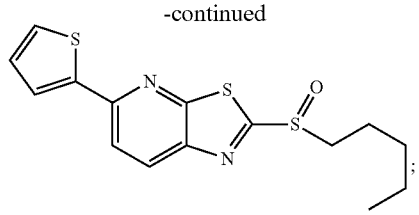
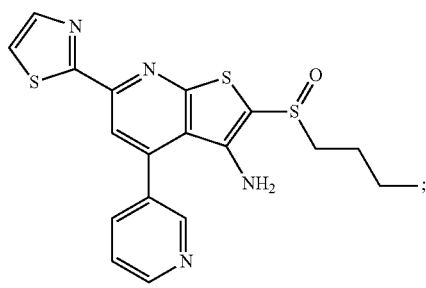
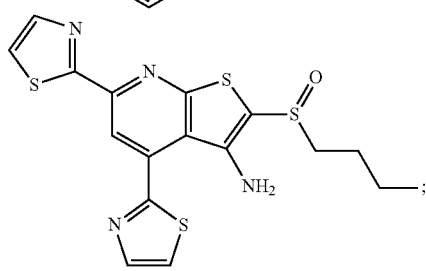
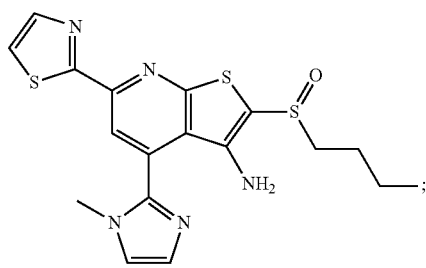
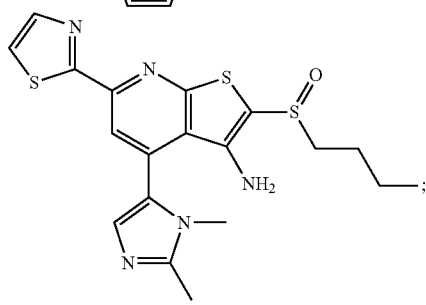
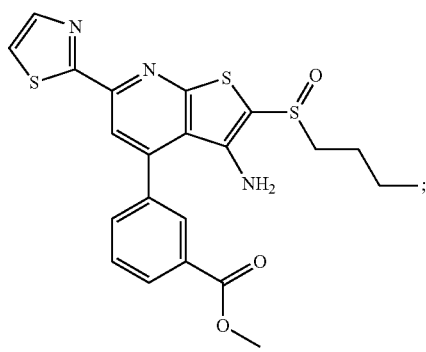
170
-continued
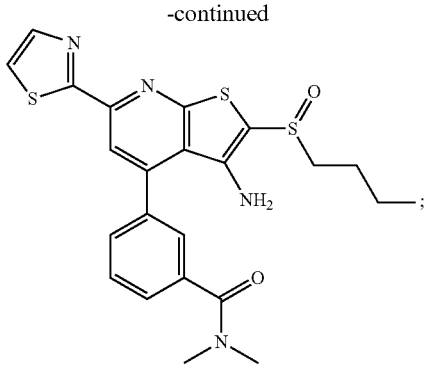
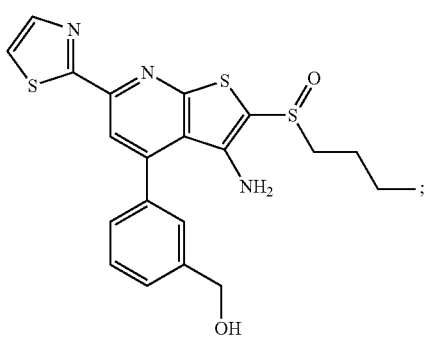
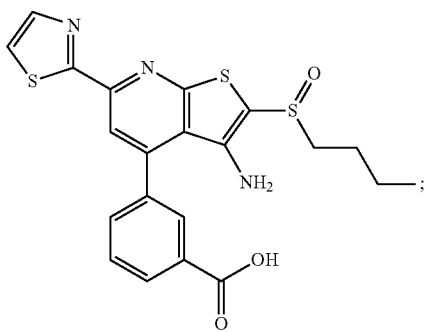
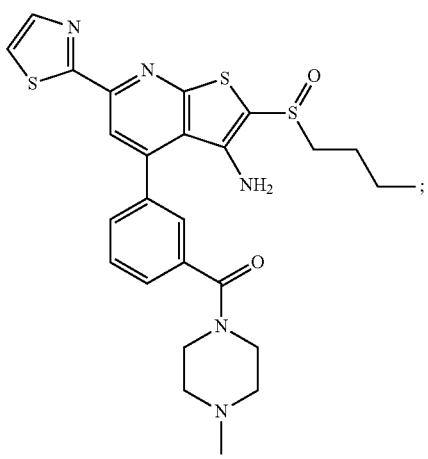

171
-continued
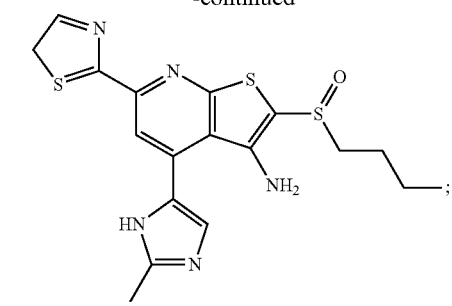
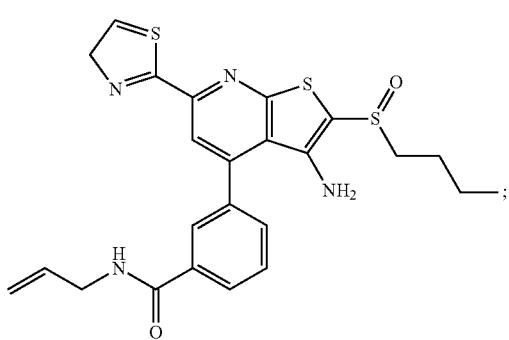
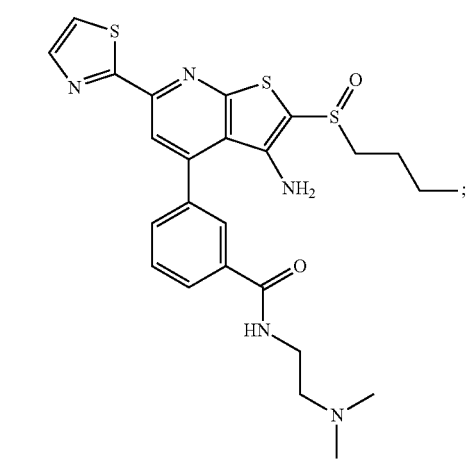
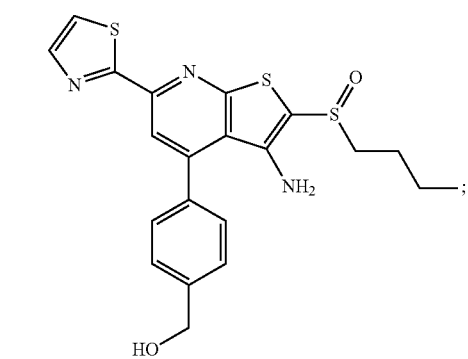
172
-continued
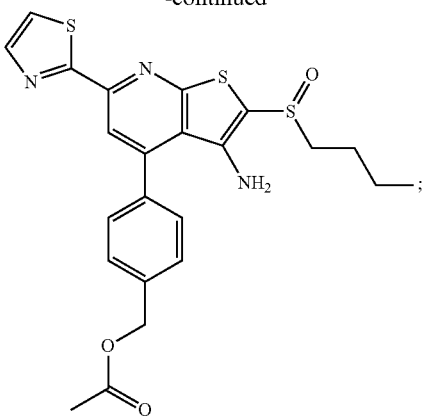
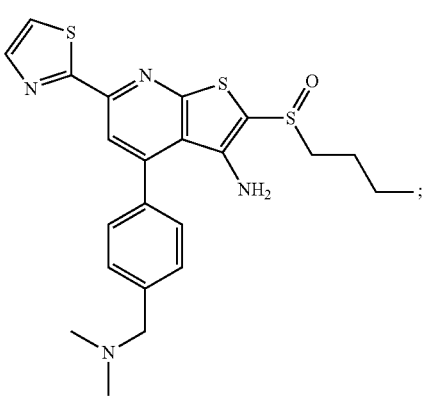
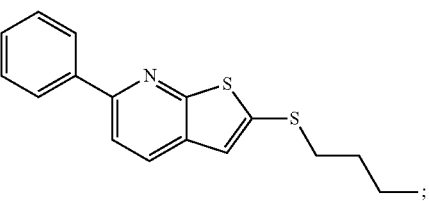
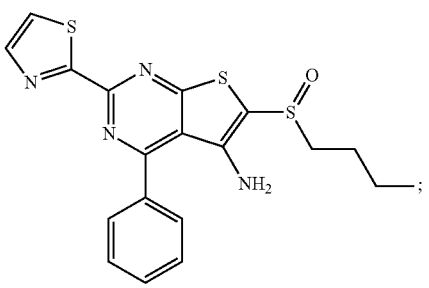
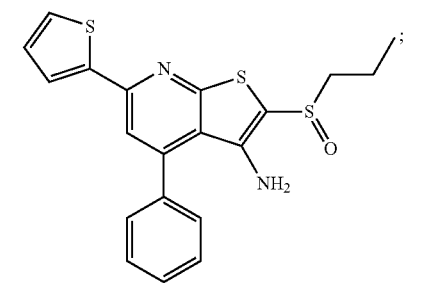

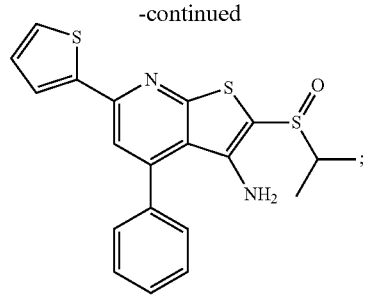
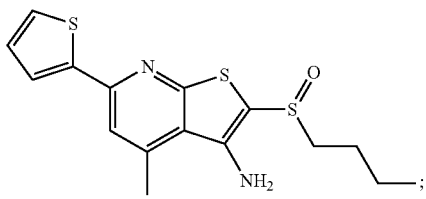
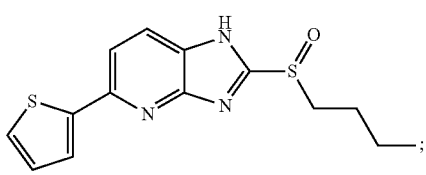
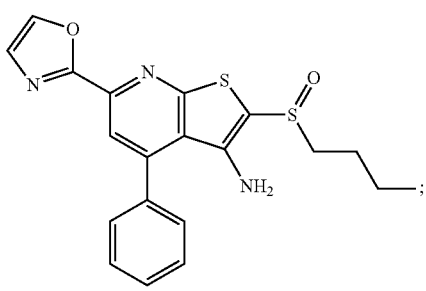
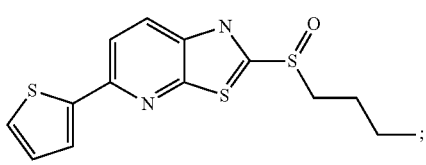
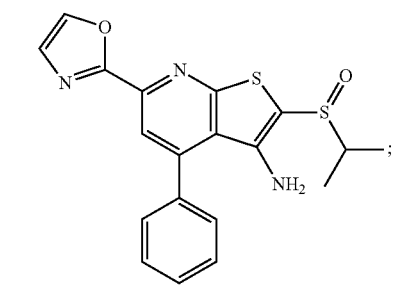
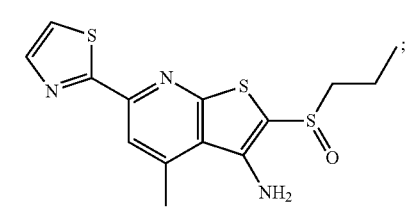
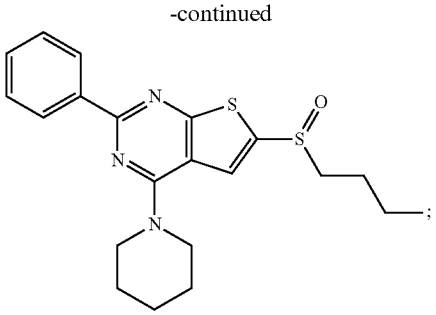
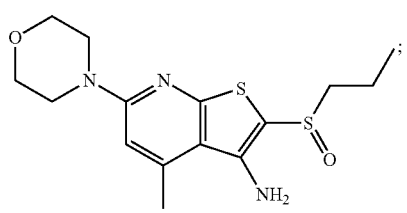
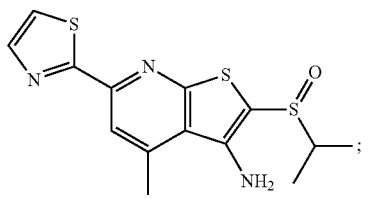
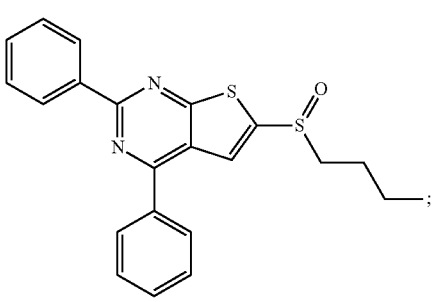
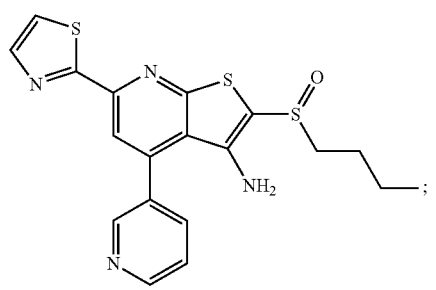
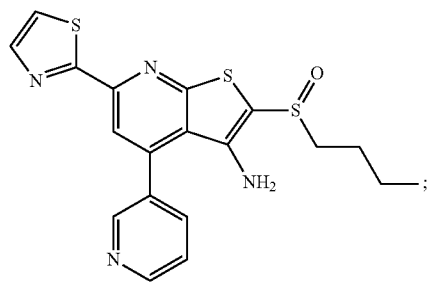

175
-continued
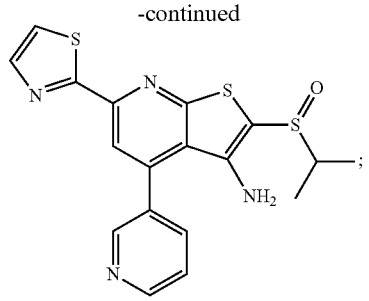
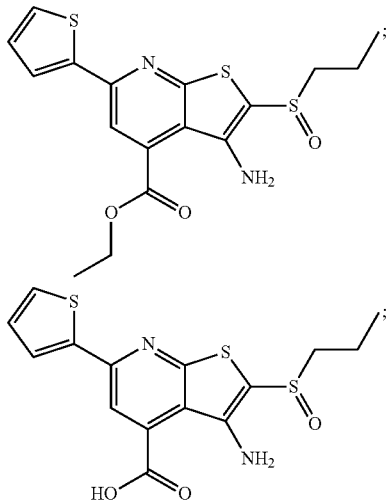
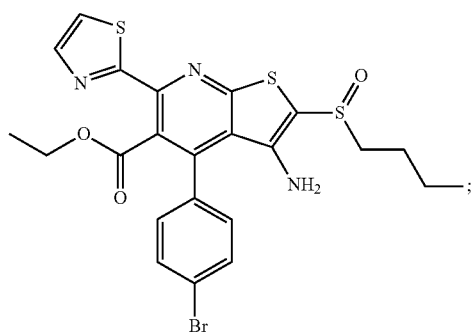
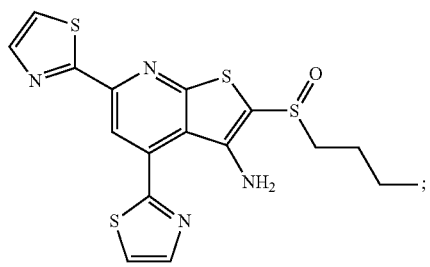
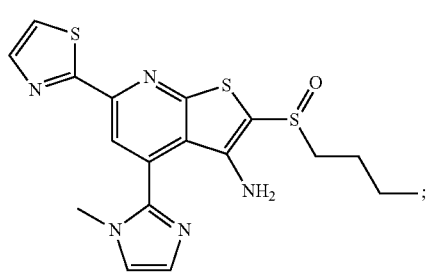
176
-continued
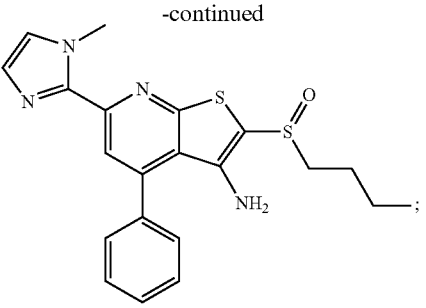
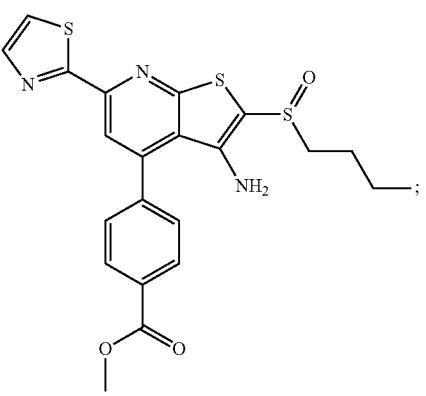
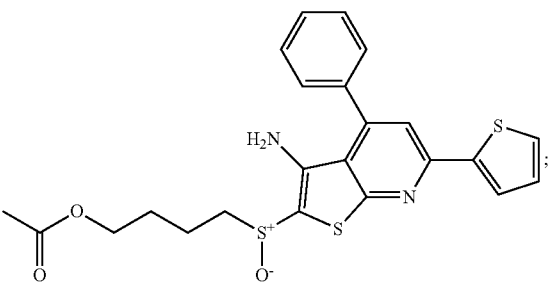
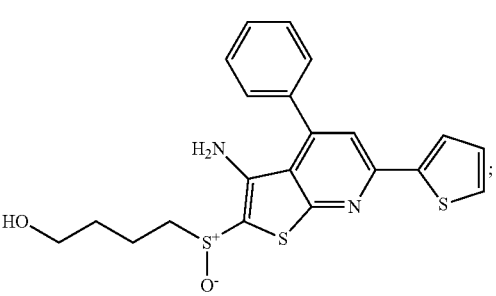
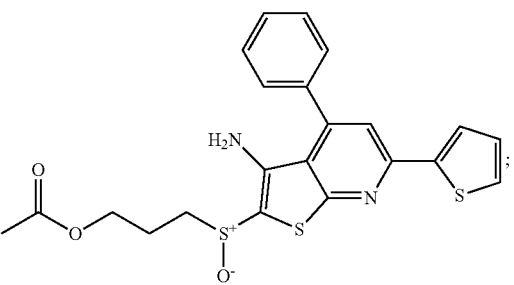

177
-continued
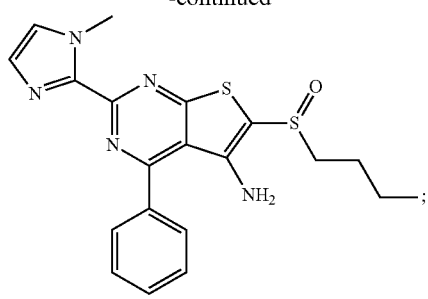
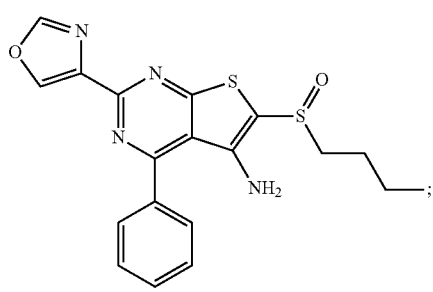
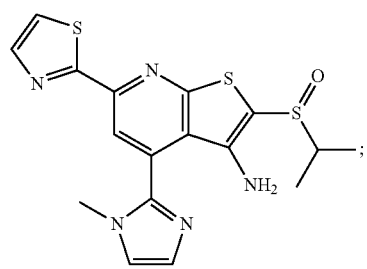
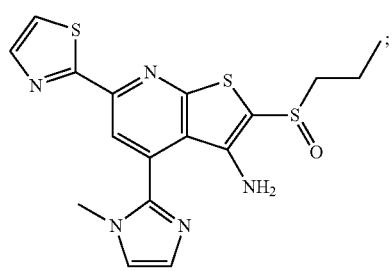
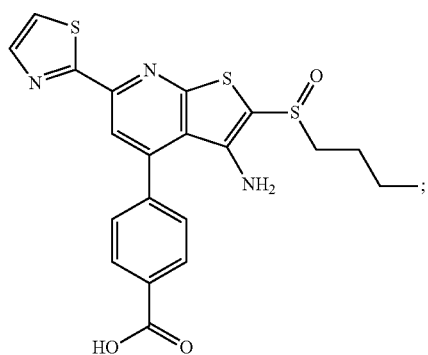
178
-continued
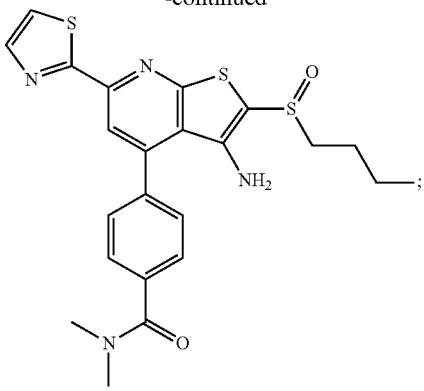
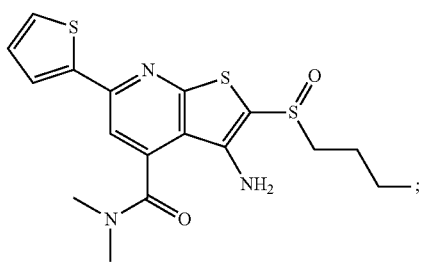
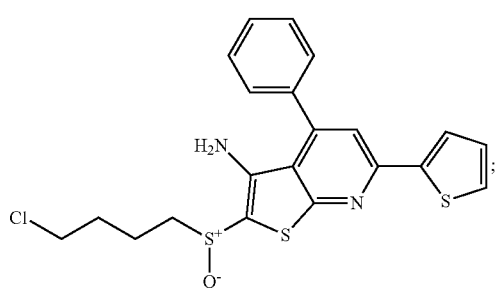
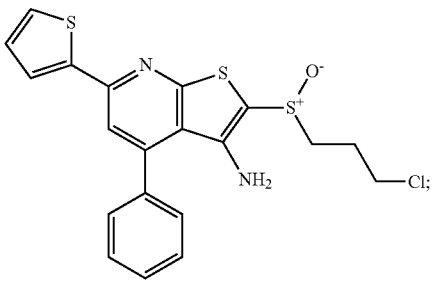
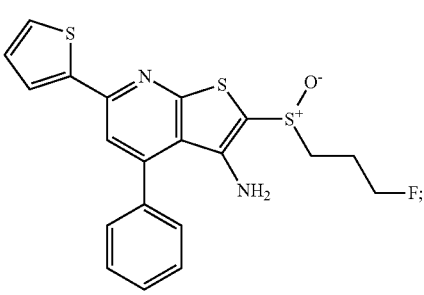

179
-continued
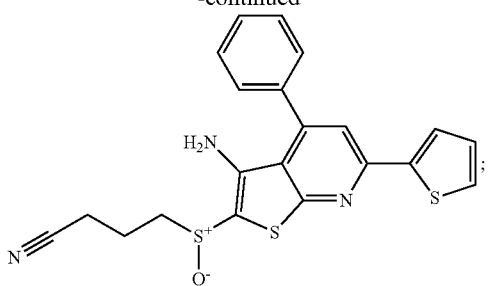
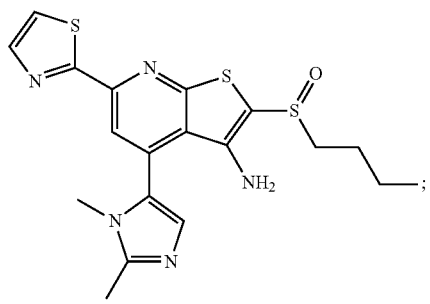
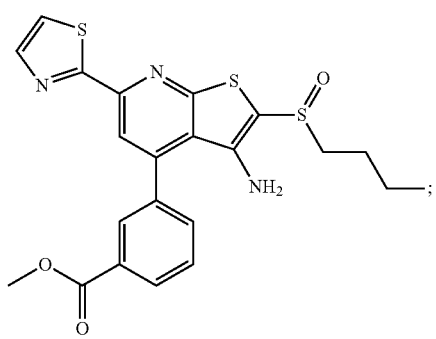
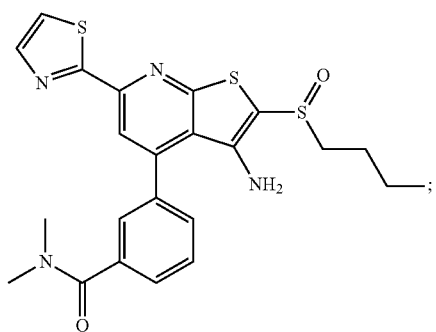
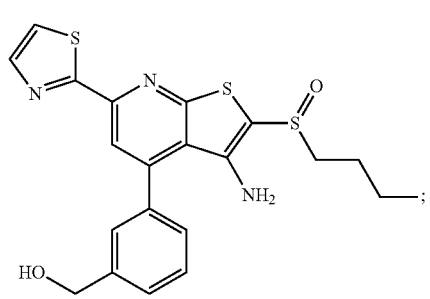
180
-continued
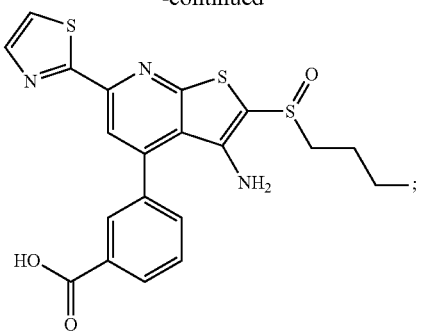
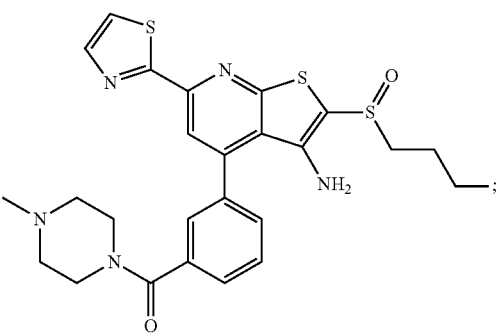
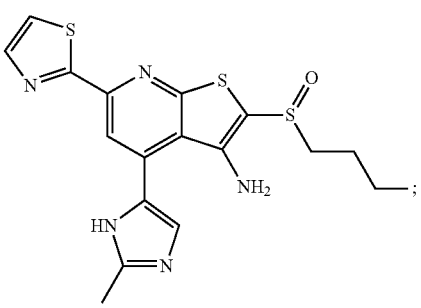
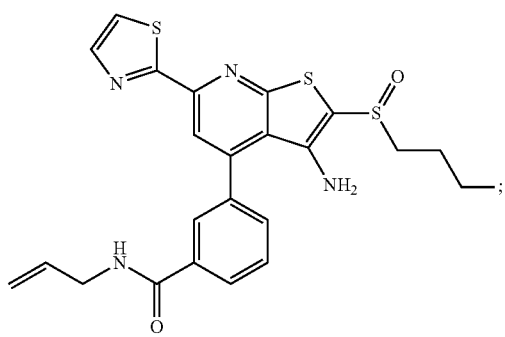
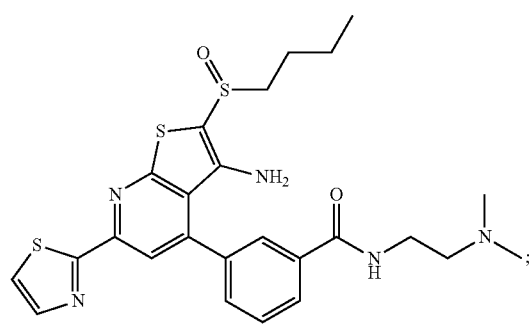

181
-continued
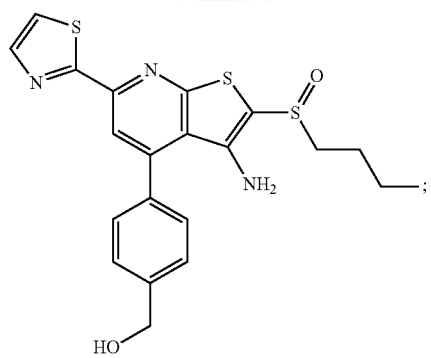
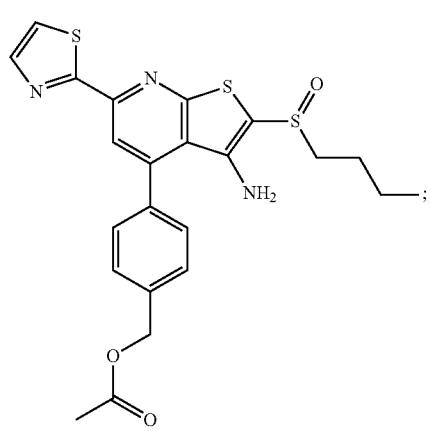
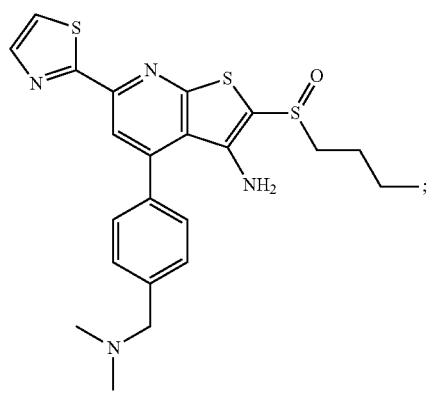
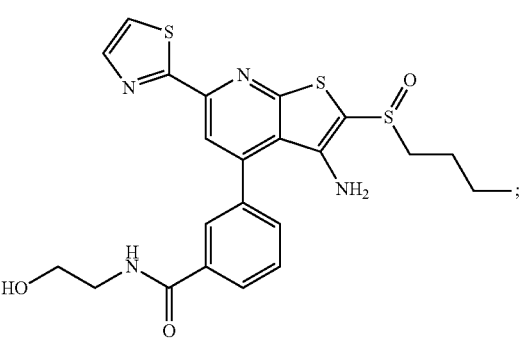
182
-continued
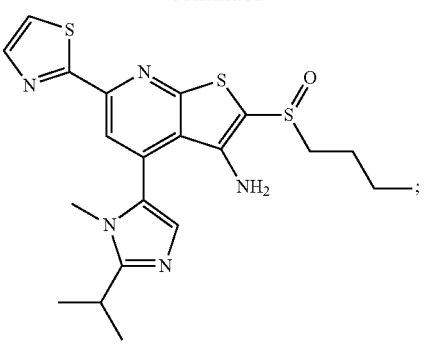
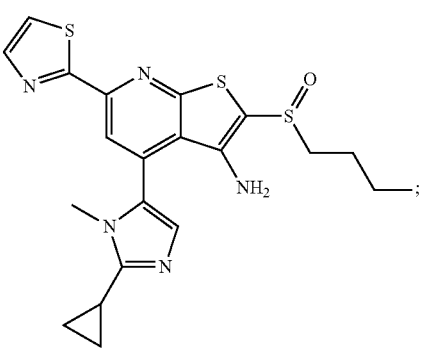
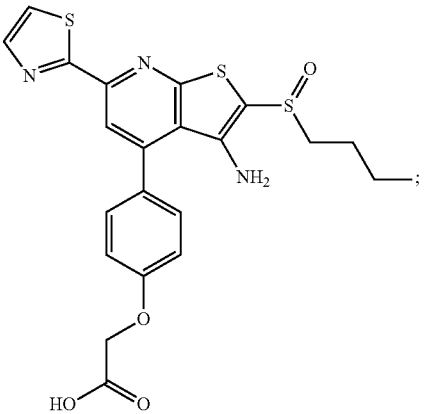
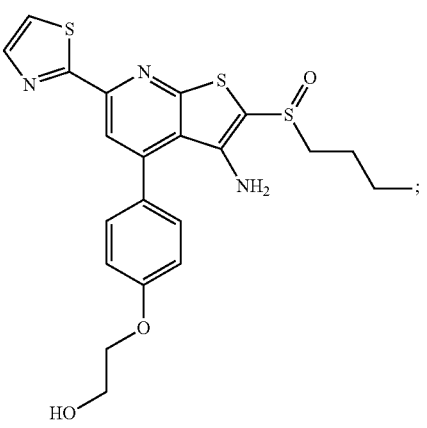

183
-continued
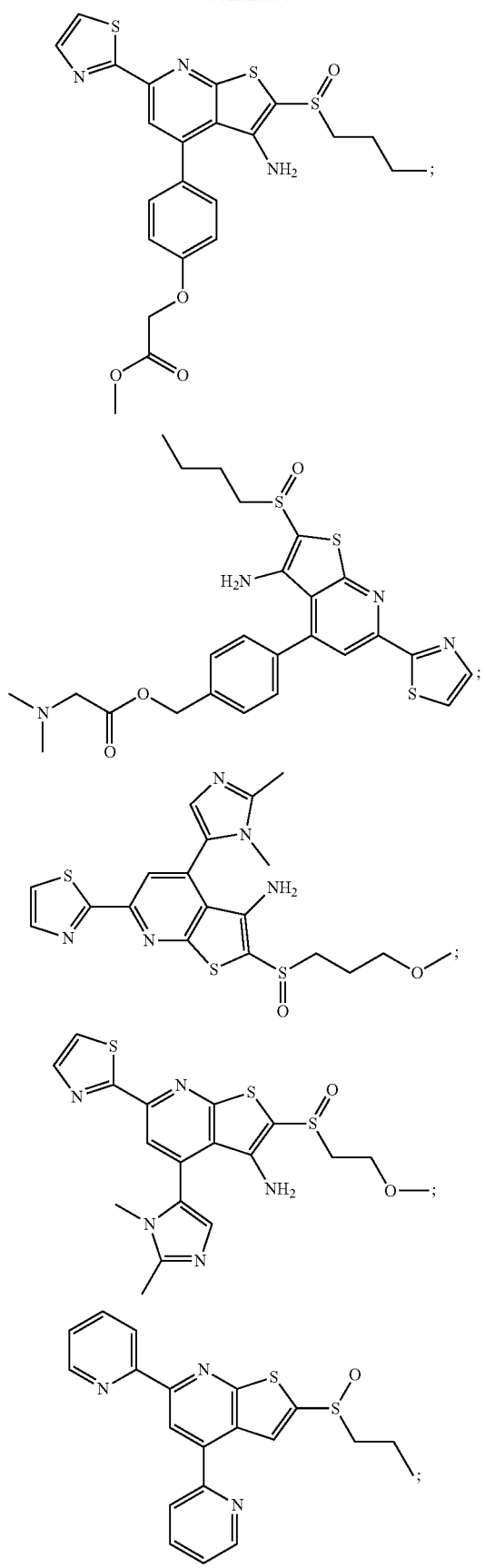
184
-continued
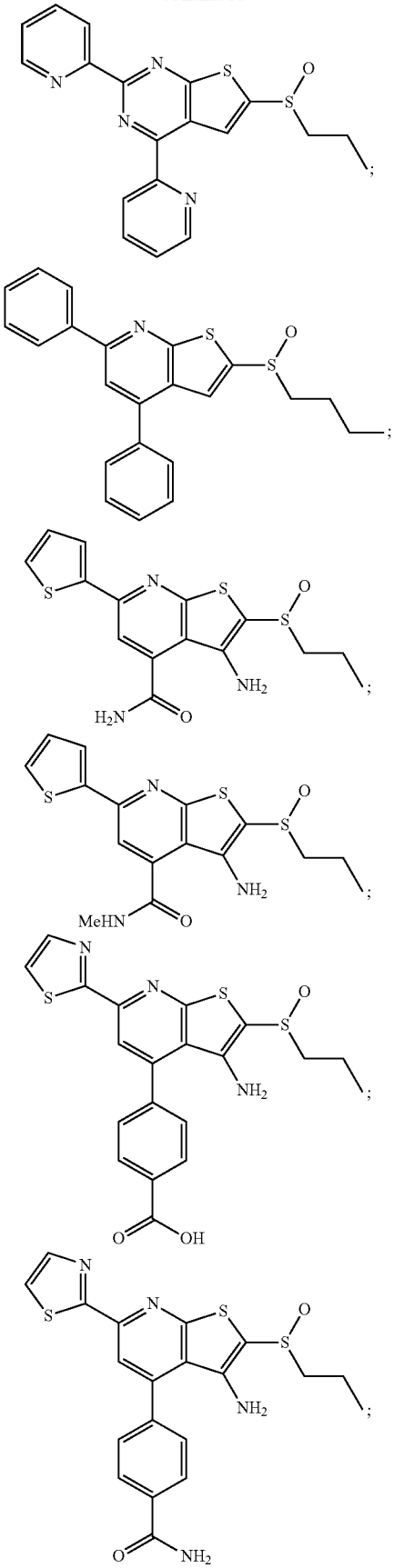

185
-continued
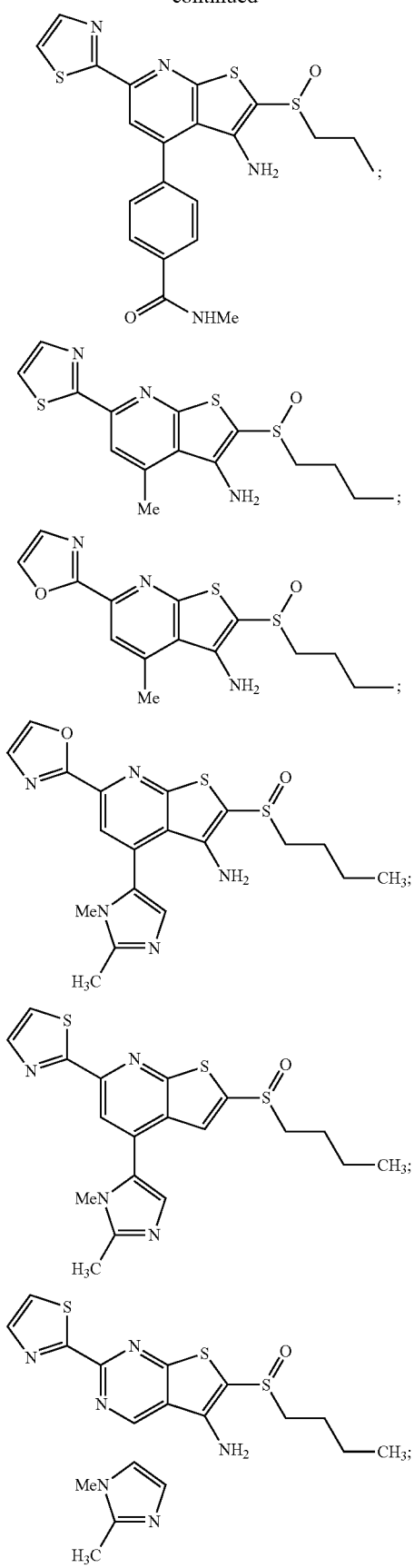
186
-continued
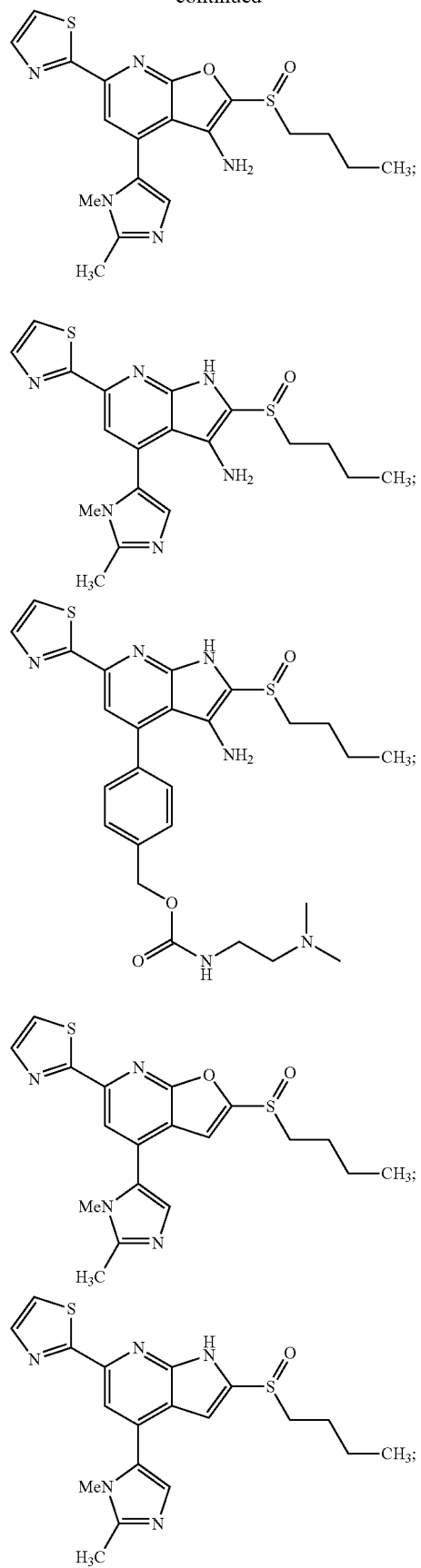

187
-continued
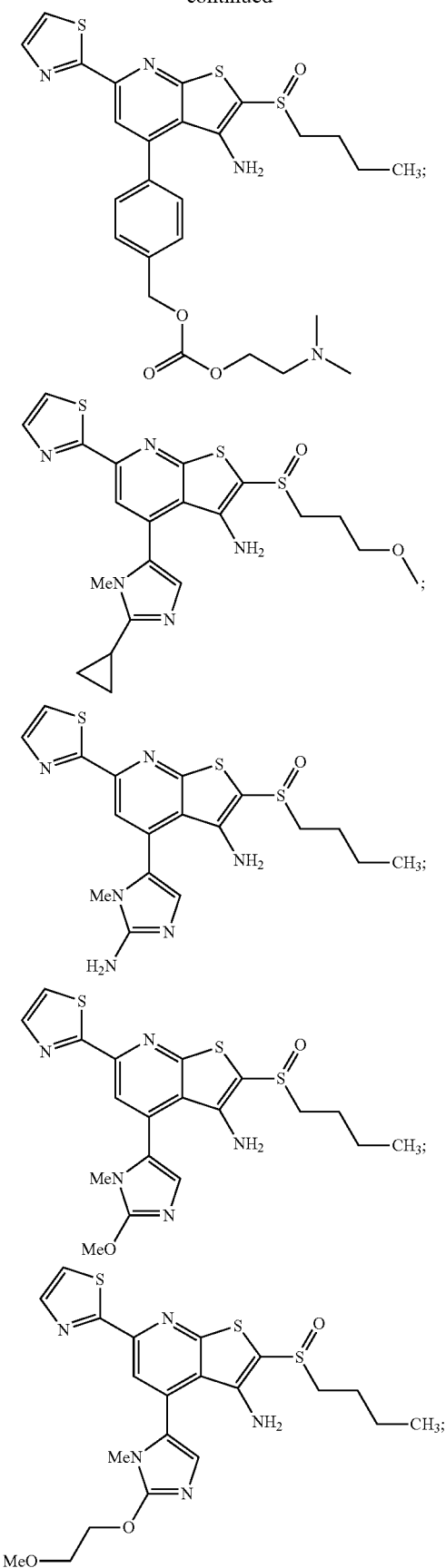
188
-continued
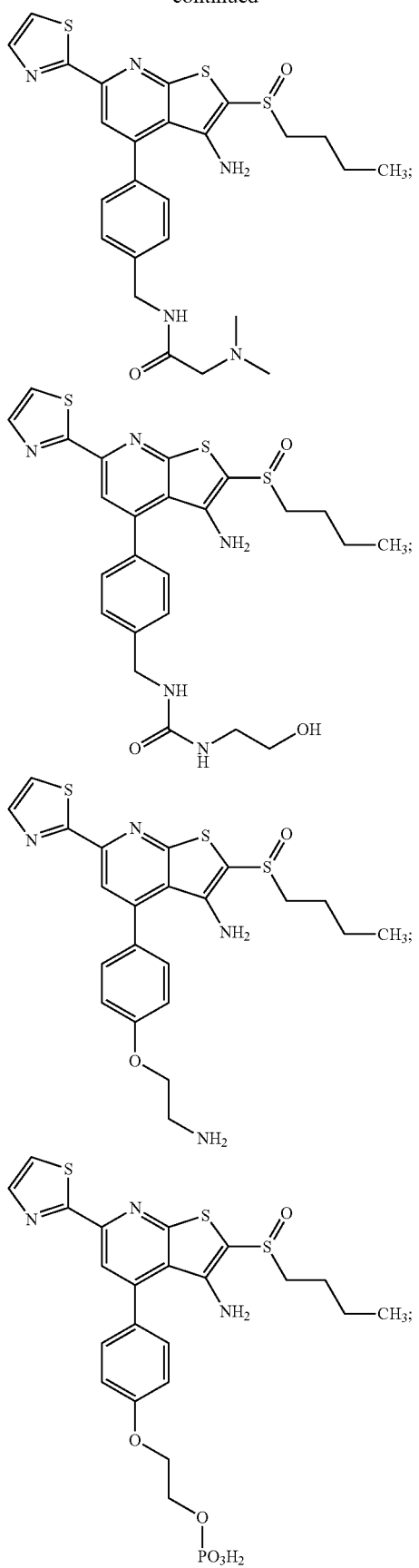

189
-continued
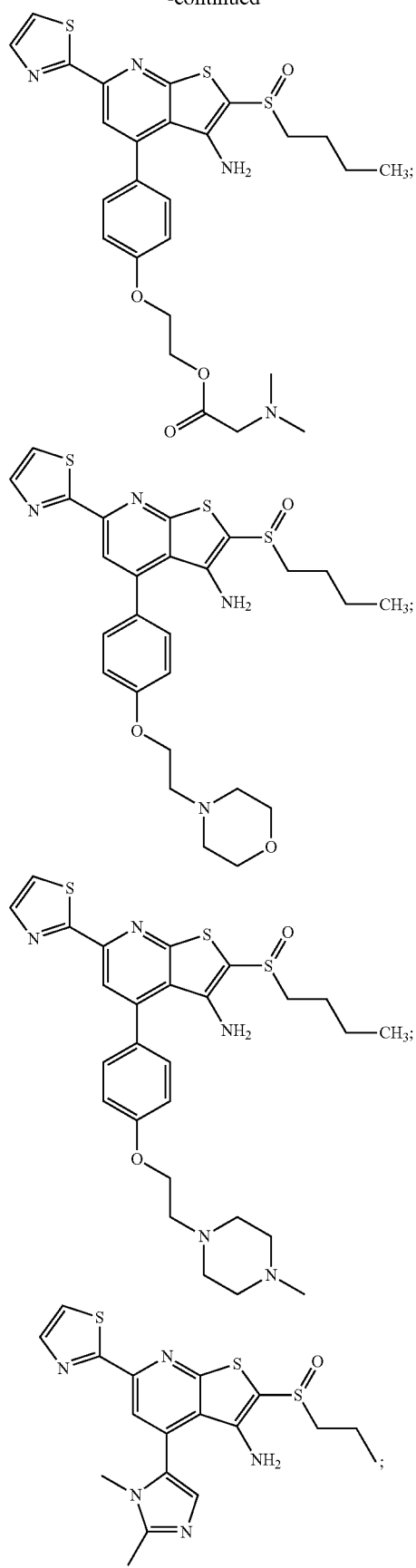
190
-continued
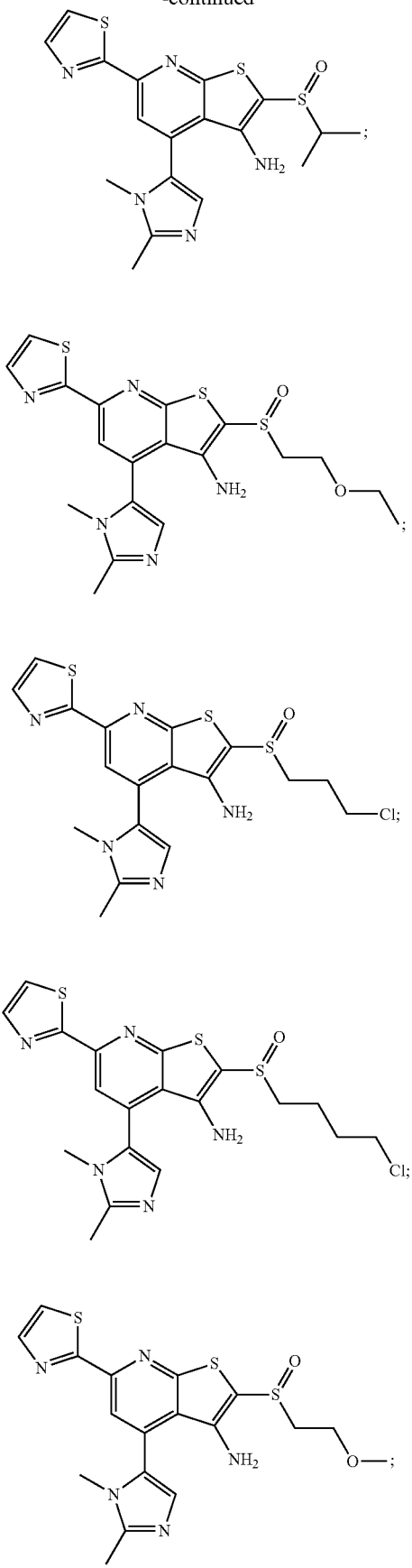

191
-continued
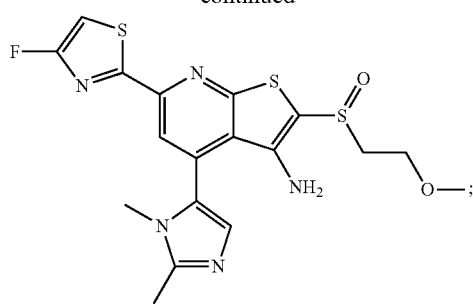
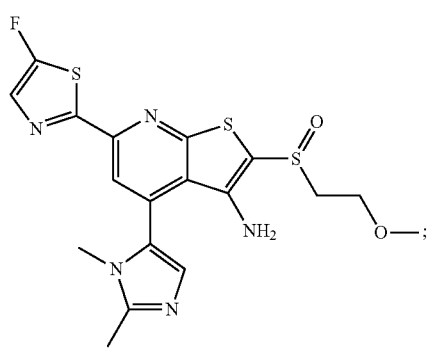
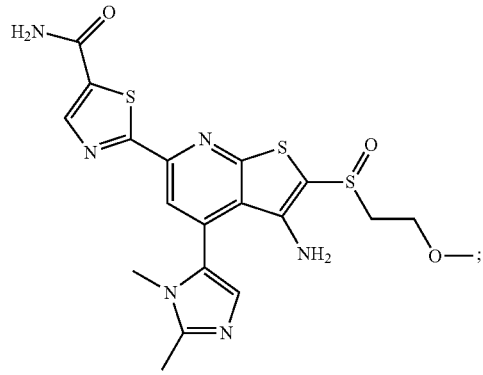
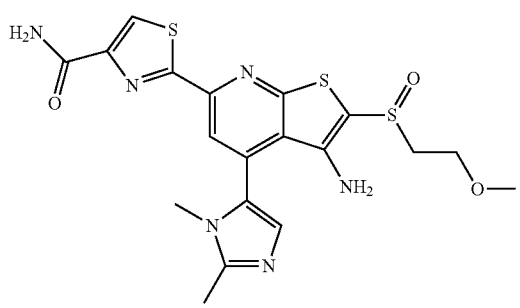
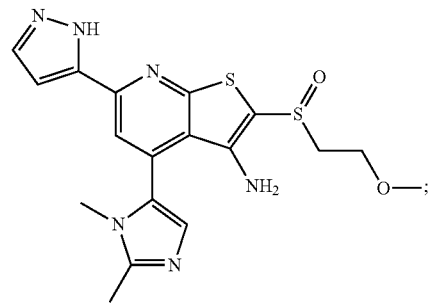
192
-continued
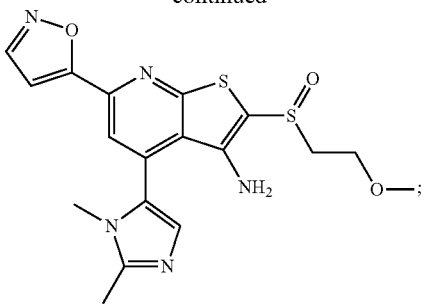
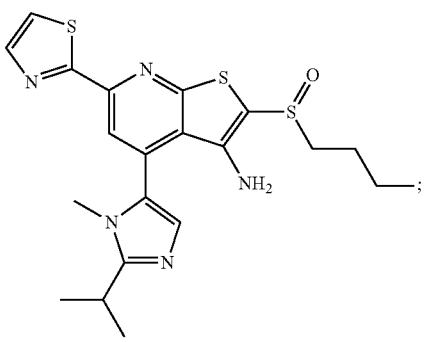
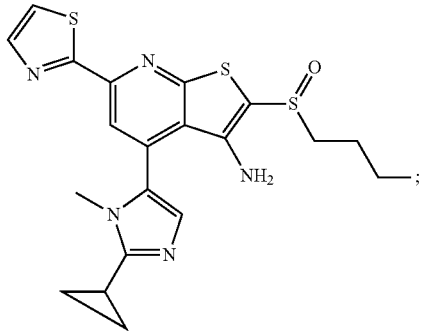
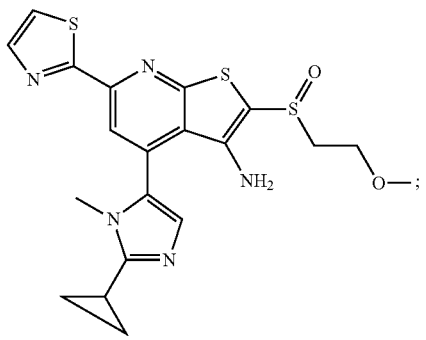
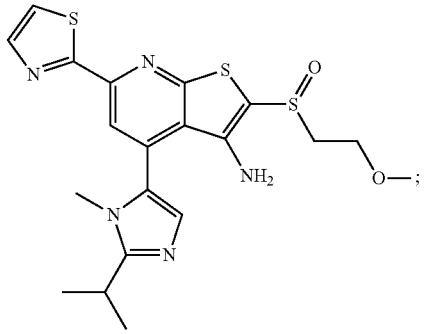

193
-continued
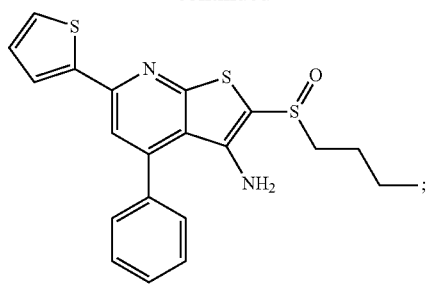
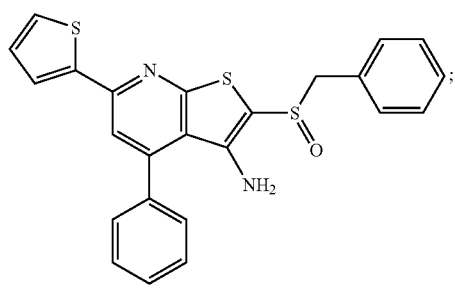
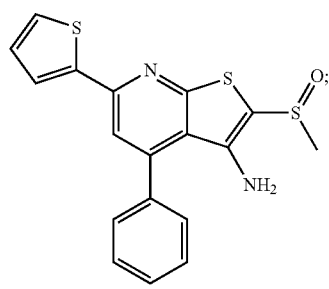
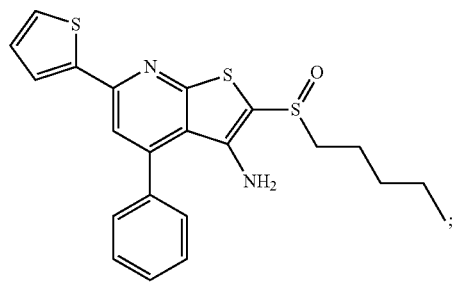
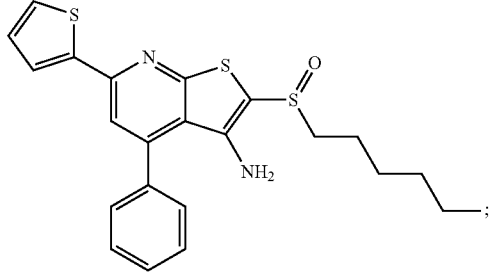
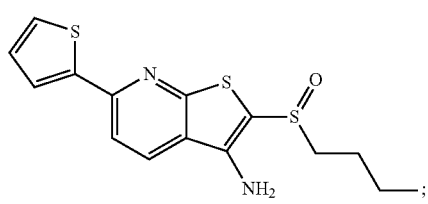
194
-continued
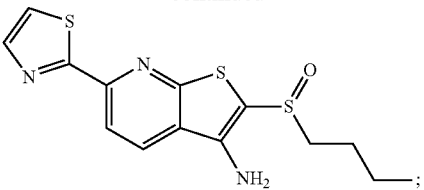
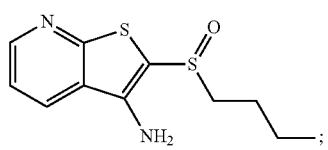
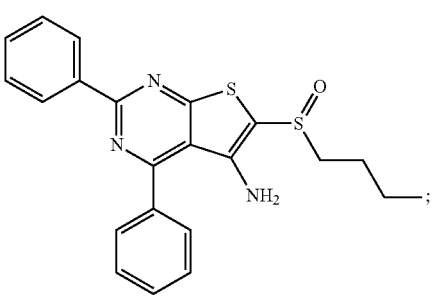
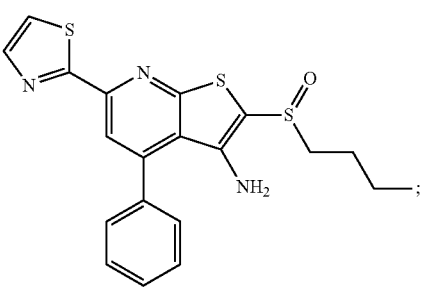
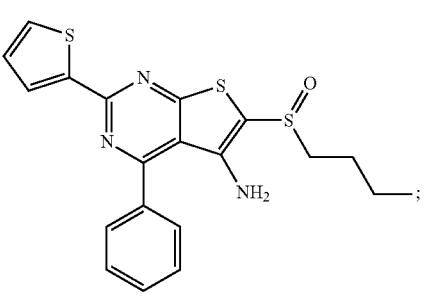
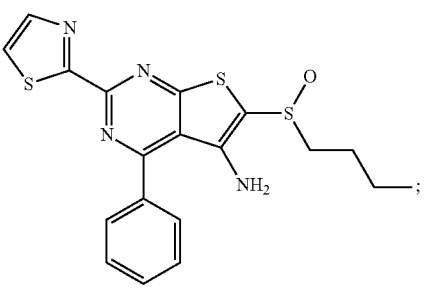

-continued

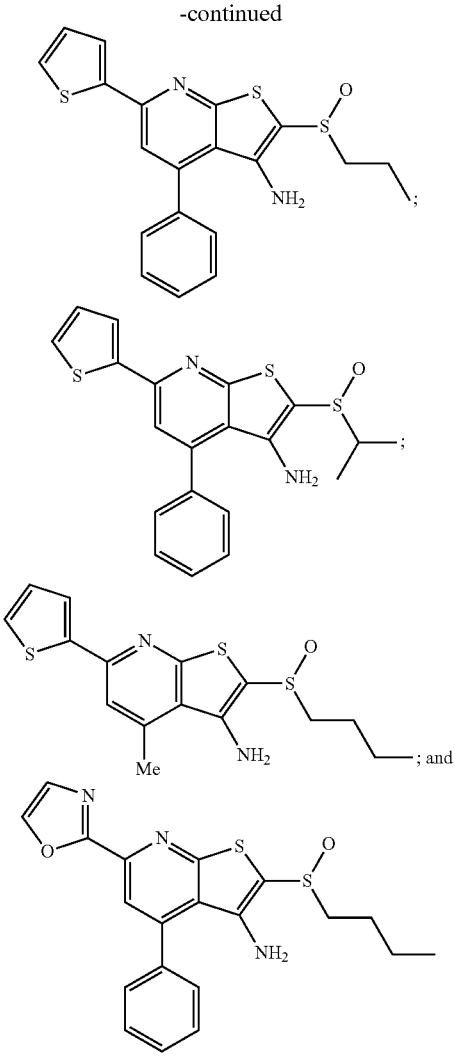

or pharmaceutically acceptable salts thereof.

8. The method of claim 1, wherein:
R$^1$ is C$_1$-C$_{24}$ alkyl; C$_1$-C$_{24}$ alkyl substituted with a halo, C$_1$-C$_{24}$alkoxy, C$_3$-C$_7$cycloalkyl or hydroxy; or C$_3$-C$_7$cycloalkyl;
R$^6$ and R$^7$ are each independently

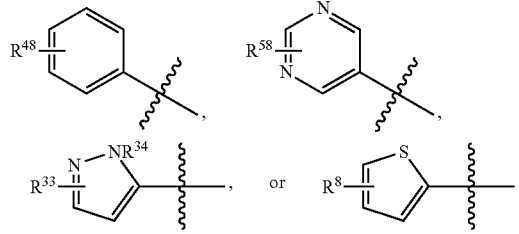

wherein R$^8$, R$^{33}$, R$^{34}$, R$^{48}$, and R$^{58}$ are the same or different and are independently selected from the group consisting of hydrogen, C$_1$-C$_{24}$ alkyl, C$_2$-C$_{24}$ alkenyl, C$_2$-C$_{24}$ alkynyl, C$_6$-C$_{20}$ aryl, heterocycloalkenyl containing from 5-6 ring atoms, heteroaryl or heterocyclyl containing from 5-14 ring atoms, C$_6$-C$_{24}$ alkaryl, C$_6$-C$_{24}$ aralkyl, halo, silyl, hydroxyl, sulfhydryl, C$_1$-C$_{24}$ alkoxy that is optionally substituted with at least one hydroxyl, C$_2$-C$_{24}$ alkenyloxy, C$_2$-C$_{24}$ alkynyloxy, C$_5$-C$_{20}$ aryloxy, acyl, acyloxy (—O-acyl), C$_2$-C$_{24}$ alkoxycarbonyl (—(CO)—O-alkyl), C$_6$-C$_{20}$ aryloxy-carbonyl (—(CO)—O-aryl), C$_2$-C$_{24}$ alkylcarbonato (—O—(CO)—O-alkyl), C$_6$-C$_{20}$ arylcarbonato (—O—(CO)—O-aryl), carboxy (—COOH), carboxylato (—COO—), carbamoyl (—(CO)—NH$_2$), C$_1$-C$_{24}$ alkyl-carbamoyl (—(CO)—NH(C$_1$-C$_{24}$ alkyl)), arylcarbamoyl (—(CO)—NH-aryl), thiocarbamoyl (—(CS)—NH$_2$), carbamido (—NH—(CO)—NH$_2$), cyano (—CN), isocyano (—N+C—), cyanato (—O—CN), isocyanato (—O—N+=C—), isothiocyanato (—S—CN), azido (—N=N+=N—), formyl (—(CO)—H), thioformyl (—(CS)—H), amino (—NH$_2$), mono- or di-(C$_1$-C$_{24}$ alkyl)-amino, mono- or di-(C$_1$-C$_{24}$ alkyl)-amino that is substituted with at least one hydroxyl, C$_5$-C$_{20}$ aryl amino, C$_2$-C$_{24}$ alkylamido (—NH—(CO)-alkyl), C$_6$-C$_{20}$ arylamido (—NH—(CO)-aryl), sulfanamido (—SO$_2$N(R)$_2$ where R is independently H, alkyl, aryl or heteroaryl), imino, alkylimino, arylimino, nitro (—NO$_2$), nitroso (—NO), sulfo (—SO$_2$—OH), sulfonato (—SO$_2$—O—), C$_1$-C$_{24}$ alkylsulfanyl, arylsulfanyl, C$_1$-C$_{24}$ alkylsulfinyl (—(SO)-alkyl), C$_5$-C$_{20}$ arylsulfinyl (—(SO)-aryl), C$_1$-C$_{24}$ alkylsulfonyl (—SO$_2$-alkyl), C$_5$-C$_{20}$ arylsulfonyl (—SO$_2$-aryl), sulfonamide (—SO$_2$—NH$_2$, —SO$_2$NY$_2$ (wherein Y is independently H, arlyl or alkyl), phosphono (—P(O)(OH)$_2$), phosphonato (—P(O)(O$^-$)$_2$), phosphinato (—P(O)(O$^-$)), phospho (—PO$_2$), phosphino (—PH$_2$), polyalkyl ethers (—[(CH$_2$)$_n$O]$_m$), phosphates, phosphate esters [—OP(O)(OR)$_2$ where R=H, methyl or other alkyl];
X$^6$ is N or CH.

9. The method of claim 1, wherein the 15-PGDH inhibitor has an IC50 for 15-PGDH of less than 1 µM.

10. The method of claim 1, wherein the 15-PGDH inhibitor has an IC50 for 15-PGDH of less than 250 nM.

11. The method of claim 1, wherein the 15-PGDH inhibitor has an IC50 for 15-PGDH of less than 50 nM.

12. The method of claim 1, wherein the 15-PGDH inhibitor has an IC50 for 15-PGDH of less than 10 nM.

13. The method of claim 1, wherein the 15-PGDH inhibitor has an IC50 of less than 5 nM.

14. The method of claim 1, wherein:
R$^1$ is C$_3$-C$_7$ cycloalkyl or C$_1$-C$_{24}$ alkoxy;
R$^6$ is

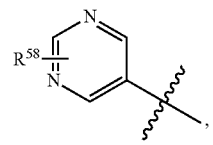

and R$^{58}$ is halo, C(O)NH$_2$, C$_1$-C$_{24}$ alkyl, amino, or mono- or di-(C$_1$-C$_{24}$ alkyl)-amino that is optionally substituted with at least one hydroxyl;
R$^7$ is

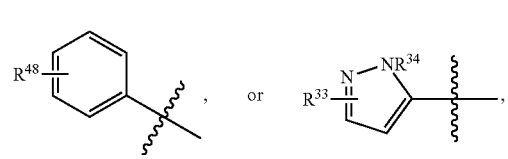

and R$^{33}$, R$^{34}$, and R$^{48}$ are the same or different and are independently C$_1$-C$_{24}$ alkyl, —OOH, mono- or di-(C$_1$-C$_{24}$ alkyl)-amino, —C(O)NH$_2$, or —C(O)NH(C$_1$-C$_{24}$ alkyl); and
X$^6$ is N or CH.

* * * * *

UNITED STATES PATENT AND TRADEMARK OFFICE
CERTIFICATE OF CORRECTION

PATENT NO. : 10,945,998 B2
APPLICATION NO. : 15/556972
DATED : March 16, 2021
INVENTOR(S) : Sanford Markowitz et al.

Page 1 of 1

It is certified that error appears in the above-identified patent and that said Letters Patent is hereby corrected as shown below:

In the Specification

Please replace the paragraph starting at Line 14, Column 1:
--GOVERNMENT FUNDING
This invention was made with government support under Grant Nos. CA127306, CA150964,CA095471, EB005583, and DK107156 awarded by The National Institutes of Health. The government has certain rights in the invention.--

Signed and Sealed this
Eighteenth Day of May, 2021

Drew Hirshfeld
*Performing the Functions and Duties of the
Under Secretary of Commerce for Intellectual Property and
Director of the United States Patent and Trademark Office*